(12) United States Patent
Nambu et al.

(10) Patent No.: US 7,868,026 B2
(45) Date of Patent: Jan. 11, 2011

(54) THERAPEUTIC COMPOUNDS

(75) Inventors: Mitchell David Nambu, San Diego, CA (US); Leena Bharat Kumar Patel, San Diego, CA (US); Brian Douglas Patterson, San Diego, CA (US); Sylvie Kim Sakata, San Diego, CA (US); John Howard Tatlock, San Diego, CA (US)

(73) Assignee: Pfizer Inc., New York, NY (US)

( * ) Notice: Subject to any disclaimer, the term of this patent is extended or adjusted under 35 U.S.C. 154(b) by 1018 days.

(21) Appl. No.: 11/621,410

(22) Filed: Jan. 9, 2007

(65) Prior Publication Data

US 2007/0167497 A1 Jul. 19, 2007

Related U.S. Application Data

(63) Continuation of application No. PCT/IB2006/002639, filed on Sep. 11, 2006.

(60) Provisional application No. 60/720,151, filed on Sep. 23, 2005, provisional application No. 60/723,115, filed on Oct. 3, 2005, provisional application No. 60/725,469, filed on Oct. 11, 2005, provisional application No. 60/762,256, filed on Jan. 25, 2006, provisional application No. 60/821,664, filed on Aug. 7, 2006.

(51) Int. Cl.
| | |
|---|---|
| *A61K 31/4406* | (2006.01) |
| *A61K 31/44* | (2006.01) |
| *C07D 213/75* | (2006.01) |
| *C07D 213/76* | (2006.01) |

(52) U.S. Cl. .............. 514/345; 514/344; 514/348; 514/349; 514/352; 546/286; 546/287; 546/289; 546/290; 546/296; 546/297; 546/307; 546/312

(58) Field of Classification Search ........... 546/286, 546/287, 288, 289, 290, 296, 297, 307, 312; 514/344, 345, 348, 349, 352
See application file for complete search history.

(56) References Cited

U.S. PATENT DOCUMENTS

2003/0166584 A1 9/2003 Hu

OTHER PUBLICATIONS

Vippagunta et al., "Crystalline Solid", Advanced Drug Delivery Reviews 48 (2001) 3-26.*
Guillory (in Bruittain ed.), "Polymorphism, etc.," NY: Marcel Dekker, Inc., 1999, 1-2, 183-226.*
Dresser, G.K., et al. "Pharmacolkinetic-Pharmacodynamic Consequences and clinical relevance of Cytochrome P450 3A4 Inhibition" Clinical Pharmacokinetics, Lea & Febiger, Philadelphia, PA, US vol. 38, No. 1, Jan. 2000, pp. 41-57, table II.
International Search Report from corresponding PCT International application No. PCT/IB2006/002639.

* cited by examiner

*Primary Examiner*—Patricia L Morris
(74) *Attorney, Agent, or Firm*—Jennifer A. Kispert; J. Michael Dixon

(57) ABSTRACT

The present invention provides compounds of formula (I),

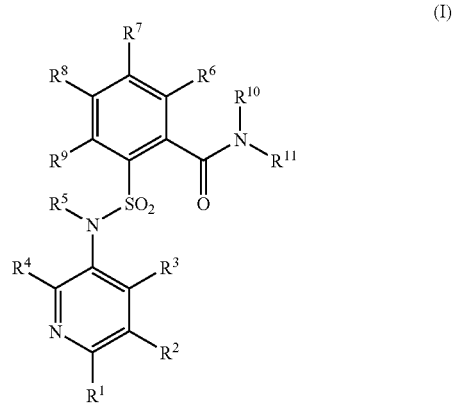

or pharmaceutically acceptable salts or solvates thereof, methods for their preparation, methods for their use, and pharmaceutical formulations comprising them.

12 Claims, No Drawings

THERAPEUTIC COMPOUNDS

This application is a continuation of International Application No. PCT/IB2006/002639, filed Sep. 11, 2006, which claims the benefit of U.S. Provisional Application No. 60/720,151, filed Sep. 23, 2005, U.S. Provisional Application No. 60/723,115, filed Oct. 3, 2005, U.S. Provisional Application No. 60/725,469, filed Oct. 11, 2005, U.S. Provisional Application No. 60/762,256, filed Jan. 25, 2006, and U.S. Provisional Application No. 60/821,664, filed Aug. 7, 2006, all of which are hereby incorporated by reference in their entirety.

BACKGROUND

The cytochrome P450 (CYP450) enzyme system is responsible for the biotransformation of drugs from active to inactive metabolites that are readily excreted by the body. Furthermore, the rapid metabolism of certain drugs by the CYP450 enzyme system can markedly alter their pharmacokinetic (PK) profile and can result in sub-therapeutic plasma levels of those drugs over time. In the area of anti-infective therapy, such as treating viral infections such as human immunodeficiency virus (HIV) infections, such sub-therapeutic drug plasma levels can lead to an increase in resistance of the virus.

Ritonavir (RTV) is a marketed HIV protease inhibitor (PI) that, due to its ability to inhibit the cytochrome P450 3A4 enzyme, is also used to "boost" the pharmacokinetic exposure of many co-administered anti-retrovirals. However, RTV is associated with clinically significant gastrointestinal and metabolic side effects including nausea, emesis, diarrhea, and dyslipidemia. Administering low doses of a compound with potent antiviral activity may also contribute to the selection of drug-resistant strains of HIV. A novel CYP3A4 inhibitor capable of boosting antivirals as effectively as RTV but devoid of antiviral activity and significant side-effects would offer significant advantages and therapeutic value in the treatment of those suffering from infection with the HIV virus. The present invention discloses compounds that are useful in the inhibition of the CYP450 enzyme system and may be used to boost the pharmacokinetic exposure of co-administered drugs, including anti-retrovirals. It also discloses pharmaceutical formulations comprising such compounds, methods of making them, and methods of using them.

SUMMARY

In one embodiment are provided compounds of formula (I),

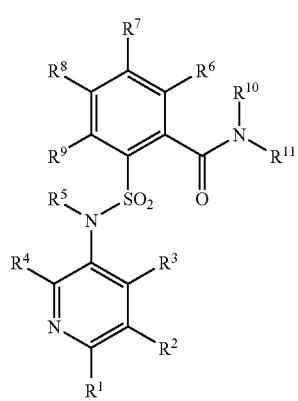

(I)

wherein:
$R^1$, $R^2$, $R^3$, $R^4$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$OR$^{12a}$, —$(CR^{12a}R^{12b})_t$N($R^{12a}R^{12b}$), —$(CR^{12a}R^{12b})_t$CF$_3$, and —$(CR^{12a}R^{12b})_t$C$_6$-C$_{10}$ aryl;

$R^5$ is hydrogen or $C_1$-$C_6$ alkyl;

$R^6$, $R^7$, $R^8$ and $R^9$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$CF$_3$, —$(CR^{12a}R^{12b})_t$OR$^{12a}$, —$(CR^{12a}R^{12b})_t$N($R^{12a}R^{12b}$), —$(CR^{12a}R^{12b})_t$R$^{12a}$, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, —$(CR^{12a}R^{12b})_t$heteroaryl, —O$(CR^{12a}R^{12b})_t$R$^{12a}$, —O$(CR^{12a}R^{12b})_t$C$_3$-C$_{11}$ cycloalkyl, —O$(CR^{12a}R^{12b})_t$C$_6$-C$_{10}$ aryl, —O$(CR^{12a}R^{12b})_t$C$_2$-C$_{10}$ heterocyclyl, —O$(CR^{12a}R^{12b})_t$heteroaryl, —O$(CR^{12a}R^{12b})_t$OR$^{12a}$, and —O$(CR^{12a}R^{12b})_t$N($R^{12a}R^{12b}$), wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl is optionally substituted with one or more $R^{14}$;

$R^{10}$ and $R^{11}$ are independently selected from hydrogen, —$(CR^{12a}R^{12b})_t$C$_1$-C$_6$ alkyl, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, and —$(CR^{12a}R^{12b})_t$heteroaryl, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{13}$; or $R^{10}$ and $R^{11}$, together with the atom to which they are attached, form a $C_2$-$C_{10}$ heterocyclyl group, optionally substituted with one or more $R^{13}$;

each $R^{12a}$ and $R^{12b}$ is independently selected from hydrogen and $C_1$-$C_6$ alkyl; or $R^{12a}$ and $R^{12b}$ together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t$CN, —$(CR^{12a}R^{12b})_t$CF$_3$, —$(CR^{12a}R^{12b})_t$OCF$_3$, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, —$(CR^{12a}R^{12b})_t$heteroaryl, —O$(CR^{12a}R^{12b})_t$R$^{12a}$, —O$(CR^{12a}R^{12b})_t$C$_6$-C$_{10}$ aryl, —O$(CR^{12a}R^{12b})_t$C$_2$-C$_{10}$ heterocyclyl, —O$(CR^{12a}R^{12b})_t$heteroaryl, —$(CR^{12a}R^{12b})_t$CO$_2$($C_1$-$C_6$ alkyl), —$(CR^{12a}R^{12b})_t$N($R^{12a}R^{12b}$), —$(CR^{12a}R^{12b})_t$C(O)NR$^{12a}$R$^{12b}$, —$(CR^{12a}R^{12b})_t$OR$^{12a}$, —$(CR^{12a}R^{12b})_t$S(O)R$^{12a}$, and —$(CR^{12a}R^{12b})_t$S(O)$_2$R$^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

In another embodiment are provided compounds of formula (I), wherein:

$R^1$, $R^2$, $R^3$, $R^4$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$OR$^{12a}$, —$(CR^{12a}R^{12b})_t$N($R^{12a}R^{12b}$), and —$(CR^{12a}R^{12b})_t$CF$_3$;

$R^5$ is hydrogen or $C_1$-$C_6$ alkyl;

$R^6$, $R^7$, $R^8$, and $R^9$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$CF$_3$, —$(CR^{12a}R^{12b})_t$OR$^{12a}$, —$(CR^{12a}R^{12b})_t$N($R^{12a}R^{12b}$), —$(CR^{12a}R^{12b})_t$R$^{12a}$, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, —$(CR^{12a}R^{12b})_t$heteroaryl, —O$(CR^{12a}R^{12b})_t$R$^{12a}$, —O$(CR^{12a}R^{12b})_t$C$_3$-C$_{11}$ cycloalkyl, —$(CR^{12a}R^{12b})_t$C$_6$-C$_{10}$ aryl, —O$(CR^{12a}R^{12b})_t$C$_2$-C$_{10}$ heterocyclyl, —O(CR$^{12a}$R$^{12b}$)$_t$heteroaryl, —O(CR$^{12a}$R$^{12b}$)$_t$OR$^{12a}$, and —O(CR$^{12a}$R$^{12b}$)$_t$N(R$^{12a}$R$^{12b}$), wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl is optionally substituted with one or more R$^{14}$;

R$^{10}$ and R$^{11}$ are independently selected from hydrogen, —(CR$^{12a}$R$^{12b}$)$_t$C$_1$-C$_6$ alkyl, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, and —(CR$^{12a}$R$^{12b}$)$_t$heteroaryl wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl groups is optionally substituted with one or more R$^{13}$;

each R$^{12a}$ and R$^{12b}$ is independently selected from hydrogen and C$_1$-C$_6$ alkyl; or R$^{12a}$ and R$^{12b}$ together with the atom to which they are attached, form a C$_3$-C$_{11}$ cycloalkyl or a C$_2$-C$_{10}$ heterocyclyl group;

each R$^{13}$ is independently selected from C$_1$-C$_6$ alkyl, halogen, —(CR$^{12a}$R$^{12b}$)$_t$CN, —(CR$^{12a}$R$^{12b}$)$_t$CF$_3$, —(CR$^{12a}$R$^{12b}$)$_t$OCF$_3$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, —(CR$^{12a}$R$^{12b}$)$_t$heteroaryl, —O(CR$^{12a}$R$^{12b}$)$_t$R$^{12a}$, —O(CR$^{12a}$R$^{12b}$)$_t$C$_6$-C$_{10}$ aryl, —O(CR$^{12a}$R$^{12b}$)$_t$C$_2$-C$_{10}$ heterocyclyl, —O(CR$^{12a}$R$^{12b}$)$_t$heteroaryl, —(CR$^{12a}$R$^{12b}$)$_t$CO$_2$ (C$_1$-C$_6$ alkyl), —(CR$^{12a}$R$^{12b}$)$_t$N(R$^{12a}$R$^{12b}$), —(CR$^{12a}$R$^{12b}$)$_t$C(O)NR$^{12a}$R$^{12b}$, —(CR$^{12a}$R$^{12b}$)$_t$OR$^{12a}$, —(CR$^{12a}$R$^{12b}$)$_t$S(O)R$^{12a}$, and —(CR$^{12a}$R$^{12b}$)$_t$S(O)$_2$R$^{12a}$, wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl groups is optionally substituted with one or more R$^{14}$;

each R$^{14}$ is independently selected from C$_1$-C$_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

In yet another embodiment are provided compounds of formula (I), wherein:

R$^1$, R$^2$, R$^3$, R$^4$ are independently selected from hydrogen, C$_1$-C$_6$ alkyl, halo, —CN, —OR$^{12a}$, and —CF$_3$;

R$^5$ is hydrogen;

R$^6$, R$^7$, R$^8$, and R$^9$ are independently selected from hydrogen, C$_1$-C$_6$ alkyl, —(CR$^{12a}$R$^{12b}$)$_t$halo, —(CR$^{12a}$R$^{12b}$)$_t$CN, —(CR$^{12a}$R$^{12b}$)$_t$CF$_3$, —(CR$^{12a}$R$^{12b}$)$_t$OR$^{12a}$, —(CR$^{12a}$R$^{12b}$)$_t$N(R$^{12a}$R$^{12b}$), —(CR$^{12a}$R$^{12b}$)$_t$R$^{12a}$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, —(CR$^{12a}$R$^{12b}$)$_t$heteroaryl, —O(CR$^{12a}$R$^{12b}$)$_t$R$^{12a}$, —O(CR$^{12a}$R$^{12b}$)$_t$C$_3$-C$_{11}$ cycloalkyl, —O(CR$^{12a}$R$^{12b}$)$_t$C$_6$-C$_{10}$ aryl, —O(CR$^{12a}$R$^{12b}$)$_t$C$_2$-C$_{10}$ heterocyclyl, —O(CR$^{12a}$R$^{12b}$)$_t$heteroaryl, —O(CR$^{12a}$R$^{12b}$)$_t$OR$^{12a}$, and —O(CR$^{12a}$R$^{12b}$)$_t$N(R$^{12a}$R$^{12b}$), wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl is optionally substituted with one or more R$^{14}$;

R$^{10}$ and R$^{11}$ are independently selected from hydrogen, —(CR$^{12a}$R$^{12b}$)$_t$C$_1$-C$_6$ alkyl, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, and —(CR$^{12a}$R$^{12b}$)$_t$heteroaryl, wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl groups is optionally substituted with one or more R$^{13}$;

each R$^{12a}$ and R$^{12b}$ is independently selected from hydrogen and C$_1$-C$_6$ alkyl; or R$^{12a}$ and R$^{12b}$, together with the atom to which they are attached, form a C$_3$-C$_{11}$ cycloalkyl or a C$_2$-C$_{10}$ heterocyclyl group;

each R$^{13}$ is independently selected from C$_1$-C$_6$ alkyl, halogen, —(CR$^{12a}$R$^{12b}$)$_t$CN, —(CR$^{12a}$R$^{12b}$)$_t$CF$_3$, —(CR$^{12a}$R$^{12b}$)$_t$OCF$_3$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, —(CR$^{12a}$R$^{12b}$)$_t$heteroaryl, —O(CR$^{12a}$R$^{12b}$)$_t$R$^{12a}$, —O(CR$^{12a}$R$^{12b}$)$_t$C$_6$-C$_{10}$ aryl, —O(CR$^{12a}$R$^{12b}$)$_t$C$_2$-C$_{10}$ heterocyclyl, —O(CR$^{12a}$R$^{12b}$)$_t$heteroaryl, —(CR$^{12a}$R$^{12b}$)$_t$CO$_2$ (C$_1$-C$_6$ alkyl), —(CR$^{12a}$R$^{12b}$)$_t$N(R$^{12a}$R$^{12b}$), —(CR$^{12a}$R$^{12b}$)$_t$C(O)NR$^{12a}$R$^{12b}$, —(CR$^{12a}$R$^{12b}$)$_t$OR$^{12a}$, —(CR$^{12a}$R$^{12b}$)$_t$S(O)R$^{12a}$, and —(CR$^{12a}$R$^{12b}$)$_t$S(O)$_2$R$^{12a}$, wherein each of said C$_1$-C$_6$ alkyl, C$_3$-C$_{11}$, cycloalkyl, C$_6$-C$_{10}$ aryl, C$_2$-C$_{10}$ heterocyclyl, and heteroaryl groups is optionally substituted with one or more R$^{14}$;

each R$^{14}$ is independently selected from C$_1$-C$_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

Still another embodiment provides compounds of formula (I), wherein:

R$^1$, R$^2$, R$^3$, R$^4$ are independently selected from hydrogen, C$_1$-C$_6$ alkyl, halo, —CN, —OR$^{12a}$, and —CF$_3$;

R$^5$ is hydrogen;

R$^6$, R$^7$, R$^8$, and R$^9$ are independently selected from hydrogen, C$_1$-C$_6$ alkyl, —(CR$^{12a}$R$^{12b}$)$_t$halo, —(CR$^{12a}$R$^{12b}$)$_t$CN, —(CR$^{12a}$R$^{12b}$)$_t$CF$_3$, —(CR$^{12a}$R$^{12b}$)$_t$OR$^{12a}$, —(CR$^{12a}$R$^{12b}$)$_t$N(R$^{12a}$R$^{12b}$), —(CR$^{12a}$R$^{12b}$)$_t$R$^{12a}$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, —(CR$^{12a}$R$^{12b}$)$_t$heteroaryl, —O(CR$^{12a}$R$^{12b}$)$_t$R$^{12a}$, —O(CR$^{12a}$R$^{12b}$)$_t$C$_3$-C$_{11}$ cycloalkyl, —O(CR$^{12a}$R$^{12b}$)$_t$C$_6$-C$_{10}$ aryl, —O(CR$^{12a}$R$^{12b}$)$_t$C$_2$-C$_{10}$ heterocyclyl, —O(CR$^{12a}$R$^{12b}$)$_t$heteroaryl, —O(CR$^{12a}$R$^{12b}$)$_t$OR$^{12a}$, and —O(CR$^{12a}$R$^{12b}$)$_t$N(R$^{12a}$R$^{12b}$), wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl is optionally substituted with one or more R$^{14}$;

R$^{10}$ is hydrogen or C$_1$-C$_6$ alkyl;

R$^{11}$ is selected from —(CR$^{12a}$R$^{12b}$)$_t$C$_1$-C$_6$ alkyl, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, and —(CR$^{12a}$R$^{12b}$)$_t$heteroaryl, wherein each of said C$_1$-C$_6$ alkyl, C$_3$-C$_{11}$ cycloalkyl, C$_6$-C$_{10}$ aryl, C$_2$-C$_{10}$ heterocyclyl, and heteroaryl groups is optionally substituted with one or more R$^{13}$;

each R$^{12a}$ and R$^{12b}$ is independently selected from hydrogen and C$_1$-C$_6$ alkyl; or R$^{12a}$ and R$^{12b}$, together with the atom to which they are attached, form a C$_3$-C$_{11}$, cycloalkyl or a C$_2$-C$_{10}$ heterocyclyl group;

each R$^{13}$ is independently selected from C$_1$-C$_6$ alkyl, halogen, —(CR$^{12a}$R$^{12b}$)$_t$CN, —(CR$^{12a}$R$^{12b}$)$_t$CF$_3$, —(CR$^{12a}$R$^{12b}$)$_t$OCF$_3$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —(CR$^{12a}$R$^{12b}$)$_t$C$_2$-C$_{10}$ heterocyclyl, —(CR$^{12a}$R$^{12b}$)$_t$heteroaryl, —O(CR$^{12a}$R$^{12b}$)$_t$R$^{12a}$, —O(CR$^{12a}$R$^{12b}$)$_t$C$_6$-C$_{10}$ aryl, —O(CR$^{12a}$R$^{12b}$)$_t$C$_2$-C$_{10}$ heterocyclyl, —O(CR$^{12a}$R$^{12b}$)$_t$heteroaryl, —(CR$^{12a}$R$^{12b}$)$_t$CO$_2$ (C$_1$-C$_6$ alkyl), —(CR$^{12a}$R$^{12b}$)$_t$N(R$^{12a}$R$^{12b}$), —(CR$^{12a}$R$^{12b}$)$_t$C(O)NR$^{12a}$R$^{12b}$, —(CR$^{12a}$R$^{12b}$)$_t$OR$^{12a}$, —(CR$^{12a}$R$^{12b}$)$_t$S(O)R$^{12a}$, and —(CR$^{12a}$R$^{12b}$)$_t$S(O)$_2$R$^{12a}$, wherein each of said C$_1$-C$_6$ alkyl, C$_3$-C$_{11}$, cycloalkyl, C$_6$-C$_{10}$ aryl, C$_2$-C$_{10}$ heterocyclyl, and heteroaryl groups is optionally substituted with one or more R$^{14}$;

each R$^{14}$ is independently selected from C$_1$-C$_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

Further provided herein are compounds of formula (I), wherein:

$R^1$, $R^2$, $R^3$, $R^4$ are independently selected from hydrogen, $C_1$-$C_6$ alkyl, halo, —CN, —$OR^{12a}$, and —$CF_3$;

$R^5$ is hydrogen;

$R^6$, $R^7$, $R^8$, and $R^9$ are hydrogen;

$R^{10}$ is hydrogen or $C_1$-$C_6$ alkyl;

$R^{11}$ is selected from —$(CR^{12a}R^{12b})_t C_1$-$C_6$ alkyl, —$(CR^{12a}R^{12b})_t C_3$-$C_{11}$ cycloalkyl, —$(CR^{12a}R^{12b})_t C_6$-$C_{10}$ aryl, —$(CR^{12a}R^{12b})_t C_2$-$C_{10}$ heterocyclyl, and —$(CR^{12a}R^{12b})_t$heteroaryl, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^3$;

each $R^{12a}$ and $R^{12b}$ is independently selected from hydrogen and $C_1$-$C_6$ alkyl; or $R^{12a}$ and $R^{12b}$ together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t CN$, —$(CR^{12a}R^{12b})_t CF_3$, —$CR^{12a}R^{12b})_t OCF_3$, —$(CR^{12a}R^{12b})_t C_3$-$C_{11}$ cycloalkyl, —$(CR^{12a}R^{12b})_t C_6$-$C_{10}$ aryl, —$(CR^{12a}R^{12b})_t C_2$-$C_{10}$ heterocyclyl, —$(CR^{12a}R^{12b})_t$heteroaryl, —$O(CR^{12a}R^{12b})_t R^{12a}$, —$O(CR^{12a}R^{12b})_t C_6$-$C_{10}$ aryl, —$O(CR^{12a}R^{12b})_t C_2$-$C_{10}$ heterocyclyl, —$O(CR^{12a}R^{12b})_t$heteroaryl, —$(CR^{12a}R^{12b})_t CO_2$($C_1$-$C_6$ alkyl), —$(CR^{12a}R^{12b})_t N(R^{12a}R^{12b})$, —$(CR^{12a}R^{12b})_t C(O)NR^{12a}R^{12b}$, —$(CR^{12a}R^{12b})_t OR^{12a}$, —$(CR^{12a}R^{12b})_t S(O)R^{12a}$, and —$(CR^{12a}R^{12b})_t S(O)_2 R^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —$CF_3$, and —$OR^{12a}$; and each t is independently selected from 0, 1, 2, 3, 4, 5, and 6; or a pharmaceutically acceptable salt or solvate thereof.

Still another embodiment affords compounds of formula (I), wherein:

$R^1$, $R^2$, $R^3$, $R^4$ are independently selected from hydrogen, $C_1$-$C_6$ alkyl, halo, —CN, —$OR^{12a}$, and —$CF_3$;

$R^5$ is hydrogen;

$R^6$, $R^7$, $R^8$, and $R^9$ are hydrogen;

$R^{10}$ is hydrogen or $C_1$-$C_6$ alkyl;

$R^{11}$ is —$(CR^{12a}R^{12b})_t C_6$-$C_{10}$ aryl, wherein said $C_6$-$C_{10}$ aryl is optionally substituted with one or more $R^{13}$;

each $R^{12a}$ and $R^{12b}$ is independently selected from hydrogen and $C_1$-$C_6$ alkyl; or $R^{12a}$ and $R^{12b}$, together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t CN$, —$(CR^{12a}R^{12b})_t CF_3$, —$(CR^{12a}R^{12b})_t OCF_3$, —$(CR^{12a}R^{12b})_t C_3$-$C_{11}$ cycloalkyl, —$(CR^{12a}R^{12b})_t C_6$-$C_{10}$ aryl, —$(CR^{12a}R^{12b})_t C_2$-$C_{10}$ heterocyclyl, —$(CR^{12a}R^{12b})_t$heteroaryl, —$O(CR^{12a}R^{12b})_t R^{12a}$, —$O(CR^{12a}R^{12b})_t C_6$-$C_{10}$ aryl, —$O(CR^{12a}R^{12b})_t C_2$-$C_{10}$ heterocyclyl, —$O(CR^{12a}R^{12b})_t$heteroaryl, —$(CR^{12a}R^{12b})_t CO_2$($C_1$-$C_6$ alkyl), —$(CR^{12a}R^{12b})_t N(R^{12a}R^{12b})$, —$(CR^{12a}R^{12b})_t C(O)NR^{12a}R^{12b}$, —$(CR^{12a}R^{12b})_t OR^{12a}$, —$(CR^{12a}R^{12b})_t S(O)R^{12a}$, and —$(CR^{12a}R^{12b})_t S(O)_2 R^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —$CF_3$, and —$OR^{12a}$; and each t is independently selected from 0, 1, 2, 3, 4, 5, and 6; or a pharmaceutically acceptable salt or solvate thereof.

Yet another embodiment provides compounds of formula (I), wherein:

$R^1$, $R^2$, $R^3$, $R^4$ are independently selected from hydrogen, $C_1$-$C_6$ alkyl, halo, —CN, —$OR^{12a}$; and —$CF_3$;

$R^5$ is hydrogen;

$R^6$, $R^7$, $R^8$, and $R^9$ are hydrogen;

$R^{10}$ is hydrogen or $C_1$-$C_6$ alkyl;

$R^{11}$ is —$(CR^{12a}R^{12b})C_6$-$C_{10}$ aryl or —$(CR^{12a}R^{12b})_2 C_6$-$C_{10}$ aryl, wherein said $C_6$-$C_{10}$ aryl is optionally substituted with one or more $R^{13}$;

each $R^{12a}$ and $R^{12b}$ is independently selected from hydrogen and $C_1$-$C_6$ alkyl; or $R^{12a}$ and $R^{12b}$ together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t CN$, —$(CR^{12a}R^{12b})_t CF_3$, —$(CR^{12a}R^{12b})_t OCF_3$, —$(CR^{12a}R^{12b})_t C_3$-$C_{11}$ cycloalkyl, —$(CR^{12a}R^{12b})_t C_6$-$C_{10}$ aryl, —$(CR^{12a}R^{12b})_t C_2$-$C_{10}$ heterocyclyl, —$(CR^{12a}R^{12b})_t$heteroaryl, —$O(CR^{12a}R^{12b})_t R^{12a}$, —$O(CR^{12a}R^{12b})_t C_6$-$C_{10}$ aryl, —$O(CR^{12a}R^{12b})_t C_2$-$C_{10}$ heterocyclyl, —$O(CR^{12a}R^{12b})_t$heteroaryl, —$(CR^{12a}R^{12b})_t CO_2$($C_1$-$C_6$ alkyl), —$(CR^{12a}R^{12b})_t N(R^{12a}R^{12b})$, —$(CR^{12a}R^{12b})_t C(O)NR^{12a}R^{12b}$, —$(CR^{12a}R^{12b})_t OR^{12a}$, —$(CR^{12a}R^{12b})_t S(O)R^{12a}$, and —$(CR^{12a}R^{12b})_t S(O)_2 R^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —$CF_3$, and —$OR^{12a}$; and each t is independently selected from 0, 1, 2, 3, 4, 5, and 6; or a pharmaceutically acceptable salt or solvate thereof.

Still another embodiment provides compounds of formula (I), wherein:

$R^1$, $R^2$, $R^3$, $R^4$ are independently selected from hydrogen, $C_1$-$C_6$ alkyl, halo, —CN, —$OR^{12a}$, and —$CF_3$;

$R^5$ is hydrogen;

$R^6$, $R^7$, $R^8$, and $R^9$ are hydrogen;

$R^{10}$ is hydrogen or $C_1$-$C_6$ alkyl;

$R^{11}$ is —$(CH_2)C_6$-$C_{10}$ aryl or —$(CH_2)_2 C_6$-$C_{10}$ aryl, wherein said $C_6$-$C_{10}$ aryl is optionally substituted with one or more $R^{13}$;

$R^{12a}$ is hydrogen or $C_1$-$C_6$ alkyl; and each $R^{13}$ is independently selected from $C_1$-$C_6$ alkyl, halogen, —CN, —$CF_3$, and —$OCF_3$; or a pharmaceutically acceptable salt or solvate thereof.

A further embodiment provides compounds of formula (I), wherein:

$R^1$, $R^3$, and $R^4$ are hydrogen;

$R^2$ is $C_1$-$C_6$ alkyl, halo, —CN, —$OR^{12a}$, or —$CF_3$;

$R^5$ is hydrogen;

$R^6$, $R^7$, $R^8$ and $R^9$ are hydrogen;

$R^{10}$ is hydrogen or $C_1$-$C_6$ alkyl;

$R^{11}$ is —$(CH_2)C_6$-$C_{10}$ aryl or —$(CH_2)_2 C_6$-$C_{10}$ aryl, wherein said $C_6$-$C_{10}$ aryl is optionally substituted with one or more $R^{13}$;

$R^{12a}$ is hydrogen or $C_1$-$C_6$ alkyl; and each $R^{13}$ is independently selected from $C_1$-$C_6$ alkyl, halogen, —CN, —$CF_3$, and —$OCF_3$; or a pharmaceutically acceptable salt or solvate thereof.

In another embodiment are provided compounds of formula (I), wherein:
$R^1$, $R^3$, and $R^4$ are hydrogen;
$R^2$ is $C_1$-$C_6$ alkyl, —Cl, —F, —CN, —$OCH_3$, —$OCH_2CH_3$, or —$CF_3$;
$R^5$ is hydrogen;
$R^6$, $R^7$, $R^8$ and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or
a pharmaceutically acceptable salt or solvate thereof.

In still another embodiment are provided compounds of formula (I), wherein:
$R^1$, $R^3$, and $R^4$ are hydrogen;
$R^2$ is $C_1$-$C_6$ alkyl, —$OCH_3$, or —$OCH_2CH_3$;
$R^5$ is hydrogen;
$R^6$, $R^7$, $R^8$ and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or
a pharmaceutically acceptable salt or solvate thereof.

In still another embodiment are provided compounds of formula (I), wherein:
$R^1$, $R^3$, and $R^4$ are hydrogen;
$R^2$ is —$CH_3$, —$OCH_3$, or —$OCH_2CH_3$;
$R^5$ is hydrogen;
$R^6$, $R^7$, $R^8$ and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or
a pharmaceutically acceptable salt or solvate thereof.

In a further embodiment are provided compounds of formula (I), wherein:
$R^1$, $R^2$, and $R^4$ are hydrogen;
$R^3$ is $C_1$-$C_6$ alkyl, —Cl, —F, —CN, —$OCH_3$, —$OCH_2CH_3$, or —$CF_3$;
$R^5$ is hydrogen;
$R^6$, $R^7$, $R^8$ and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or
a pharmaceutically acceptable salt or solvate thereof.

In a further embodiment are provided compounds of formula (I), wherein:
$R^1$, $R^2$, and $R^4$ are hydrogen;
$R^3$ is —$CH_3$, —$OCH_3$ or —$OCH_2CH_3$;
$R^5$ is hydrogen;
$R^6$, $R^7$, $R^8$, and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or
a pharmaceutically acceptable salt or solvate thereof.

In yet another embodiment are provided compounds of formula (I), wherein:
$R^1$, $R^2$, and $R^4$ are hydrogen;
$R^3$ is —$OCH_3$ or —$OCH_2CH_3$;
$R^5$ is hydrogen;
$R^6$, $R^7$, $R^8$, and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more substituents independently selected from —Cl and —F; or
a pharmaceutically acceptable salt or solvate thereof.

In another embodiment are provided compounds of formula (I), wherein:
$R^1$, $R^2$, $R^3$, $R^4$, $R^5$, $R^6$, $R^7$, $R^8$, and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, halogen, —CN, —$CF_3$, and —$OCF_3$; or
a pharmaceutically acceptable salt or solvate thereof.

In another embodiment are provided compounds of formula (I), wherein:
$R^1$, $R^2$, $R^3$, $R^4$, $R^5$, $R^6$, $R^7$, $R^8$, $R^9$, and $R^{10}$ are hydrogen;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, halogen, —CN, —$CF_3$, and —$OCF_3$; or
a pharmaceutically acceptable salt or solvate thereof.

In still another embodiment are provided compounds of formula (I), wherein:
$R^1$, $R^2$, $R^3$, $R^4$, $R^5$, $R^6$, $R^7$, $R^8$, and $R^9$ are hydrogen;
$R^{10}$ —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, halogen, —CN, —$CF_3$, and —$OCF_3$; or
a pharmaceutically acceptable salt or solvate thereof.

Further provided are compounds of formula (I), wherein:
$R^1$, $R^2$, $R^3$, $R^4$ are independently selected from hydrogen, $C_1$-$C_6$ alkyl, halo, —CN, —$OR^{12a}$, and —$CF_3$;
$R^5$ is hydrogen;
$R^6$, $R^7$, $R^8$, and $R^9$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$$CF_3$, —$(CR^{12a}R^{12b})_t$$OR^{12a}$, —$(CR^{12a}R^{12b})_t$$N(R^{12a}R^{12b})$, —$(CR^{12a}R^{12b})_t$$R^{12a}$, —$(CR^{12a}R^{12b})_t$$C_3$-$C_{11}$ cycloalkyl, —$(CR^{12a}R^{12b})_t$$C_6$-$C_{10}$ aryl, —$(CR^{12a}R^{12b})_t$$C_2$-$C_{10}$ heterocyclyl —$(CR^{12a}R^{12b})_t$heteroaryl, —$O(CR^{12a}R^{12b})_t$$R^{12a}$, —$O(CR^{12a}R^{12b})_t$$C_3$-$C_{11}$ cycloalkyl, —$O(CR^{12a}R^{12b})_t$$C_6$-$C_{10}$ aryl, —$O(CR^{12a}R^{12b})_t$$C_2$-$C_{10}$ heterocyclyl, —$O(CR^{12a}R^{12b})_t$heteroaryl, —$O(CR^{12a}R^{12b})_t$$OR^{12a}$, and —$O(CR^{12a}R^{12b})_t$$N(R^{12a}R^{12b})$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl is optionally substituted with one or more $R^{14}$;
$R^{10}$ and $R^{11}$, together with the atom to which they are attached, form a $C_2$-$C_{10}$ heterocyclyl group, optionally substituted with one or more $R^{13}$;
each $R^{12a}$ and $R^{12b}$ is independently selected from hydrogen and $C_1$-$C_6$ alkyl; or
$R^{12a}$ and $R^{12b}$ together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t$CN, —$(CR^{12a}R^{12b})_t$CF$_3$, —$(CR^{12a}R^{12b})_t$OCF$_3$, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, —$(CR^{12a}R^{12b})_t$heteroaryl, —O$(CR^{12a}R^{12b})_t$R$^{12a}$, —O$(CR^{12a}R^{12b})_t$C$_6$-C$_{10}$ aryl —O$(CR^{12a}R^{12b})_t$C$_2$-C$_{10}$ heterocyclyl, —O$(CR^{12a}R^{12b})_t$heteroaryl, —$(CR^{12a}R^{12b})_t$CO$_2$(C$_1$-C$_6$ alkyl), —$(CR^{12a}R^{12b})_t$N(R$^{12a}$R$^{12b}$), —$(CR^{12a}R^{12b})_t$C(O)NR$^{12a}$R$^{12b}$, —$(CR^{12a}R^{12b})_t$OR$^{12a}$, —$(CR^{12a}R^{12b})_t$S(O)R$^{12a}$, and —$(CR^{12a}R^{12b})_t$S(O)$_2$R$^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

Yet another embodiment provides compounds of formula (I), wherein:

$R^1$, $R^2$, $R^3$, $R^4$ are independently selected from hydrogen, $C_1$-$C_6$ alkyl, halo, —CN, —OR$^{12a}$, and —CF$_3$;

$R^5$ is hydrogen;

$R^6$, $R^7$, $R^8$, and $R^9$ are hydrogen;

$R^{10}$ and $R^{11}$, together with the atom to which they are attached, form a $C_2$-$C_{10}$ heterocyclyl group, optionally substituted with one or more $R^{13}$;

each $R^{12a}$ and $R^{12b}$ is independently selected from hydrogen and $C_1$-$C_6$ alkyl; or $R^{12a}$ and $R^{12b}$ together with the atom to which they are attached, form a $C_3$-$C_{11}$ cycloalkyl or a $C_2$-$C_{10}$ heterocyclyl group;

each $R^{13}$ is independently selected from $C_1$-$C_6$ alkyl, halogen, —$(CR^{12a}R^{12b})_t$CN, —$(CR^{12a}R^{12b})_t$CF$_3$, —$(CR^{12a}R^{12b})_t$OCF$_3$, —$(CR^{12a}R^{12b})_t$C$_3$-C$_{11}$ cycloalkyl, —$(CR^{12a}R^{12b})_t$C$_6$-C$_{10}$ aryl, —$(CR^{12a}R^{12b})_t$C$_2$-C$_{10}$ heterocyclyl, —$(CR^{12a}R^{12b})_t$heteroaryl, —O$(CR^{12a}R^{12b})_t$R$^{12a}$, —O$(CR^{12a}R^{12b})_t$C$_6$-C$_{10}$ aryl, —O$(CR^{12a}R^{12b})_t$C$_2$-C$_{10}$ heterocyclyl, —O$(CR^{12a}R^{12b})_t$heteroaryl, —$(CR^{12a}R^{12b})_t$CO$_2$(C$_1$-C$_6$ alkyl), —$(CR^{12a}R^{12b})_t$N(R$^{12a}$R$^{12b}$), —$(CR^{12a}R^{12b})_t$C(O)NR$^{12a}$R$^{12b}$, —$(CR^{12a}R^{12b})_t$OR$^{12a}$, —$(CR^{12a}R^{12b})_t$S(O)R$^{12a}$, and —$(CR^{12a}R^{12b})_t$S(O)$_2$R$^{12a}$, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with one or more $R^{14}$;

each $R^{14}$ is independently selected from $C_1$-$C_6$ alkyl, halogen, —CN, —CF$_3$, and —OR$^{12a}$; and each t is independently selected from 0, 1, 2, 3, 4, 5, and 6; or a pharmaceutically acceptable salt or solvate thereof.

In another embodiment are provided compounds of formula (I), wherein:

$R^1$, $R^2$, $R^3$, $R^4$ are independently selected from hydrogen, $C_1$-$C_6$ alkyl, halo, —CN, —OR$^{12a}$, and —CF$_3$;

$R^5$ is hydrogen;

$R^6$, $R^7$, $R^8$ and $R^9$ are hydrogen;

$R^{10}$ and $R^{11}$, together with the atom to which they are attached, form a $C_2$-$C_{10}$ heterocyclyl group, optionally substituted with one or more $R^{13}$;

$R^{12a}$ is hydrogen or $C_1$-$C_6$ alkyl; and each $R^{13}$ is independently selected from $C_1$-$C_6$ alkyl, halogen, —CN, —CF$_3$, and —OCF$_3$; or a pharmaceutically acceptable salt or solvate thereof.

In still another embodiment are afforded compounds of formula (I), wherein:

$R^1$, $R^3$, and $R^4$ are hydrogen;

$R^2$ is $C_1$-$C_6$ alkyl, halo, —CN, —OR$^{12a}$, or —CF$_3$;

$R^5$ is hydrogen;

$R^6$, $R^7$, $R^8$, and $R^9$ are hydrogen;

$R^{10}$ and $R^{11}$, together with the atom to which they are attached, form a $C_2$-$C_{10}$ heterocyclyl group, optionally substituted with one or more $R^{13}$;

$R^{12a}$ is hydrogen or $C_1$-$C_6$ alkyl; and each $R^{13}$ is independently selected from $C_1$-$C_6$ alkyl, halogen, —CN, —CF$_3$, and —OCF$_3$; or a pharmaceutically acceptable salt or solvate thereof.

In a further embodiment are provided compounds of formula (I), wherein:

$R^1$, $R^3$, and $R^4$ are hydrogen;

$R^2$ is $C_1$-$C_6$ alkyl, —Cl, —F, —CN, —OCH$_3$, —OCH$_2$CH$_3$, or —CF$_3$;

$R^5$ is hydrogen;

$R^6$, $R^7$, $R^8$ and $R^9$ are hydrogen;

$R^{10}$ and $R^{11}$, together with the atom to which they are attached, form a $C_2$-$C_{10}$ heterocyclyl group, optionally substituted with one or more $R^{13}$; and each $R^{13}$ is independently selected from $C_1$-$C_6$ alkyl, halogen, —CN, —CF$_3$, and —OCF$_3$; or a pharmaceutically acceptable salt or solvate thereof.

A further embodiment affords compounds of formula (I), wherein:

$R^1$, $R^2$, and $R^3$ are hydrogen;

$R^3$ is $C_1$-$C_6$ alkyl, —Cl, —F, —CN, —OCH$_3$, —OCH$_2$CH$_3$, or —CF$_3$;

$R^5$ is hydrogen;

$R^6$, $R^7$, $R^8$, and $R^9$ are hydrogen;

$R^{10}$ and $R^{11}$, together with the atom to which they are attached, form a $C_2$-$C_{10}$ heterocyclyl group, optionally substituted with one or more $R^{13}$; and each $R^{13}$ is independently selected from $C_1$-$C_6$ alkyl, halogen, —CN, —CF$_3$, and —OCF$_3$; or a pharmaceutically acceptable salt or solvate thereof.

In still a further embodiment are provided compounds of formula (I), wherein:

$R^1$, $R^2$, $R^3$, $R^4$, $R^5$, $R^6$, $R^7$, $R^8$, and $R^9$ are hydrogen;

$R^{10}$ and $R^{11}$, together with the atom to which they are attached, form a $C_2$-$C_{10}$ heterocyclyl group, optionally substituted with one or more $R^{13}$; and each $R^{13}$ is independently selected from $C_1$-$C_6$ alkyl, halogen, —CN, —CF$_3$, and —OCF$_3$; or a pharmaceutically acceptable salt or solvate thereof.

In another embodiment are provided compounds of formula (I),

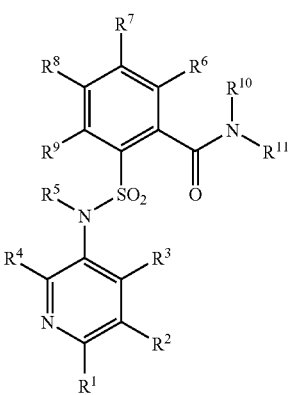

wherein:

$R^1$, $R^2$, $R^3$, $R^4$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_tOR^{12a}$, and $(CR^{12a}R^{12b})_tN(R^{12a}R^{12b})$;

$R^5$ is hydrogen or $C_1$-$C_6$ alkyl;

$R^6$, $R^7$, $R^8$, and $R^9$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_tOR^{12a}$, and $(CR^{12a}R^{12b})_tN(R^{12a}R^{12b})$;

$R^{10}$ and $R^{11}$ are independently selected from hydrogen, —$(CR^{12a}R^{12b})_tC_1$-$C_6$ alkyl, —$(CR^{12a}R^{12b})_tC_3$-$C_{11}$ cycloalkyl, —$(CR^{12a}R^{12b})_tC_6$-$C_{10}$ aryl, —$(CR^{12a}R^{12b})_tC_2$-$C_{10}$ heterocyclyl, and —$(CR^{12a}R^{12b})_t$heteroaryl, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with at least one $R^{13}$; or $R^{10}$ and $R^{11}$, together with the atom to which they are attached, form a $C_2$-$C_{10}$ heterocyclyl group, optionally substituted with at least one $R^{13}$;

each $R^{12a}$ and $R^{12b}$ is independently selected from hydrogen and $C_1$-$C_6$ alkyl; or $R^{12a}$ and $R^{12b}$ together with the atom to which they are attached, form a $C_3$-$C_{11}$ cycloalkyl group;

each $R^{13}$ is independently selected from $C_1$-$C_6$ alkyl, halogen, —$O(CR^{12a}R^{12b})_tR^{12a}$, —$O(CR^{12a}R^{12b})_tC_6$-$C_{10}$ aryl, —$O(CR^{12a}R^{12b})_tC_2$-$C_{10}$ heterocyclyl, —$O(CR^{12a}R^{12b})_t$heteroaryl, —$CO_2(C_1$-$C_6$ alkyl), —$(CR^{12a}R^{12b})_tN(R^{12a}R^{12b})$, —$C(O)NR^{12a}R^{12b}$, and —$(CR^{12a}R^{12b})_tOR^{12a}$ wherein each of said $C_1$-$C_6$ alkyl, $C_6$-$C_{10}$ aryl, $C_2$-$C_{10}$ heterocyclyl, and heteroaryl groups is optionally substituted with at least one $R^{14}$;

each $R^{14}$ is independently selected from $C_1$-$C_6$ alkyl, halogen, and —$OR^{12a}$; and each t is independently selected from 0, 1, 2, 3, 4, 5, and 6; or a pharmaceutically acceptable salt or solvate thereof.

In other embodiments are provided compounds of formula (I), wherein:

$R^1$, $R^2$, $R^3$, $R^4$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_tOR^{12a}$, and $(CR^{12a}R^{12b})_tN(R^{12a}R^{12b})$;

$R^5$ is hydrogen or $C_1$-$C_6$ alkyl;

$R^6$, $R^7$, $R^8$, and $R^9$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_tOR^{12a}$, and $(CR^{12a}R^{12b})_tN(R^{12a}R^{12b})$;

$R^{10}$ and $R^{11}$ are independently selected from hydrogen, —$(CR^{12a}R^{12b})_tC_1$-$C_6$ alkyl, —$(CR^{12a}R^{12b})_tC_3$-$C_{11}$ cycloalkyl, —$(CR^{12a}R^{12b})_tC_6$-$C_{10}$ aryl, —$(CR^{12a}R^{12b})_tC_2$-$C_{10}$ heterocyclyl, and —$(CR^{12a}R^{12b})_t$heteroaryl wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with at least one $R^{13}$; or $R^{10}$ and $R^{11}$, together with the atom to which they are attached, form a $C_2$-$C_{10}$ heterocyclyl group, optionally substituted with at least one $R^{13}$;

each $R^{12a}$ and $R^{12b}$ is independently selected from hydrogen and $C_1$-$C_6$ alkyl; or $R^{12a}$ and $R^{12b}$, together with the atom to which they are attached, form a $C_3$-$C_{11}$ cycloalkyl group;

each $R^{13}$ is independently selected from $C_1$-$C_6$ alkyl, halogen, —$O(CR^{12a}R^{12b})_tR^{12a}$, —$O(CR^{12a}R^{12b})_tC_6$-$C_{10}$ aryl, —$O(CR^{12a}R^{12b})_tC_2$-$C_{10}$ heterocyclyl, —$O(CR^{12a}R^{12b})_t$heteroaryl, —$CO_2(C_1$-$C_6$ alkyl), and —$(CR^{12a}R^{12b})_tN(R^{12a}R^{12b})$, wherein each of said $C_1$-$C_6$ alkyl, $C_6$-$C_{10}$ aryl, $C_2$-$C_{10}$ heterocyclyl, and heteroaryl groups is optionally substituted with at least one $R^{14}$;

each $R^{14}$ is independently selected from $C_1$-$C_6$ alkyl, halogen, and —$OR^{12a}$; and each t is independently selected from 0, 1, 2, 3, 4, 5, and 6; or a pharmaceutically acceptable salt or solvate thereof.

In other embodiments are provided compounds of formula (I), wherein $R^1$, $R^2$, $R^3$ and $R^4$ are hydrogen.

In other embodiments are provided compounds of formula (I), wherein $R^6$, $R^7$, $R^8$ and $R^9$ are hydrogen.

In other embodiments are provided compounds of formula (I), wherein $R^1$, $R^2$, $R^3$, $R^4$, $R^5$, $R^6$, $R^7$, $R^8$, and $R^9$ are hydrogen.

In other embodiments are provided compounds of formula (I), wherein $R^5$ is hydrogen.

In other embodiments are provided compounds of formula (I), wherein $R^{10}$ is hydrogen and $R^{11}$ is —$(CR^{12a}R^{12b})_tC_1$-$C_6$ alkyl, —$(CR^{12a}R^{12b})_tC_3$-$C_{11}$ cycloalkyl, —$(CR^{12a}R^{12b})_tC_6$-$C_{10}$ aryl, —$(CR^{12a}R^{12b})_tC_2$-$C_{10}$ heterocyclyl, and —$(CR^{12a}R^{12b})_t$heteroaryl, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with at least one $R^{13}$.

In other embodiments are provided compounds of formula (I), wherein:

$R^{11}$ is selected from —$(CR^{12a}R^{12b})_tC_1$-$C_6$ alkyl, —$(CR^{12a}R^{12b})_tC_3$-$C_{11}$ cycloalkyl, —$(CR^{12a}R^{12b})_tC_6$-$C_{10}$ aryl, —$(CR^{12a}R^{12b})_tC_2$-$C_{10}$ heterocyclyl, and —$(CR^{12a}R^{12b})_t$heteroaryl, wherein each of said $C_1$-$C_6$ alkyl, $C_3$-$C_{11}$ cycloalkyl, $C_6$-$C_{10}$ aryl, $C_2$-$C_{10}$ heterocyclyl, and heteroaryl groups is optionally substituted with at least one $R^{13}$; and t is 1 or 2.

In other embodiments are provided compounds of formula (I), wherein $R^{11}$ is $C_1$-$C_6$ alkyl and —$(CH_2)C_6$-$C_{10}$ aryl, wherein said $C_1$-$C_6$ and aryl groups are optionally substituted with at least one substituent independently selected from $C_1$-$C_6$ alkyl, halogen, and —$OR^{12a}$.

In other embodiments are provided compounds of formula (I), wherein $R^{11}$ is $C_1$-$C_6$ alkyl.

In other embodiments are provided compounds of formula (I), wherein $R^{10}$ and $R^{11}$, together with the atom to which they are attached, form a $C_2$-$C_{10}$ heterocyclyl group, optionally substituted with at least one $R^{13}$.

In other embodiments are provided compounds of formula (I), wherein said $C_2$-$C_{10}$ heterocyclyl group is optionally substituted with at least one substituent independently selected from $C_1$-$C_6$ alkyl, $C_6$-$C_{10}$ aryl, —OH, —$OCH_3$, heteroaryl, and —$CO_2(C_1$-$C_6$ alkyl), wherein said $C_6$-$C_{10}$ aryl and heteroaryl groups are optionally substituted with at least one halogen or $C_1$-$C_6$ alkyl group.

In other embodiments are provided compounds of formula (I), wherein said $C_2$-$C_{10}$ heterocyclyl group is selected from 2,7-diazaspiro[3.5]non-7-yl, 2,7-diazaspiro[3.5]non-2-yl, piperazinyl, piperdinyl morpholinyl, and pyrrolidinyl.

In other embodiments are provided compounds of formula (I), selected from N-[1,1-dimethyl-2-(4-methylpiperidin-1-yl)ethyl]-2-[(pyridin-3-ylamino)sulfonyl]benzamide; N-(1,1-dimethyl-2-piperidin-1-ylethyl)-2-[(pyridin-3-ylamino) sulfonyl]benzamide; N-(1,1-dimethyl-2-pyrrolidin-1-ylethyl)-2-[(pyridin-3-ylamino)sulfonyl]benzamide; N-(1-cyclopropyl-1-methylethyl)-2-[(pyridin-3-ylamino) sulfonyl]benzamide; N-(2-fluorobenzyl)-2-[(pyridin-3-ylamino)sulfonyl]benzamide; 2-(2,7-diazaspiro[3.5]non-7-ylcarbonyl)-N-pyridin-3-ylbenzenesulfonamide; 2-(2,7-diazaspiro[3.5]non-2-ylcarbonyl)-N-pyridin-3-ylbenzenesulfonamide; N-cyclohexyl-2-[(pyridin-3-ylamino)sulfonyl]benzamide; N-(4-fluorobenzyl)-2-[(pyridin-3-ylamino)sulfonyl]benzamide; tert-butyl 7-{2-[(pyridin-3-ylamino)sulfonyl]benzoyl}-2,7-diazaspiro[3.5] nonane-2-carboxylate; tert-butyl 2-{2-[(pyridin-3-ylamino)

sulfonyl]benzoyl}-2,7-diazaspiro[3.5]nonane-7-carboxylate; N-benzyl-2-[(pyridin-3-ylamino)sulfonyl]benzamide; 2-{[4-(4-fluorophenyl)piperazin-1-yl]carbonyl}-N-pyridin-3-ylbenzenesulfonamide; N-(tert-butyl)-2-[(pyridin-3-ylamino)sulfonyl]benzamide; N-methyl-2-(piperidin-1-ylcarbonyl)-N-pyridin-3-ylbenzenesulfonamide; N-(5-methoxypyridin-3-yl)-2-(piperidin-1-ylcarbonyl)benzenesulfonamide; N-butyl-2-{[(5-methoxypyridin-3-yl)amino]sulfonyl}benzamide; N-(4-methoxypyridin-3-yl)-2-(piperidin-1-ylcarbonyl)benzenesulfonamide; N-butyl-2-{[(4-methoxypyridin-3-yl)amino]sulfonyl}benzamide; N-pyridin-3-yl-2-(pyrrolidin-1-ylcarbonyl)benzenesulfonamide; 2-(morpholin-4-ylcarbonyl)-N-pyridin-3-ylbenzenesulfonamide; N-(5-cyanopyridin-3-yl)-2-(piperidin-1-ylcarbonyl)benzenesulfonamide; N-[1-(hydroxymethyl)cyclopentyl]-2-[(pyridin-3-ylamino)sulfonyl]benzamide; N-butyl-2-{[(5-cyanopyridin-3-yl)amino]sulfonyl}benzamide; 2-[(3,5-dimethylpiperidin-1-yl)carbonyl]-N-pyridin-3-ylbenzenesulfonamide; 2-[(4-methoxypiperidin-1-yl)carbonyl]-N-pyridin-3-ylbenzenesulfonamide; 2-{[(2R,6S)-2,6-dimethylmorpholin-4-yl]carbonyl}-N-pyridin-3-ylbenzenesulfonamide; 2-[(4-hydroxypiperidin-1-yl)carbonyl]-N-pyridin-3-ylbenzenesulfonamide; 2-[(3,3-dimethylpiperidin-1-yl)carbonyl]-N-pyridin-3-ylbenzenesulfonamide; N-(5-methylpyridin-3-yl)-2-(piperidin-1-ylcarbonyl)benzenesulfonamide; N-butyl-2-{[(5-methylpyridin-3-yl)amino]sulfonyl}benzamide; N-(2-methyl-2-morpholin-4-ylpropyl)-2-[(pyridin-3-ylamino)sulfonyl]benzamide; N-(1-dimethyl-2-morpholin-4-ylethyl)-2-[(pyridin-3-ylamino)sulfonyl]benzamide; N-[2-(benzyloxy)-1,1-dimethylethyl]-2-[(pyridin-3-ylamino)sulfonyl]benzamide; 2-[(4-methyl piperazin-1-yl)carbonyl]-N-pyridin-3-ylbenzenesulfonamide; ethyl 4-{2-[(pyridin-3-ylamino)sulfonyl]benzoyl}piperazine-1-carboxylate; N-[2-(dimethylamino)ethyl]-2-[(pyridin-3-ylamino)sulfonyl]benzamide; N-(1,1-dimethylpropyl)-2-[(pyridin-3-ylamino)sulfonyl]benzamide; N-(2-hydroxy-1,1-dimethylethyl)-2-[(pyridin-3-ylamino)sulfonyl]benzamide; N-ethyl-N-[2-(1H-pyrazol-1-yl)ethyl]-2-[(pyridin-3-ylamino)sulfonyl]benzamide; 2-[(4-methylpiperidin-1-yl)carbonyl]-N-pyridin-3-ylbenzenesulfonamide; N-(3-methylbutyl)-2-[(pyridin-3-ylamino)sulfonyl]benzamide; N-(3-fluorobenzyl)-2-[(pyridin-3-ylamino)sulfonyl]benzamide; N-(2,2-dimethylpropyl)-2-[(pyridin-3-ylamino)sulfonyl]benzamide; N-(2,6-dimethoxybenzyl)-2-[(pyridin-3-ylamino)sulfonyl]benzamide; N-(3-methoxybenzyl)-2-[(pyridin-3-ylamino)sulfonyl]benzamide; N-methyl-N-pentyl-2-[(pyridin-3-ylamino)sulfonyl]benzamide; N-(cyclopropylmethyl)-2-[(pyridin-3-ylamino)sulfonyl]benzamide; N-isopropyl-2-[(pyridin-3-ylamino)sulfonyl]benzamide; N-propyl-2-[(pyridin-3-ylamino)sulfonyl]benzamide; N-(3,5-dimethoxybenzyl)-2-[(pyridin-3-ylamino)sulfonyl]benzamide; N-(1H-indol-4-yl methyl)-2-[(pyridin-3-ylamino)sulfonyl]benzamide; N-(2,4-dimethoxybenzyl)-2-[(pyridin-3-ylamino)sulfonyl]benzamide; N-(cyclopropylmethyl)-N-propyl-2-[(pyridin-3-ylamino)sulfonyl]benzamide; N-(1H-benzyl-N-methyl-2-[(pyridin-3-ylamino)sulfonyl]benzamide; N-(2-phenoxyethyl)-2-[(pyridin-3-ylamino)sulfonyl]benzamide; N-(4-methoxybenzyl)-2-[(pyridin-3-ylamino)sulfonyl]benzamide; N-(2,3-dihydro-1H-inden-2-yl)-2-[(pyridin-3-ylamino)sulfonyl]benzamide; N-(3-butoxypropyl)-2-[(pyridin-3-ylamino)sulfonyl]benzamide; N-[2-(3-methoxyphenyl)ethyl]-2-[(pyridin-3-ylamino)sulfonyl]benzamide; N-pentyl-2-[(pyridin-3-ylamino)sulfonyl]benzamide; N-pyridin-3-yl-2-[(4-pyridin-2-ylpiperazin-1-yl)carbonyl]benzenesulfonamide; N-butyl-2-[(pyridin-3-ylamino)sulfonyl]benzamide; N-(cyclopentylmethyl)-2-[(pyridin-3-ylamino)sulfonyl]benzamide; N-cyclobutyl-2-[(pyridin-3-ylamino)sulfonyl]benzamide; 2-[(pyridin-3-ylamino)sulfonyl]-N-(2-pyridin-2-ylethyl)benzamide; 2-(piperidin-1-ylcarbonyl)-N-pyridin-3-ylbenzenesulfonamide; N-methyl-N-(2-phenylethyl)-2-[(pyridin-3-ylamino)sulfonyl]benzamide; 2-[(pyridin-3-ylamino)sulfonyl]-N-(3-pyridin-2-ylpropyl)benzamide; N-(1,1-dimethyl-2-morpholin-4-ylethyl)-2-[(pyridin-3-ylmethyl)sulfinyl]benzamide; N-[3-(difluoromethoxy)benzyl]-2-[(pyridin-3-ylamino)sulfonyl]benzamide; N-(2-ethoxybenzyl)-2-[(pyridin-3-ylamino)sulfonyl]benzamide; N-(2-fluorobenzyl)-N-methyl-2-[(pyridin-3-ylamino)sulfonyl]benzamide; N-(2-methylbenzyl)-2-[(pyridin-3-ylamino)sulfonyl]benzamide; N-[2-(2-methylphenyl)ethyl]-2-[(pyridin-3-ylamino)sulfonyl]benzamide; N-[2-(3-methylphenyl)ethyl]-2-[(pyridin-3-ylamino)sulfonyl]benzamide; N-(2-phenylethyl)-2-[(pyridin-3-ylamino)sulfonyl]benzamide; N-benzyl-N-ethyl-2-[(pyridin-3-ylamino)sulfonyl]benzamide; N-(4-methylbenzyl)-2-[(pyridin-3-ylamino)sulfonyl]benzamide; N-(3-methylbenzyl)-2-[(pyridin-3-ylamino)sulfonyl]benzamide; N-(4-[(methylamino)carbonyl]benzyl-2-[(pyridin-3-ylamino)sulfonyl]benzamide; N-(2,3-dihydro-1-benzofuran-5-ylmethyl)-2-[(pyridin-3-ylamino)sulfonyl]benzamide; 2-(3,4-dihydroisoquinolin-2(1H)-ylcarbonyl)-N-pyridin-3-ylbenzenesulfonamide; N-{4-[(dimethylamino)methyl]benzyl}-2-[(pyridin-3-ylamino)sulfonyl]benzamide; N-(3,4-difluorobenzyl)-2-[(pyridin-3-ylamino)sulfonyl]benzamide; N-[4-(1-hydroxy-1-methylethyl)benzyl]-2-[(pyridin-3-ylamino)sulfonyl]benzamide; N-(2,3-difluorobenzyl)-2-[(pyridin-3-ylamino)sulfonyl]benzamide; 2-(1,3-dihydro-2H-isoindol-2-ylcarbonyl)-N-pyridin-3-ylbenzenesulfonamide; 2-(anilinosulfonyl)-N-(quinolin-6-ylmethyl)benzamide; 2-(anilinosulfonyl)-N-(2-methoxybenzyl)benzamide; and N-(3,4-difluorobenzyl)-2-{[(4-methoxypyridin-3-yl)amino]sulfonyl}-N-methylbenzamide; or a pharmaceutically acceptable salt or solvate thereof.

Another embodiment provides a compound selected from N-(3,4-difluorobenzyl)-2-{[(5-methoxypyridin-3-yl)amino]sulfonyl}benzamide; N-(3,4-difluorobenzyl)-2-{[(5-methylpyridin-3-yl)amino]sulfonyl}benzamide; N-(3,4-dichlorobenzyl)-2-{[(5-methylpyridin-3-yl)amino]sulfonyl}benzamide; N-[4-fluoro-3-(trifluoromethyl)benzyl]-2-{[(5-methylpyridin-3-yl)amino]sulfonyl}benzamide; N-(3,4-dichlorobenzyl)-2-{[(5-methoxypyridin-3-yl)amino]sulfonyl}benzamide; N-[4-fluoro-3-(trifluoromethyl)benzyl]-2-{[(5-methoxypyridin-3-yl)amino]sulfonyl}benzamide; N-(3,4-dichlorobenzyl)-2-{[(5-ethoxypyridin-3-yl)amino]sulfonyl}benzamide; N-(3,4-difluorobenzyl)-2-{[(5-ethoxypyridin-3-yl)amino]sulfonyl}benzamide; N-(3,4-difluorobenzyl)-2-{[(5-ethoxypyridin-3-yl)amino]sulfonyl}-N-methylbenzamide; 2-{[(5-ethoxypyridin-3-yl)amino]sulfonyl}-N-[4-fluoro-3-(trifluoromethyl)benzyl]benzamide; N-(3,4-difluorobenzyl)-N-methyl-2-{[(5-methylpyridin-3-yl)amino]sulfonyl}benzamide; N-(3,4-difluorobenzyl)-2-{[(5-methoxypyridin-3-yl)amino]sulfonyl}-N-methylbenzamide; N-(4-fluorobenzyl)-2-{[(5-methoxypyridin-3-yl)amino]sulfonyl}-5-(2-morpholin-4-ylethoxy)benzamide; N-(4-fluorobenzyl)-2-{[(5-methoxypyridin-3-yl)amino]sulfonyl}-5-(piperidin-4-yloxy)benzamide; N-(3-chloro-4-fluorobenzyl)-2-{[(5-methoxypyridin-3-yl)amino]sulfonyl}benzamide; N-(3,4-difluorobenzyl)-2-{[(4-methoxypyridin-3-yl)amino]sulfonyl}-N-methylbenzamide; N-[4-fluoro-3-(trifluoromethyl)benzyl]-2-{[(4-methoxypyridin-3-yl)amino]sulfonyl}benzamide; N-(3,4-difluorobenzyl)-2-{[(4-ethoxypyridin-3-yl)amino]sulfonyl}benzamide; N-(3,4-difluorobenzyl)-2-{[(4-ethoxypyridin-3-yl)amino]sulfonyl}-N-methylbenzamide; 2-{[(4-ethoxypyridin-3-yl)amino]sulfonyl}-N-[4-fluoro-3-(trifluoromethyl)benzyl]benzamide; N-(4-chloro-2-methylbenzyl)-2-{[(5-methoxypyridin-3-yl)amino]sulfonyl}benzamide; N-(2-chloro-6-fluorobenzyl)-2-{[(5-methoxypyridin-3-yl)amino]sulfonyl}benzamide; N-(2,4-difluorobenzyl)-2-{[(5-methoxypyridin-3-yl)amino]sulfonyl}benzamide; N-(3-chloro-2-methylbenzyl)-2-{[(5-methoxypyridin-3-yl)amino]sulfonyl}benzamide; N-(2-fluorobenzyl)-2-{[(5-methoxypyridin-3-yl)amino]sulfonyl}-N-methylbenzamide; N-(3-chlorobenzyl)-2-{[(5-methoxypyridin-3-yl)amino]sulfonyl}benzamide; N-(2,3-dichlorobenzyl)-2-{[(5-methoxypyridin-3-yl)amino]sulfonyl}benzamide; N-(2-chloro-4-fluorobenzyl)-2-{[(5-methoxypyridin-3-yl)amino]sulfonyl}benzamide; N-[1-(4-chlorophenyl)ethyl]-2-{[(5-methoxypyridin-3-yl)amino]sulfonyl}benzamide; N-(3-chloro-2-fluorobenzyl)-2-{[(5-methoxypyridin-3-yl)amino]sulfonyl}benzamide; N-(3-chloro-4-fluorobenzyl)-2-{[(5-methylpyridin-3-yl)amino]sulfonyl}benzamide; N-(3-fluoro-4-methylbenzyl)-2-{[(5-methylpyridin-3-yl)amino]sulfonyl}benzamide; N-(3,5-dichlorobenzyl)-2-{[(5-methylpyridin-3-yl)amino]sulfonyl}benzamide; N-[1-(3,4-difluorophenyl)-1-methylethyl]-2-{[(5-methoxypyridin-3-yl)amino]sulfonyl}benzamide; N-methyl-2-{[(5-methylpyridin-3-yl)amino]sulfonyl}-N-[4-(trifluoromethyl)benzyl]benzamide; N-(3-chloro-4-methylbenzyl)-2-{[(5-methoxypyridin-3-yl)amino]sulfonyl}benzamide; N-(4-chloro-3-fluorobenzyl)-2-{[(5-methoxypyridin-3-yl)amino]sulfonyl}benzamide; 2-{[(4-ethoxypyridin-3-yl)amino]sulfonyl}-N-methyl-N-[4-(trifluoromethyl)benzyl]benzamide; and N-(4-fluorobenzyl)-5-methoxy-2-{[(5-methoxypyridin-3-yl)amino]sulfonyl}benzamide; or a pharmaceutically acceptable salt or solvate thereof.

A further embodiment provides a compound selected from N-(3,4-difluorobenzyl)-2-{[(4-methoxypyridin-3-yl)amino]sulfonyl}benzamide; N-(3,4-difluorobenzyl)-2-{[(4-methoxypyridin-3-yl)amino]sulfonyl}-N-methylbenzamide; N-[4-fluoro-3-(trifluoromethyl)benzyl]-2-{[(4-methoxypyridin-3-yl)amino]sulfonyl}benzamide; N-(3,4-difluorobenzyl)-2-{[(4-ethoxypyridin-3-yl)amino]sulfonyl}benzamide; N-(3,4-difluorobenzyl)-2-{[(4-ethoxypyridin-3-yl)amino]sulfonyl}-N-methylbenzamide; 2-{[(4-ethoxypyridin-3-yl)amino]sulfonyl}-N-[4-fluoro-3-(trifluoromethyl)benzyl]benzamide; N-(4-fluorobenzyl)-2-{[(4-methoxypyridin-3-yl)amino]sulfonyl}-N-methylbenzamide; 2-{[(4-ethoxypyridin-3-yl)amino]sulfonyl}-N-(4-fluorobenzyl)-N-methylbenzamide; N-(2-fluorobenzyl)-2-{[(4-methoxypyridin-3-yl)amino]sulfonyl}-N-methylbenzamide; 2-{[(4-ethoxypyridin-3-yl)amino]sulfonyl}-N-(2-fluorobenzyl)-N-methylbenzamide; 2-{[(4-methoxypyridin-3-yl)amino]sulfonyl}-N-methyl-N-[4-(trifluoromethyl)benzyl]benzamide; 2-{[(4-ethoxypyridin-3-yl)amino]sulfonyl}-N-methyl-N-[4-(trifluoromethyl)benzyl]benzamide; N-(3-fluorobenzyl)-2-{[(4-methoxypyridin-3-yl)amino]sulfonyl}-N-methylbenzamide; and 2-{[(4-ethoxypyridin-3-yl)amino]sulfonyl}-N-(3-fluorobenzyl)-N-methylbenzamide; or a pharmaceutically acceptable salt or solvate thereof.

Still another embodiment provides a compound selected from N-butyl-2-{[(4-methoxypyridin-3-yl)amino]sulfonyl}benzamide; N-(4-methoxypyridin-3-yl)-2-(piperidin-1-ylcarbonyl)benzenesulfonamide; N-butyl-2-{[(4-methoxypyridin-3-yl)amino]sulfonyl}-N-methylbenzamide; N-isopropyl-2-{[(4-methoxypyridin-3-yl)amino]sulfonyl}-N-methylbenzamide; 2-{[(4-methoxypyridin-3-yl)amino]sulfonyl}-N-methyl-N-pentylbenzamide; 2-{[(4-methoxypyridin-3-yl)amino]sulfonyl}-N-(3-methylbutyl)benzamide; N-(1-cyclopropylethyl)-2-{[(4-methoxypyridin-3-yl)amino]sulfonyl}benzamide; 2-{[(4-methoxypyridin-3-yl)amino]sulfonyl}-N-[2-(2-methylphenyl)ethyl]benzamide; N-butyl-2-{[(4-ethoxypyridin-3-yl)amino]sulfonyl}-N-methylbenzamide; 2-{[(4-ethoxypyridin-3-yl)amino]sulfonyl}-N-isopropyl-N-methylbenzamide; 2-{[(4-ethoxypyridin-3-yl)amino]sulfonyl}-N-methyl-N-pentylbenzamide; 2-{[(4-ethoxypyridin-3-yl)amino]sulfonyl}-N-(3-methylbutyl)benzamide; N-(1-cyclopropylethyl)-2-{[(4-ethoxypyridin-3-yl)amino]sulfonyl}benzamide; 2-{[(4-ethoxypyridin-3-yl)amino]sulfonyl}-N-[2-(2-methylphenyl)ethyl]benzamide; N-(3,4-difluorobenzyl)-2-{[(4-methoxypyridin-3-yl)amino]sulfonyl}benzamide; N-(3,4-difluorobenzyl)-2-{[(4-methoxypyridin-3-yl)amino]sulfonyl}-N-methylbenzamide; N-[4-fluoro-3-(trifluoromethyl)benzyl]-2-{[(4-methoxypyridin-3-yl)amino]sulfonyl}benzamide; N-(tert-butyl)-2-{[(4-methoxypyridin-3-yl)amino]sulfonyl}benzamide; N-(3,4-difluorobenzyl)-2-{[(4-ethoxypyridin-3-yl)amino]sulfonyl}benzamide; N-(3,4-difluorobenzyl)-2-{[(4-ethoxypyridin-3-yl)amino]sulfonyl}-N-methylbenzamide; 2-{[(4-ethoxypyridin-3-yl)amino]sulfonyl}-N-[4-fluoro-3-(trifluoromethyl)benzyl]benzamide; N-(tert-butyl)-2-{[(4-ethoxypyridin-3-yl)amino]sulfonyl}benzamide; 2-{[(4-methoxypyridin-3-yl)amino]sulfonyl}-N-(2-phenoxyethyl)benzamide; N-(2-ethoxyethyl)-2-{[(4-methoxypyridin-3-yl)amino]sulfonyl}benzamide; N-[2-(2-fluorophenyl)ethyl]-2-{[(4-methoxypyridin-3-yl)amino]sulfonyl}benzamide; 2-{[(4-methoxypyridin-3-yl)amino]sulfonyl}-N-{2-[2-(trifluoromethoxy)phenyl]ethyl}benzamide; N-[2-(2-chlorophenyl)ethyl]-2-{[(4-methoxypyridin-3-yl)amino]sulfonyl}benzamide; 2-{[(4-ethoxypyridin-3-yl)amino]sulfonyl}-N-(2-phenoxyethyl)benzamide; N-(2-ethoxyethyl)-2-{[(4-ethoxypyridin-3-yl)amino]sulfonyl}benzamide; 2-{[(4-ethoxypyridin-3-yl)amino]sulfonyl}-N-(2-methoxyethyl)benzamide; N-(2-methoxyethyl)-2-{[(4-methoxypyridin-3-yl)amino]sulfonyl}-N-methylbenzamide; 2-{[(4-ethoxypyridin-3-yl)amino]sulfonyl}-N-(2-methoxyethyl)-N-methylbenzamide; N-(4-fluorobenzyl)-2-{[(4-methoxypyridin-3-yl)amino]sulfonyl}-N-methylbenzamide; 2-{[(4-ethoxypyridin-3-yl)amino]sulfonyl}-N-(4-fluorobenzyl)-N-methylbenzamide; N-isopropyl-N-(2-methoxyethyl)-2-{[(4-methoxypyridin-3-yl)amino]sulfonyl}benzamide; 2-{[(4-ethoxypyridin-3-yl)amino]sulfonyl}-N-isopropyl-N-(2-methoxyethyl)benzamide; N-(2-fluorobenzyl)-2-{[(4-methoxypyridin-3-yl)amino]sulfonyl}-N-methylbenzamide; 2-{[(4-ethoxypyridin-3-yl)amino]sulfonyl}-N-(2-fluorobenzyl)-N-methylbenzamide; 2-{[(4-methoxypyridin-3-yl)amino]sulfonyl}-N-methyl-N-[4-(trifluoromethyl)benzyl]benzamide; 2-{[(4-ethoxypyridin-3-yl)amino]sulfonyl}-N-methyl-N-[4-(trifluoromethyl)benzyl]benzamide; N-(sec-butyl)-2-{[(4-methoxypyridin-3-yl)amino]sulfonyl}benzamide; N-(sec-butyl)-2-{[(4-ethoxypyridin-3-yl)amino]sulfonyl}benzamide; 2-{[(4-methoxypyridin-3-yl)amino]sulfonyl}-N-(2-methylbutyl)benzamide; 2-{[(4-ethoxypyridin-3-yl)amino]sulfonyl}-N-(2-methylbutyl)benzamide; N-[(1R)-1,2-dimethylpropyl]-2-{[(4-methoxypyridin-3-yl)amino]sulfonyl}benzamide; N-[(1R)-1,2-dimethylpropyl]-2-{[(4-ethoxypyridin-3-yl)amino]sulfonyl}benzamide; N-[(1S)-1,2-dimethylpropyl]-2-{[(4-methoxypyridin-3-yl)sulfonyl}benzamide; N-[(1S)-1,2-dimethylpropyl]-2-{[(4-ethoxypyridin-3-yl)amino]sulfonyl}benzamide; N-(1,1-dimethylpropyl)-2-{[(4- methoxypyridin-3-yl)amino]sulfonyl}benzamide; N-(1,1-dimethylpropyl)-2-{[(4-ethoxypyridin-3-yl)amino]sulfonyl}benzamide; N-(3-fluorobenzyl)-2-{[(4-methoxypyridin-3-yl)amino]sulfonyl}-N-methylbenzamide; and 2-{[(4-ethoxypyridin-3-yl)amino]sulfonyl}-N-(3-fluorobenzyl)-N-methylbenzamide; or a pharmaceutically acceptable salt of solvate thereof.

A still further embodiment provides a compound selected from 2-{[(5-methoxypyridin-3-yl)amino]sulfonyl}-N-[2-(2-methylphenyl)ethyl]benzamide; N-(3,4-difluorobenzyl)-2-{[(5-methoxypyridin-3-yl)amino]sulfonyl}benzamide; N-butyl-2-{[(5-methoxypyridin-3-yl)amino]sulfonyl}-N-methylbenzamide; 2-{[(5-methoxypyridin-3-yl)amino]sulfonyl}-N-methyl-N-pentylbenzamide; 2-{[(5-methoxypyridin-3-yl)amino]sulfonyl}-N-methyl-N-(3-methylbutyl)benzamide; N-(cyclopropylmethyl)-2-{[(5-methoxypyridin-3-yl)(methyl)amino]sulfonyl}-N-propylbenzamide; N-(3,4-dichlorobenzyl)-2-{[(5-methoxypyridin-3-yl)amino]sulfonyl}benzamide; N-[4-fluoro-3-(trifluoromethyl)benzyl]-2-{[(5-methoxypyridin-3-yl)amino]sulfonyl}benzamide; 2-{[(5-ethoxypyridin-3-yl)amino]sulfonyl}-N-(3-methylbutyl)benzamide; 2-{[(5-ethoxypyridin-3-yl)amino]sulfonyl}-N-[2-(2-methylphenyl)ethyl]benzamide; N-(3,4-dichlorobenzyl)-2-{[(5-ethoxypyridin-3-yl)amino]sulfonyl}benzamide; N-(3,4-difluorobenzyl)-2-{[(5-ethoxypyridin-3-yl)amino]sulfonyl}benzamide; N-(3,4-difluorobenzyl)-2-{[(5-ethoxypyridin-3-yl)amino]sulfonyl}-N-methylbenzamide; 2-{[(5-ethoxypyridin-3-yl)amino]sulfonyl}-N-[4-fluoro-3-(trifluoromethyl)benzyl]benzamide; N-(3,4-difluorobenzyl)-2-{[(5-methoxypyridin-3-yl)amino]sulfonyl}-N-methylbenzamide; N-(4-fluorobenzyl)-2-{[(5-methoxypyridin-3-yl)amino]sulfonyl}-5-(2-morpholin-4-ylethoxy)benzamide; N-(4-fluorobenzyl)-2-{[(5-methoxypyridin-3-yl)amino]sulfonyl}-5-(piperidin-4-yloxy)benzamide; N-(3-chloro-4-fluorobenzyl)-2-{[(5-methoxypyridin-3-yl)amino]sulfonyl}benzamide; N-isopropyl-2-{[(5-methoxypyridin-3-yl)amino]sulfonyl}-N-methyl-5-(2-morpholin-4-ylethoxy)benzamide; N-isopropyl-N-(2-methoxyethyl)-2-{[(5-methoxypyridin-3-yl)amino]sulfonyl}benzamide; N-isopropyl-2-{[(5-methoxypyridin-3-yl)amino]sulfonyl}-N-methyl-5-(piperidin-4-yloxy)benzamide; N-[2-(2-chlorophenyl)ethyl]-2-{[(5-methoxypyridin-3-yl)amino]sulfonyl}benzamide; N-[3-(2-methoxyphenyl)propyl]-2-{[(5-methoxypyridin-3-yl)amino]sulfonyl}benzamide; N-(4-chloro-2-methylbenzyl)-2-{[(5-methoxypyridin-3-yl)amino]sulfonyl}benzamide; N-(2-chloro-6-fluorobenzyl)-2-{[(5-methoxypyridin-3-yl)amino]sulfonyl}benzamide; N-(2,4-difluorobenzyl)-2-{[(5-methoxypyridin-3-yl)amino]sulfonyl}benzamide N-(1-isopropyl-2-methylpropyl)-2-{[(5-methoxypyridin-3-yl)amino]sulfonyl}benzamide; N-(2-cyclopentylethyl)-2-{[(5-methoxypyridin-3-yl)amino]sulfonyl}benzamide; N-(3-chloro-2-methylbenzyl)-2-{[(5-methoxypyridin-3-yl)amino]sulfonyl}benzamide; N-2-adamantyl-2-{[(5-methoxypyridin-3-yl)amino]sulfonyl}benzamide; N-(cyclohexylmethyl)-2-{[(5-methoxypyridin-3-yl)amino]sulfonyl}benzamide; N-[1-(4-chlorobenzyl)-2-hydroxyethyl]-2-{[(5-methoxypyridin-3-yl)amino]sulfonyl}benzamide; N-(2-fluorobenzyl)-2-{[(5-methoxypyridin-3-yl)amino]sulfonyl}-N-methylbenzamide; N-(1-ethylpropyl)-2-{[(5-methoxypyridin-3-yl)amino]sulfonyl}benzamide; N-(3-chlorobenzyl)-2-{[(5-methoxypyridin-3-yl)amino]sulfonyl}benzamide; N-[(1S)-2-cyclohexyl-1-(hydroxymethyl)ethyl]-2-{[(5-methoxypyridin-3-yl)amino]sulfonyl}benzamide; N-[(2-hydroxy-2-adamantyl)methyl]-2-{[(5-methoxypyridin-3-yl)amino]sulfonyl}benzamide; N-(2,3-dichlorobenzyl)-2-{[(5-methoxypyridin-3-yl)amino]sulfonyl}benzamide; N-(2-chloro-4-fluorobenzyl)-2-{[(5-methoxypyridin-3-yl)amino]sulfonyl}benzamide; N-[1-(4-chlorophenyl)ethyl]-2-{[(5-methoxypyridin-3-yl)amino]sulfonyl}benzamide; N-(3-chloro-2-fluorobenzyl)-2-{[(5-methoxypyridin-3-yl)amino]sulfonyl}benzamide; N-[2-(3-chlorophenyl)ethyl]-2-{[(5-methoxypyridin-3-yl)amino]sulfonyl}benzamide; N-[1-(3,4-difluorophenyl)-1-methylethyl]-2-{[(5-methoxypyridin-3-yl)amino]sulfonyl}benzamide; N-(3-chloro-4-methylbenzyl)-2-{[(5-methoxypyridin-3-yl)amino]sulfonyl}benzamide; N-[2-(3,4-difluorophenyl)-1-methylethyl]-2-{[(5-methoxypyridin-3-yl)amino]sulfonyl}benzamide; N-(4-chloro-3-fluorobenzyl)-2-{[(5-methoxypyridin-3-yl)amino]sulfonyl}benzamide; and N-(4-fluorobenzyl)-5-methoxy-2-{[(5-methoxypyridin-3-yl)amino]sulfonyl}benzamide; or a pharmaceutically acceptable salt or solvate thereof.

In another embodiment is provided a compound selected from N-methyl-N-(3-methylbutyl)-2-{[(5-methylpyridin-3-yl)amino]sulfonyl}benzamide; N-(cyclopentylmethyl)-N-methyl-2-{[(5-methylpyridin-3-yl)amino]sulfonyl}benzamide; N-methyl-2-{[(5-methylpyridin-3-yl)amino]sulfonyl}-N-pentylbenzamide; N-(3,4-difluorobenzyl)-2-{[(5-methylpyridin-3-yl)amino]sulfonyl}benzamide; N-[2-(2-methylphenyl)ethyl]-2-{[(5-methylpyridin-3-yl)amino]sulfonyl}benzamide; N-(3,4-dichlorobenzyl)-2-{[(5-methylpyridin-3-yl)amino]sulfonyl}benzamide; N-[4-fluoro-3-(trifluoromethyl)benzyl]-2-{[(5-methylpyridin-3-yl)amino]sulfonyl}benzamide; N-(3,4-difluorobenzyl)-N-methyl-2-{[(5-methylpyridin-3-yl)amino]sulfonyl}benzamide; N-[2-(2-chlorophenyl)ethyl]-2-{[(5-methylpyridin-3-yl)amino]sulfonyl}benzamide; 2-{[(5-methylpyridin-3-yl)amino]sulfonyl}-N-{2-[2-(trifluoromethoxy)phenyl]ethyl}benzamide; N-(3-chloro-4-fluorobenzyl)-2-{[(5-methylpyridin-3-yl)amino]sulfonyl}benzamide; N-(3-fluoro-4-methylbenzyl)-2-{[(5-methylpyridin-3-yl)amino]sulfonyl}benzamide; N-(3,5-dichlorobenzyl)-2-{[(5-methylpyridin-3-yl)amino]sulfonyl}benzamide; N-methyl-N-[2-(2-methylphenyl)ethyl]-2-{[(5-methylpyridin-3-yl)amino]sulfonyl}benzamide; N-methyl-2-{[(5-methylpyridin-3-yl)amino]sulfonyl}-N-[4-(trifluoromethyl)benzyl]benzamide; and N-(1-isopropyl-2-methylpropyl)-2-{[(5-methylpyridin-3-yl)amino]sulfonyl}benzamide; or a pharmaceutically acceptable salt or solvate thereof.

In another embodiment is provided a compound selected from N-methyl-N-(2-phenylethyl)-2-[(pyridin-3-ylamino)sulfonyl]benzamide; N-[2-(3-methoxyphenyl)ethyl]-2-[(pyridin-3-ylamino)sulfonyl]benzamide; N-(2-phenylethyl)-2-[(pyridin-3-ylamino)sulfonyl]benzamide; N-[2-(3-methylphenyl)ethyl]-2-[(pyridin-3-ylamino)sulfonyl]benzamide; N-[2-(2-methylphenyl)ethyl]-2-[(pyridin-3-ylamino)sulfonyl]benzamide; 2-{[(5-methoxypyridin-3-yl)amino]sulfonyl}-N-[2-(2-methylphenyl)ethyl]benzamide; 2-{[(5-methoxypyridin-3-yl)amino]sulfonyl}-N-methyl-N-(2-phenylethyl)benzamide; N-methyl-2-{[(5-methylpyridin-3-yl)amino]sulfonyl}-N-(2-phenylethyl)benzamide; N-[2-(2-methylphenyl)ethyl]-2-{[methyl(pyridin-3-yl)amino]sulfonyl}benzamide; N-[2-(2-methylphenyl)ethyl]-2-{[(5-methylpyridin-3-yl)amino]sulfonyl}benzamide; 2-{[(5-ethoxypyridin-3-yl)amino]sulfonyl}-N-[2-(2-methylphenyl)ethyl]benzamide; 2-{[(4-methoxypyridin-3-yl)amino]sulfonyl}-N-[2-(2-methylphenyl)ethyl]benzamide; 2-{[(4-ethoxypyridin-3-yl)amino]sulfonyl}-N-[2-(2-methylphenyl)ethyl]benzamide; N-[2-(2-methoxyphenyl)ethyl]-2-{[(5-methoxypyridin-3-yl)amino]sulfonyl}benzamide; N-[2-(2-fluorophenyl)ethyl]-2-{[(5-methoxypyridin-3-yl)amino]

sulfonyl}benzamide; N-[2-(2-chlorophenyl)ethyl]-2-{[(5-methoxypyridin-3-yl)amino]sulfonyl}benzamide; N-[2-(2-fluorophenyl)ethyl]-2-{[(5-methylpyridin-3-yl)amino] sulfonyl}benzamide; N-[2-(2-chlorophenyl)ethyl]-2-{[(5-methylpyridin-3-yl)amino]sulfonyl}benzamide; 2-{[(5-methylpyridin-3-yl)amino]sulfonyl}-N-{2-[2-(trifluoromethoxy)phenyl]ethyl}benzamide; N-[2-(2-fluorophenyl)ethyl]-2-{[(4-methoxypyridin-3-yl)amino] sulfonyl}benzamide; 2-{[(4-methoxypyridin-3-yl)amino] sulfonyl}-N-{2-[2-(trifluoromethoxy)phenyl] ethyl}benzamide; N-[2-(2-chlorophenyl)ethyl]-2-{[(4-methoxypyridin-3-yl)amino]sulfonyl}benzamide; N-[1-(4-chlorobenzyl)-2-hydroxyethyl]-2-{[(5-methoxypyridin-3-yl)amino]sulfonyl}benzamide; N-[2-(2,5-difluorophenyl) ethyl]-2-{[(5-methoxypyridin-3-yl)amino] sulfonyl}benzamide; N-[2-(2,4-difluorophenyl)ethyl]-2-{[(5-methoxypyridin-3-yl)amino]sulfonyl}benzamide; N-[2-(2-methylphenyl)ethyl]-2-{[(4-methylpyridin-3-yl)amino] sulfonyl}benzamide; N-methyl-N-[2-(2-methylphenyl) ethyl]-2-{[(5-methylpyridin-3-yl)amino] sulfonyl}benzamide; N-[2-(3-chlorophenyl)ethyl]-2-{[(5-methoxypyridin-3-yl)amino]sulfonyl}benzamide; N-[2-(3,4-difluorophenyl)ethyl]-2-{[(5-methoxypyridin-3-yl) amino]sulfonyl}benzamide; N-[2-(2,3-difluoro-4-methylphenyl)ethyl]-2-{[(5-methoxypyridin-3-yl)amino] sulfonyl}benzamide; N-[2-(3,4-difluorophenyl)-1-methylethyl]-2-{[(5-methoxypyridin-3-yl)amino] sulfonyl}benzamide; and N-{2-[3-fluoro-4-(trifluoromethyl)phenyl]ethyl}-2-{[(5-methoxypyridin-3-yl)amino]sulfonyl}benzamide; or a pharmaceutically acceptable salt or solvate thereof.

Another embodiment provides a compound selected from N-(3,4-difluorobenzyl)-2-{[(5-methoxypyridin-3-yl)amino] sulfonyl}benzamide; N-[2-(2-methylphenyl)ethyl]-2-{[(5-methylpyridin-3-yl)amino]sulfonyl}benzamide; N-(3,4-dichlorobenzyl)-2-{[(5-methylpyridin-3-yl)amino] sulfonyl}benzamide; N-[4-fluoro-3-(trifluoromethyl) benzyl]-2-{[(5-methylpyridin-3-yl)amino] sulfonyl}benzamide; N-[4-fluoro-3-(trifluoromethyl) benzyl]-2-{[(5-methoxypyridin-3-yl)amino] sulfonyl}benzamide; 2-{[(5-ethoxypyridin-3-yl)amino] sulfonyl}-N-[2-(2-methylphenyl)ethyl]benzamide; N-(3,4-dichlorobenzyl)-2-{[(5-ethoxypyridin-3-yl)amino] sulfonyl}benzamide; N-(3,4-difluorobenzyl)-2-{[(5-ethoxypyridin-3-yl)amino]sulfonyl}-N-methylbenzamide; 2-{[(4-ethoxypyridin-3-yl)amino]sulfonyl}-N-[4-fluoro-3-(trifluoromethyl)benzyl]benzamide; 2-{[(5-ethoxypyridin-3-yl)amino]sulfonyl}-N-[4-fluoro-3-(trifluoromethyl)benzyl]benzamide; N-(3,4-difluorobenzyl)-2-{[(4-ethoxypyridin-3-yl)amino]sulfonyl}-N-methylbenzamide; N-(4-chloro-2-methylbenzyl)-2-{[(5-methoxypyridin-3-yl) amino]sulfonyl}benzamide; N-(3-chloro-2-methylbenzyl)-2-{[(5-methoxypyridin-3-yl)amino]sulfonyl}benzamide; and N-(3,5-dichlorobenzyl)-2-{[(5-methylpyridin-3-yl) amino]sulfonyl}benzamide; N-(3,4-difluorobenzyl)-2-{[(4-methoxypyridin-3-yl)amino]sulfonyl}-N-methylbenzamide; or a pharmaceutically acceptable salt or solvate thereof.

In another embodiment is provided a compound selected from N-(3,4-difluorobenzyl)-2-{[(4-methoxypyridin-3-yl) amino]sulfonyl}-N-methylbenzamide; N-(3,4-difluorobenzyl)-2-{[(4-methoxypyridin-3-yl)amino] sulfonyl}benzamide; N-[2-(2-fluorophenyl)ethyl]-2-{[(5-methoxypyridin-3-yl)amino]sulfonyl}benzamide; N-[4-fluoro-3-(trifluoromethyl)benzyl]-2-{[(4-methoxypyridin-3-yl)amino]sulfonyl}benzamide; N-(3,4-difluorobenzyl)-2-{[(4-ethoxypyridin-3-yl)amino]sulfonyl}benzamide; and N-(3,4-difluorobenzyl)-2-{[(4-ethoxypyridin-3-yl)amino] sulfonyl}-N-methylbenzamide; or a pharmaceutically acceptable salt or solvate thereof.

In another embodiment is provided N-(3,4-difluorobenzyl)-2-{[(4-methoxypyridin-3-yl)amino]sulfonyl}-N-methylbenzamide, or a pharmaceutically acceptable salt or solvate thereof. Another embodiment provides N-(3,4-difluorobenzyl)-2-{[(4-methoxypyridin-3-yl)amino] sulfonyl}benzamide, or a pharmaceutically acceptable salt or solvate thereof. Another embodiment provides N-[2-(2-fluorophenyl)ethyl]-2-{[(5-methoxypyridin-3-yl)amino] sulfonyl}benzamide, or a pharmaceutically acceptable salt or solvate thereof. Another embodiment provides N-[4-fluoro-3-(trifluoromethyl)benzyl]-2-{[(4-methoxypyridin-3-yl) amino]sulfonyl}benzamide, or a pharmaceutically acceptable salt or solvate thereof. Another embodiment provides N-(3,4-difluorobenzyl)-2-{[(4-ethoxypyridin-3-yl)amino] sulfonyl}benzamide, or a pharmaceutically acceptable salt or solvate thereof. Another embodiment provides N-(3,4-difluorobenzyl)-2-{[(4-ethoxypyridin-3-yl)amino]sulfonyl}-N-methylbenzamide, or a pharmaceutically acceptable salt or solvate thereof.

In other embodiments are provided pharmaceutical compositions, comprising an effective amount of at least one compound of formula (I), and a pharmaceutically acceptable carrier. In other embodiments are provided pharmaceutical compositions, further comprising an effective amount of at least one compound that is metabolized by cytochrome P4503A4 enzyme. In other embodiments are provided pharmaceutical compositions, wherein said at least one compound that is metabolized by cytochrome P4503A4 enzyme is an anti-HIV compound.

Further provided herein are pharmaceutical compositions, comprising an effective amount of at least one compound that is metabolized by cytochrome P450 enzyme and an effective amount of any of the compounds of formula (I). In other embodiments are provided pharmaceutical compositions, wherein said at least one anti-HIV compound is an HIV protease inhibitor. In other embodiments are provided such pharmaceutical compositions, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl) amino]-4-phenylbutanoyl}-5,5-dimethyl-1,3-thiazolidine-4-carboxamide, and fosamprenavir calcium. In other embodiments are provided such pharmaceutical compositions, wherein said HIV protease inhibitor is selected from amprenavir, nelfinavir, ritonavir, saquinavir, invirase, lopinavir, atazanavir, palinavir, indinavir, tipranavir, darunavir, brecanavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. A further embodiment provides such pharmaceutical compositions, wherein said at least one additional compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Another embodiment provides pharmaceutical compositions, comprising an effective amount of (N-{(1S)-3-[3-isopropyl-5-methyl-4H-1,2,4-triazole-4-yl]-exo-8-azabicyclo [3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo

[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide), at least one compound of formula (I), and a pharmaceutically acceptable carrier. Further provided herein are such pharmaceutical compositions, comprising an effective amount of (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), at least compound of formula (I), and a pharmaceutically acceptable carrier.

Another embodiment affords pharmaceutical compositions, comprising at least one compound of formula (I), and an anti-HIV compound as a combined preparation for simultaneous, separate, or sequential administration to an HIV-infected mammal for the treatment of HIV in said mammal.

In other embodiments are provided methods of inhibiting the metabolism of a first compound that is metabolized by cytochrome P4503A4 enzyme, comprising administering said first compound and an effective amount of a second compound to said mammal, wherein said second compound is selected from those of formula (I). Further provided herein are such methods, wherein said first compound is 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one, or a pharmaceutically acceptable salt thereof. In another embodiment are provided such methods wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Further provided herein are such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). In other embodiments are provided such methods, wherein said first compound is an anti-HIV compound. In other embodiments are provided such methods, wherein said anti-HIV compound is an HIV protease inhibitor. In other embodiments are provided such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In other embodiments are provided such methods, wherein said HIV protease inhibitor is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide and fosamprenavir calcium. In another embodiment are provided such methods wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide).

In other embodiments are provided methods of improving the pharmacokinetics in a mammal of a first compound, comprising administering said first compound and an effective amount of a second compound to said mammal, wherein said second compound is selected from those of formula (I). Another embodiment provides such methods, wherein said first compound is 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one, or a pharmaceutically acceptable salt thereof. Further provided herein are such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). A further embodiment provides such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). In other embodiments are provided such methods, wherein said first compound is an anti-HIV compound. In other embodiments are provided such methods, wherein said anti-HIV compound is an HIV protease inhibitor. In other embodiments are provided such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In other embodiments are provided such methods, wherein said HIV protease inhibitor is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide and fosamprenavir calcium. In still another embodiment are provided such methods, wherein said HIV protease inhibitor is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Another embodiment provides methods of inhibiting HIV replication in an HIV-infected mammal, comprising administering to said mammal an effective amount of a first compound and an effective amount of a second compound, wherein said first compound is an HIV replication-inhibiting compound and said second compound is selected from those of formula (I). Still another embodiment provides such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-

Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Yet another embodiment provides such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Still another embodiment affords such methods, wherein said anti-HIV compound is an HIV protease inhibitor. A further embodiment provides such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Still another embodiment provides such methods, wherein said HIV protease inhibitor is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. A further embodiment provides such methods, wherein said first compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Also provided herein are uses of a first compound and a second compound in the preparation of a medicament for the treatment of HIV infection in an HIV-infected mammal, wherein said first compound is selected from those of formula (I), and said second compound is an anti-HIV compound. Further provided herein are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). A further embodiment affords such methods, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Yet another embodiment provides such uses, wherein said second compound is an HIV protease inhibitor. A further embodiment affords such uses, wherein said second compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Another embodiment provides such uses, wherein said second compound is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. A further embodiment provides such uses, wherein said second compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide. Further embodiments provide such uses, wherein said medicament is for simultaneous, separate, or sequential administration to said mammal for the treatment of HIV.

Use of a first compound and a second compound in the preparation of a medicament for improving the pharmacokinetics of said second compound in a mammal, wherein said first compound is selected from those of formula (I), and said second compound is metabolized by cytochrome P450. Further provided are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Also provided are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Further provided are such uses, wherein said second compound is an HIV protease inhibitor. Another embodiment affords such uses, wherein said second compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Also included herein are such uses, wherein said second compound is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Another embodiment provides such uses, wherein said second compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Also included herein are the use of a first compound in the preparation of a medicament for improving the pharmacokinetics in a mammal of a second compound, wherein said first compound is selected from those according of formula (I), and said second compound is metabolized by cytochrome P450. Further provided are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Also provided are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Further provided are such uses, wherein said second compound is an HIV protease inhibitor. Another embodiment affords such uses, wherein said second compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Also included herein are such uses, wherein said second compound is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Another embodiment provides such uses, wherein said second compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

In other embodiments are provided any of the methods described herein, wherein the administration of said first and second compounds occurs sequentially.

In other embodiments are provided any of the methods described herein, wherein the administration of said first and second compounds occurs at the same time.

In other embodiments are provided methods of treating HIV in an HIV-infected mammal, comprising administering to said mammal an effective amount of an anti-HIV compound and an effective amount of a compound according to formula (I). In other embodiments are provided such methods, where said anti-HIV compound is an HIV protease inhibitor. In other embodiments are provided such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In other embodiments are provided such methods, wherein said HIV protease inhibitor is selected from amprenavir, nelfinavir, ritonavir, saquinavir, invirase, lopinavir, atazanavir, palinavir, indinavir, tipranavir, darunavir, brecanavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In other embodiments are provided such methods wherein the HIV protease inhibitor is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide. In other embodiments are provided such methods wherein the anti-HIV compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). In other embodiments are provided such methods wherein the anti-HIV compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide).

In other embodiments are provided such methods, wherein the first compound is 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one.

As used herein, the terms "comprising" and "including" are used in their open, non-limiting sense.

As used herein, the term "HIV" means Human Immunodeficiency Virus. The term "HIV integrase," as used herein, means the Human Immunodeficiency Virus integrase enzyme.

The term "$C_1$-$C_6$ alkyl," as used herein, means saturated monovalent hydrocarbon radicals having straight or branched moieties and containing from 1 to 6 carbon atoms. Examples of such groups include, but are not limited to, methyl, ethyl, propyl, iso-propyl, n-butyl, iso-butyl, and tert-butyl.

The term "$C_3$-$C_{11}$ cycloalkyl" means a saturated, monocyclic, fused, or spiro, polycyclic ring structure having a total of from 3 to 11 carbon ring atoms. Examples of such groups include, but are not limited to, cyclopropyl, cyclobutyl, cyclopentyl, cyclopentenyl, cyclohexyl, cycloheptyl, and adamantyl.

The term "$C_6$-$C_{10}$ aryl", as used herein, means a group derived from an aromatic hydrocarbon containing from 6 to 10 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "$C_2$-$C_{10}$ heterocyclyl" as used herein, means a non-aromatic, monocyclic, bicyclic, tricyclic, or tetracyclic group having a total of from 4 to 10 atoms in its ring system, and containing from 2 to 10 carbon atoms and from one to four heteroatoms each independently selected from O, S and N, and with the proviso that the ring of said group does not contain two adjacent 0 atoms or two adjacent S atoms. Furthermore, such $C_2$-$C_{10}$ heterocyclyl groups may comprise polycyclic, spiro ring systems. Also, such groups may be optionally benzofused. Additionally, such $C_2$-$C_{10}$ heterocyclyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$-$C_{10}$ heterocyclyl group contains a sulfur atom, said sulfur atom may be oxidized with one or two oxygen atoms to afford either a sulfoxide or sulfone. An example of a 4-membered heterocyclic group is azetidinyl (derived from azetidine). An example of a 5-membered heterocyclic group is thiazolyl and an example of a 10 membered heterocyclic group is quinolinyl. Further examples of such $C_2$-$C_{10}$ heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

The term "heteroaryl," as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The terms "halogen" and "halo," as used herein, mean fluorine, chlorine, bromine or iodine.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The terms "cytochrome P450-inhibiting amount" and "cytochrome P450 enzyme activity-inhibiting amount," as used herein, refer to an amount of a compound required to decrease the activity of cytochrome P450 enzymes or a particular cytochrome P450 enzyme isoform in the presence of such compound. Whether a particular compound decreases cytochrome P450 enzyme activity, and the amount of such a compound required to do so, can be determined by methods known to those of ordinary skill in the art and the methods described herein.

The terms "inhibiting" or "inhibition," as used herein, refer to decreasing the activity of a cytochrome P450 enzyme or enzymes using an agent that is capable of decreasing such activity either in vitro or in vivo after administration to a mammal, such as a human. Such inhibition may take place by the compound binding directly to the cytochrome P450 enzyme or enzymes. In addition, the activity of such cytochrome P450 enzymes may be decreased in the presence of such a compound when such direct binding between the enzyme and the compound does not take place. Furthermore, such inhibition may be competitive, non-competitive, or uncompetitive, as described in T. F. Woolf, *Handbook of Drug Metabolism*, Marcel Dekker, Inc., New York, 1999. Such inhibition may be determined using in vitro or in vivo systems, or a combination of both, using methods known to those of ordinary skill in the art.

As used herein, the term "bioavailability" refers to the systemic availability of a given amount of a chemical compound administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the Area Under the Curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, *Modern Pharmaceutics, Drugs and the Pharmaceutical Sciences*, v. 72, Marcel Dekker, New York, Inc., 1996. The $C_{max}$ value is defined as the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first compound, measured as AUC, $C_{max}$, or $C_{min}$ in a mammal is greater when co-administered with a compound of the present invention than when such co-administration does not take place.

The terms "administration", "administering", "dosage," and "dosing," as used herein refer to the delivery of a compound, or a pharmaceutically acceptable salt or solvate thereof, or of a pharmaceutical composition containing the compound, or a pharmaceutically acceptable salt or solvate thereof, to a mammal such that the compound is absorbed into the serum or plasma of the mammal.

The terms "co-administration" or "co-administering," as used herein, refer to the administration of a combination of a first compound and a compound of the present invention, or a pharmaceutically acceptable salt or solvate thereof. Such co-administration can be performed such that the first compound and the compound of the present invention are part of the same composition or part of the same unitary dosage form. Co-administration also includes administering a first compound and a compound of the present invention separately, but as part of the same therapeutic regimen. The two components, if administered separately, need not necessarily be administered at essentially the same time, although they can be if so desired. Thus co-administration includes, for example, administering a first compound and a compound of the present invention as separate dosages or dosage forms, but at the same time. Co-administration also includes separate administration at different times and in any order.

The terms "pharmaceutically acceptable formulation" or "pharmaceutical composition," as used herein, mean a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissollution such as paraffin; resorption accelerators such as quaternary ammonium compounds; surfacelactive agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional anti-HIV agents.

The term "inhibiting HIV replication" means inhibiting human immunodeficiency virus (HIV) replication in a cell. Such a cell may be present in vitro, or it may be present in vivo, such as in a mammal, such as a human. Such inhibition may be accomplished by administering one or more anti-HIV compounds to the cell, such as in a mammal, in an HIV-inhibiting amount. The quantification of inhibition of HIV replication in a cell, such as in a mammal, can be measured using methods known to those of ordinary skill in the art. For example, an anti-HIV compound may be administered to a mammal, either alone or as part of a pharmaceutically acceptable formulation. Blood samples may then be withdrawn from the mammal and the amount of HIV virus in the sample may be quantified using methods known to those of ordinary skill in the art. A reduction in the amount of HIV virus in the sample compared to the amount found in the blood before administration of one or more anti-HIV compounds would represent inhibition of the replication of HIV virus in the mammal. The administration of one or more anti-HIV compounds to the cell, such as in a mammal, may be in the form of single dose or a series of doses. In the case of more than one dose, the doses may be administered in one day or they may be administered over more than one day.

The terms "anti-HIV compound" and "HIV-inhibiting agent," as used herein, mean a compound or combination of compounds capable of inhibiting the replication of HIV in a cell, such as a cell in a mammal. Such compounds may inhibit the replication of HIV through any mechanism known to those of ordinary skill in the art.

The terms "human immunodeficiency virus-inhibiting amount," "HIV-inhibiting amount," and "HIV replication-inhibiting amount" as used herein, refer to the amount of an anti-HIV compound, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods described herein and those known to those of ordinary skill in the art.

The terms "therapeutically effective amount" or "effective amount," as used herein, means an amount of a compound that, when administered to a mammal in need of such treatment, is sufficient to effect treatment, as defined herein. Thus, a therapeutically effective amount or effective amount of a compound is a quantity sufficient to modulate or inhibit the activity of a particular enzyme target or biological process such that a disease condition that is mediated by activity of such an enzyme target or biological process is reduced or alleviated. Examples of the modulation or inhibition of a particular target enzyme target or biological process include, but are not limited to, inhibition of the HIV protease enzyme and inhibition of the CYP450 enzymes, such as the CYP3A4 enzyme.

The terms "treat", "treating", and "treatment" refer to any treatment of any disease or condition in a mammal, particularly a human, and include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition.

The terms "resistant," "resistance," and "resistant HIV," as used herein, refer to HIV virus demonstrating a reduction in sensitivity to a particular drug. A mammal infected with HIV that is resistant to a particular anti-HIV agent or combination of agents usually manifests an increase in HIV viral load despite continued administration of the agent or agents. Resistance may be either genotypic, meaning that a mutation in the HIV genetic make-up has occurred, or phenotypic, meaning that resistance is discovered by successfully growing laboratory cultures of HIV virus in the presence of an anti-HIV agent or a combination of such agents.

The terms "protease inhibitor" and "HIV protease inhibitor," as used herein, refer to compounds or combinations of compounds that interfere with the proper functioning of the HIV protease enzyme that is responsible for cleaving long strands of viral protein into the separate proteins making up the viral core.

The terms "viral load" and "HIV viral load," as used herein, mean the amount of HIV in the circulating blood of a mammal, such as a human. The amount of HIV virus in the blood of mammal can be determined by measuring the quantity of HIV RNA in the blood using methods known to those of ordinary skill in the art.

The term, "compound of the present invention" refers to any compound of formula (I), including those in the Examples that follow, and also include those generically described or those described as species. The term also refers to pharmaceutically acceptable salts or solvates of these compounds.

DETAILED DESCRIPTION

The compounds of the present invention may be administered to a mammal, such as a human, in combination with an additional compound so that there is an increase of the exposure, or an increase in the bioavailability of the additional compound, or an improvement in the pharmacokinetics, of the additional compound in the mammal. The term "exposure," as used herein, refers to the concentration of an additional or second compound in the plasma of a mammal as measured over a period of time. An increase of the exposure of a mammal to an additional or second compound can be measured by first administering the additional or second compound to a mammal in an appropriate form and in the absence of the administration of a compound of the invention, withdrawing plasma samples at predetermined times, and measuring the amount of the compound in the plasma using an appropriate analytical technique, such as liquid chromatography or liquid chromatography-tandem mass spectroscopy. The same study is then repeated, except that a compound of the present invention is co-administered with the additional or second compound. The amount of the additional or second compound present in the plasma at a certain time is determined and the concentration and time data from all the samples are plotted to afford a curve. The area under this curve is calculated and affords the exposure of the mammal to the compound. The difference in the areas under the curve in the presence and absence of a compound of the present invention affords a measure of the increase of the exposure to the additional or second compound in the plasma of the mammal. The terms "exposure," "area under the curve," and "area under the concentration/time curve" are intended to have the same meaning and may be used interchangeably throughout.

Such co-administration to a mammal of a compound of the present invention and a second or additional compound, as described above, may occur such that a compound or compounds of the present invention are present in the same formulation as the additional agents described above. Alternatively, such a combination may be administered such that the compound or compounds of the present invention are present in a formulation that is separate from the formulation in which the additional agent is found. If the compound or compounds of the present invention are administered separately from the additional agent, such administration may take place at the same or sequentially with an appropriate period of time in between. The choice of whether to include the compound or compounds of the present invention in the same formulation as the additional agent or agents is within the knowledge of one of ordinary skill in the art.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

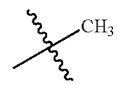

represents a methyl group,

represents an ethyl group,

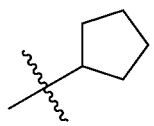

represents a cyclopentyl group, etc.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The compounds of the present invention may have asymmetric carbon atoms. The bonds of the compounds of the present invention may be depicted herein using a solid line ( ____ ), a solid wedge ( ▬ ) or a dotted wedge ( ........ ). The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of the invention may contain more than one asymmetric carbon atom. In those compounds, the use of a solid line to depict bonds from asymmetric carbon atoms is meant to indicate that all possible stereoisomers are meant to be included. The use of a solid line to depict bonds from one or more asymmetric carbon atoms in a compound of the invention and the use of a solid or dotted wedge to depict bonds from other asymmetric carbon atoms in the same compound is meant to indicate that a mixture of diastereomers is present.

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "solvate" is intended to mean a pharmaceutically acceptable solvate form of a specified compound that retains the biological effectiveness of such compound. Examples of solvates include, but are not limited to, compounds of the invention in combination with water, isopropanol, ethanol, methanol, dimethylsulfoxide (DMSO), N,N-dimethylformamide (DMF), ethyl acetate, acetic acid, ethanolamine, or mixtures thereof.

A "pharmaceutically acceptable salt" is intended to mean a salt that retains the biological effectiveness of the free acids and bases of the specified derivative, containing pharmacologically acceptable anions, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycol late, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol®, Gelucire® or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

To treat or prevent diseases or conditions mediated by HIV, a pharmaceutical composition of the invention in a suitable formulation is administered in combination with at least one anti-HIV agent. A combined formulation of a compound of the present invention and an at least anti-HIV agent may be prepared by combining a therapeutically effective amount (i.e., a cytochrome P450-inhibiting amount) of at least one compound of the present invention (as an active ingredient) with one or more anti-HIV agents and at least one pharmaceutically suitable carrier, which may be selected, for example, from diluents, excipients and auxiliaries that facilitate processing of the active compounds into the final pharmaceutical preparations.

Alternatively, to treat or prevent diseases or conditions mediated by HIV, a pharmaceutical composition of the invention in a suitable formulation is administered at the same time as at least one anti-HIV agent that is in a separate, pharmaceutically acceptable formulation. Such a dosing regimen may be designed such that a compound of the present invention is administered to an HIV-infected mammal prior to, at the same time as, or after the administration of the pharmaceutical formulation containing at least one anti-HIV agent. The pharmaceutically acceptable formulation of the compound of the present invention may be prepared by combining the compound and at least one pharmaceutically suitable carrier, which may be selected, for example, from diluents, excipients and auxiliaries that facilitate processing of the active compounds into the final pharmaceutical preparations.

The compounds of the present invention, or a pharmaceutically acceptable salt or solvate thereof, may be administered to a mammal suffering from infection with HIV, such as a human, either alone or as part of a pharmaceutically acceptable formulation, once a day, twice a day, or three times a day in combination with an anti-HIV agent.

Those of ordinary skill in the art will understand that with respect to the compounds of the present invention, the particular pharmaceutical formulation, the dosage, and the number of doses given per day to a mammal requiring such treatment, and the choice of a particular anti-HIV agent or agents are all choices within the knowledge of one of ordinary skill in the art and can be determined without undue experimentation. For example, see "Guidelines for the Use of Antiretroviral Agents in HIV-1 Infected Adults and Adolescents,"

United States Department of Health and Human Services, available at http://www.aidsinfo.nih.gov/quidelines/ as of Apr. 16, 2004.

The compounds of the present invention may be administered in combination with an additional agent or agents for the treatment of a mammal, such as a human, that is suffering from an infection with the HIV virus, AIDS, AIDS-related complex (ARC), or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, inhibitors of HIV integrase, CCR5 inhibitors, HIV fusion inhibitors, compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compounds of the present invention include, but are not limited to, 141 W94 (amprenavir), CGP-73547, CGP-61755, DMP-450, nelfinavir, ritonavir, saquinavir (invirase), lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, darunavir, brecanavir, DPC-681, DPC-684, fosamprenavir calcium (Lexiva), benzenesulfonamide derivatives disclosed in WO 03053435, R-944, Ro-03-34649, VX-385, GS-224338, OPT-TL3, PL-100, SM-309515, AG-148, DG-35-VIII, DMP-850, GW-5950X, KNI-1039, L-756423, LB-71262, LP-130, RS-344, SE-063, UIC-94-003, Vb-19038, A-77003, BMS-182193, BMS-186318, SM-309515, JE-2147, GS-9005, and (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Compounds useful as inhibitors of the HIV reverse transcriptase enzyme that may be used in combination with the compounds of the present invention include, but are not limited to, abacavir, FTC, GS-840, lamivudine, adefovir dipivoxil, beta-fluoro-ddA, zalcitabine, didanosine, stavudine, zidovudine, tenofovir, amdoxovir, SPD-754, SPD-756, racivir, reverset (DPC-817), MIV-210 (FLG), beta-L-Fd4C (ACH-126443), MIV-310 (alovudine, FLT), dOTC, DAPD, entecavir, GS-7340, emtricitabine, and alovudine.

Compounds useful as non-nucleoside inhibitors of the HIV reverse transcriptase enzyme that may be used in combination with the compounds of the present invention include, but are not limited to, efavirenz, HBY-097, nevirapine, TMC-120 (dapivirine), TMC-125, etravirine, delavirdine, DPC-083, DPC-961, TMC-120, capravirine, GW-678248, GW-695634, calanolide, and tricyclic pyrimidinone derivatives as disclosed in WO 03062238.

Compounds useful as CCR5 inhibitors that may be used in combination with the compounds of the present invention include, but are not limited to, TAK-779, SC-351125, SCH-D, (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo [3.2.1]oct-3-yl}-2-methyl-4,5,6,7-tetrahydro-1H-imidazo[4,5-c]pyridine-5-carboxylate, N-{(1S)-3-[3-endo-(5-Isobutyryl-2-methyl-4,5,6,7-tetrahydro-1H-imidazo[4,5-c] pyridin-1-yl)-8-azabicyclo[3.2.1]oct-8-yl]-1-(3-fluorophenyl)propyl}acetamide), PRO-140, and GW-873140 (Ono-4128, AK-602).

Compounds useful as inhibitors of HIV integrase enzyme that may be used in combination with the compounds of the present invention include, but are not limited to, GW-810781, 1,5-naphthyridine-3-carboxamide derivatives disclosed in WO 03062204, compounds disclosed in WO 03047564, compounds disclosed in WO 03049690, and 5-hydroxypyrimidine-4-carboxamide derivatives disclosed in WO 03035076.

Fusion inhibitors for the treatment of HIV that may be used in combination with the compounds of the present invention include, but are not limited to enfuvirtide (T-20), T-1249, AMD-3100, and fused tricyclic compounds disclosed in JP 2003171381.

Other compounds that are useful inhibitors of HIV that may be used in combination with the compounds of the present invention include, but are not limited to, Soluble CD4, TNX-355, PRO-542, BMS-806, tenofovir disoproxil fumarate, and compounds disclosed in JP 2003119137.

Compounds useful in the treatment or management of infection from viruses other than HIV that may be used in combination with the compounds of the present invention include, but are not limited to, acyclovir, fomivirsen, penciclovir, HPMPC, oxetanocin G, AL-721, cidofovir, cytomegalovirus immune globin, cytovene, fomivganciclovir, famciclovir, foscarnet sodium, Isis 2922, KNI-272, valacyclovir, virazole ribavirin, valganciclovir, ME-609, PCL-016

Compounds that act as immunomodulators and may be used in combination with the compounds of the present invention include, but are not limited to, AD-439, AD-519, Alpha Interferon, AS-101, bropirimine, acemannan, CL246, 738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compounds of the present invention include, but are not limited to, atovaquone, azithromycin, clarithromycin, trimethoprim, trovafloxacin, pyrimethamine, daunorubicin, clindamycin with primaquine, fluconazole, pastill, ornidyl, eflornithine pentamidine, rifabutin, spiramycin, intraconazole-R51211, trimetrexate, daunorubicin, recombinant human erythropoietin, recombinant human growth hormone, megestrol acetate, testerone, and total enteral nutrition.

Antifungals that may be used in combination with the compounds of the present invention include, but are not limited to, anidulafungin, C31G, caspofungin, DB-289, fluconzaole, itraconazole, ketoconazole, micafungin, posaconazole, and voriconazole.

Other compounds that may be used in combination with the compounds of the present invention include, but are not limited to, acmannan, ansamycin, LM 427, AR177, BMS-232623, BMS-234475, Cl-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with anti-proliferative agents for the treatment of conditions such as Kaposi's sarcoma. Such agents include, but are not limited to, inhibitors of metallo-matrix proteases, A-007, bevacizumab, BMS-275291, halofuginone, interleukin-12, rituximab, paclitaxel, porfimer sodium, rebimastat, and COL-3.

The particular choice of an additional agent or agents will depend on a number of factors that include, but are not limited to, the condition of the mammal being treated, the particular condition or conditions being treated, the identity of the compound or compounds of the present invention and the additional agent or agents, and the identity of any additional compounds that are being used to treat the mammal. The particular choice of the compound or compounds of the invention and the additional agent or agents is within the knowledge of one of ordinary skill in the art and can be made without undue experimentation.

The compounds of the present invention may be administered in combination with any of the above additional agents for the treatment of a mammal, such as a human, that is suffering from an infection with the HIV virus, AIDS, AIDS-related complex (ARC), or any other disease or condition which is related to infection with the HIV virus. Such a combination may be administered to a mammal such that a compound or compounds of the present invention are present in the same formulation as the additional agents described above. Alternatively, such a combination may be administered to a mammal suffering from infection with the HIV virus such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

The inventive agents may be prepared using the reaction routes and synthesis schemes as described below, employing the techniques available in the art using starting materials that are readily available. The preparation of certain embodiments of the present invention are described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

The compounds of Formula (I) can be prepared from compounds of formulae 3 and 4, as shown below in Scheme 1. In general, compounds of formula 3, wherein $R^1$, $R^2$, $R^3$, $R^4$, $R^5$, $R^6$, $R^7$, $R^8$, and $R^9$ are as hereinbefore defined, and $R^{15}$ is $C_1$-$C_{10}$ alkyl, may be allowed to react with compounds of formula 4, wherein $R^{10}$ and $R^{11}$ are as hereinbefore defined. Such reactions may be performed in an aprotic solvent, such as acetonitrile for example, at a temperature in the range of from about 50° C. to about 150° C., for example about 110° C., and optionally in the presence of microwave energy. For example, compounds of formula (I) may be prepared using methyl 2-[(pyridin-3-ylamino)sulfonyl]benzoate by preparing a mixture of methyl 2-[(pyridin-3-ylamino)sulfonyl]benzoate (1 eq) and an appropriate compound of formula 4 (1.5 eq) in $CH_3CN$ (0.35 M) and heating the resulting mixture to about 110° C. for 30 minutes in a microwave. The reaction mixtures are then allowed to cool to about room temperature and the solvents are removed by evaporation. The resulting crude products may be further purified by methods known to those of ordinary skill in the art, such as the use of silica gel chromatography using an appropriate solvent or mixture of solvents as the eluant.

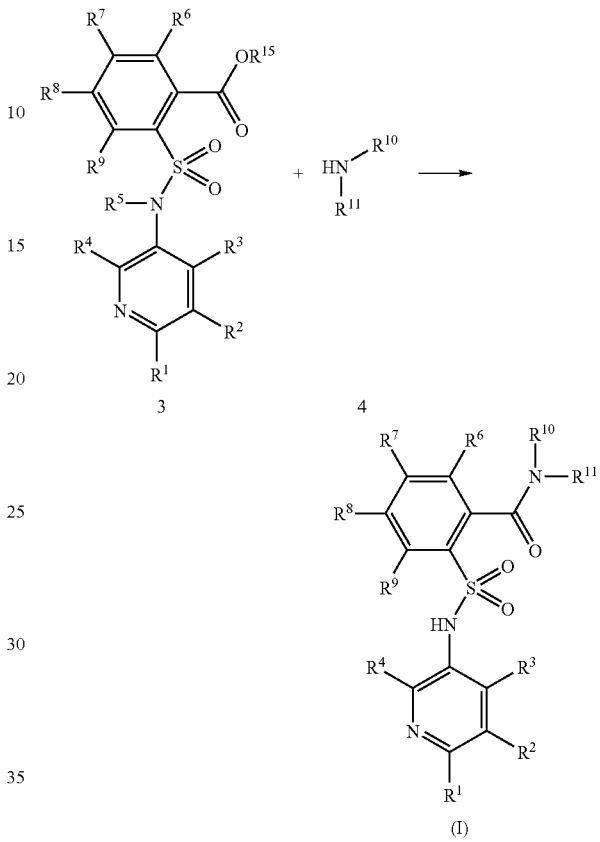

Compounds of formula 3 may be prepared from compounds of formulae 1 and 2, wherein $R^1$, $R^2$, $R^3$, $R^4$, $R^5$, $R^6$, $R^7$, $R^8$, and $R^9$ are as hereinbefore defined, and $R^{15}$ is $C_1$-$C_{10}$ alkyl, as shown below in Scheme 2. Generally, these reactions may be performed in an aprotic solvent, such as acetonitrile for example, at a temperature in the range of from about 0° C. to about 75° C., for example about 25° C., and in the presence of a base. Suitable bases include, but are not limited to, inorganic bases, such as potassium carbonate or sodium carbonate for example, or organic bases, such as triethyl amine or N,N-4,4-dimethylaminopyridine for example. Alternatively, a second equivalent of the compound of formula 2 may be used as a suitable base. The choice of whether to use an additional base or an additional equivalent of compound 2 as the base is within the knowledge of one of ordinary skill in the art and can be determined without undue experimentation.

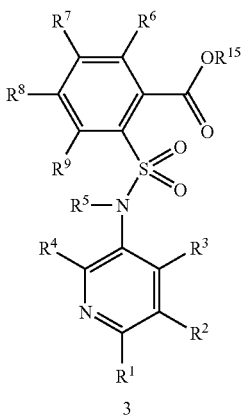

Compounds of formula 1 are commercially available or may be prepared by those of ordinary skill in the art without undue experimentation using methods found in the literature, such as those found in Kim et al., *Synthesis* (1992), (12), 1203-4; Bastide et al., *Pesticide Science* (1994), 40(4), 293-7; and Diehr et al., U.S. Pat. No. 4,743,294.

Compounds of formula 2 are either commercially available, may be prepared by those of ordinary skill in the art without undue experimentation using methods found in the literature, or may be prepared using methods described herein.

The inhibition of the cytochrome P450 enzyme system by a compound of the present invention can be determined according to methods known to those of skill in the art and the methods described herein. For example, see Morrison, J. F., *Biochim Biophys Acta.*, 1969, 185: 269-86; and Szedlascek, S. E., Ostafe, V., Serban, M., and Vlad, M. O., *Biochem. J.*, 1988, 254:311-312.

EXAMPLES

The examples below are intended only to illustrate particular embodiments of the present invention and are not meant to limit the scope of the invention in any manner.

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromotagraphy (HPLC) or thin-layer chromatography (TLC) and terminated as judged by the consumption of starting material. The TLC plates were visualized by UV, phosphomolybdic acid stain, or iodine stain.

Unless otherwise indicated, $^1$H-NMR spectra were recorded on a Bruker instrument operating at 300 MHz and $^{13}$C-NMR spectra were recorded at 75 MHz. NMR spectra were obtained as DMSO-d6 or CDCl$_3$ solutions (reported in ppm), using chloroform as the reference standard (7.25 ppm and 77.00 ppm) or DMSO-d6 ((2.50 ppm and 39.52 ppm)). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCl. All melting points are uncorrected.

All final products had greater than 95% purity (by HPLC at wavelengths of 220 nm and 254 nm).

All elemental analyses for compounds herein, unless otherwise specified, provided values for C, H, and N analysis that were within 0.4% of the theoretical value, and are reported as "C, H, N."

In the following examples and preparations, "LDA" means lithium diisopropyl amide, "Et" means ethyl, "Ac" means acetyl, "Me" means methyl, "Ph" means phenyl, (PhO)$_2$POCl means chlorodiphenylphosphate, "HCl" means hydrochloric acid, "EtOAc" means ethyl acetate, "Na$_2$CO$_3$" means sodium carbonate, "NaOH" means sodium hydroxide, "NaCl" means sodium chloride, "NEt$_3$" means triethylamine, "THF" means tetrahydrofuran, "DIC" means diisopropylcarbodiimide, "HOBt" means hydroxy benzotriazole, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "AcCl" means acetyl chloride, "CH$_2$Cl$_2$" means methylene chloride, "MTBE" means methyl t-butyl ether, "DMF" means dimethyl formamide, "SOCl$_2$" means thionyl chloride, "H$_3$PO$_4$" means phosphoric acid, "CH$_3$SO$_3$H" means methanesulfonic acid, "Ac$_2$O" means acetic anhydride, "CH$_3$CN" means acetonitrile, and "KOH" means potassium hydroxide.

Example A

Methyl 2-[(pyridin-3-ylamino)sulfonyl]benzoate

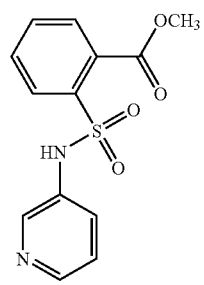

Methyl 2-(chlorosulfonyl)benzoate (14.1 g, 60.0 mmol) was added to a stirred solution of 3-pyridinamine (15.0 g, 159.4 mmol) in CH$_3$CN (0.4 M). The temperature rose to 25° C. and a small amount of reddish oil separated out. CHCl$_3$ (2.0 M, protected with amylenes) was added to return all materials to solution. After 1 h, the solvents were evaporated and the residual oil was partitioned between EtOAc and water. The organic layer was washed with water and was evaporated to give the crude product. The crude product was dissolved in the minimum amount of hot EtOAc and was diluted with ether. The product rapidly crystallized out and after 1 hour filtered off and washed with ether to provide the title compound. $^1$H NMR (400 MHz, CDCl$_3$) δ 8.38 (d, 1H) 8.31 (d, 2H) 7.93 (d, 2H) 7.80 (d, 2H) 7.76 (t, 1H) 7.64 (t, 1H) 7.53 (t, 1H) 7.25 (m, 1H) 4.12 (s, 3H).

Compounds of formula (I) were prepared using methyl 2-[(pyridin-3-ylamino)sulfonyl]benzoate by preparing a mixture of methyl 2-[(pyridin-3-ylamino)sulfonyl]benzoate (1 eq) and an appropriate amine (1.5 eq) in CH$_3$CN (0.35 M) and heating to about 110° C. for 30 minutes in a microwave. The solutions were allowed to cool to room temperature and the solvent was evaporated. The crude products were purified by SiO$_2$ column chromatography.

Example B
Methyl 2-{[(5-methylpyridin-3-yl)amino]sulfonyl}benzoate

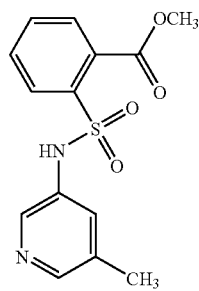

To a solution of 5-methylpyridin-3-amine (0.5 g, 4.62 mmol) in CH$_2$Cl$_2$ (50 ml) were added triethylamine (0.64 mL, 4.62 mmol) and methyl 2-(chlorosulfonyl)benzoate (1.08 g, 4.62 mmol). The resulting mixture was stirred at room temperature for 1 hour. The mixture was then diluted with saturated aqueous NaHCO$_3$ and extracted with CH$_2$Cl$_2$. The organic layer was dried over Na$_2$SO$_4$, filtered and concentrated. The crude residue was purified by flash chromatography (0-8% MeOH/CH$_2$Cl$_2$) to give the title compound (0.476 g, 34%). $^1$H NMR (400 MHz, DMSO-D6) δ ppm 10.25-10.62 (m, 1H) 8.6 (s, 2H) 7.81-7.93 (m, 1H) 7.64-7.76 (m, 2H) 7.54-7.64 (m, 1H) 7.28 (s, 1H) 3.80 (s, 3H) 2.18 (s, 3H).

Compounds of formula (I) were prepared using methyl 2-{[(5-methylpyridin-3-yl)amino]sulfonyl}benzoate by preparing a mixture of methyl 2-{[(5-methylpyridin-3-yl)amino]sulfonyl}benzoate (1 eq) and an appropriate amine (1.5 eq) in CH$_3$CN (0.35 M) and heating to about 110° C. for 30 minutes in a microwave. The solutions were allowed to cool to room temperature and the solvent was evaporated. The crude products were purified by SiO$_2$ column chromatography.

Example C

Preparation of methyl 2-{[(5-methoxypyridin-3-yl)amino]sulfonyl}benzoate

Step 1: 3-bromo-5-methoxypyridine

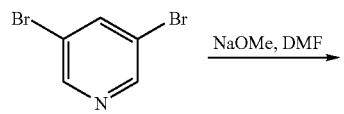

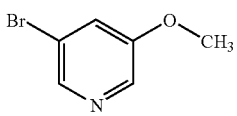

To a solution of 3,5-dibromopyridine (10.0 g, 42.2 mmol) in DMF (10 mL) in a flask with a distillation head was added NaOMe solution 25% wt/wt (10 mL) and the mixture was heated to 100° C. for 3 hours. At the end of 3 hours ~8 mL of MeOH was collected. The DMF solution was cooled to room temperature and diluted with H$_2$O (25 mL) and extracted with MTBE (2×25 mL). The combined organic layers were washed with H$_2$O (2×25 mL), dried over Na$_2$SO$_4$, filtered and concentrated. The residue was then dried under high vacuum for 10 hours to give the title compound (5.2 g, 66%). $^1$H NMR (400 MHz, DMSO-D6) δ 8.26-8.31 (m, 2H) 7.69-7.72 (m, 1H) 3.84 (s, 3H).

Step 2: 5-methoxypyridin-3-amine

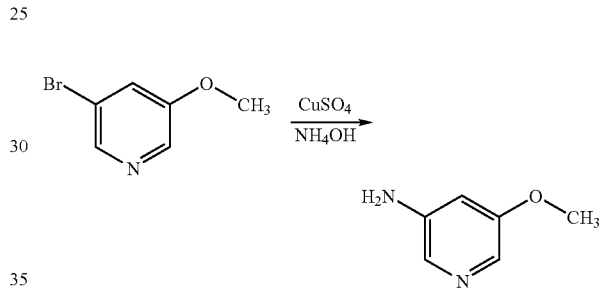

A solution of 3-bromo-5-methoxypyridine (5.2 g, 27.5 mmol) and CuSO$_4$.H2O (1.37 g, 5.5 mmol) in NH$_4$OH (5 mL) was placed in a sealed tube and heated at 120° C. for 10 hours. The reaction mixture was then cooled to room temperature, diluted with H$_2$O (40 mL), and extracted with EtOAc (3×30 mL). The combined organic layers were dried over Na$_2$SO$_4$, filtered and concentrated to afford the title compound that was used in the next step with no further purification.

Step 3: methyl 2-{[(5-methoxypyridin-3-yl)amino]sulfonyl}benzoate

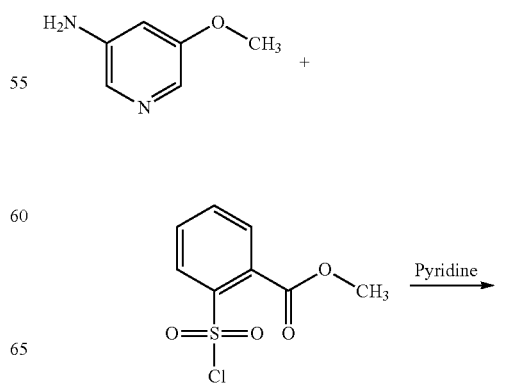

-continued

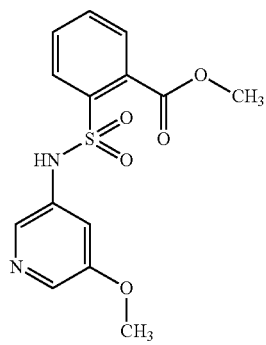

To a solution of 5-methoxypyridin-3-amine (1 eq) in pyridine (0.4 M) was added methyl 2-(chlorosulfonyl)benzoate (1 eq) and the mixture was stirred overnight at room temperature. The mixture was diluted with saturated aqueous NaHCO$_3$ and extracted with CH$_2$Cl$_2$. The organic layer was dried over Na$_2$SO$_4$, filtered and concentrated. The crude residue was purified by flash chromatography (0-8% MeOH/CH$_2$Cl$_2$) to give afford the title compound. $^1$H NMR (400 MHz, DMSO-D6) δ ppm 10.56-10.66 (m, 1H) 8.55-8.61 (m, 1H) 7.95-8.01 (m, 1H) 7.86-7.94 (m, 1H) 7.67-7.73 (m, 2H) 7.34-7.40 (m, 1H) 7.02 (s, 1H) 3.83 (s, 3H) 3.73 (s, 3H).

Compounds of formula (I) were prepared using methyl 2-{[(5-methoxypyridin-3-yl)amino]sulfonyl}benzoate by preparing a mixture of methyl 2-{[(5-methoxypyridin-3-yl)amino]sulfonyl}benzoate (1 eq) and an appropriate amine (1.5 eq) in CH$_3$CN (0.35 M) and heating to about 110° C. for 30 minutes in a microwave. The solutions were allowed to cool to room temperature and the solvent was evaporated. The crude products were purified by SiO$_2$ column chromatography.

Example D

Preparation of methyl 2-{[(4-methoxypyridin-3-yl)amino]sulfonyl}benzoate

Step 1: 4-methoxypyridin-3-amine

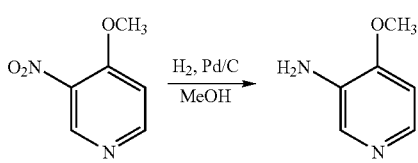

To a solution of 4-methoxy-3-nitropyridine (2.5 g, 16.2 mmol) in MeOH (50 mL) was added Pd/C 10% wt/wt (0.5 g) and the mixture was stirred under 1 atm H$_2$ for 10 hours at room temperature. The reaction mixture was filtered through celite and filtrate was concentrated. The crude residue was purified by flash chromatography (0-10% MeOH/CH$_2$Cl$_2$) to give compound 16 (0.875 g, 44%). $^1$H NMR (400 MHz, DMSO-D6) δ 7.83 (s, 1H) 7.70 (d, 1H) 6.79 (d, 1H) 4.79 (s, 2H) 3.79 (s, 3H).

Step 2: methyl 2-{[(4-methoxypyridin-3-yl)amino]sulfonyl}benzoate

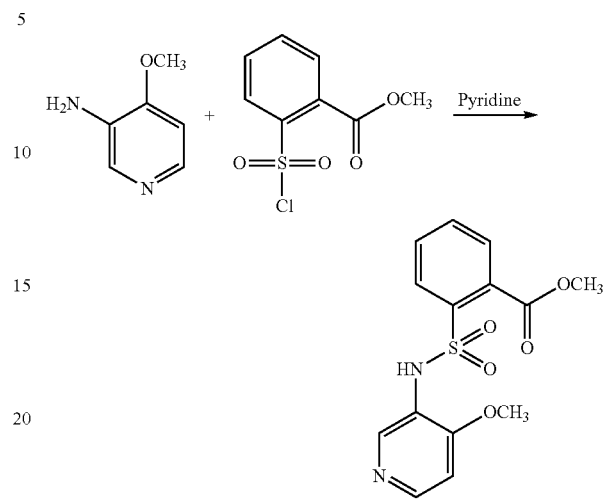

To a solution of 5-methoxypyridin-3-amine (1 eq) in pyridine (0.4 M) was added methyl 2-(chlorosulfonyl)benzoate (1 eq) and the mixture was stirred overnight at room temperature. The mixture was diluted with saturated aqueous NaHCO$_3$ and extracted with CH$_2$Cl$_2$. The organic layer was dried over Na$_2$SO$_4$, filtered and concentrated. The crude residue was purified by flash chromatography to give afford the title compound. $^1$H NMR (400 MHz, DMSO-D6) δ 9.35-9.57 (m, 1H) 8.54-8.61 (m, 1H) 8.17-8.23 (m, 1H) 7.74-7.85 (m, 2H) 7.61-7.73 (m, 1H) 7.32-7.42 (m, 1H) 6.91-7.00 (m, 1H) 3.73 (s, 3H) 3.51 (s, 3H)

Compounds of formula (I) were prepared using methyl 2-{[(4-methoxypyridin-3-yl)amino]sulfonyl}benzoate by preparing a mixture of methyl 2-{[(4-methoxypyridin-3-yl)amino]sulfonyl}benzoate (1 eq) and an appropriate amine (1.5 eq) in CH$_3$CN (0.35 M) and heating to about 110° C. for 30 minutes in a microwave. The solutions were allowed to cool to room temperature and the solvent was evaporated. The crude products were purified by SiO$_2$ column chromatography.

Example E

Preparation of methyl 2-{[(5-cyanopyridin-3-yl)amino]sulfonyl}benzoate

Methyl 2-{[(5-cyanopyridin-3-yl)amino]sulfonyl}benzoate was prepared following the procedure published in Schareina, T. et al., *J. Organometallic Chemistry* 2004, 689, 4576.

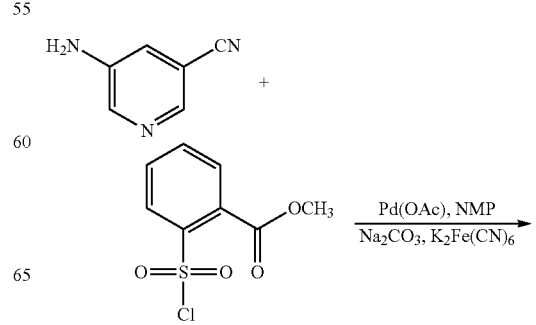

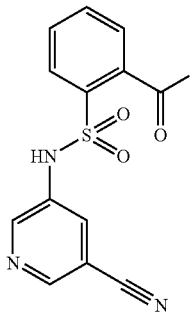

5

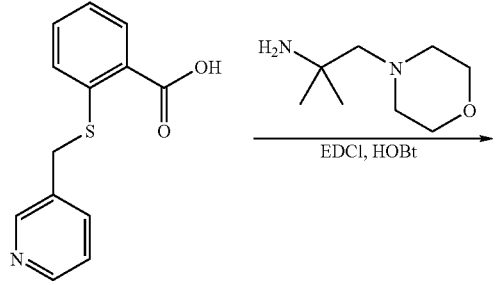

Compounds of formula (I) were prepared using methyl 2-{[(5-cyanopyridin-3-yl)amino]sulfonyl}benzoate by preparing a mixture of methyl 2-{[(5-cyanopyridin-3-yl)amino]sulfonyl}benzoate (1 eq) and an appropriate amine (1.5 eq) in CH₃CN (0.35 M) and heating to about 110° C. for 30 minutes in a microwave. The solutions were allowed to cool to room temperature and the solvent was evaporated. The crude products were purified by SiO₂ column chromatography.

Example F

Synthesis of N-(1,1-dimethyl-2-morpholin-4-yl-ethyl)-2-[(pyridin-3-ylmethyl)sulfinyl]benzamide

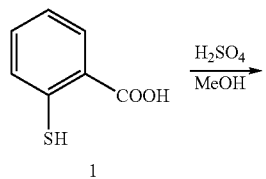

1

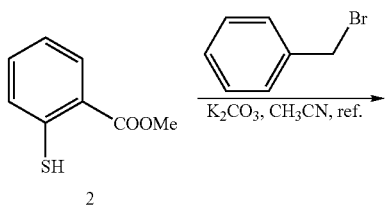

2

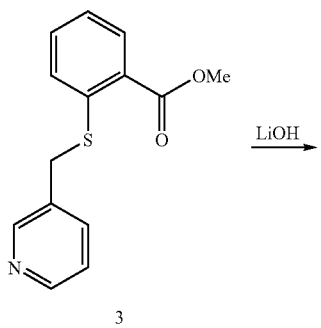

3

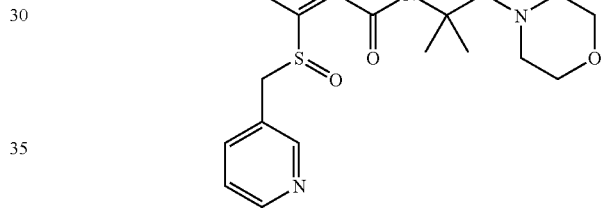

4

25

30

35

40

Step 1: Methyl 2-mercaptobenzoate (2): Acid 1 (170.0 g, 1.1 mol), H₂SO₄ (20 mL, 0.37 mol) and anhydrous MeOH (300 mL) were refluxed for 2 days. The solvent was evaporated under reduced pressure. Water was added and the mixture was extracted with CH₂Cl₂ (3×1000 mL). The organic layers were combined, washed with aq. NaHCO₃ (2×300 mL), water (2×250 mL), brine (500 mL) and dried over Na₂SO₄ to afford crude compound 2 (165.0 g, 89.6%). This was used without further purification.

Step 2: Methyl 2-(pyridin-3-ylmethylthio)benzoate (3): A mixture of compound 2 (70.0 g, 0.4167 mol), 1-(bromomethyl)benzene (82.8 g, 0.5 mol), K₂CO₃ (350 g, 2.49 mol) and CH₃CN (500 mL) was refluxed overnight. The mixture was allowed to cool to room temperature and filtered. The filtrate was concentrated under reduced pressure. After addition of water, the mixture was extracted with CH₂Cl₂ (3×500 mL). The organic layers were combined, washed with aq. Na₂CO₃ (2×200 mL), water (2×300 mL), brine (300 mL) and dried over Na₂SO₄. After evaporation, crude compound 3 was obtained (64.0 g, 59.4%). This was used without further purification.

Step 3: 2-(pyridin-3-ylmethylthio)benzoic acid (4): To a solution of compound 3 (55.0 g, 0.212 mol) in MeOH/H₂O (300 mL/50 mL) was added LiOH. H₂O (17.8 g, 0.425 mol) in portions at 0° C. The reaction mixture was stirred at room temperature overnight and TLC showed the starting material was consumed. The solvent was removed under reduced pressure. The residue was diluted with water, and extracted with Et₂O (2×1 L) to remove neutral impurities. The aqueous layer was adjusted to pH 3-4 with 1 N aq. HCl (50 mL) and extracted with EtOAc (2×1 L). The combined organic phases were washed with water (2×200 mL), brine (300 mL), dried over Na₂SO₄ and concentrated to afford compound 4 (35.0 g, 67%). This was used without further purification.

Step 4: N-(2-methyl-1-morpholinopropan-2-yl)-2-(pyridin-3-ylmethylthio)benzamide(5): To a solution of acid 4 (2.75 g, 11.2 mmol) and 2-methyl-1-morpholinopropan-2-amine (1.12 mL, 7.4 mmol)) in anhydrous DMF/DMSO were added EDCl (2.58 g, 13.32 mmol), HOBt (0.182 g, 13.32 mmol) and NMM (3.35 mL, 29.6 mmol) and the mixture was stirred at room temperature overnight. The solvent was removed in vacuo. After addition of water (10 mL), the mixture was extracted with CH₂Cl₂. The organic layers were combined, washed with 1 N aq. NaOH (15 mL), water (3×10 mL), brine (50 mL) and dried over MgSO₄. The solvent was removed under reduced pressure; the residue was purified via column chromatography (silica gel, EtOAc/petroleum 1:5) to afford 5 (2.0 g, 50%). ¹H NMR (400 MHz, CHLOROFORM-D) □ ppm 8.46 (d, 1H) 8.43 (dd, 1H) 7.52-7.56 (m, 1H) 7.45-7.50 (m, 1H) 7.20-7.24 (m, 2H) 7.13-7.19 (m, 1H) 6.66 (s, 1H) 4.08 (s, 2H) 3.63 (t, 4H) 2.57-2.62 (m, 6H) 1.44 (s, 6H)

Step 5: N-(2-methyl-1-morpholinopropan-2-yl)-2-(pyridin-3-ylmethylsulfinyl)benzamide (6): To a solution of intermediate 5 (0.143, 0.370 mmol) in CHCl₃ (6 ml) were added Et₄NBr (0.004 g, 0.018 mmol) and IBX (0.142 g, 0.507 mmol) and the reaction mixture was stirred at room temperature for 1 hour. The mixture was diluted with saturated aqueous NaHCO₃ and extracted with CH₂Cl₂. The organic layer was dried over Na₂SO₄, filtered and concentrated. The crude residue was purified by flash chromatography (0-5% MeOH/CH₂Cl₂) to give compound 17 (0.026 g, 18%). ¹H NMR (400 MHz, CHLOROFORM-D) d ppm 8.45 (d, 1H) 8.07-8.11 (m, 1H) 7.39-7.53 (m, 5H) 7.13-7.20 (m, 1H) 7.05 (s, 1H) 4.40 (d, 1H) 4.19 (d, 1H) 3.61-3.70 (m, 4H) 2.48-2.65 (m, 6H) 1.46 (d, 6H)

Example G

General Method for BOC Deprotection

To a solution of an appropriate BOC-protected amine (1 eq) in MeOH (0.1 M) is added DOWEX 50WX2-400 ion exchange resin (10 eq) and the mixture is heated to 40° C. for 3 hours. The mixture is then allowed to cool to room temperature and filtered. The resin is washed with 3 portions of MeOH. The product is then liberated from the resin by treatment with a solution of 20% NH₄OH/MeOH that is applied in 3 portions. The basic alcohol washes are concentrated in vacuo to provide the desired, deprotected amine.

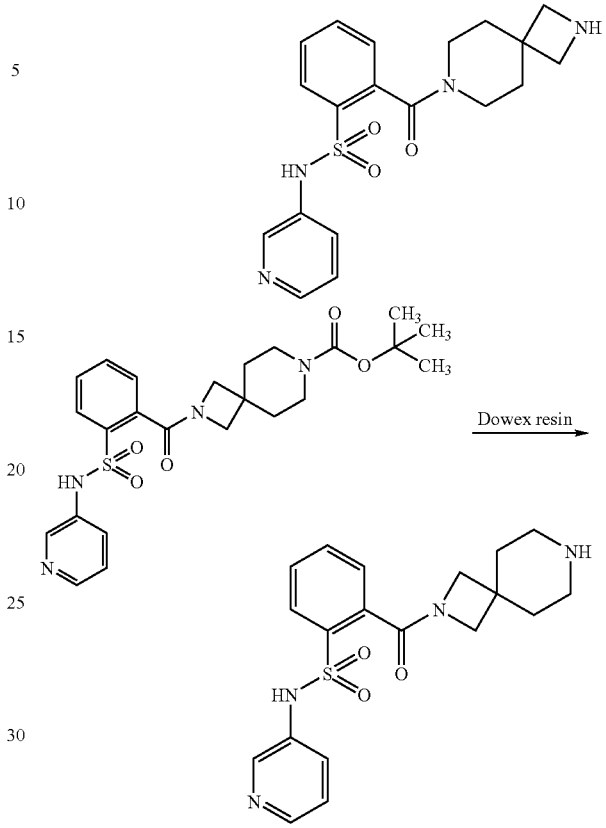

Example 42

N-(3-methylbutyl)-2-[(pyridin-3-ylamino)sulfonyl]benzamide

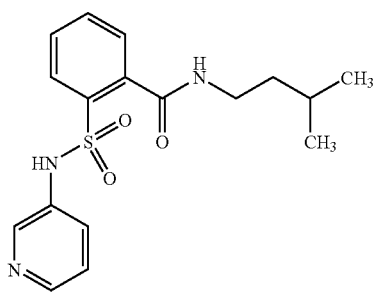

The title compound was prepared according to procedures described above, using methyl 2-[(pyridin-3-ylamino)sulfonyl]benzoate and 3-methylbutylamine. The title compound was further purified by dissolving 2.0 g in ethyl acetate (20 mL) and heating to reflux. When compound had fully dissolved the resultant solution was left to cool very slowly to room temperature. The resulting crystals were left to stand at RT for 30 min, after which time they were filtered using a funnel, washed with cold ethyl acetate (20 mL), and dried under high vacuum for 16 h to afford the title compound as a white crystalline solid (1.67 g, 84%). ¹H NMR (400 MHz, CDCl₃) δ 8.64 (s, 1H) 8.26-8.43 (m, 2H) 7.60-7.68 (m, 2H) 7.45-7.59 (m, 2H) 7.39 (t, 1H) 7.12-7.21 (m, 1H) 6.08-6.17 (m, 1H) 3.52 (q, 2H) 1.67-1.79 (m, 1H) 1.57 (q, 2H) 0.98 (d, 6H).

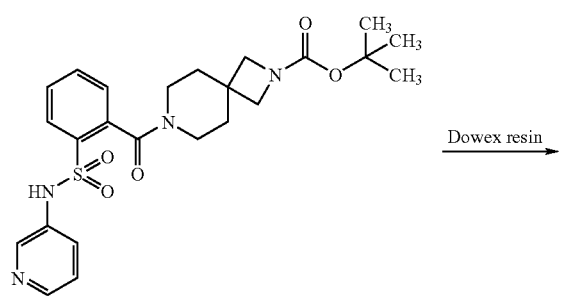

Example 43

N-(3-fluorobenzyl)-2-[(pyridin-3-ylamino)sulfonyl]benzamide

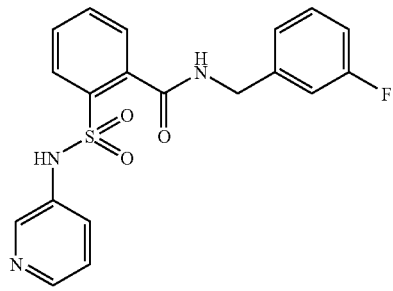

The title compound was prepared according to procedures described above, using methyl 2-[(pyridin-3-ylamino)sulfonyl]benzoate and 3-fluorobenzylamine. The title compound was further purified by dissolving 25 g in EtOH (300 mL) and gently heating using water bath to 80° C. The resulting solids material were then slowly dissolved and more EtOH (50 mL) was added to completely dissolve all the solids. The solution left at room temperature to crystallize for 1 h. The resulting crystals were collected and dried under high vacuum for 16 h to afford the title compound as a crystalline solid (21 g, 84%). $^1$H NMR (400 MHz, DMSO-D6) δ 9.76 (s, 1H) 9.32 (t, 1H) 8.31 (d, 1H) 8.25 (d, 1H) 7.66-7.78 (m, 2H) 7.50-7.65 (m, 3H) 7.39 (q, 1H) 7.23-7.29 (m, 3H) 7.09 (t, 1H) 4.54 (d, 2H).

Example 63

N-butyl-2-[(pyridin-3-ylamino)sulfonyl]benzamide

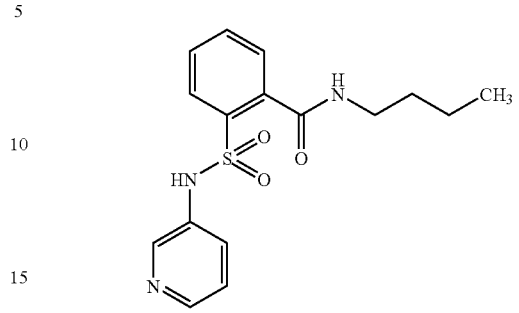

The title compound was prepared according to procedures described above, using methyl 2-[(pyridin-3-ylamino)sulfonyl]benzoate and n-butylamine. The title compound was further purified by dissolving 2.0 g in ethyl acetate (10 mL). Hexane was then added dropwise to the solution until it became cloudy. A few drops of ethyl acetate were then added to obtain a clear solution. The resulting solution was left at rt for approximately 48 h. The resulting solids were collected, washed with 20% ethyl acetate/hexane (3×150 mL), and dried under high vacuum overnight at rt to afford the title compound as a crystalline solid (1.64 g, 82%). $^1$H NMR (400 MHz, DMSO-D6) δ 9.90-10.00 (m, 1H) 8.73 (t, 1H) 8.28-8.37 (m, 2H) 7.71-7.76 (m, 1H) 7.61-7.70 (m, 2H) 7.49-7.57 (m, 2H) 7.35-7.44 (m, 1H) 3.25 (q, 2H) 1.51-1.54 (m, 2H) 1.29-1.40 (m, 2H) 0.90 (t, 3H).

Examples 1 to 393

The following examples were prepared according to Example 2, using the appropriate compound of formulae 3 and 4 (as described in Schemes 1 and 2). Compounds of formula 3 were prepared as described above and compounds of formula 4 are commercially available or were prepared using methods known to those of ordinary skill in the art.

| Example No. | Structure | Name | $^1$H NMR |
|---|---|---|---|
| 1 | 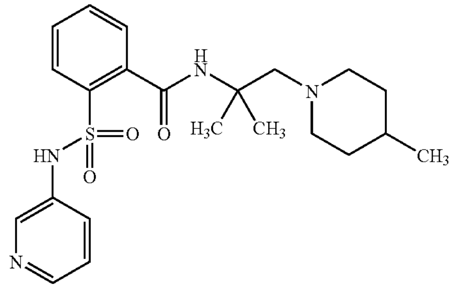 | N-[1,1-dimethyl-2-(4-methylpiperidin-1-yl)ethyl]-2-[(pyridin-3-ylamino)sulfonyl]benzamide | (400 MHz, CHLOROFORM-D) d ppm 8.33-8.38(m, 1H) 8.25-8.30(m, 1H) 7.72 (d, 1H) 7.59 (d, 1H) 7.52 (d, 2H) 7.42-7.47(m, 1H) 7.32-7.40(m, 1H) 7.08-7.17(m, 1H) 2.95-3.05(m, 2H) 2.71(s, 2H) 2.33(t, 2H) 1.56-1.63(m, 1H) 1.54 (s, 6H) 1.29-1.42(m, 1H) 1.14-1.27(m, 3H) 0.85(d, 3H) |

-continued

| Example No. | Structure | Name | $^1$H NMR |
|---|---|---|---|
| 2 | 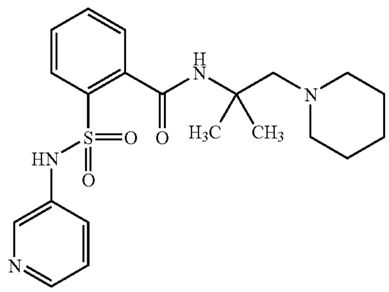 | N-(1,1-dimethyl-2 piperidin-1-ylethyl)-2-[(pyridin-3-ylamino)sulfonyl]benzamide | (400 MHz, DMSO-D6) d ppm 8.53-8.64(m, 1H) 8.19-8.23(m, 1H) 8.07-8.14(m, 1H) 7.71(d, 1H) 7.60(t, 1H) 7.47-7.53(m, 2H) 7.41-7.47(m, 1H) 7.15-7.22(m, 1H) 2.90-2.97(m, 2H) 2.70-2.80(m, 4H) 1.53-1.63(m, 4H) 1.41(s, 8H) |
| 3 | 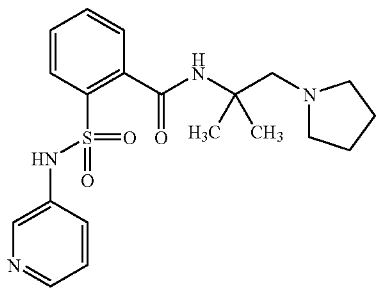 | N-(1,1-dimethyl-2-pyrrolidin-1-ylethyl)-2-(pyridin-3-ylamino)sulfonyl]benzamide | (400 MHz, DMSO-D6) d ppm 8.35-8.43(m, 1H) 8.11-8.16(m, 1H) 7.92-7.99(m, 1H) 7.74(d, 1H) 7.46-7.53(m, 1H) 7.39-7.45(m, 2H) 7.31-7.37(m, 1H) 7.02-7.10(m, 1H) 3.51-3.57(m, 2H) 3.16-3.24(m, 4H) 1.79-1.86(m, 4H) 1.45(s, 6H) |
| 4 | 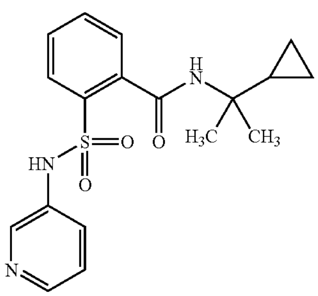 | N-(1-cyclopropyl-1-methylethyl)-2-[(pyridin-3-ylamino)sulfonyl]benzamide | (400 MHz, CHLOROFORM-D) d ppm 8.55-8.63(m, 1H) 8.30-8.42(m, 2H) 7.57-7.71(m, 2H) 7.46-7.57(m, 2H) 7.31-7.43(m, 1H) 7.08-7.20(m, 1H) 6.08(s, 1H) 1.42(s, 6H) 1.26-1.38(m, 1H) 0.43-0.56(m, 4H) |
| 5 | 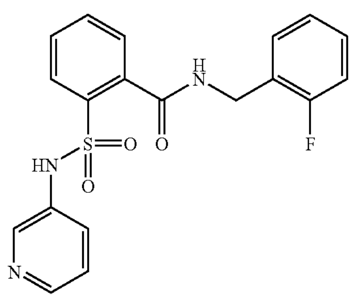 | N-(2-fluorobenzyl)-2-[(pyridin-3-ylamino)sulfonyl]benzamide | (400 MHz, DMSO-D6) d ppm 9.74(s, 1H) 9.24-9.39(m, 1H) 8.24(d, 2H) 7.63-7.80(m, 2H) 7.46-7.65(m, 4H) 7.21-7.36(m, 2H) 7.14-7.22(m, 2H) 4.54(d, 2H) |
| 6 | 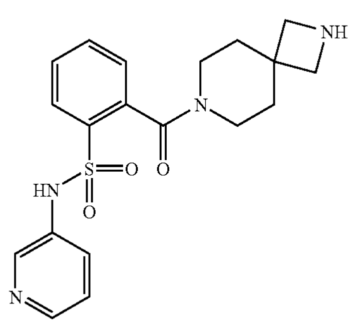 | 2-(2,7-diazaspiro[3.5]non-7-ylcarbonyl)-N-pyridin-3-ylbenzenesulfonamide | (400 MHz, DMSO-D6) d ppm 8.01(s, 1H) 7.61-7.77(m, 2H) 7.28-7.46(m, 2H) 7.05-7.23(m, 2H) 6.84-6.93(m, 1H) 3.57-3.81(m, 5H) 3.39-3.46(m, 1H) 2.93-3.03(m, 2H) 1.77-1.93(m, 2H) 1.63-1.77(m, 1H) 1.41-1.57(m, 1H) |

| Example No. | Structure | Name | ¹H NMR |
|---|---|---|---|
| 7 | 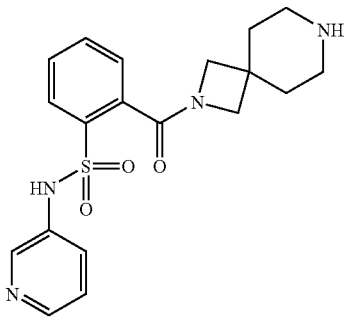 | 2-(2,7-diazaspiro[3.5]non-2-ylcarbonyl)-N-pyridin-3-ylbenzenesulfonamide | (400 MHz, DMSO-D6) d ppm 8.03(s, 1H) 7.70-7.85(m, 2H) 7.36-7.49(m, 2H) 7.17-7.27(m, 2H) 6.90-6.99(m, 1H) 3.72(s, 2H) 3.56(s, 2H) 2.86-2.99(m, 2H) 2.71-2.84(m, 2H) 1.68-1.86(m, 4H) |
| 8 | 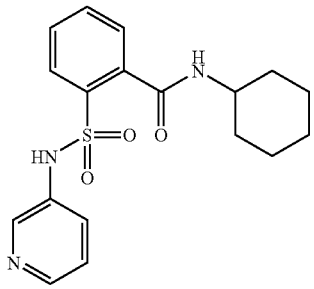 | N-cyclohexyl-2-[(pyridin-3-ylamino)sulfonyl]benzamide | (400 MHz, DMSO-D6) d ppm 9.67(s, 1H) 8.62-8.79(m, 1H) 8.18-8.36(m, 2H) 7.57-7.79(m, 2H) 7.42-7.57(m, 3H) 7.18-7.36(m, 1H) 3.71-3.91(m, 1H) 1.85-1.97(m, 2H) 1.69-1.84(m, 2H) 1.51-1.64(m, 1H) 1.22-1.39(m, 4H) 1.03-1.20(m, 1H) |
| 9 | 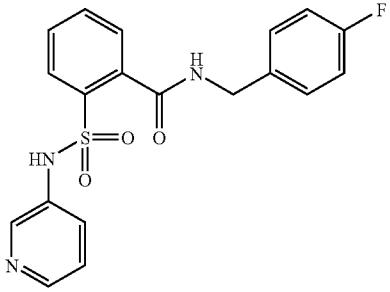 | N-(4-fluorobenzyl)-2-[(pyridin-3-ylamino)sulfonyl]benzamide | (400 MHz, DMSO-D6) d ppm 9.75(s, 1H) 9.24-9.37(m, 1H) 8.26(d, 2H) 7.64-7.78(m, 2H) 7.50-7.64(m, 3H) 7.40-7.49(m, 2H) 7.23-7.32(m, 1H) 7.11-7.21(m, 2H) 4.50(d, 2H) |
| 10 | 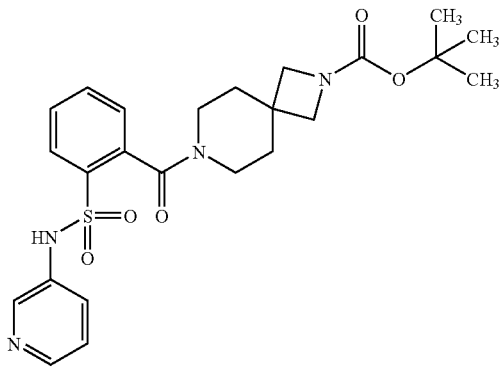 | tert-butyl 7-{2-[(pyridin-3-ylamino)sulfonyl]benzoyl}-2,7-diazaspiro[3.5]nonane-2-carboxylate | (400 MHz, DMSO-D6) d ppm 10.16(s, 1H) 8.24-8.29(m, 1H) 8.18-8.23(m, 1H) 7.79(d, 1H) 7.64(t, 1H) 7.50-7.58(m, 1H) 7.43-7.50(m, 1H) 7.33-7.42(m, 1H) 7.18-7.28(m, 1H) 3.48-3.66(m, 6H) 2.88-3.02(m, 2H) 1.69-1.77(m, 2H) 1.48-1.65(m, 2H) 1.36(s, 9H) |

| Example No. | Structure | Name | $^1$H NMR |
|---|---|---|---|
| 11 | 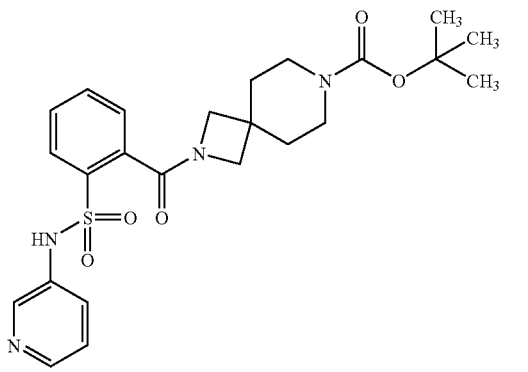 | tert-butyl 2-{2-[(pyridin-3-ylamino)sulfonyl]benzoyl}-2,7-diazaspiro[3.5]nonane-7-carboxylate | (400 MHz, DMSO-D6) d ppm 8.28-8.32(m, 1H) 8.23(d, 1H) 7.81(d, 1H) 7.66(t, 1H) 7.54-7.61(m, 1H) 7.46-7.52(m, 2H) 7.23-7.30(m, 1H) 3.77(s, 2H) 3.46(s, 2H) 3.25-3.31 (m, 2H) 3.07-3.18(m, 2H) 1.56-1.64(m, 4H) 1.38(s, 9H) |
| 12 | 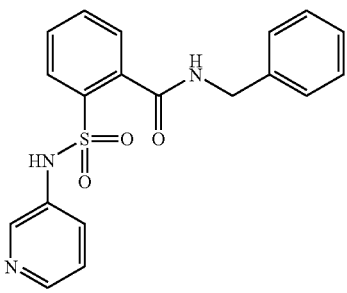 | N benzyl-2-[(pyridin-3-ylamino)sulfonyl]benzamide | (400 MHz, DMSO-D6) d ppm 9.75(s, 1H) 9.26-9.37(m, 1H) 8.22-8.34(m, 2H) 7.65-7.79(m, 2H) 7.49-7.65(m, 3H) 7.40-7.48(m, 2H) 7.32-7.39(m, 2H) 7.23-7.33(m, 2H) 4.54(d, 2H) |
| 13 | 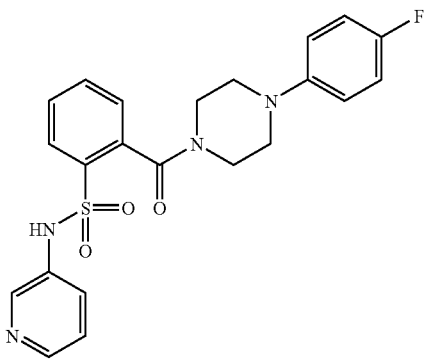 | 2-{[4-(4-fluorophenyl)piperazin-1-yl]carbonyl}-N-pyridin-3-ylbenzenesulfonamide | (400 MHz, DMSO-D6) d ppm 10.27(s, 1H) 8.18-8.32(m, 2H) 7.81-7.91(m, 1H) 7.65-7.75(m, 1H) 7.54-7.62(m, 1H) 7.41-7.55(m, 2H) 7.22-7.31(m, 1H) 7.01-7.10(m, 2H) 6.90-7.00(m, 2H) 3.66-3.88(m, 2H) 2.92-3.25(m, 6H) |
| 14 | 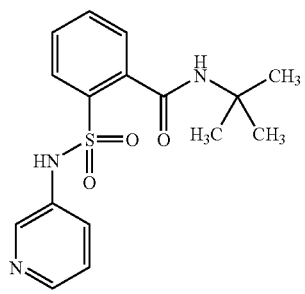 | N-(tert-butyl)-2-[(pyridin-3-ylamino)sulfonyl]benzamide | (400 MHz, DMSO-D6) d ppm 9.56(s, 1H) 8.33-8.40(m, 1H) 8.22-8.30(m, 2H) 7.58-7.68(m, 2H) 7.44-7.55(m, 3H) 7.20-7.32(m, 1H) 1.39(s, 9H) |

| Example No. | Structure | Name | ¹H NMR |
|---|---|---|---|
| 15 | 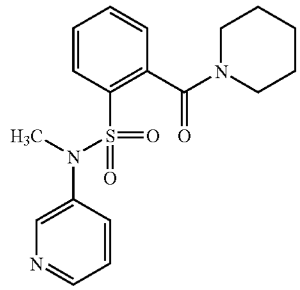 | N-methyl-2-(piperidin-1-ylcarbonyl)-N-pyridin-3-ylbenzenesulfonamide | (400 MHz, CHLOROFORM-d ppm 8.46-8.55(m, 2H) 7.50-7.69(m, 2H) 7.29-7.41(m, 3H) 7.20-7.27(m, 1H) 3.80-3.96(m, 1H) 3.45-3.58(m, 1H) 3.29(s, 3H) 3.02-3.18(m, 2H) 1.52-1.70(m, 5H) 1.29-1.43(m, 1H) |
| 16 | 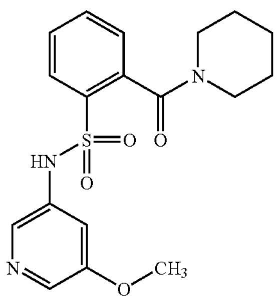 | N-(5-methoxypyridin-3-yl)-2-(piperidin-1-ylcarbonyl)benzenesulfonamide | (400 MHz, DMSO-D6) d ppm 8.09(d, 1H) 7.99(d, 1H) 7.88(d, 1H) 7.68(t, 1H) 7.58(t, 1H) 7.39(d, 1H) 7.28-7.32(m, 1H) 3.80(s, 3H) 3.62-3.70(m, 1H) 3.42-3.56(m, 1H) 2.93-3.08(m, 2H) 1.41-1.66(m, 5H) 1.29-141(m, 1H) |
| 17 | 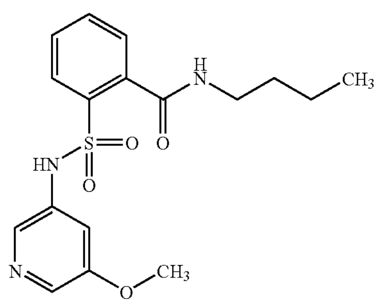 | N-butyl-2-{[(5-methoxypyridin-3-yl)amino]sulfonyl}benzamide | (400 MHz, DMSO-D6) d ppm 10.16-10.37(m, 1H) 8.65-8.77(m, 1H) 8.12(d, 1H) 7.98-8.04(m, 1H) 7.83(d, 1H) 7.69(t, 1H) (7.59(t, 1H) 7.50(d, 1H) 7.30-7.35(m, 1H) 3.80(s, 3H) 3.24(q, 2H) 1.46-1.57(m, 2H) 1.29-1.42(m, 2H) 0.90(t, 3H) |
| 18 | 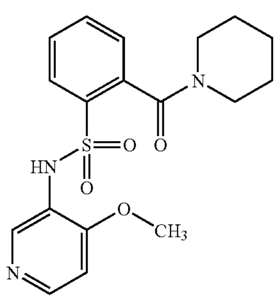 | N-(4-methoxypyridin-3-yl)-2-(piperidin-1-ylcarbonyl)benzenesulfonamide | (400 MHz, DMSO-D6) d ppm 9.07-9.23(m, 1H) 8.19-8.29(m, 2H) 7.71-7.77(m, 1H) 7.63-7.71(m, 1H) 7.50-7.59(m, 1H) 7.41(d, 1H) 6.99(d, 1H) 3.57-3.67(m, 2H) 3.54(s, 3H) 2.88-3.10(m, 2H) 1.26-1.65(m, 6H) |
| 19 | 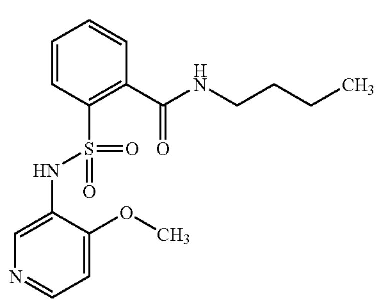 | N-butyl-2-{[(4-methoxypyridin-3-yl)amino]sulfonyl}benzamide | (400 MHz, DMSO-D6) d ppm 8.84(t, 1H) 8.67(s, 1H) 8.60(d, 1H) 7.82(d, 1H) 7.69-7.78(m, 1H) 7.56-7.65(m, 2H) 7.50(d, 1H) 3.80(s, 3H) 3.23(q, 2H) 1.46-1.57(m, 2H) 1.28-1.42(m, 2H) 0.90(t, 3H) |

-continued

| Example No. | Structure | Name | ¹H NMR |
|---|---|---|---|
| 20 | 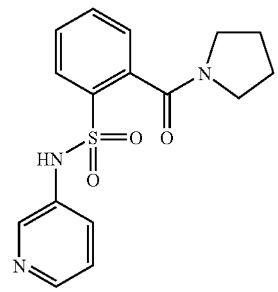 | N-pyridin-3-yl-2-(pyrrolidin-1-ylcarbonyl)benzenesulfonamide | (400 MHz, DMSO-D6) d ppm 10.10(s, 1H) 8.31(d, 1H) 8.24(d, 1H) 7.77-7.84(m, 1H) 7.64-7.72(m, 1H) 7.52-7.60(m, 1H) 7.41-7.53(m, 2H) 7.21-7.31(m, 1H) 3.43-3.52(m, 2H) 2.88-3.01(m, 2H) 1.82-1.88(m, 2H) 1.66-1.81(m, 2H) |
| 21 | 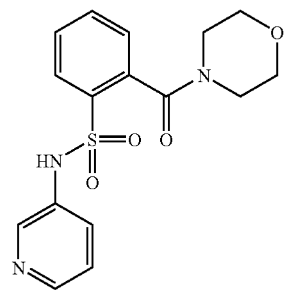 | 2-(morpholin-4-ylcarbonyl)-N-pyridin-3-ylbenzenesulfonamide | |
| 22 | 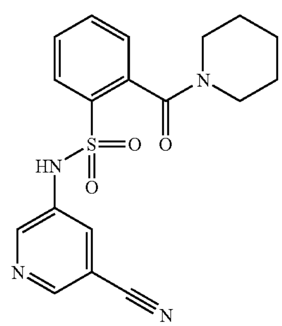 | N-(5-cyanopyridin-3-yl)-2-(piperidin-1-ylcarbonyl)benzenesulfonamide | (400 MHz, DMSO-D6) d ppm 10.56-11.12(m, 1H) 8.65(d, 1H) 8.52(d, 1H) 7.86-8.00(m, 2H) 7.69(t, 1H) 7.58(t, 1H) 7.40(d, 1H) 3.61-3.70(m, 1H) 3.48-3.57(m, 1H) 2.95-3.09(m, 2H) 1.31-1.64(m, 6H) |
| 23 | 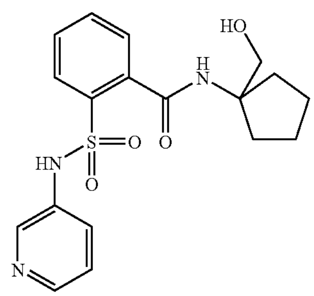 | N-[1-(hydroxymethyl)cyclopentyl]-2-[(pyridin-3-ylamino)sulfonyl]benzamide | (400 MHz, DMSO-D6) d ppm 9.52-10.02(m, 1H) 8.18-8.38(m, 3H) 7.61-7.72(m, 2H) 7.41-7.62(m, 3H) 7.16-7.37(m, 1H) 3.70(s, 2H) 1.98-2.11(m, 2H) 1.62-1.78(m, 4H) 1.45-1.61(m, 2H) |
| 24 | 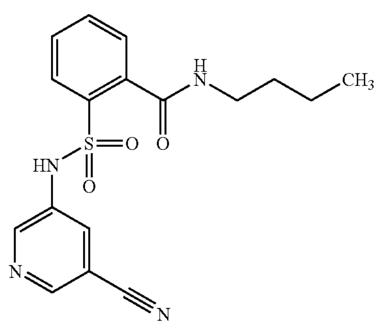 | N-butyl-2-{[(5-cyanopyridin-3-yl)amino]sulfonyl}benzamide | (400 MHz, DMSO-D6) d ppm 10.33-10.49(m, 1H) 8.72(t, 1H) 8.65-8.68(m, 1H) 8.52(d, 1H) 7.91-7.95(m, 1H) 7.85(d, 1H) 7.69(t, 1H) 7.59(t, 1H) 7.47-7.54(m, 1H) 3.23(q, 2H) 1.44-1.59(m, 2H) 1.29-1.43(m, 2H) 0.90(t, 3H) |

| Example No. | Structure | Name | $^1$H NMR |
|---|---|---|---|
| 25 | 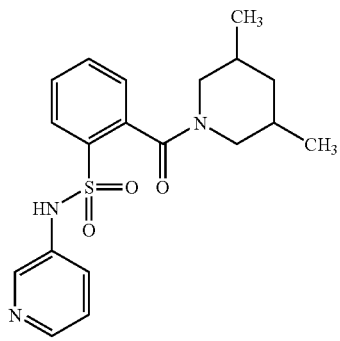 | 2-[(3,5-dimethylpiperidin-1-yl)carbonyl]-N-pyridin-3-ylbenzenesulfonamide | (400 MHz, DMSO-D6) d ppm 8.11-8.21(m, 1H) 7.98-8.08(m, 1H) 7.77 (dd, 1H) 7.51-7.60(m, 1H) 7.41-7.51(m, 1H) 7.32-7.41(m, 1H) 7.24-7.31 (m, 1H) 7.05-7.15(m, 1H) 4.38-4.57(m, 1H) 3.07-3.18(m, 1H) 2.86-2.97(m, 1H) 1.85-1.96(m, 1H) 1.66-1.79(m, 1H) 0.93-0.95(m, 1H) 0.87-0.93(m, 3H) 0.80-0.87(m, 1H) 0.72-0.79(m, 1H) 0.55-0.65(m, 3H) |
| 26 | 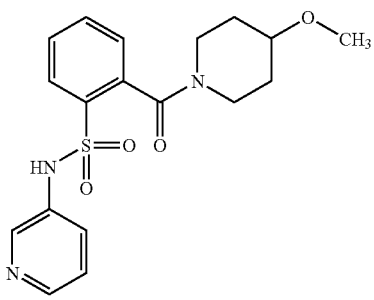 | 2-[(4-methoxypiperidin-1-yl)carbonyl]-N-pyridin-3-ylbenzenesulfonamide | |
| 27 | 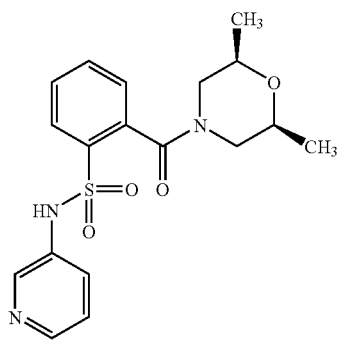 | 2-{[(2R,6S)-2,6-dimethylmorpholin-4-yl]carbonyl}-N-pyridin-3-ylbenzenesulfonamide | |
| 28 | 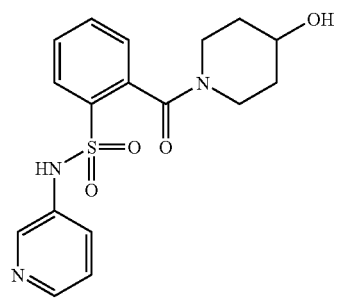 | 2-[(4-hydroxypiperidin-1-yl)carbonyl]-N-pyridin-3-ylbenzenesulfonamide | (400 MHz, DMSO-D6) d ppm 10.13-10.16(m, 1H) 8.27-8.34(m, 1H) 8.21(d, 1H) 7.73-7.84(m, 1H) 7.63-7.71(m, 1H) 7.42-7.60(m, 2H) 7.34-7.44(m, 1H) 7.22-7.28(m, 1H) 4.78(dd, 1H) 3.86-4.08 (m, 1H) 3.67-3.78(m, 1H) 3.09-3.25(m, 1H) 2.82-2.98(m, 1H) 1.71-1.88(m, 1H) 1.51-1.68(m, 1H) 1.34-1.50(m, 2H) 1.19-1.31(m, 1H) |

| Example No. | Structure | Name | ¹H NMR |
|---|---|---|---|
| 29 | 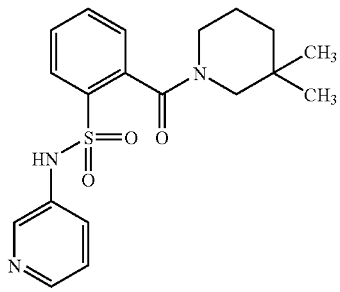 | 2-[(3,3-dimethylpiperidin-1-yl)carbonyl]-N-pyridin-3-ylbenzenesulfonamide | (400 MHz, DMSO-D6) d ppm 10.06-10.26(m, 1H) 8.28(s, 1H) 8.13-8.25(m, 1H) 7.75-7.86(m, 1H) 7.61-7.71(m, 1H) 7.51-7.60(m, 1H) 7.43-7.51(m, 1H) 7.26-7.43(m, 1H) 7.18-7.29(m, 1H) 3.46-3.58(m, 1H) 3.07-3.19(m, 1H) 2.79-3.02(m, 2H) 1.51-1.64(m, 1H) 1.32-1.48(m, 3H) 0.93-1.03(m, 4H) 0.76-0.83(m, 1H) 0.62-0.72(m, 1H) |
| 30 | 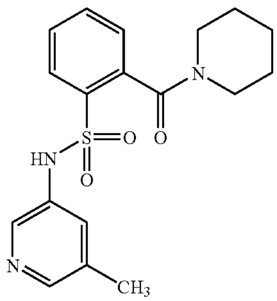 | N-(5-methylpyridin-3-yl)-2-(piperidin-1-ylcarbonyl)benzenesulfonamide | (400 MHz, CHLOROFORM-D) d ppm 8.06-8.14(m, 2H) 7.95-8.05(m, 1H) 7.41-7.58(m, 2H) 7.24-7.35(m, 3H) 3.82-3.95(m, 1H) 3.45-3.57(m, 2H) 2.17(s, 3H) 1.37-1.80(m, 7H) |
| 31 | 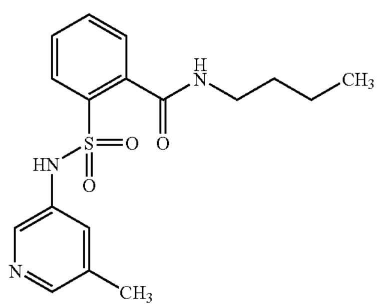 | N-butyl-2-{[(5-methylpyridin-3-yl)amino]sulfonyl}benzamide | (400 MHz, CHLOROFORM-D) d ppm 8.49-8.78(m, 1H) 8.04-8.15(m, 2H) 7.44-7.59(m, 3H) 7.28-7.41(m, 2H) 6.68-6.80(m, 1H) 3.46(q, 2H) 2.21(s, 3H) 1.57-1.70(m, 2H) 1.34-1.50(m, 2H) 0.98(t, 3H) |
| 32 | 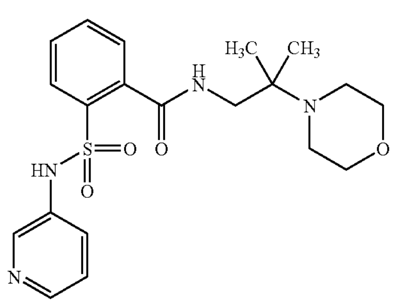 | N-(2-methyl-2-morpholin-4-ylpropyl)-2-[(pyridin-3-ylamino)sulfonyl]benzamide | (400 MHz, DMSO-D6) d ppm 8.45-8.57(m, 1H) 8.17-8.30(m, 2H) 7.64-7.75(m, 2H) 7.45-7.60(m, 3H) 7.19-7.29(m, 1H) 3.54-3.60(m, 4H) 3.34-3.37(m, 2H) 2.54-2.62(m, 4H) 1.06(s, 6H) |
| 33 | 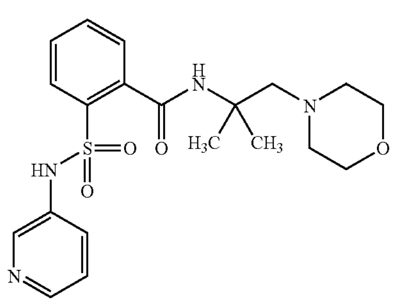 | N-(1,1-dimethyl-2-morpholin-4-ylethyl)-2-[(pyridin-3-ylamino)sulfonyl]benzamide | (400 MHz, CHLOROFORM-D) d ppm 8.26-8.34(m, 2H) 7.53-7.63(m, 2H) 7.43-7.52(m, 2H) 7.29-7.37(m, 1H) 7.09-7.16(m, 1H) 6.86(s, 1H) 3.59-3.63(m, 4H) 2.61-2.63(m, 2H) 2.56-2.61(m, 4H) 1.47(s, 6H) |

-continued

| Example No. | Structure | Name | ¹H NMR |
|---|---|---|---|
| 34 | 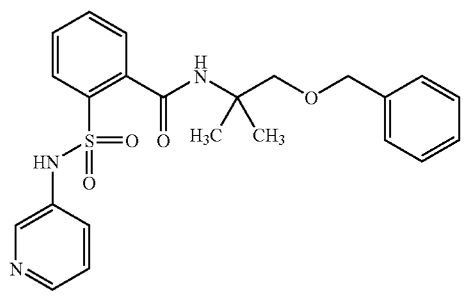 | N-[2-(benzyloxy)-1,1-dimethylethyl]-2-[(pyridin-3-ylamino)sulfonyl]benzamide | (400 MHz, DMSO-D6) d ppm 8.22-8.27(m, 1H) 8.18-8.23(m, 1H) 7.93-7.96(m, 1H) 7.84-7.89(m, 1H) 7.59-7.65(m, 2H) 7.42-7.50(m, 2H) 7.34-7.42(m, 6H) 5.59(s, 2H) 3.57(d, 2H) 1.24(s, 6H) |
| 35 | 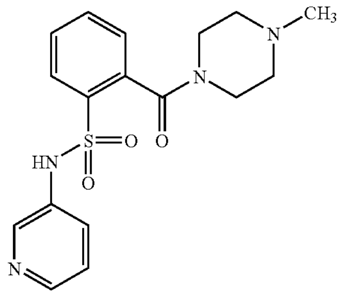 | 2-[(4-methylpiperazin-1-yl)carbonyl]-N-pyridin-3-ylbenzenesulfonamide | (400 MHz, DMSO-D6) d ppm 10.15-10.31(m, 1H) 8.26-8.30(m, 1H) 8.19-8.24(m, 1H) 7.81(d, 1H) 7.66(t, 1H) 7.56(t, 1H) 7.46-7.51(m, 1H) 7.37-7.41(m, 1H) 7.20-7.28(m, 1H) 3.66-3.74(m, 1H) 3.48-3.59(m, 1H) 2.86-3.07(m, 2H) 2.40-2.46(m, 1H) 2.24-2.36(m, 2H) 2.19(s, 3H) 2.09-2.15(m, 1H) |
| 36 | 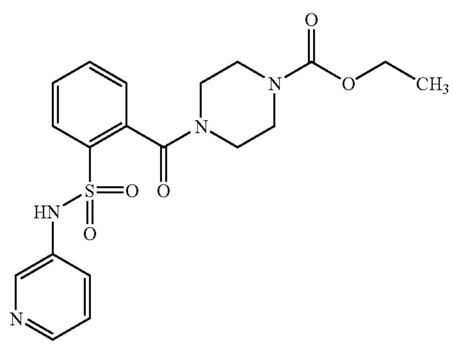 | ethyl 4-{2-[(pyridin-3-ylamino)sulfonyl]benzoyl}piperazine-1-carboxylate | (400 MHz, CHLOROFORM-D) d ppm 8.29-8.37(m, 2H) 7.51-7.63(m, 3H) 7.29-7.38(m, 2H) 7.09-7.18 (m, 1H) 4.17-4.25(m, 1H) 4.11(q, 2H) 3.74-3.85(m, 1H) 3.53-3.69(m, 1H) 3.24-3.50(m, 5H) 1.21-1.30(m, 3H) |
| 37 | 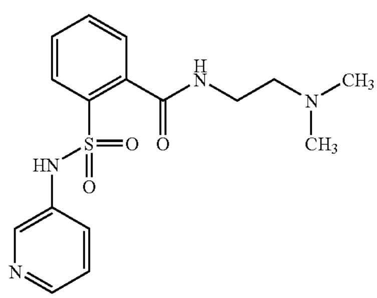 | N-[2-(dimethylamino)ethyl]-2-(pyridin-3-ylamino)sulfonyl]benzamide | (400 MHz, CHLOROFORM-D) d ppm 8.37-8.41(m, 1H) 8.21-8.26(m, 1H) 7.86-7.92(m, 1H) 7.60-7.65 (m, 1H) 7.35-7.54(m, 4H) 7.02-7.11(m, 1H) 3.62-3.72(m, 2H) 2.81(t, 2H) 2.38(s, 6H) |
| 38 | 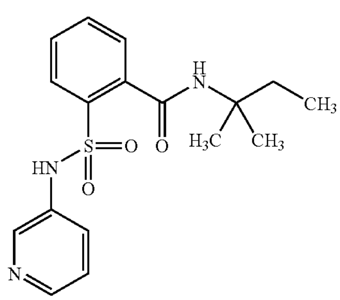 | N-(1,1-dimethylpropyl)-2-[(pyridin-3-ylamino)sulfonyl]benzamide | (400 MHz, CHLOROFORM-D) d ppm 8.54-8.65(m, 1H) 8.26-8.36(m, 2H) 7.55-7.63(m, 2H) 7.46-7.56 (m, 2H) 7.30-7.39(m, 1H) 7.08-7.20(m, 1H) 1.88(q, 2H) 1.46(s, 6H) 0.99 (t, 3H) |

-continued

| Example No. | Structure | Name | $^1$H NMR |
|---|---|---|---|
| 39 | 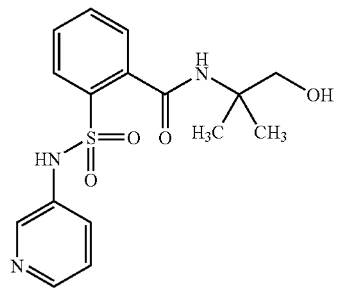 | N-(2-hydroxy-1,1-dimethylethyl)-2-[(pyridin-3-ylamino)sulfonyl]benzamide | (400 MHz, DMSO-D6) d ppm 9.69-9.86(m, 1H) 8.19-8.32(m, 2H) 8.05-8.12(m, 1H) 7.60-7.74(m, 2H) 7.49-7.53(m, 3H) 7.20-7.34(m, 1H) 4.70-5.05 (m, 1H) 3.58(s, 2H) 1.31 (s, 6H) |
| 40 | 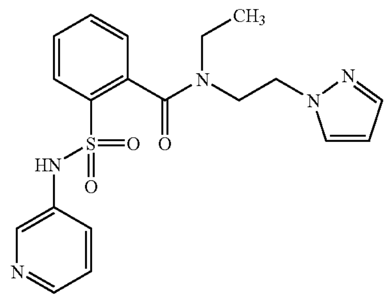 | N-ethyl-N-[2-(1H-pyrazol-1-yl)ethyl]-2-[(pyridin-3-ylamino)sulfonyl]benzamide | (400 MHz, CHLOROFORM-D) d ppm 8.29-8.36(m, 2H) 8.08-8.22(m, 1H) 7.60-7.65(m, 1H) 7.47-7.60 (m, 4H) 7.28-7.37(m, 2H) 7.09-7.18(m, 1H) 6.22(t, 1H) 4.53(t, 2H) 3.87-4.04 (m, 2H) 2.86-2.98(m, 1H) 2.55-2.70(m, 1H) 0.93 (t, 3H) |
| 41 | 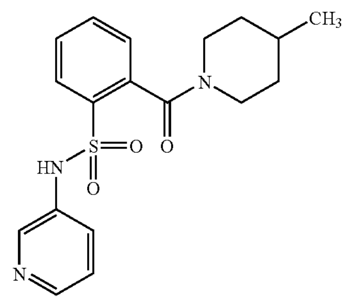 | 2-[(4-methylpiperidin-1-yl)carbonyl]-N-pyridin-3-ylbenzenesulfonamide | (400 MHz, CHLOROFORM-D) d ppm 8.27-8.36(m, 2H) 7.44-7.63(m, 3H) 7.27-7.37(m, 2H) 7.04-7.19 (m, 1H) 4.47-4.79(m, 1H) 3.37-3.59(m, 1H) 2.69-3.16(m, 2H) 1.78-1.97(m, 1H) 1.55-1.78(m, 2H) 1.32-1.51(m, 1H) 1.04-1.30(m, 1H) 0.88-1.03 (m, 3H) |
| 42 | 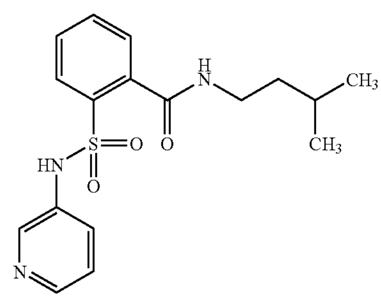 | N-(3-methylbutyl)-2-[(pyridin-3-ylamino)sulfonyl]benzamide | (400 MHz, CHLOROFORM-D) d ppm 8.64(s, 1H) 8.26-8.43(m, 2H) 7.60-7.68(m, 2H) 7.45-7.59(m, 2H) 7.39(t, 1H) 7.12-7.21(m, 1H) 6.08-6.17(m, 1H) 3.52(q, 2H) 1.67-1.79(m, 1H) 1.57(q, 2H) 0.98 (d, 6H) |
| 43 | 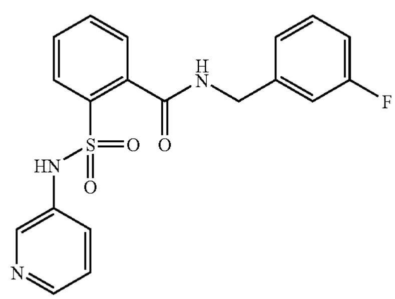 | N-(3-fluorobenzyl)-2-[(pyridin-3-ylamino)sulfonyl]benzamide | (400 MHz, DMSO-D6) d ppm 9.76(s, 1H) 9.32(t, 1H) 8.31(d, 1H) 8.25(d, 1H) 7.66-7.78(m, 2H) 7.50-7.65(m, 3H) 7.39(q, 1H) 7.23-7.29(m, 3H) 7.09(t, 1H) 4.54(d, 2H) |

-continued

| Example No. | Structure | Name | $^1$H NMR |
|---|---|---|---|
| 44 | 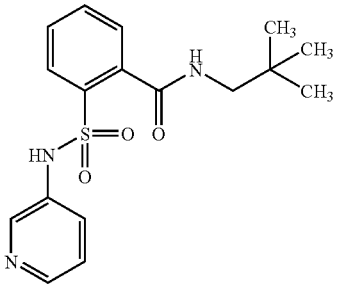 | N-(2,2-dimethylpropyl)-2-[(pyridin-3-ylamino)sulfonyl]benzamide | (400 MHz, DMSO-D6) d ppm 9.68(s, 1H) 8.72-8.83(m, 1H) 8.22-8.33(m, 2H) 7.63-7.74(m, 2H) 7.46-7.61(m, 3H) 7.24-7.32(m, 1H) 3.14(d, 2H) 0.96(s, 9H) |
| 45 | 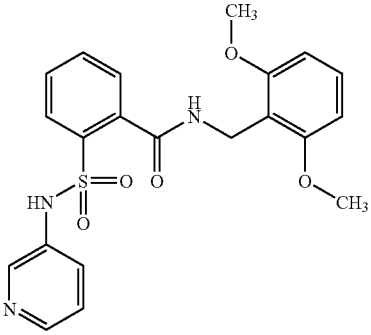 | N-(2,6-dimethoxybenzyl)-2-[(pyridin-3-ylamino)sulfonyl]benzamide | (400 MHz, DMSO-D6) d ppm 9.69(s, 1H) 8.59-8.73(m, 1H) 8.21-8.36(m, 2H) 7.57-7.70(m, 2H) 7.45-7.56(m, 2H) 7.37-7.45(m, 1H) 7.22-7.33(m, 2H) 6.68(d, 2H) 4.50(d, 2H) 3.79(s, 6H) |
| 46 | 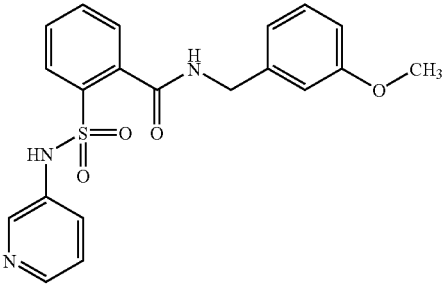 | N-(3-methoxybenzyl)-2-[(pyridin-3-ylamino)sulfonyl]benzamide | (400 MHz, DMSO-D6) d ppm 9.71-9.83(m, 1H) 9.18-9.44(m, 1H) 8.16-8.39(m, 2H) 7.64-7.81(m, 2H) 7.45-7.63(m, 3H) 7.20-7.31(m, 2H) 6.92-7.11(m, 2H) 6.73-6.89(m, 1H) 4.49(d, 2H) 3.74(s, 3H) |
| 47 | 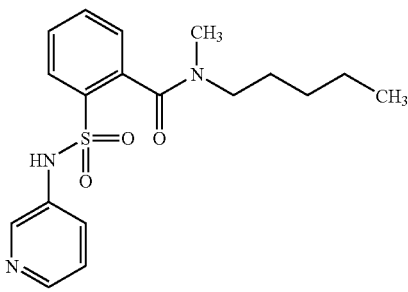 | N-methyl-N-pentyl-2-[(pyridin-3-ylamino)sulfonyl]benzamide | |
| 48 | 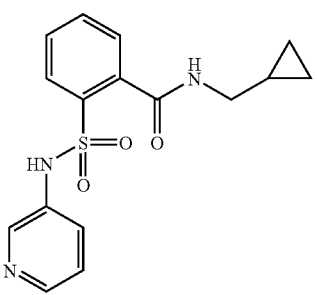 | N-(cyclopropylmethyl)-2-[(pyridin-3-ylamino)sulfonyl]benzamide | (400 MHz, DMSO-D6) d ppm 9.70(s, 1H) 8.83-8.94(m, 1H) 8.20-8.32(m, 2H) 7.62-7.75(m, 2H) 7.47-7.59(m, 3H) 7.20-7.33(m, 1H) 3.18(d, 2H) 0.98-1.10(m, 1H) 0.41-0.48(m, 2H) 0.23-0.31(m, 2H) |

-continued

| Example No. | Structure | Name | $^1$H NMR |
|---|---|---|---|
| 49 | 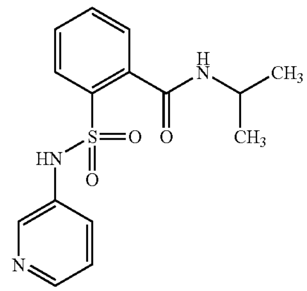 | N-isopropyl-2-[(pyridin-3-ylamino)sulfonyl]benzamide | (400 MHz, DMSO-D6) d ppm 9.71(s, 1H) 8.61-8.81(m, 1H) 8.13-8.39(m, 2H) 7.60-7.77(m, 2H) 7.43-7.61(m, 3H) 7.19-7.36(m, 1H) 3.95-4.20(m, 1H) 1.19(s, 6H) |
| 50 | 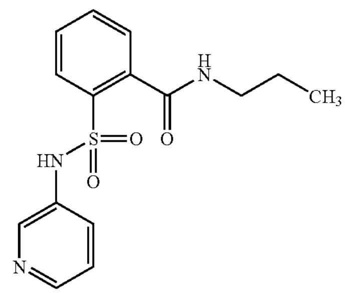 | N-propyl-2-[(pyridin-3-ylamino)sulfonyl]benzamide | |
| 51 | 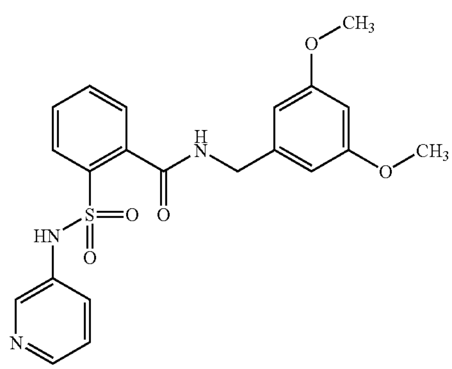 | N-(3,5-dimethoxybenzyl)-2-[(pyridin-3-ylamino)sulfonyl]benzamide | (400 MHz, DMSO-D6) d ppm 7.83-7.96(m, 2H) 7.63-7.74(m, 2H) 7.39-7.50(m, 2H) 7.12-7.24(m, 1H) 6.83-6.96(m, 1H) 6.63-6.72(m, 2H) 6.49-6.63(m, 1H) 6.26-6.43(m, 1H) 4.43(d, 2H) 3.72 (s, 6H) |
| 52 | 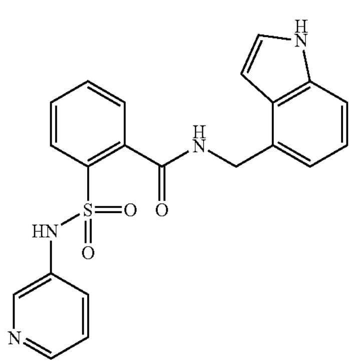 | N-(1H-indol-4-ylmethyl)-2-[(pyridin-3-ylamino)sulfonyl]benzamide | (400 MHz, DMSO-D6) d ppm 11.15(s, 1H) 9.61-9.84(m, 1H) 9.13-9.44(m, 1H) 8.16-8.44(m, 2H) 7.63-7.86(m, 2H) 7.46-7.63(m, 3H) 7.27-7.42(m, 3H) 6.99-7.13(m, 2H) 6.65(s, 1H) 4.75(d, 2H) |

| Example No. | Structure | Name | ¹H NMR |
|---|---|---|---|
| 53 | 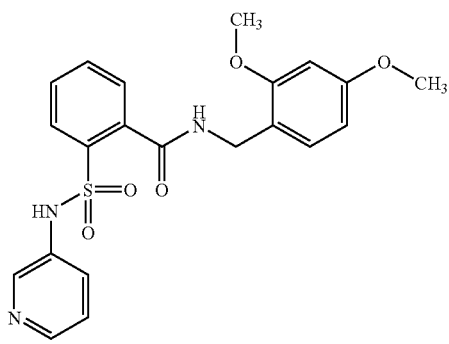 | N-(2,4-dimethoxybenzyl)-2-[(pyridin-3-ylamino)sulfonyl]benzamide | (400 MHz, DMSO-D6) d ppm 9.72(s, 1H) 9.01-9.15(m, 1H) 8.22-8.36(m, 2H) 7.64-7.78(m, 2H) 7.45-7.61(m, 3H) 7.17-7.35(m, 2H) 6.55(s, 1H) 6.45-6.54(m, 1H) 4.40(d, 2H) 3.80(s, 3H) 3.74 (s, 3H) |
| 54 | 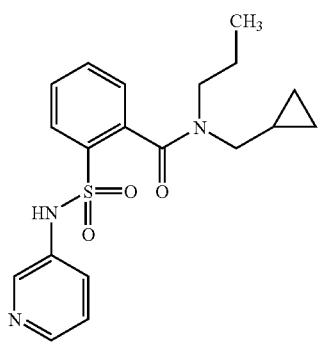 | N-(cyclopropylmethyl)-N-propyl-2-[(pyridin-3-ylamino)sulfonyl]benzamide | |
| 55 | 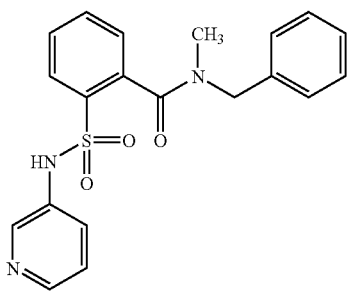 | N-benzyl-N-methyl-2-[(pyridin-3-ylamino)sulfonyl]benzamide | |
| 56 | 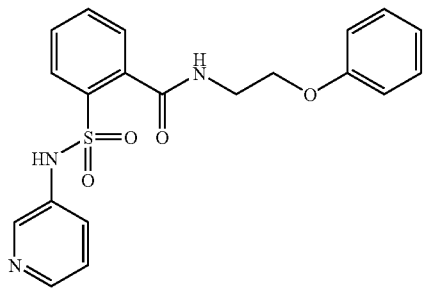 | N-(2-phenoxyethyl)-2-[(pyridin-3-ylamino)sulfonyl]benzamide | (400 MHz, DMSO-D6) d ppm 9.72(s, 1H) 8.93-9.07(m, 1H) 8.15-8.34(m, 2H) 7.59-7.81(m, 2H) 744-7.60(m, 3H) 7.19-7.35(m, 3H) 6.83-7.05(m, 3H) 4.09(t, 2H) 3.66 (q, 2H) |

| Example No. | Structure | Name | $^1$H NMR |
|---|---|---|---|
| 57 | 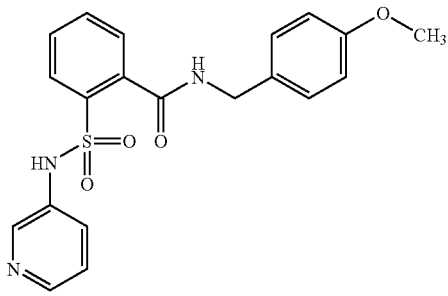 | N-(4-methoxybenzyl)-2-[(pyridin-3-ylamino)sulfonyl]benzamide | (400 MHz, DMSO-D6) d ppm 9.75(s, 1H) 9.24(t, 1H) 8.32(d, 1H) 8.26(d, 1H) 7.64-7.76(m, 2H) 7.52-7.59(m, 3H) 7.25-7.36(m, 3H) 6.90(d, 2H) 4.46 (d, 2H) 3.73(s, 3H) |
| 58 | 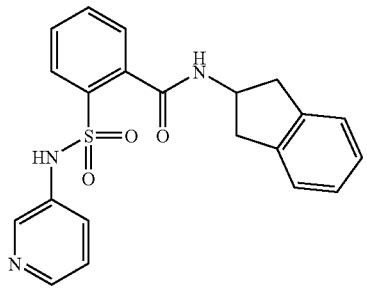 | N-(2,3-dihydro-1H-inden-2-yl)-2-[(pyridin-3-ylamino)sulfonyl]benzamide | (400 MHz, DMSO-D6) d ppm 9.72(s, 1H) 9.00-9.13(m, 1H) 8.22-8.37(m, 2H) 7.60-7.75(m, 2H) 7.47-7.58(m, 3H) 7.19-7.29(m, 3H) 7.11-7.18(m, 2H) 4.60-4.75(m, 1H) 3.26(t, 2H) 2.99(dd, 2H) |
| 59 | 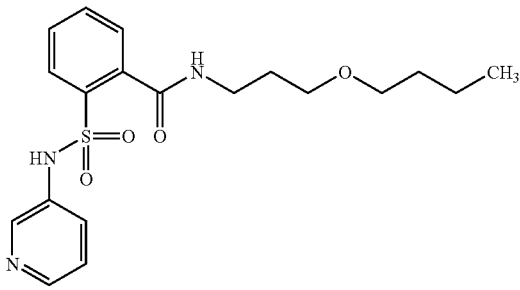 | N-(3-butoxypropyl)-2-[(pyridin-3-ylamino)sulfonyl]benzamide | (400 MHz, CHLOROFORM-D) d ppm 8.74-8.93(m, 1H) 8.25-8.37(m, 2H) 7.57-7.69(m, 2H) 7.48-7.54 (m, 2H) 7.31-7.40(m, 1H) 7.19-7.25(m, 1H) 7.09-7.18(m, 1H) 3.56-3.66(m, 4H) 3.40(t, 2H) 1.87-1.98 (m, 2H) 1.36-1.47(m, 2H) 1.11-1.29(m, 2H) 0.77 (t, 3H) |
| 60 | 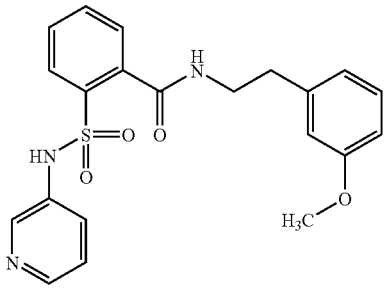 | N-[2-(3-methoxyphenyl)ethyl]-2-[(pyridin-3-ylamino)sulfonyl]benzamide | (400 MHz, DMSO-D6) d ppm 9.75(s, 1H) 8.87(t, 1H) 8.31(d, 1H) 8.25(d, 1H) 7.62-7.73(m, 2H) 7.49-7.58(m, 2H) 7.40-7.48(m, 1H) 7.16-7.31(m, 2H) 6.81-6.91(m, 2H) 6.74-6.81(m, 1H) 3.74(s, 3H) 3.50(q, 2H) 2.84(t, 2H) |

| Example No. | Structure | Name | ¹H NMR |
|---|---|---|---|
| 61 | 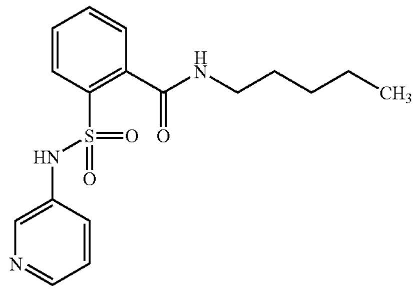 | N-pentyl-2-[(pyridin-3-ylamino)sulfonyl]benzamide | |
| 62 | 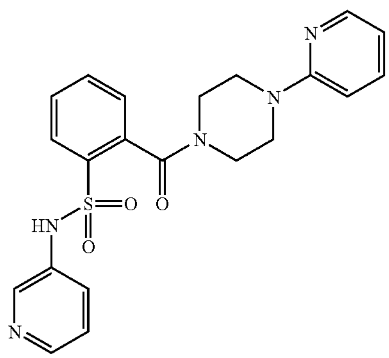 | N-pyridin-3-yl-2-[(4-pyridin-2-ylpiperazin-1-yl)carbonyl]benzenesulfonamide | (400 MHz, DMSO-D6) d ppm 10.23(s, 1H) 8.31(s, 1H) 8.20-8.26(m, 1H) 8.06-8.16(m, 1H) 7.80-7.89 (m, 1H) 7.65-7.73(m, 1H) 7.40-7.64(m, 4H) 7.21-7.30(m, 1H) 6.84(d, 1H) 6.58-6.70(m, 1H) 3.54-3.84(m, 4H) 3.34-3.56(m, 2H) 3.00-3.24(m, 2H) |
| 63 | 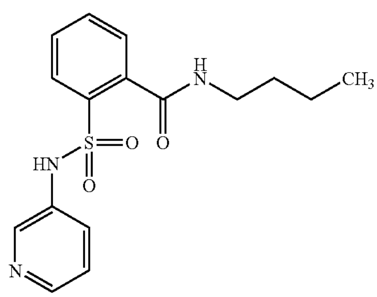 | N-butyl-2-[(pyridin-3-ylamino)sulfonyl]benzamide | (400 MHz, DMSO-D6) d ppm 9.90-10.00(m, 1H) 8.73(t, 1H) 8.28-8.37(m, 2H) 7.71-7.76(m, 1H) 7.61-7.70(m, 2H) 7.49-7.57(m, 2H) 7.35-7.44(m, 1H) 3.25(q, 2H) 1.51-1.54 (m, 2H) 1.29-1.40(m, 2H) 0.90(t, 3H) |
| 64 | 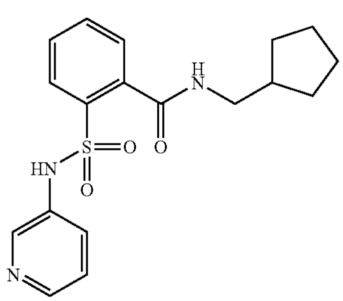 | N-(cyclopentylmethyl)-2-[(pyridin-3-ylamino)sulfonyl]benzamide | (400 MHz, DMSO-D6) d ppm 9.68(S, 1H) 8.75-8.91(m, 1H) 8.21-8.36(m, 2H) 7.64-7.73(m, 2H) 7.45-7.60(m, 3H) 7.19-7.32(m, 1H) 3.14-3.27(m, 2H) 2.10-2.24(m, 1H) 1.67-1.80(m, 2H) 1.43-1.66(m, 4H) 1.19-1.36 (m, 2H) |
| 65 | 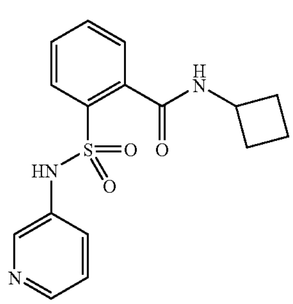 | N-cyclobutyl-2-[(pyridin-3-ylamino)sulfonyl]benzamide | (400 MHz, CHLOROFORM-D6) d ppm 8.62(s, 1H) 8.31-8.42(m, 2H) 7.62-7.69 (m, 2H) 7.7.53-7.59(m, 2H) 7.35-7.39(m, 1H) 7.15-7.22 (m, 1H) 6.29-6.41(m, 1H) 4.48-4.52(m, 1H) 2.43-2.59 (m, 2H) 2.02-2.15(m, 2H) 1.81-1.92(m, 2H) |

| Example No. | Name | ¹H NMR |
|---|---|---|
| 66 | 2-[(pyridin-3-ylamino)sulfonyl]-N-(2-pyridin-2-ylethyl)benzamide | (400 MHz, CHLOROFORM-D) d ppm 8.51-8.59(m, 1H) 8.28-8.35(m, 2H) 7.73-7.80 (m, 1H) 7.51-7.72(m, 5H) 7.43-7.49(m, 1H) 7.20-7.27 (m, 2H) 7.11-7.19(m, 2H) 3.88-3.92(m, 2H) 3.12-3.21 (m, 2H) |
| 67 | 2-(piperidin-1-ylcarbonyl)-N-pyridin-3-ylbenzenesulfonamide | (400 MHz, CHLOROFORM-D6) d ppm 8.42(s, 2H) 7.61-7.69(m, 3H) 7.31-7.42 (m, 2H) 7.15-7.21(m, 1H) 3.92-4.12(m, 1H) 3.61-3.65 (m, 1H) 3.21-3.49(m, 2H) 1.35-1.76(m, 6H) |
| 68 | N-methyl-N-(2-phenylethyl)-2-[(pyridin-3-ylamino)sulfonyl]benzamide | (400 MHz, CHLOROFORM-D) d ppm 8.31-8.42(m, 3H) 7.88-8.03(m, 1H) 7.51-760 (m, 3H) 7.14-7.42(m, 4H) 6.95-7.04(m, 2H) 6.62-6.74 (m, 1H) 3.72-3.94(m, 2H) 3.31-3.51(m, 2H) 2.81 (s, 3H) |
| 69 | 2-[(pyridin-3-ylamino)sulfonyl]-N-(3-pyridin-2-ylpropyl)benzamide | (400 MHz, CHLOROFORM-D) d ppm 8.28-8.39(m, 3H) 8.03-8.11(m, 1H) 7.65-7.72(m, 1H) 7.58-7.65 (m, 2H) 7.48-7.57(m, 2H) 7.32-7.43(m, 1H) 7.19-7.26(m, 1H) 7.05-7.18(m, 2H) 3.54(q, 2H) 2.95-3.02(m, 2H) 2.06-2.16 (m, 2H) |
| 70 | N-(1,1-dimethyl-2-morpholin-4-ylethyl)-2-[(pyridin-3-ylmethyl)sulfinyl]benzamide | (400 MHz, CHLOROFORM-D) d ppm 8.45(d, 1H) 8.07-8.11(m, 1H) 7.39-7.53 (m, 5H) 7.13-7.20(m, 1H) 7.05(s, 1H) 4.40(d, 1H) 4.19(d, 1H) 3.61-3.70(m, 4H) 2.48-2.65(m, 6H) 1.46(d, 6H) |

| Example No. | Structure | Name | $^1$H NMR |
|---|---|---|---|
| 71 | 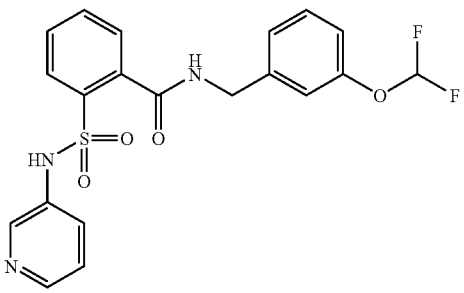 | N-[3-(difluoromethoxy)benzyl]-2-[(pyridin-3-ylamino)sulfonyl]benzamide | 1H NMR (400 MHz, CHLOROFORM-D) d ppm 8.30-8.43(m, 2H) 7.62-7.77(m, 2H) 7.54-7.61(m, 2H) 7.40-7.50(m, 2H) 7.25-7.34(m, 1H) 7.13-7.22(m, 3H) 7.07(d, 1H) 6.46-6.56(m, 1H) 4.73(d, 2H) 1.6-1.66(m, 1H) |
| 72 | 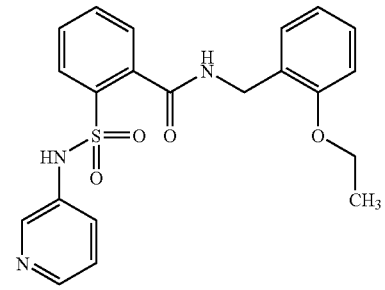 | N-(2-ethoxybenzyl)-2-[(pyridin-3-ylamino)sulfonyl]benzamide | 1H NMR (400 MHz, DMSO-D6) d ppm 9.72(s, 1H) 9.20 (br.s, 1H) 8.24(d, 2H) 7.62-7.78(m, 3H) 7.47-7.59(m, 2H) 7.40(d, 1H) 7.18-7.32(m, 2H) 6.81-7.07(m, 2H) 4.50(d, 2H) 4.07(q, 2H) 1.37(t, 3H) |
| 73 | 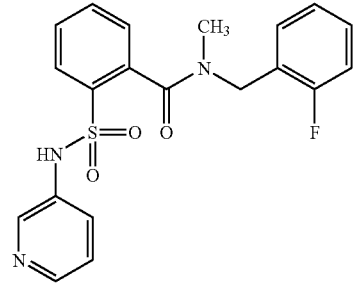 | N-(2-fluorobenzyl)-N-methyl-2-[(pyridin-3-ylamino)sulfonyl]benzamide | 1H NMR (400 MHz, CHLOROFORM-D) of major rotational isomer: d ppm 8.30-8.40(m, 2H) 7.52-7.67(m, 3H) 7.28-7.43(m, 4H) 6.96-7.23(m, 4H) 4.99-5.12(m, 1H) 4.68-4.81(m, 1H) 2.89(s, 3H) |
| 74 | 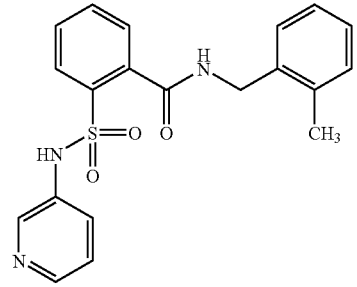 | N-(2-methylbenzyl)-2-[(pyridin-3-ylamino)sulfonyl]benzamide | 1H NMR (400 MHz, DMSO-D6) d ppm 9.43-9.62(m, 1H) 8.14(d, 2H) 7.78(d, 1H) 7.58-7.67(m, 2H) 7.49-7.57(m, 1H) 7.32-7.47(m, 2H) 7.11-7.29(m, 5H) 4.48(d, 2H) 2.35(s, 3H) |
| 75 | 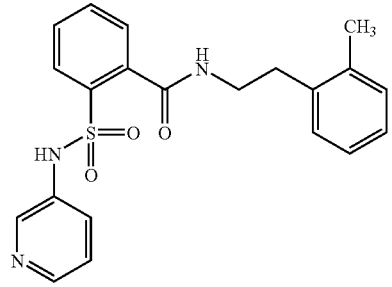 | N-[2-(2-methylphenyl)ethyl]-2-[(pyridin-3-ylamino)sulfonyl]benzamide | 1H NMR (400 MHz, DMSO-D6) d ppm 9.78(br.s, 1H) 8.87(br.s, 1H) 8.21-8.32(m, 2H) 7.62-7.77(m, 2H) 7.41-7.59(m, 3H) 7.24-7.30(m, 1H) 7.18-7.24(m, 1H) 7.08-7.20(m, 1H) 3.46(q, 2H) 2.87(t, 2H) 2.32-2.35(m, 3H) |

-continued

| Example No. | Structure | Name | ¹H NMR |
|---|---|---|---|
| 76 | 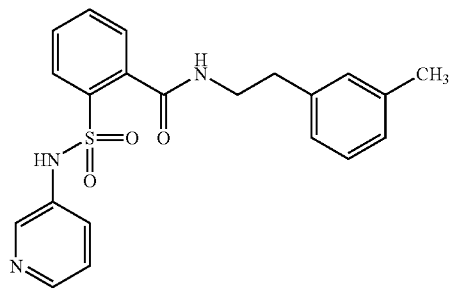 | N-[2-(3-methylphenyl)ethyl]-2-[(pyridin-3-ylamino)sulfonyl]benzamide | 1H NMR (400 MHz, DMSO-D6) d ppm 9.75(br.s, 1H) 8.90(br.s, 1H) 8.13-8.37 (m, 2H) 7.61-7.76(m, 2H) 7.40-7.56(m, 3H) 7.14-7.30(m, 2H) 6.92-7.13(m, 3H) 3.47(q, 2H) 2.82 (t, 2H) 2.30(s, 3H) |
| 77 | 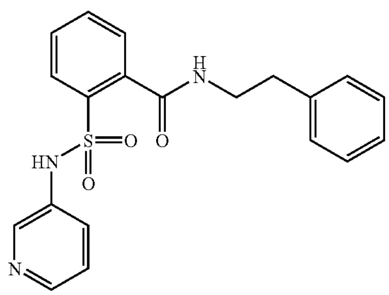 | N-(2-phenylethyl)-2-[(pyridin-3-ylamino)sulfonyl]benzamide | 1H NMR (400 MHz, DMSO-D6) d ppm 9.75(s, 1H) 8.95 (s, 1H) 8.19-8.35(m, 2H) 7.62-7.76(m, 2H) 7.47-7.58(m, 2H) 7.42-7.47(m, 1H) 7.19-7.36(m, 6H) 3.50(q, 2H) 2.88(t, 2H) |
| 78 | 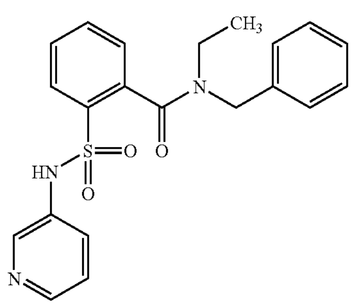 | N-benzyl-N-ethyl-2-[(pyridin-3-ylamino)sulfonyl]benzamide | 1H NMR (400 MHz, DMSO-D6) of major rotational isomer: d ppm 8.16-8.22 (m, 1H) 8.00-8.08(m, 1H) 7.73-7.83(m, 1H) 7.45-7.54(m, 2H) 7.32-7.41(m, 5H) 7.24-7.33(m, 2H) 7.17-7.23(m, 1H) 7.04-7.16(m, 1H) 2.86-3.06(m, 2H) 2.66(q, 2H) 1.09 (t, 3H) |
| 79 | 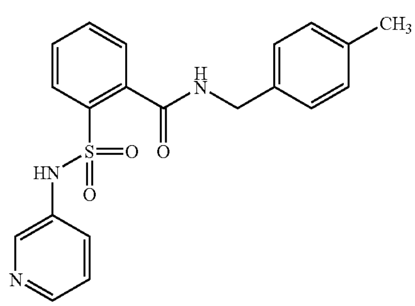 | N-(4-methylbenzyl)-2-[(pyridin-3-ylamino)sulfonyl]benzamide | 1H NMR (400 MHz, DMSO-D6) d ppm 9.76(br.s, 1H) 9.32(br.s, 1H) 8.24(d, 2H) 7.63-7.78(m, 2H) 7.44-7.60(m, 3H) 7.22-7.33(m, 3H) 7.11-7.18(m, 2H) 4.47(d, 2H) 2.29(s, 3H) |
| 80 | 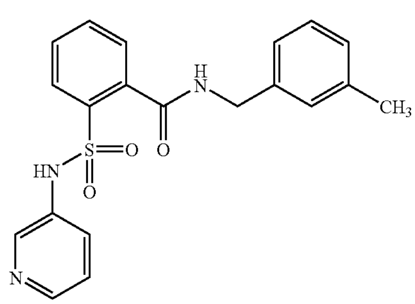 | N-(3-methylbenzyl)-2-[(pyridin-3-ylamino)sulfonyl]benzamide | 1H NMR (400 MHz, DMSO-D6) d ppm 9.75(br.s, 1H) 9.39(br.s, 1H) 8.16-8.32 (m, 2H) 7.64-7.79(m, 2H) 7.44-7.64(m, 3H) 7.17-7.29(m, 4H) 7.06(d, 1H) 4.48(d, 2H) 2.29(s, 3H) |

| Example No. | Name | 1H NMR |
|---|---|---|
| 81 | N-{4-[(methylamino)carbonyl]benzyl}-2-[(pyridin-3-ylamino)sulfonyl]benzamide | 1H NMR (400 MHz, DMSO-D6) d ppm 9.75(br.s, 1H) 9.36(br.s, 1H) 8.41(d, 1H) 8.28-8.33(m, 1H) 8.24(d, 1H) 7.83(d, 2H) 7.65-7.78(m, 2H) 7.51-7.64(m, 3H) 7.47(d, 2H) 7.19-7.30(m, 1H) 4.55(d, 2H) 2.78(d, 3H) |
| 82 | N-(2,3-dihydro-1-benzofuran-5-ylmethyl)-2-[(pyridin-3-ylamino)sulfonyl]benzamide | 1H NMR (400 MHz, DMSO-D6) d ppm 9.72(br.s, 1H) 9.23(br.s, 1H) 8.21-8.31(m, 2H) 7.64-7.75(m, 2H) 7.48-7.58(m, 3H) 7.23-7.30(m, 2H) 7.08-7.14(m, 1H) 6.64-6.74(m, 1H) 4.46-4.53(m, 2H) 4.43(d, 2H) 3.11-3.19(m, 2H) |
| 83 | 2-(3,4-dihydroisoquinolin-2(1H)-ylcarbonyl)-N-pyridin-3-ylbenzenesulfonamide | 1H NMR (400 MHz, DMSO-D6) d ppm 10.28(br.s, 1H) 8.25-8.33(m, 1H) 8.13-8.24(m, 1H) 7.78-7.89(m, 1H) 7.65-7.73(m, 1H) 7.55-7.64(m, 1H) 7.45-7.54(m, 1H) 7.36-7.44(m, 1H) 7.08-7.28(m, 5H) 4.51-4.94(br.m, 1H) 4.05-4.35(br.m, 1H) 3.69-4.03(br.m, 1H) 3.16-3.29(m, 1H) 2.81-3.01(m, 1H) 2.70-2.78(m, 1H) |
| 84 | N-{4-[(dimethylamino)methyl]benzyl}-2-[(pyridin-3-ylamino)sulfonyl]benzamide | 1H NMR (400 MHz, DMSO-D6) d ppm 9.58(br.s, 1H) 8.20(d, 2H) 7.77(d, 1H) 7.58-7.68(m, 2H) 7.48-7.58(m, 1H) 7.45(d, 1H) 7.38(d, 2H) 7.27(d, 2H) 7.12-7.22(m, 1H) 4.50(d, 2H) 2.21(s, 6H) 1.89(s, 2H) |
| 85 | N-(3,4-difluorobenzyl)-2-[(pyridin-3-ylamino)sulfonyl]benzamide | 1H NMR (400 MHz, DMSO-D6) d ppm 9.77(br.s, 1H) 9.34(br.s, 1H) 8.21-8.34(m, 2H) 7.66-7.79(m, 2H) 7.34-7.65(m, 5H) 7.22-7.30(m, 2H) 4.51(d, 2H) |

| Example No. | Structure | Name | ¹H NMR |
|---|---|---|---|
| 86 | 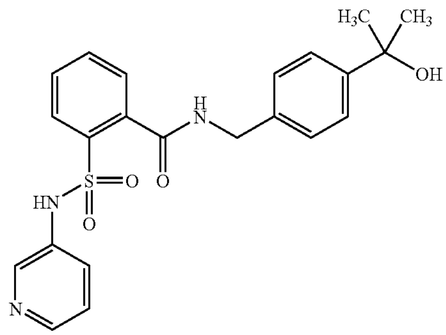 | N-[4-(1-hydroxy-1-methylethyl)benzyl]-2-[(pyridin-3-ylamino)sulfonyl]benzamide | 1H NMR (400 MHz, DMSO-D6) d ppm 9.72(br.s, 1H) 9.31(br.s, 1H) 8.20-8.35 (m, 2H) 7.65-7.77(m, 2H) 7.47-7.61(m, 3H) 7.40-7.45(m, 3H) 7.25-7.37(m, 3H) 4.50(d, 2H) 1.38 (s, 6H) |
| 87 | 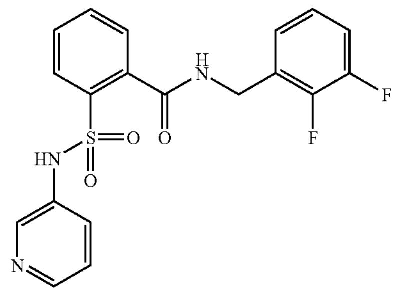 | N-(2,3-difluorobenzyl)-2-[(pyridin-3-ylamino)sulfonyl]benzamide | 1H NMR (400 MHz, DMSO-D6) d ppm 9.81(br.s, 1H) 9.41(br.s, 1H) 8.01-8.37 (m, 2H) 7.65-7.80(m, 2H) 7.46-7.62(m, 3H) 7.30-7.40(m, 2H) 7.12-7.29(m, 2H) 3.31(s, 2H) |
| 88 | 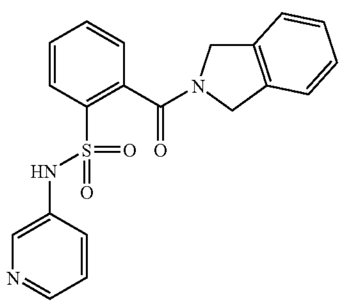 | 2-(1,3-dihydro-2H-isoindol-2-ylcarbonyl)-N-pyridin-3-ylbenzenesulfonamide | 1H NMR (400 MHz, DMSO-D6) d ppm 10.29(br.s, 1H) 8.15-8.33(m, 2H) 7.88(d, 1H) 7.68-7.79(m, 1H) 7.56-7.66(m, 2H) 7.45-7.54(m, 1H) 7.37-7.47(m, 1H) 7.13-7.35(m, 5H) 4.79-4.94(m, 2H) 4.25-4.52(m, 2H) |
| 89 | 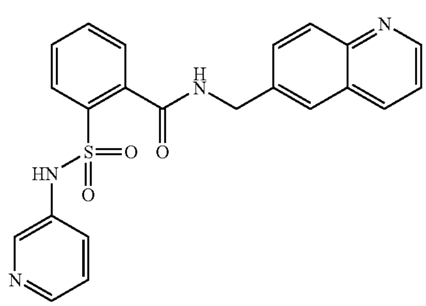 | 2-[(pyridin-3-ylamino)sulfonyl]-N-(quinolin-6-ylmethyl)benzamide | 1H NMR (400 MHz, DMSO-D6) d ppm 9.88(br.s, 1H) 9.37-9.53(m, 1H) 8.91-9.09 (m, 1H) 8.54-8.67(m, 1H) 8.24-8.40(m, 2H) 8.09(d, 2H) 7.93 (d, 1H) 7.78(d, 1H) 7.64-7.75 (m, 3H) 7.51-7.64(m, 2H) 7.25-7.37(m, 1H) 4.73(d, 2H) |
| 90 | 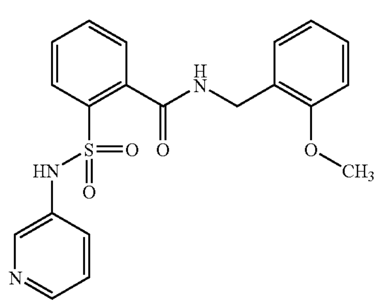 | N-(2-methoxybenzyl)-2-[(pyridin-3-ylamino)sulfonyl]benzamide | 1H NMR (400 MHz, DMSO-D6) d ppm 9.56-9.82(br.s 1H) 8.99 (br.s, 1H) 8.16-8.34(m, 2H) 7.66-7.81(m, 2H) 7.59-7.65 (m, 1H) 7.44-7.59(m, 2H) 7.38(d, 1H) 7.18-7.30(m, 2H) 7.00(d, 1H) 6.93(t, 1H) 4.49 (d, 2H) 3.83(s, 3H) |

| Example No. | Structure | Name | ¹H NMR |
|---|---|---|---|
| 91 | 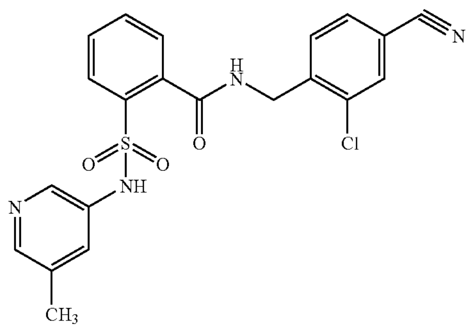 | N-(2-chloro-4-cyanobenzyl)-2-{[(5-methylpyridin-3-yl)amino]sulfonyl}benzamide | (400 MHz, DMSO-d6) d ppm 9.69(s, 1H), 9.44(s, 1H), 8.06-8.15(m, 3H), 7.79-7.89(m, 2H), 7.68-7.79(m, 3H), 7.61(t, J=6.95Hz, 1H), 7.37(s, 1H), 4.63(d, J=5.05Hz, 2H), 2.19(s, 3H) |
| 92 | 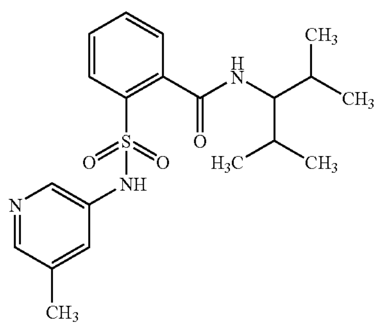 | N-(1-isopropyl-2-methylpropyl)-2-{[(5-methylpyridin-3-yl)amino]sulfonyl}benzamide | (400 MHz, DMSO-d6) d ppm 9.51(s, 1H), 8.53(d, J=9.60Hz, 1H), 8.11(d, J=8.08Hz, 1H), 8.10(s, 1H), 7.68-7.74(m, 2H), 7.52-7.62(m, 2H), 7.36(s, 1H), 3.66(dt, J=9.60, 6.57 Hz, 1H), 2.21(s, 3H), 1.84-1.95(m, J=13.39, 6.82, 6.69, 6.69Hz, 2H), 0.94 (dd, J=14.40, 6.82Hz, 12H) |
| 93 | 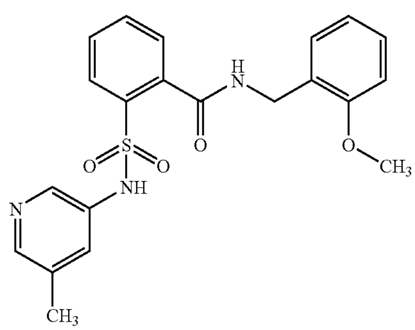 | N-(2-methoxybenzyl)-2-{[(5-methylpyridin-3-yl)amino]sulfonyl}benzamide | (400 MHz, DMSO-d6) d ppm 9.64(s, 1H), 9.22(s, 1H), 8.10(s, 2H), 7.68-7.77 (m, 2H), 7.63-7.68(m, 1H), 7.57(td, J=7.64, 1.39 Hz, 1H), 7.40(d, J=6.06Hz, 1H), 7.39(s, 1H), 7.36(s, 1H), 7.27(td, J=7.77, 1.64 Hz, 1H), 7.01(d, J=7.58Hz, 1H), 6.95(t, J=7.33Hz, 1H), 4.49(d, J=5.31Hz, 2H), 3.82-3.86(m, 3H), 2.20 (s, 3H) |
| 94 | 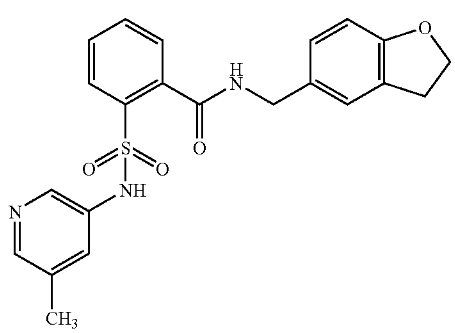 | N-(2,3-dihydro-1-benzofuran-5-ylmethyl)-2-{[(5-methylpyridin-3-yl)amino]sulfonyl}benzamide | (400 MHz, DMSO-d6) d ppm 9.64(s, 1H), 9.22(s, 1H), 8.10(s, 1H), 7.68-7.77 (m, 1H), 7.62-7.67(m, 1H), 7.57(td, J=7.58 1.52 Hz, 1H), 7.40(d, J=5.81Hz, 1H), 7.39(s, 1H), 7.36(s, 1H), 7.27(td, J=7.77, 1.64 Hz, 1H), 7.01(d, J=7.58Hz, 1H), 6.95(t, J=7.45Hz, 1H), 4.49(d, J=5.56Hz, 2H), 3.84(s, 3H), 2.20(s, 3H), 2.07(m, 1H) |

-continued

| Example No. | Structure | Name | $^1$H NMR |
|---|---|---|---|
| 95 | 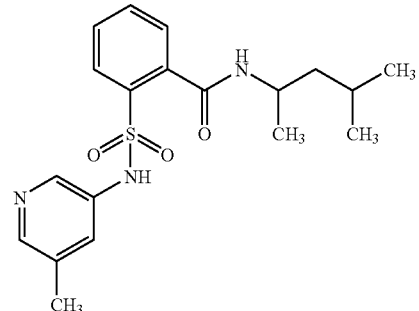 | N-(1,3-dimethylbutyl)-2-{[(5-methylpyridin-3-yl)amino]sulfonyl}benzamide | (400 MHz, DMSO-d6) d ppm 9.60(s, 1H), 8.63(s, 1H), 8.10(d, J=4.55Hz, 1H), 8.09(s, 1H), 7.68(t, J=7.58 Hz, 2H), 7.49-7.56(m, 2H), 7.35(s, 1H), 4.05-4.15 (m, 1H), 2.21(s, 3H), 1.69-1.79(m, 1H), 1.46-1.55 (m, 1H), 1.24(ddd, J=13.58, 8.40, 5.56Hz, 1H), 1.15(d, J=6.57Hz, 3H), 0.91(dd, J=9.60, 6.57Hz, 6H) |
| 96 | 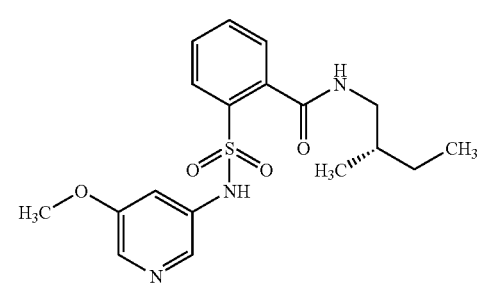 | 2-{[(5-methoxypyridin-3-yl)amino]sulfonyl}-N-[(2S)-2-methylbutyl]benzamide | (400 MHz, CHLOROFORM-d) d ppm 0.97(s, 1H) 0.98-1.05(m, 5H) 1.28(m, 1H) 1.30(m, 1H) 1.52(m, 1H) 1.79(m, 1H) 3.29-3.39(m, 1H) 3.43-3.54(m, 1H) 3.83(s, 3H) 6.16(s,1H) 7.44(td, J=7.71, 1.52Hz, 1H) 7.51-7.61(m, 2H) 7.73 (d, J=7.83Hz, 1H) 7.97(s, 1H) 8.06(s, 1H) 8.70 (s, 1H) |
| 97 | 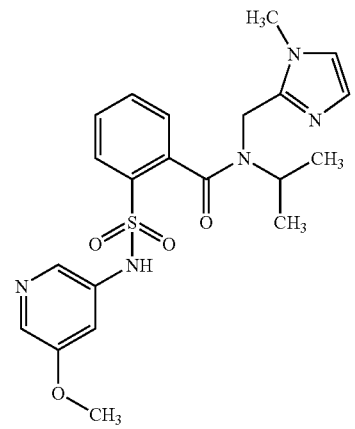 | N-isopropyl-2-{[(5-methoxypyridin-3-yl)amino]sulfonyl}-N-[(1-methyl-1H-imidazol-2-yl)methyl]benzamide | (400 MHz, DMSO-d6) d ppm 8.05(d, J=7.33Hz, 1H), 7.87-7.95(m, 1H), 7.78-7.84(m, 1H), 7.65-7.76(m, 2H), 7.54(d, J=7.33Hz, 1H), 7.52(dd, J=3.92, 2.65Hz, 1H), 7.32 (s, 1H), 7.17(s, 1H), 6.90 (s, 1H), 4.91(d, J=16.67 Hz, 1H), 4.62(d, J=16.67 Hz, 1H), 3.74-3.81(m, 3H), 3.63-3.73(m, 3H), 1.02-1.12(m, 6H) |
| 98 | 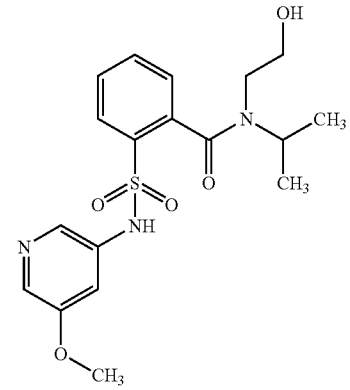 | N-(2-hydroxyethyl)-N-isopropyl-2-{[(5-methoxypyridin-3-yl)amino]sulfonyl}benzamide | (400 MHz, DMSO-d6) d ppm 10.25(s, 1H), 7.90-8.01(m, 2H), 7.81(t, J=8.72Hz, 1H), 7.63-7.73 (m, 1H), 7.54-7.63(m, 1H), 7.43(t, J=7.45Hz, 1H), 7.10-7.20(m, 1H), 4.77(s, 1H), 3.71-3.82(m, 4H), 3.52-3.59(m, 1H), 3.43-3.49(m, 1H), 3.32-3.41 (m, 2H), 1.08(dd, J=14.65, 6.57Hz, 6H) |

| Example No. | Structure | Name | ¹H NMR |
|---|---|---|---|
| 99 | 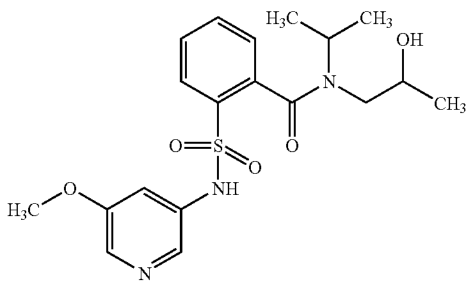 | N-(2-hydroxypropyl)-N-isopropyl-2-{[(5-methoxypyridin-3-yl)amino]sulfonyl}benzamide | (400 MHz, CHLOROFORM-d) d ppm 1.18-1.26(m, 7H) 1.28-1.32(m, 3H) 3.32 (m, 1H) 3.41(m, 1H) 3.53-3.65(m, 1H) 3.76-3.84(m, 4H) 3.87-3.92(m, 1H) 4.38-4.26(m, 1H) 7.14(m, 1H) 7.33-7.43(m, 2H) 7.55-7.65(m, 2H) 7.91 (bs, 1H) 8.08(bs, 1H) |
| 100 | 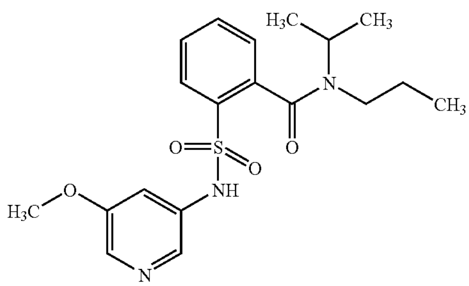 | N-isopropyl-2-{[(5-methoxypyridin-3-yl)amino]sulfonyl}-N-propylbenzamide | (400 MHz, CHLOROFORM-d) d ppm 0.68(t, J=7.45Hz, 0.6H) 1.02(t, J=7.45Hz, 2.5H) 1.22(dd, J=6.57, 3.28 Hz, 5H) 1.40(d, J=6.82Hz, 1.4H) 1.77-1.86(m, 2H) 2.96-3.09(m, 0.4H) 3.24 (m, 1H) 3.47(m, 1H) 3.80 (s, 3H) 7.22(s, 1H) 7.32-7.39(m, 2H) 7.56(td, J=7.58, 1.26Hz, 1H) 7.61-7.65(m, 1H) 7.96(bs, 1H) 8.07(bs, 1H) 8.14 (bs, 1H) |
| 101 | 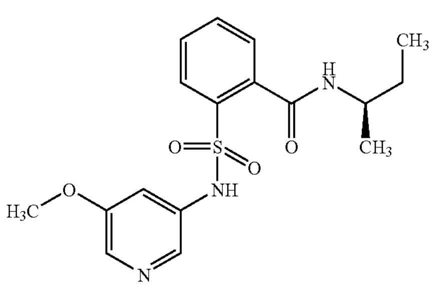 | 2-{[(5-methoxypyridin-3-yl)amino]sulfonyl}-N-[(1R)-1-methylpropyl]benzamide | (400 MHz, CHLOROFORM-d) d ppm 1.04(m, 3H) 1.31 (m, 3H) 1.64(m, 2H) 3.82 (s, 3H) 4.10-4.20(m, 1H) 5.91(m, 1H) 7.21-7.26(m, 1H) 7.43(m, 1H) 7.54(m, 2H) 7.72(m, 1H) 7.97(s, 1H) 8.05(s, 1H) 8.68 (bs, 1H) |
| 102 | 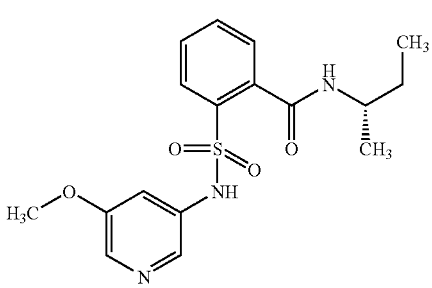 | 2-{[(5-methoxypyridin-3-yl)amino]sulfonyl}-N-[(1S)-1-methylpropyl]benzamide | (400 MHz, CHLOROFORM-d) d ppm 1.05(m, 3H) 1.32 (m, 1H) 1.33(m, 2H) 1.61-1.73(m, 3H) 3.83(s, 3H) 4.11-4.21(m, 1H) 5.90 m, 1H) 7.41-7.47(m, 1H) 7.51-7.61(m, 2H) 7.74(m, 1H) 7.99(s, 1H) 8.07 (s, 1H) 8.72(bs, 1H) |
| 103 | 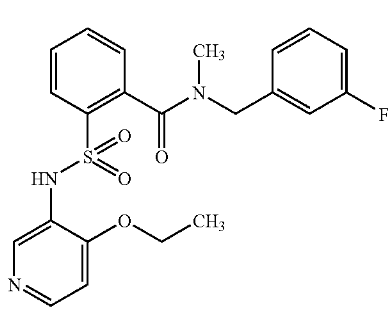 | 2-{[(4-ethoxypyridin-3-yl)amino]sulfonyl}-N-(3-fluorobenzyl)-N-methylbenzamide | (400 MHz, CHLOROFORM-d) d ppm 0.88-1.34(m, 3H) 2.85(s, 2H) 3.10(s, 1H) 3.64-4.04 (m, 2H) 4.28-4.99(m, 2H) 6.65(d, J=5.79Hz, 1H) 6.79-7.10(m, 2H) 7.13-7.28(m, 1H) 7.32-7.45(m, 3H) 7.47-7.64(m, 1H) 7.74(t, J=8.94Hz, 1H) 7.85-8.05(m, 1H) 8.27(dd, J=5.54, 3.02Hz, 1H) 8.49-8.75(m, 1H) |

| Example No. | Structure | Name | ¹H NMR |
|---|---|---|---|
| 104 | 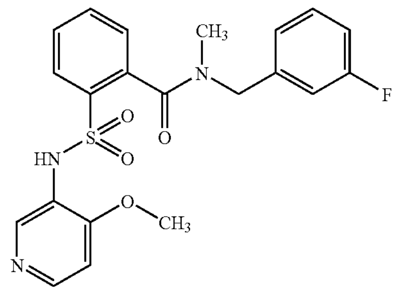 | N-(3-fluorobenzyl)-2-{[(4-methoxypyridin-3-yl)amino]sulfonyl}-N-methylbenzamide | (400 MHz, CHLOROFORM-d) d ppm 2.83(s, 2H) 3.10(s, 1H) 3.36-3.74(m, 3H) 4.11-4.98(m, 2H) 6.68(d, J=5.54Hz, 1H) 6.92-7.09 (m, 2H) 7.13-7.25(m, 2H) 7.30-7.47(m, 2H) 7.47-7.65(m, 1H) 7.75(t, J=7.81 Hz, 1H) 7.89(d, J=3.02Hz, 1H) 8.29(d, J=5.54Hz, 1H) 8.50-8.82(m, 1H) |
| 105 | 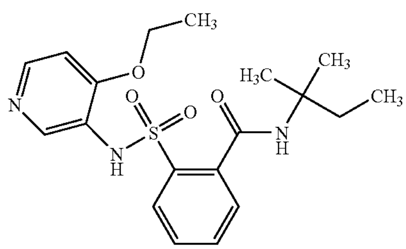 | N-(1,1-dimethylpropyl)-2-{[(4-ethoxypyridin-3-yl)amino]sulfonyl}benzamide | (400 MHz, CHLOROFORM-d) d ppm 0.99(t, J=7.43Hz, 3H) 1.16 (t, J=6.92Hz, 3H) 1.47(s, 6H) 1.89(q, J=7.55Hz, 2H) 3.83(q, J=6.97Hz, 2H) 5.75(s, 1H) 6.62(d, J=5.54 Hz, 1H) 7.33-7.47(m, 1H) 7.48-7.64(m, 2H) 7.76(d, J=7.81Hz, 1H) 8.23(d, J=5.54Hz, 1H) 8.62(s, 1H) 8.73(s, 1H) |
| 106 | 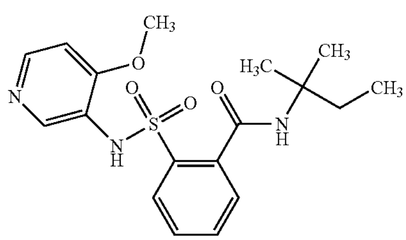 | N-(1,1-dimethylpropyl)-2-{[(4-methoxypyridin-3-yl)amino]sulfonyl}benzamide | (400 MHz, CHLOROFORM-d) d ppm 0.99(t, J=7.43Hz, 3H) 1.48 (s, 6H) 1.89(q, J=7.55Hz, 2H) 3.50-3.65(m, 3H) 5.77(s, 1H) 6.66(d, J=5.54 Hz, 1H) 7.42(t, J=7.43Hz, 1H) 7.48-7.59(m, 2H) 7.75(d, J=7.81Hz, 1H) 8.27(d, J=5.54Hz, 1H) 8.47-8.54(m, 1H) 8.56 (s, 1H) |
| 107 | 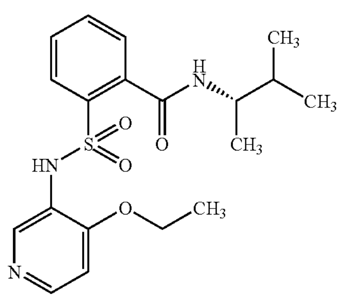 | N-[(1S)-12-dimethylpropyl]-2-{[(4-ethoxypyridin-3-yl)amino]sulfonyl}benzamide | (400 MHz, CHLOROFORM-d) d ppm 1.02(t, J=6.67Hz, 6H) 1.14 (t, J=7.05Hz, 3H) 1.21-1.31(m, 3H) 1.79-1.97(m, 1H) 3.61-3.92(m, 2H) 4.00-4.22(m, 1H) 5.89(d, J=8.56Hz, 1H) 6.62(d, J=5.54Hz, 1H) 7.44(t, J=7.68Hz, 1H) 7.48-7.60 (m, 2H) 7.77(d, J=7.81Hz, 1H) 8.23(d, J=5.54Hz, 1H) 8.63(s, 1H) 8.68(s, 1H) |
| 108 | 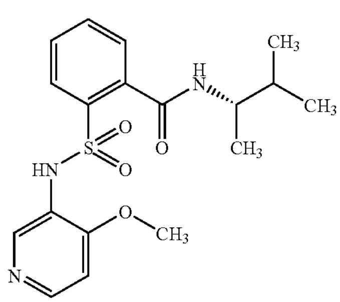 | N-(1S)-12-dimethylpropyl]-2-{[(4-methoxypyridin-3-yl)amino]sulfonyl}benzamide | (400 MHz, CHLOROFORM-d) d ppm 1.02(t, J=7.05Hz, 6H) 1.15-1.38(m, 3H) 1.75-2.00 (m, 1H) 3.60(s, 3H) 3.86-4.18(m, 1H) 5.91(d, J=8.81Hz, 1H) 6.66(d, J=5.54Hz, 1H) 7.37-7.49 (m, 1H) 7.50-7.62(m, 2H) 7.78(d, J=7.81Hz, 1H) 8.26(d, J=5.54Hz, 1H) 8.53(s, 1H) 8.62(s, 1H) |

| Example No. | Structure | Name | ¹H NMR |
|---|---|---|---|
| 109 | 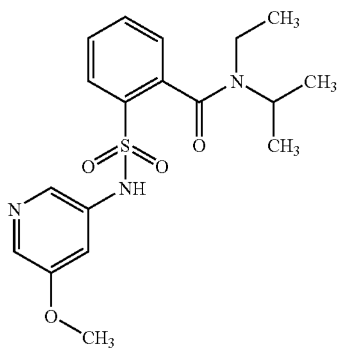 | N-ethyl-N-isopropyl-2-{[(5-methoxypyridin-3-yl)amino]sulfonyl}benzamide | (400 MHz, DMSO-d6) d ppm 10.19(s, 1H), 7.90-7.94(m, 1H), 7.80(d, J=7.83Hz, 1H), 7.64-7.71 (m, 1H), 7.54-7.61(m, 1H), 7.42(s, 1H), 7.38-7.42 (m, 1H), 7.13(t, J=2.40Hz, 1H), 3.74-3.80(m, 3H), 3.49(dt, J=13.20, 6.66Hz, 3.34-3.43(m, 2H), 3.34(s, 1H), 1.24(ddd, J=17.56, 7.20, 7.07Hz, 4H), 1.06-1.16(m, 5H) |
| 110 | 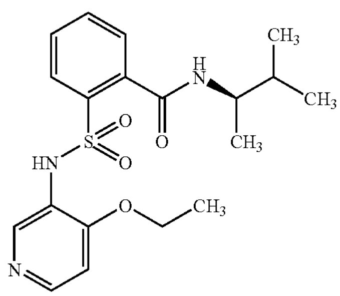 | N-[(1R)-12-dimethylpropyl]-2-{[(4-ethoxypyridin-3-yl)amino]sulfonyl}benzamide | (400 MHz, CHLOROFORM-d) d ppm 1.02(t, J=6.67Hz, 6H) 1.14 (t, J=7.05Hz, 3H) 1.21-1.31(m, 3H) 1.79-1.97(m, 1H) 3.61-3.92(m, 2H) 4.00-4.22(m, 1H) 5.89(d, J=8.56Hz, 1H) 6.62(d, J=5.54Hz, 1H) 7.44(t, J=7.68Hz, 1H) 7.48-7.60 (m, 2H) 7.77(d, J=7.81Hz, 1H) 8.23(d, J=5.54Hz, 1H) 8.63(s, 1H) 8.68(s, 1H) |
| 111 | 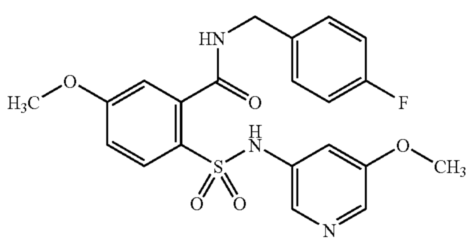 | N-(4-fluorobenzyl)-5-methoxy-2-{[(5-methoxypyridin-3-yl)amino]sulfonyl}benzamide | (400 MHz, CHLOROFORM-d) d ppm 3.84(d, J=1.26Hz, 6H) 4.67(d, J=5.81Hz, 2H) 6.45(s, 1H) 6.82(dd, J=8.84, 2.53Hz, 1H) 7.01(d, J=2.53Hz, 1H) 7.04-7.14(m, 2H) 7.41(d, J=5.31Hz, 1H) 7.42-7.51 (m, 1H) 7.66(d, J=8.59Hz, 1H) 7.98(s, 1H) 8.06(s, 1H) 8.42(s, 1H) |
| 112 | 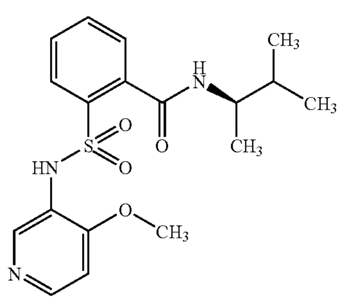 | N-[(1R)-12-dimethylpropyl]-2-{[(4-methoxypyridin-3-yl)amino]sulfonyl}benzamide | (400 MHz, CHLOROFORM-d) d ppm 1.02(t, J=7.05Hz, 6H) 1.15-1.38(m, 3H) 1.75-2.00 (m, 1H) 3.60(s, 3H) 3.86-4.18(m, 1H) 5.91(d, J=8.81Hz, 1H) 6.66(d, J=5.54Hz, 1H) 7.37-7.49 (m, 1H) 7.50-7.62(m, 2H) 7.78(d, J=7.81Hz, 1H) 8.26(d, J=5.54Hz, 1H) 8.53(s, 1H) 8.62(s, 1H) |
| 113 | 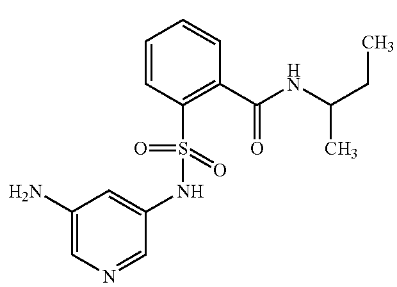 | 2-{[(5-aminopyridin-3-yl)amino]sulfonyl}-N-(sec-butyl)benzamide | (400 MHz, DMSO-d6) d ppm 0.93(t, J=7.45Hz, 3H) 1.16(d, J=6.57Hz, 3H) 1.47-1.58(m, 2H) 3.88-3.97(m, 1H) 6.81 m, 1H) 7.51(m, 1H) 7.53-7.59(m, 3H) 7.63(m, 1H) 7.70(m, 2H) 8.65(d, J=8.08Hz, 1H) |

-continued

| Example No. | Structure | Name | ¹H NMR |
|---|---|---|---|
| 114 | 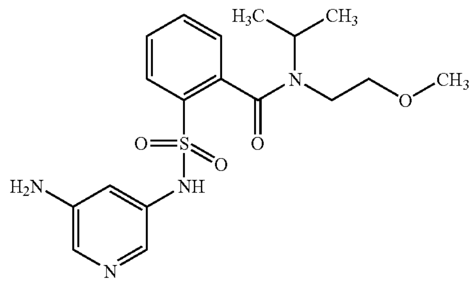 | 2-{[(5-aminopyridin-3-yl)amino]sulfonyl}-N-isopropyl-N-(2-methoxyethyl)benzamide | (400 MHz, CHLOROFORM-d) d ppm 1.18-1.27(m, 6H) 1.42(m, 1H) 2.00-2.09 (m, 1H) 3.43(s, 3H) 3.53-3.61(m, 1H) 3.61-3.71(m, 2H) 3.78(s, 1H) 3.81(m, 2H) 7.00(s, 1H) 7.32-7.43 (m, 2H) 7.51-7.61(m, 1H) 7.68(m, 1H) 7.75(s, 1H) 7.90(s, 1H) |
| 115 | 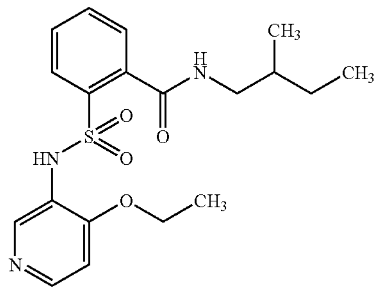 | 2-{[(4-ethoxypyridin-3-yl)amino]sulfonyl}-N-(2-methylbutyl)benzamide | (400 MHz, CHLOROFORM-d) d ppm 1.02(t, J=6.67Hz, 6H) 1.14 (t, J=7.05Hz, 3H) 1.21-1.31(m, 3H) 1.79-1.97(m, 1H) 3.61-3.92(m, 2H) 4.00-4.22(m, 1H) 5.89(d, J=8.56Hz, 1H) 6.62(d, J=5.54Hz, 1H) 7.44(t, J=7.68Hz, 1H) 7.48-7.60 2H) 7.77(d, J=7.81Hz, 1H) 8.23(d, J=5.54Hz, 1H) 8.63(s, 1H) 8.68(s, 1H) |
| 116 | 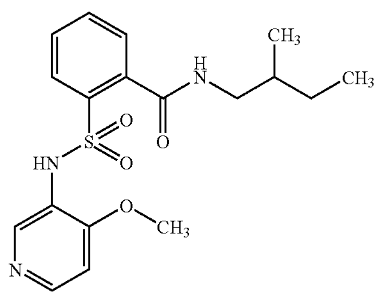 | 2-{[(4-methoxypyridin-3-yl)amino]sulfonyl}-N-(2-methylbutyl)benzamide | (400 MHz, CHLOROFORM-d) d ppm 0.69-1.19(m, 5H) 1.10-1.58(m, 2H) 1.62-1.85(m, 2H) 2.27(s, 3H) 3.19-3.40 (m, 1H) 3.38-3.54(m, 1H) 6.28(s, 1H) 7.33-7.49(m, 2H) 7.47-7.61(m, 2H) 7.67(d, J=7.81Hz, 1H) 8.17(s, 2H) 8.58(s, 1H) |
| 117 | 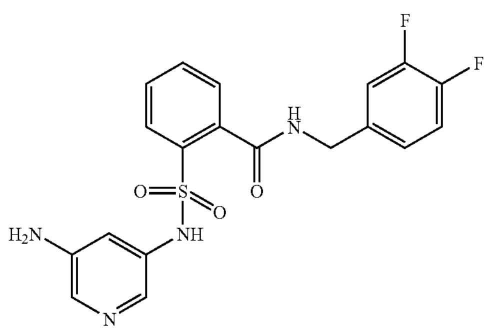 | 2-{[(5-aminopyridin-3-yl)amino]sulfonyl}-N-(34-difluorobenzyl)benzamide | (400 MHz, DMSO-d6) d ppm 4.51(d, J=5.81Hz, 2H) 5.50(bs, 1H) 6.78(s, 1H) 7.25(7.43(s, 1H) 7.45-7.53(m, 2H) 7.57-7.66(m, 4H) 7.68-7.77(m, 3H) 9.35(s, 2H) |
| 118 | 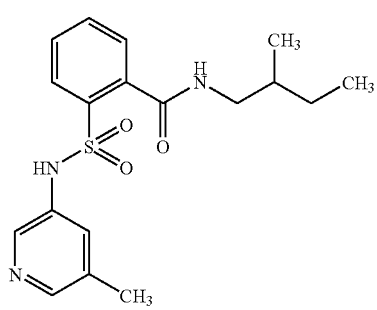 | N-(2-methylbutyl)-2-{[(5-methylpyridin-3-yl)amino]sulfonyl}benzamide | (400 MHz, CHLOROFORM-d) d ppm 0.69-1.19(m, 5H) 1.10-1.58(m, 2H) 1.62-1.85(m, 2H) 2.27(s, 3H) 3.19-3.40 (m, 1H) 3.38-3.54(m, 1H) 6.28(s, 1H) 7.33-7.49(m, 2H) 7.47-7.61(m, 2H) 7.67(d, J=7.81Hz, 1H) 8.17(s, 2H) 8.58(s, 1H) |

| Example No. | Name | ¹H NMR |
|---|---|---|
| 119 | N-(sec-butyl)-2-{[(4-ethoxypyridin-3-yl)amino]sulfonyl}benzamide | (400 MHz, CHLOROFORM-d) d ppm 0.96-1.08(m, 3H) 1.12(t, J=6.92Hz, 3H) 1.26-1.39 (m, 3H) 1.50-1.78(m, 2H) 3.68-3.91(m, 2H) 4.06-4.23(m, 1H) 6.17(d, J=7.81Hz, 1H) 6.62(d, J=5.54Hz, 1H) 7.34-7.45 (m, 1H) 7.47-7.60(m, 2H) 7.70(d, J=7.81Hz, 1H) 8.19(d, J=5.54Hz, 1H) 8.59(s, 1H) 8.69-8.87 (m, 1H) |
| 120 | N-(sec-butyl)-2-{[(4-methoxypyridin-3-yl)amino]sulfonyl}benzamide | (400 MHz, CHLOROFORM-d) d ppm 1.04(t, J=7.55Hz, 3H) 1.20-1.37(m, 3H) 1.51-1.82 (m, 2H) 3.54-3.68(m, 3H) 4.09-4.40(m, 1H) 5.89(d, J=8.06Hz, 1H) 6.67(d, J=5.29Hz, 1H) 7.35-7.66 (m, 3H) 7.78(d, J=7.81Hz, 1H) 8.26(s, 1H) 8.54 (s, 2H) |
| 121 | N-(sec-butyl)-2-{[(5-methylpyridin-3-yl)amino]sulfonyl}benzamide | (400 MHz, CHLOROFORM-d) d ppm 0.74-1.13(m, 3H) 1.16-1.43(m, 2H) 1.54-1.80(m, 3H) 2.27(s, 3H) 3.97-4.29 (m, 1H) 5.98(d, J=8.06Hz, 1H) 7.31-7.46(m, 2H) 7.46-7.59(m, 2H) 7.68(d, J=7.81Hz, 1H) 8.17(s, 2H) 8.57(s, 1H) |
| 122 | 2-{[(4-ethoxypyridin-3-yl)amino]sulfonyl}-N-methyl-N-[4-(trifluoromethyl)benzyl]benzamide | (400 MHz, CHLOROFORM-d) d ppm 0.79-1.27(m, 3H) 2.47-2.97(m, 2H) 3.09(s, 1H) 3.87(d, J=59.17Hz, 2H) 4.19-5.13(m, 2H) 6.34-6.82(m, 1H) 6.85-7.23(m, 2H) 7.29-7.46(m, 3H) 7.47-7.67(m, 2H) 7.74(t, J=8.56Hz, 1H) 8.03(s, 1H) 8.25(s, 1H) 8.66(s, 1H) |

-continued

| Example No. | Structure | Name | ¹H NMR |
|---|---|---|---|
| 123 | 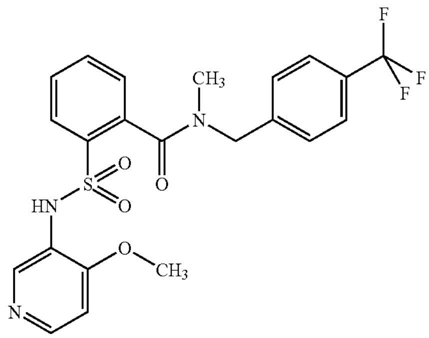 | 2-{[(4-methoxypyridin-3-yl)amino]sulfonyl}-N-methyl-N-[4-(trifluoromethyl)benzyl]benzamide | (400 MHz, CHLOROFORM-d) d ppm 2.84(s, 2H) 3.10(s, 1H) 3.37-3.71(m, 3H) 4.36-5.14(m, 2H) 6.68(d, J=5.29Hz, 1H) 7.31-7.54 (m, 4H) 7.58-7.95(m, 5H) 8.30(s, 1H) 8.47-8.69 (m, 1H) |
| 124 | 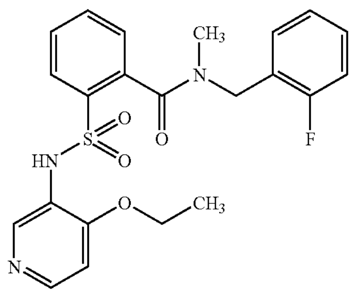 | 2-{[(4-ethoxypyridin-3-yl)amino]sulfonyl}-N-(2-fluorobenzyl)-N-methylbenzamide | (400 MHz, CHLOROFORM-d) d ppm 0.79-1.27(m, 3H) 2.47-2.97(m, 2H) 3.09(s, 1H) 3.87(d, J=59.17Hz, 2H) 4.19-5.13(m, 2H) 6.34-6.82(m, 1H) 6.85-7.23(m, 2H) 7.29-7.46(m, 3H) 7.47-7.67(m, 2H) 7.74(t, J=8.56Hz, 1H) 8.03(s, 1H) 8.25(s, 1H) 8.66(s, 1H) |
| 125 | 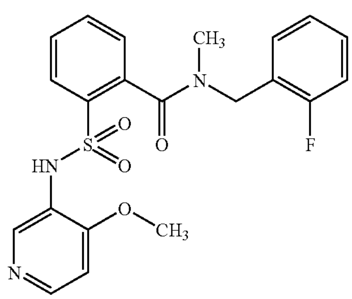 | N-(2-fluorobenzyl)-2-{[(4-methoxypyridin-3-yl)amino]sulfonyl}-N-methylbenzamide | (400 MHz, CHLOROFORM-d) d ppm 2.80(s, 2H) 3.06(s, 1H) 3.48-3.69(m, 3H) 4.31-4.96(m, 2H) 6.68(d, J=5.29Hz, 1H) 6.92-7.16 (m, 2H) 7.18-7.33(m, 1H) 7.20-7.31(m, 1H) 7.32-7.48(m, 2H) 7.48-7.65(m, 1H) 7.74(d, J=7.55Hz, 1H) 7.94(s, 1H) 8.29(s, 1H) 8.64(s, 1H) |
| 126 | 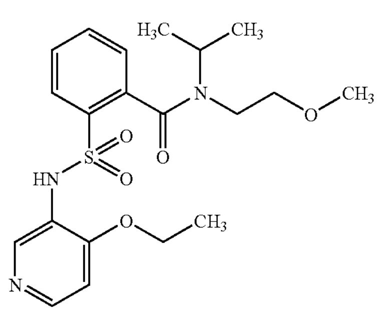 | 2-{[(4-ethoxypyridin-3-yl)amino]sulfonyl}-N-(2-methoxyethyl)benzamide | (400 MHz, CHLOROFORM-d) d ppm 0.98-1.30(m, 8H) 1.40(d, J=7.05Hz, 1H) 3.36-3.98 (m, 10H) 6.63(d, J=5.29 Hz, 1H) 7.35-7.47(m, 2H) 7.48-7.62(m, 1H) 7.69(t, J=8.44Hz, 1H) 8.01(s, 1H) 8.25(s, 1H) 8.60(s, 1H) |

| Example No. | Structure | Name | ¹H NMR |
|---|---|---|---|
| 127 | 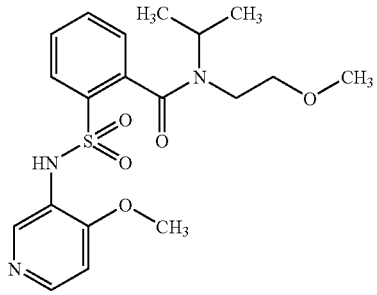 | N-isopropyl-N-(2-methoxyethyl)-2-{[(4-methoxypyridin-3-yl)amino]sulfonyl}benzamide | (400 MHz, CHLOROFORM-d) d ppm 1.21(d, J=6.80Hz, 6H) 1.40(d, J=6.80Hz, 1H) 3.38-3.48(m, 3H) 3.46-3.72(m, 5H) 3.73-3.91(m, 2H) 6.66(d, J=5.54Hz, 1H) 7.31-7.46(m, 2H) 7.49-7.61(m, 1H) 7.69(t, J=8.81Hz, 1H) 7.92(s, 1H) 8.28(d, J=5.04Hz, 1H) 8.57(s, 1H) |
| 128 | 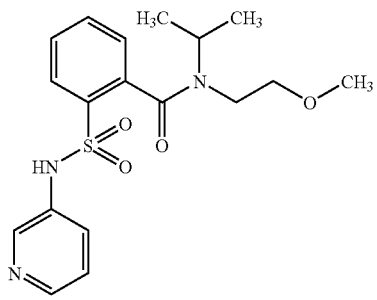 | N-isopropyl-N-(2-methoxyethyl)-2-[(pyridin-3-ylamino)sulfonyl]benzamide | (400 MHz, CHLOROFORM-d) d ppm 1.08-1.34(m, 6H) 3.35-3.56(m, 6H) 3.60-3.88(m, 4H) 7.22(s, 1H) 7.33-7.41 (m, 1H) 7.50-7.73(m, 2H) 7.92-8.12(m, 1H) 8.37(s, 2H) |
| 129 | 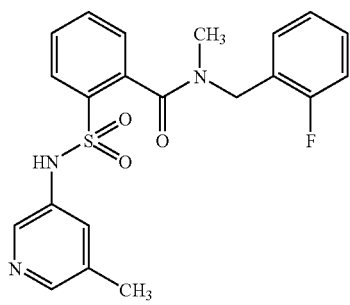 | N-(2-fluorobenzyl)-N-methyl-2-{[(5-methylpyridin-3-yl)amino]sulfonyl}benzamide | (400 MHz, CHLOROFORM-d) d ppm 2.27(s, 3H) 2.89(s, 2H) 3.11(s, 1H) 4.23-5.14(m, 2H) 6.84-7.16(m, 1H) 7.15-7.27(m, 1H) 7.30-7.49(m, 4H) 7.48-7.70(m, 3H) 7.90(s, 1H) 8.20 (s, 2H) |
| 130 | 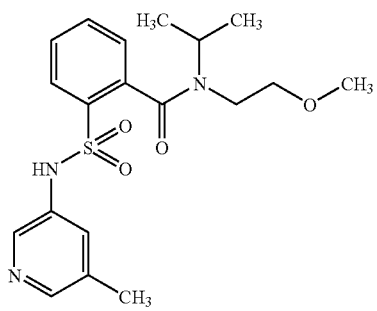 | N-isopropyl-N-(2-methoxyethyl)-2-{[(5-methylpyridin-3-yl)amino]sulfonyl}benzamide | (400 MHz, CHLOROFORM-d) d ppm 1.09-1.48(m, 5H) 2.26(s, 3H) 3.35-3.49(m, 4H) 3.53-3.73(m, 3H) 3.75-3.89(m, 2H) 7.30-7.46(m, 3H) 7.51-7.70(m, 2H) 7.80-8.00(m, 1H) 8.18(d, J=15.86Hz, 2H) |

| Example No. | Structure | Name | ¹H NMR |
|---|---|---|---|
| 131 | 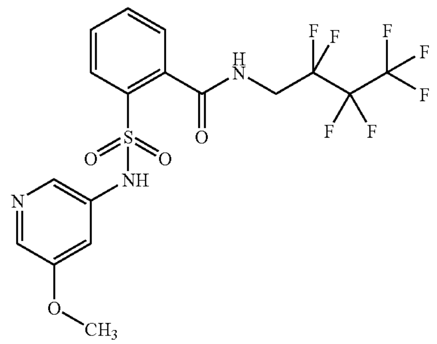 | N-(2,2,3,3,4,4,4-heptafluorobutyl)-2-{[(5-methoxypyridin-3-yl)amino]sulfonyl}benzamide | (400 MHz, CHLOROFORM-d) d ppm 9.32(s, 1H), 8.23 (d, J=1.01Hz, 1H), 8.06(s, 1H), 7.82-7.89(m, 1H), 7.79(s, 1H), 7.73(t, J=7.45 Hz, 1H), 7.59-7.69(m, 2H), 6.92(t, J=5.94Hz, 1H), 4.28(td, J=15.16, 6.06Hz, 2H), 3.98(s, 3H) |
| 132 | 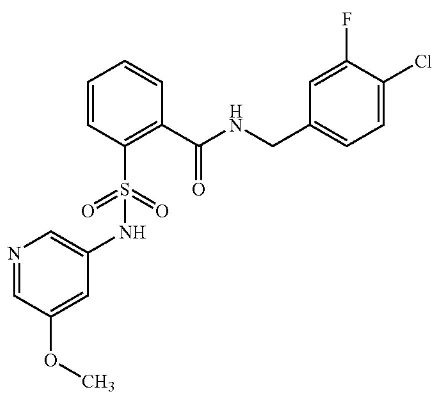 | N-(4-chloro-3-fluorobenzyl)-2-{[(5-methoxypyridin-3-yl)amino]sulfonyl}benzamide | (400 MHz, DMSO-d6) d ppm 10.35(s, 1H), 7.87-7.91(m, 1H), 7.64-7.68 (m, 2H), 7.62(s, 1H), 7.58-7.61(m, 1H), 7.46-7.57 (m, 3H), 7.29(ddd, J=15.22, 8.27, 1.52Hz, 1H), 7.01(s, 1H), 6.90(t, J=2.40Hz, 1H), 4.51(d, J=5.81Hz, 1H), 3.94(s, 1H), 3.67(s, 3H) |
| 133 | 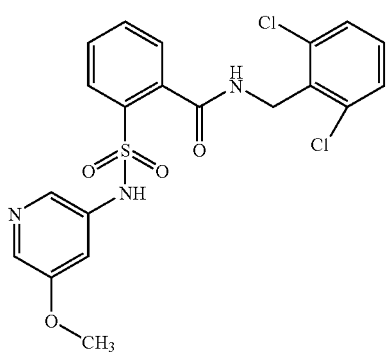 | N-(2,6-dichlorobenzyl)-2-{[(5-methoxypyridin-3-yl)amino]sulfonyl}benzamide | (400 MHz, DMSO-d6) d ppm 9.85(s, 1H), 9.08(s, 1H), 7.98(d, J=2.53Hz, 1H), 7.93(d, J=2.02Hz, 1H), 7.79(d, J=6.82Hz, 1H), 7.78(s, 1H), 7.66(td, J=7.52, 1.14Hz, 1H), 7.56 (td, J=7.71, 1.26Hz, 1H), 7.49-7.53(m, 2H), 7.46 (dd, J=7.45, 1.14Hz, 1H), 7.35-7.41(m, 1H), 7.14(t, J=2.40Hz, 1H), 4.75(d, J=4.55Hz, 2H), 3.76(s, 3H) |
| 134 | 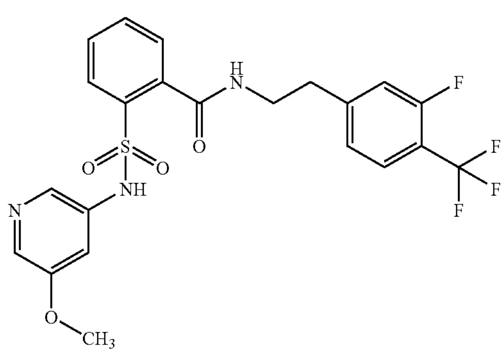 | N-{2-[3-fluoro-(trifluoromethyl)phenyl]ethyl}-2-{[(5-methoxypyridin-3-yl)amino]sulfonyl}benzamide | (400 MHz, DMSO-d6) d ppm 8.98(t, J=5.18Hz, 1H), 7.95(d, J=2.53Hz, 1H), 7.90(d, J=1.77Hz, 1H), 7.79(d, J=7.83Hz, 1H), 7.71(t, J=7.96Hz, 1H), 7.62-7.68(m, 1H), 7.53-7.59(m, 1H), 7.42-7.50 (m, 2H), 7.35(d, J=8.08Hz, 1H), 7.10(t, J=2.27Hz, 1H), 3.75(s, 3H), 3.57(q, J=6.40Hz, 2H), 2.99(t, J=6.82Hz, 2H) |

-continued

| Example No. | Structure | Name | ¹H NMR |
|---|---|---|---|
| 135 | 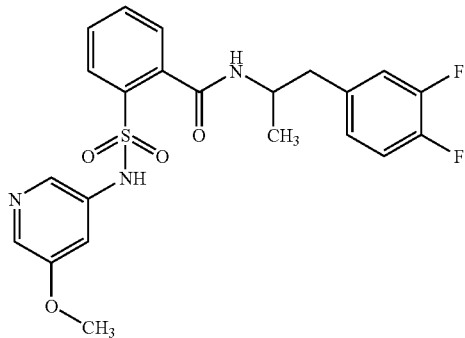 | N-[2-(3,4-difluorophenyl)-1-methylethyl-2-{[(5-methoxypyridin-3-yl)amino]sulfonyl}benzamide | (400 MHz, DMSO-d6) d ppm 9.79(s, 1H), 8.75(d, J=7.83Hz, 1H), 7.98(d, J=2.53Hz, 1H), 7.90(d, J=2.02Hz, 1H), 7.76(d, J=7.83Hz, 1H), 7.67(t, J=7.33Hz, 1H), 7.52-7.58 (m, 1H), 7.30-7.40(m, 3H), 7.08-7.16(m, 2H), 4.22(ddd, J=14.02, 7.20, 7.07Hz, 1H), 3.75(s, 3H), 2.76-2.88(m, 2H), 1.17(d, J=6.57Hz, 3H) |
| 136 | 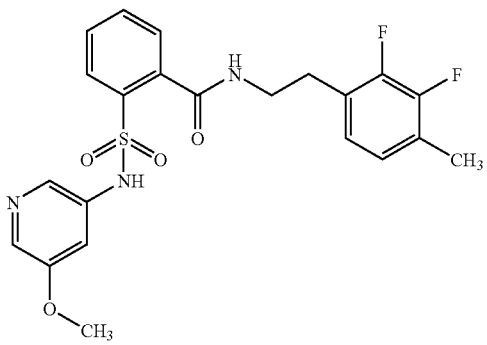 | N-[2-(2,3-difluoro-4-methylphenyl)ethyl]-2-{[(5-methoxypyridin-3-yl)amino]sulfonyl}benzamide | (400 MHz, DMSO-d6) d ppm 9.73(s, 1H), 8.97(s, 1H), 7.95(d, J=2.53Hz, 1H), 7.88(d, J=2.02Hz, 1H), 7.78(d, J=7.83Hz, 1H), 7.65(d, J=7.33Hz, 1H), 7.56(t, J=7.71Hz, 1H), J=7.58Hz, 1H), 7.00-7.11(m, 3H), 3.75(s, 3H), 3.45-3.54(m, 2H), 2.91(t, J=6.95Hz, 2H), 2.25(d, J=1.26Hz, 3H) |
| 137 | 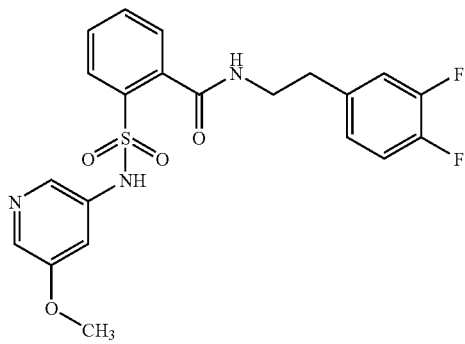 | N-[2-(3,4-difluorophenyl)ethyl]-2-{[(5-methoxypyridin-3-yl)amino]sulfonyl}benzamide | (400 MHz, DMSO-d6) d ppm 9.86(s, 1H), 8.86(t, J=5.05Hz, 1H), 7.98(d, J=2.53Hz, 1H), 7.91(d, J=2.02Hz, 1H), 7.79(s, 1H), 7.77(d, J=1.01Hz, 1H), 7.67(td, J=7.52, 1.14Hz, 1H), 7.56(td, J=7.71, 1.26 1H), 7.34-7.44(m, 2H), 7.09-7.16(m, 2H), 3.75(s, 3H), 3.46-3.55(m, 2H), 2.87(t, J=6.95Hz, 2H) |
| 138 | 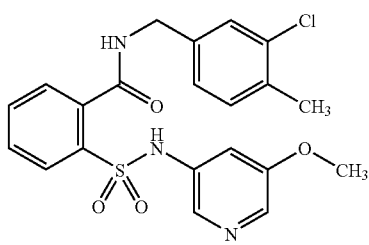 | N-(3-chloro-4-methylbenzyl)-2-{[(5-methoxypyridin-3-yl)amino]sulfonyl}benzamide | (400 MHz, DMSO-d6) d ppm 2.34(s, 3H) 3.75(s, 3H) 4.48(d, J=6.06Hz, 2H) 7.14(t, J=2.27Hz, 1H) 7.26 (dd, J=7.83, 1.77Hz, 1H) 7.38(d, J=8.08Hz, 1H) 7.42(s, 1H) 7.55-7.63(m, 2H) 7.71(t, J=7.07Hz, 1H) 7.81(d, J=7.58Hz, 1H) 7.94(s, 1H) 8.01(s, 1H) 9.28(t, J=5.94Hz, 1H) 9.88(s, 1H) |

| Example No. | Structure | Name | ¹H NMR |
|---|---|---|---|
| 139 | 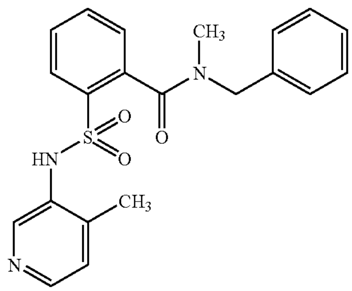 | N-benzyl-N-methyl-2-{[(4-methylpyridin-3-yl)amino]sulfonyl}benzamide | (400 MHz, CHLOROFORM-d) d ppm 1.07(s, 3H) 1.65(s, 2H) 1.90(s, 1H) 3.10-3.95(m, 2H) 5.89(s, 1H) 6.01-6.31 (m, 7H) 6.31-6.48(m, 2H) 6.63(s, 1H) 7.03(d, J=42.05Hz, 2H) |
| 140 | 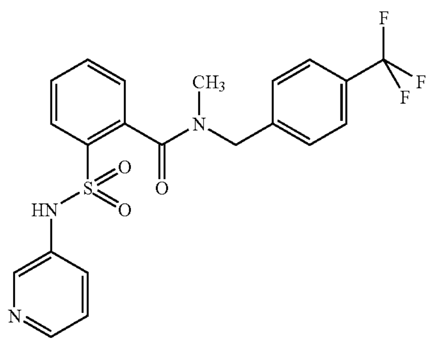 | N-methyl-2-[(pyridin-3-yl)amino)sulfonyl]-N-[4-(trifluoromethyl)benzyl]benzamide | (400 MHz, CHLOROFORM-d) d ppm 2.88(s, 2H) 3.11(s, 1H) 4.28-5.11(m, 2H) 7.05-7.23(m, 1H) 7.30-7.49(m, 3H) 7.54-7.75(m, 6H) 7.96(s, 1H) 8.40(s, 2H) |
| 141 | 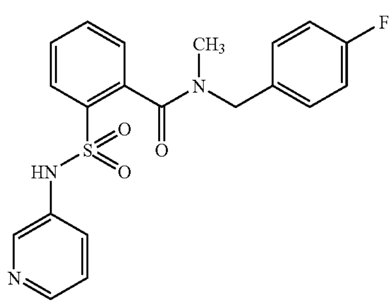 | N-(4-fluorobenzyl)-N-methyl-2-[(pyridin-3-yl)amino)sulfonyl]benzamide | (400 MHz, CHLOROFORM-d) d ppm 2.84(s, 2H) 3.07(s, 1H) 3.99-4.94(m, 2H) 6.99-7.14(m, 2H) 7.19(dd, J=7.68, 4.66Hz, 1H) 7.23-7.30(m, 1H) 7.30-7.48(m, 3H) 7.49-7.69(m, 3H) 8.01(s, 1H) 8.39(s, 2H) |
| 142 | 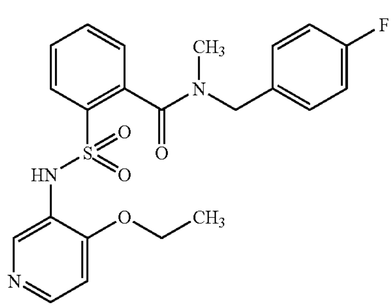 | 2-{[(4-ethoxypyridin-3-yl)amino]sulfonyl}-N-(4-fluorobenzyl)-N-methylbenzamide | (400 MHz, CHLOROFORM-d) d ppm 1.10-1.29(m, 3H) 2.81(s, 2H) 3.05(s, 1H) 3.58-4.09 (m, 2H) 4.40(s, 1H) 4.64-4.94(m, 1H) 6.65(d, J=5.29Hz, 1H) 6.97-7.15 (m, 2H) 7.20-7.33(m, 1H) 7.30-7.51(m, 3H) 7.48-7.65(m, 1H) 7.73(dd, J=7.68, 3.65Hz, 1H) 8.01 (s, 1H) 8.26(s, 1H) 8.66(s, 1H) |

| Example No. | Structure | Name | ¹H NMR |
|---|---|---|---|
| 143 | 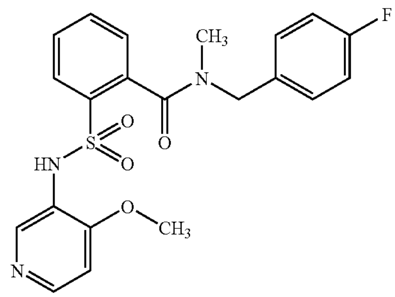 | N-(4-fluorobenzyl)-2-{[(4-methoxypyridin-3-yl)amino]sulfonyl}-N-methylbenzamide | (400 MHz, CHLOROFORM-d) d ppm 2.80(s,2H) 3.06(s,1H) 3.48-3.69(m, 3H) 4.31-4.96(m, 2H) 6.68(d, J=5.29Hz, 1H) 6.92-7.16 (m, 2H) 7.18-7.33(m, 1H) 7.20-7.31(m, 1H) 7.32-7.48(m, 2H) 7.48-7.65(m, 1H) 7.74(d, J=7.55Hz, 1H) 7.94(s, 1H) 8.29(s, 1H) 8.64(s, 1H) |
| 144 | 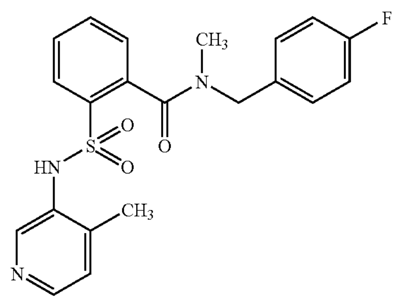 | N-(4-fluorobenzyl)-N-methyl-2-{[(4-methylpyridin-3-yl)amino]sulfonyl}benzamide | (400 MHz, CHLOROFORM-d) d ppm 2.27(s, 3H) 2.85(s, 2H) 3.07(s, 1H) 4.24-4.95(m, 2H) 6.92-7.17(m, 3H) 7.24-7.33(m, 1H) 7.36-7.50(m, 3H) 7.54-7.68(m, 2H) 7.81(s, 1H) 8.17(s, 1H) 8.29(s, 1H) |
| 145 | 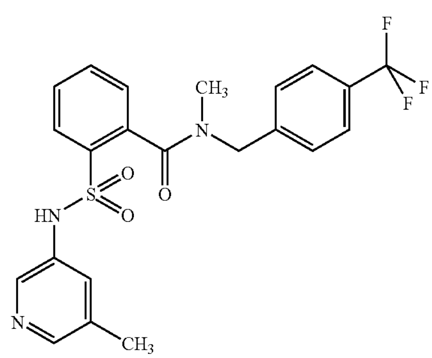 | N-methyl-2-{[(5-methylpyridin-3-yl)amino]sulfonyl}-N-[4-(trifluoromethyl)benzyl]benzamide | (400 MHz, CHLOROFORM-d) d ppm 2.28(s, 3H) 2.74-3.19(m, 3H) 4.90(d, J=43.06Hz, 1H) 7.32-7.50(m, 4H) 7.51-7.74(m, 6H) 7.88(s, 1H) 8.22(s, 2H) |
| 146 | 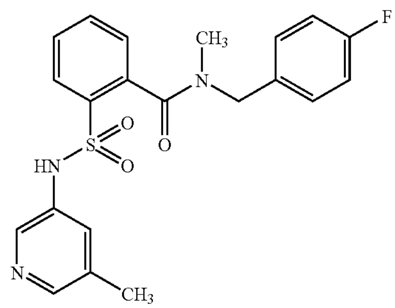 | N-(4-fluorobenzyl)-N-methyl-2-{[(5-methylpyridin-3-yl)amino]sulfonyl}benzamide | (400 MHz, CHLOROFORM-d) d ppm 2.28(s, 3H) 2.74-3.19(m, 3H) 4.90(d, J=43.06Hz, 1H) 7.32-7.50(m, 4H) 7.51-7.74(m, 6H) 7.88(s, 1H) 8.22(s, 2H) |

| Example No. | Name | ¹H NMR |
|---|---|---|
| 147 | N-(2,5-difluorobenzyl)-2-{[(5-methoxypyridin-3-yl)amino]sulfonyl}benzamide | (400 MHz, CHLOROFORM-d) d ppm 3.81(s, 3H) 4.73 (d, J=5.81Hz, 2H) 6.52(m, 1H) 7.18-7.28(m, 3H) 7.45(m, 1H) 7.49-7.58(m, 3H) 7.73(m, 1H) 7.93(m, 1H) 8.06(m, 1H) |
| 148 | N-[1-(3,4-difluorophenyl)-1-methylethyl]-2-{[(5-methoxypyridin-3-yl)amino]sulfonyl}benzamide | (400 MHz, CHLOROFORM-D) d ppm 8.16(s,1H) 8.04 (d, J=2.53Hz, 1H) 7.87(d, J=2.02Hz, 1H) 7.70(d, J=7.58Hz, 1H) 7.57-7.63 (m, 2H) 7.45(m, 1H) 7.35 (s, 1H) 7.13-7.23(m, 2H) 6.31(s, 1H) 3.79(s, 3H) 1.83(s, 6H) |
| 149 | 2-{[(5-methoxypyridin-3-yl)amino]sulfonyl}-N-(4-methylcyclohexyl)benzamide | (400 MHz, CHLOROFORM-d) d ppm 0.94(t, J=5.56Hz, 3H) 1.15(m, 2H) 1.27(m, 2H) 1.68(m, 1H) 1.71-1.83(m, 2H) 2.18(m, 1H) 3.81(s, 3H) 3.90-4.00(m, 1H) 4.27(m, 1H) 5.91-6.16 (m, 1H) 7.23(d, J=2.02Hz, 1H) 7.39-7.47(m, 1H) 7.49-7.60(m, 2H) 7.72(m, 1H) 7.96(s, 1H) 8.06 (s, 1H) 8.60(m, 1H) |
| 150 | N-(4-chloro-2-fluorobenzyl)-2-{[(5-methoxypyridin-3-yl)amino]sulfonyl}benzamide | (400 MHz, CHLOROFORM-d) d ppm 3.82(s, 3H) 4.73 (d, J=5.81Hz, 2H) 6.54(m, 1H) 7.14(dd, J=9.73, 1.89 Hz, 1H) 7.20(dd, J=8.08, 2.02Hz, 1H) 7.46(m, 1H) 7.48-7.54(m, 2H) 7.57(m, 1H) 7.74(d, J=7.83Hz, 1H) 7.95(bs, 1H) 8.05(bs, 1H) |
| 151 | N-(5-chloro-2-fluorobenzyl)-2-{[(5-methoxypyridin-3-yl)amino]sulfonyl}benzamide | (400 MHz, CHLOROFORM-d) d ppm 3.81(s, 3H) 4.73 (d, J=6.06Hz, 2H) 6.54(m, 1H) 7.05(t, J=9.09Hz, 1H) 7.21-7.31(m, 2H) 7.44(td, J=7.58, 1.52Hz, 1H) 7.51-7.60(m, 2H) 7.73(d, J=7.83Hz, 1H) 7.94(d, J=2.27Hz, 1H) 8.06(d, J=2.78Hz, 1H) |

| Example No. | Structure | Name | ¹H NMR |
|---|---|---|---|
| 152 | 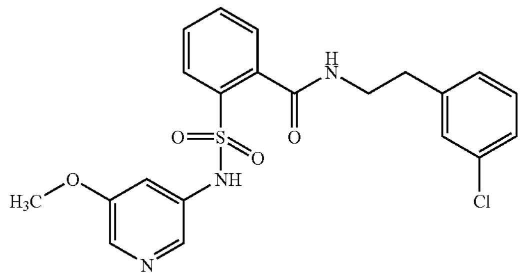 | N-[2-(3-chlorophenyl)ethyl]-2-{[(5-methoxypyridin-3-yl)amino]sulfonyl}benzamide | (400 MHz, CHLOROFORM-d) d ppm 3.00(t, J=6.82Hz, 2H) 3.74(m, 2H) 3.81(s, 3H) 6.20(t, J=5.68Hz, 1H) 7.19-7.30(m, 3H) 7.38-7.45(m, 2H) 7.49-7.57(m, 1H) 7.67-7.74(m, 1H) 7.95(d, J=2.02Hz, 1H) 8.05(d, J=2.78Hz, 1H) 8.56(s, 1H) |
| 153 | 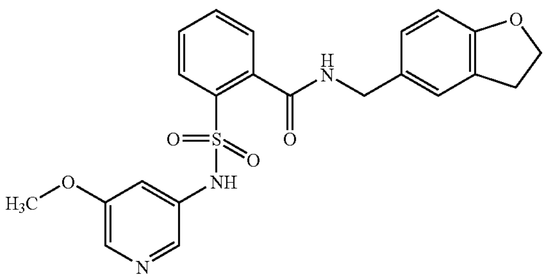 | N-(2,3-dihydro-1-benzofuran-5-ylmethyl)-2-{[(5-methoxypyridin-3-yl)amino]sulfonyl}benzamide | (400 MHz, CHLOROFORM-d) d ppm) 3.22(t, J=8.72Hz, 2H) 3.82(s, 3H) 4.58 m, 2H) 4.62(m, 2H) 6.37(s, 1H) 6.77(d, J=8.08Hz, 1H) 7.14(d, J=8.34Hz, 1H) 7.23-7.31(m, 2H) 7.39-7.47(m, 1H) 7.51-7.58(m, 2H) 7.73(d, J=7.83Hz, 1H) 7.97(d, J=1.52Hz, 1H) 8.04-8.09(m, 1H) |
| 154 | 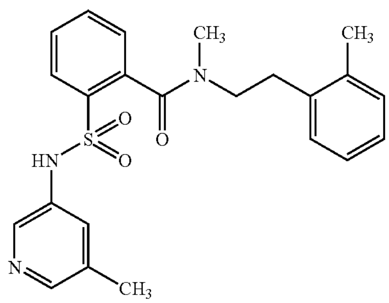 | N-methyl-N-[2-(2-methylphenyl)ethyl]-2-{[(5-methylpyridin-3-yl)amino]sulfonyl}benzamide | (400 MHz, CHLOROFORM-d) d ppm 1.84-2.06(m, 1H) 2.01-2.38(m, 3H) 2.37-2.53(m, 2H) 2.74-3.21(m, 3H) 3.29-3.55(m, 1H) 3.60-3.88(m, 1H) 6.64-6.99(m, 1H) 7.05-7.23(m, 4H) 7.27-7.45(m, 4H) 7.49-7.66(m, 2H) 7.87(d, J=49.35Hz, 1H) 8.05-8.26(m, 2H) |
| 155 | 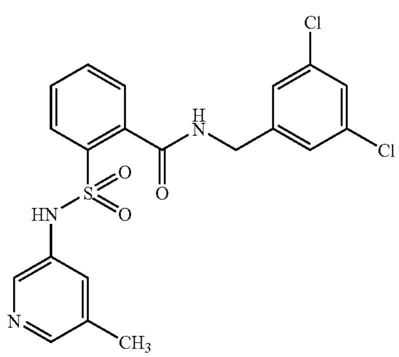 | N-(3,5-dichlorobenzyl)-2-{[(5-methylpyridin-3-yl)amino]sulfonyl}benzamide | (400 MHz, CHLOROFORM-d) d ppm 2.28(s, 3H) 4.67(d, J=5.79 Hz, 2H) 6.62(t, J=5.92Hz, 1H) 7.29-7.38(m, 3H) 7.40-7.47(m, 2H) 7.51-7.64(m, 2H) 7.70(d, J=7.81Hz, 1H) 8.17(s, 2H) 8.36(s, 1H) |
| 156 | 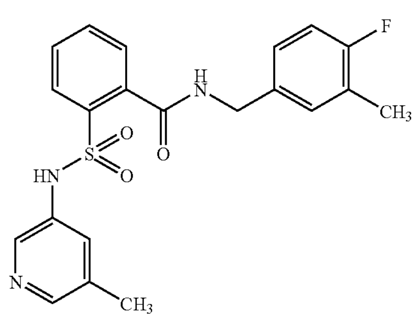 | N-(4-fluoro-3-methylbenzyl)-2-{[(5-methylpyridin-3-yl)amino]sulfonyl}benzamide | (400 MHz, CHLOROFORM-d) d ppm 2.28(s, 6H) 4.66(d, J=6.04 2H) 6.42-6.54(m, 1H) 7.04-7.15(m, 2H) 7.16-7.29(m, 1H) 7.37-7.53(m, 2H) 7.50-7.61(m, 2H) 7.70(d, J=7.55Hz, 1H) 8.17(s, 2H) 8.48(s, 1H) |

| Example No. | Structure | Name | ¹H NMR |
|---|---|---|---|
| 157 | 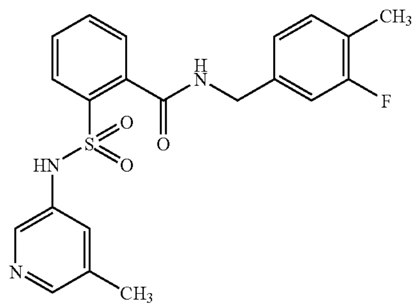 | N-(3-fluoro-4-methylbenzyl)-2-{[(5-methylpyridin-3-yl)amino]sulfonyl}benzamide | (400 MHz, CHLOROFORM-d) d ppm 2.18-2.46(m, 6H) 4.65(d, J=5.79Hz, 2H) 6.40(s, 1H) 7.01(t, J=8.81Hz, 1H) 7.16-7.25(m, 1H) 7.29(s, 1H) 7.35-7.49(m, 2H) 7.50-7.60(m, 2H) 7.72(d, J=7.55Hz, 1H) 8.18(s, 2H) 8.51(s, 1H) |
| 158 | 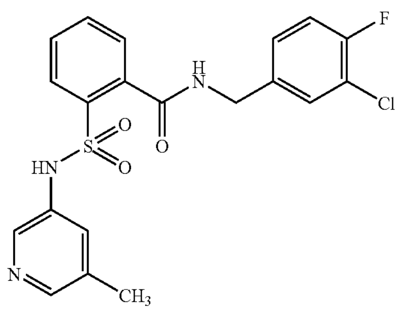 | N-(3-chloro-4-fluorobenzyl)-2-{[(5-methylpyridin-3-yl)amino]sulfonyl}benzamide | (400 MHz, CHLOROFORM-d) d ppm 2.28(s, 3H) 4.66(d, J=6.04 Hz, 2H) 6.61(t, J=5.67Hz, 1H) 7.16(t, J=8.56Hz, 1H) 7.29-7.38(m, 1H) 7.39-7.46(m, 2H) 7.49(dd, J=6.80, 2.27Hz, 1H) 7.52-7.60(m, 2H) 7.69(d, J=7.55Hz, 1H) 8.17(s, 2H) 8.42(s, 1H) |
| 159 | 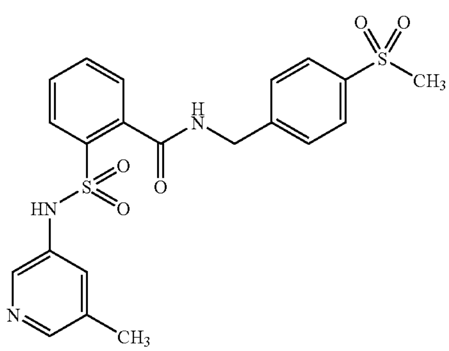 | 2-{[(5-methylpyridin-3-yl)amino]sulfonyl}-N-[4-(methylsulfonyl)benzyl]benzamide | (400 MHz, CHLOROFORM-d) d ppm 2.27(s, 3H) 3.02(s, 3H) 4.81(d, J=6.04Hz, 2H) 7.00(t, J=5.79Hz, 1H) 7.33-7.51(m, 2H) 7.52-7.72(m, 5H) 7.87(d, J=8.31Hz, 2H) 8.17(s, 2H) 8.42(s, 1H) |
| 160 | 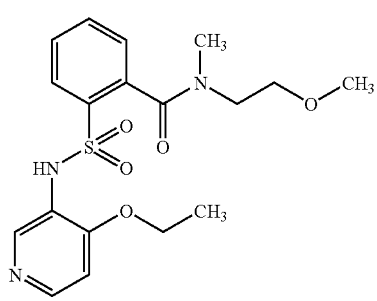 | 2-{[(4-ethoxypyridin-3-yl)amino]sulfonyl}-N-(2-methoxyethyl)-N-methylbenzamide | (400 MHz, CHLOROFORM-d) d ppm 8.61(d, J=6.04Hz, 1H) 8.25(d, J=5.29Hz, 1H) 7.99(s, 1H) 7.64-7.77(m, 1H) 7.51-7.63(m, 1H) 7.33-7.50(m, 2H) 6.64(d, J=5.54Hz, 1H) 3.50-4.00(m, 6H) 3.39-3.47(m, 2H) 3.28-3.37(m, 2H) 3.20(s, 1H) 2.99(s, 2H) 1.15(t, J=6.92Hz, 2H) |

| Example No. | Structure | Name | ¹H NMR |
|---|---|---|---|
| 161 | 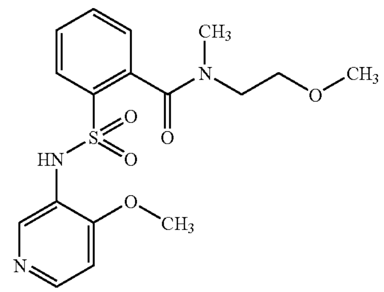 | N-(2-methoxyethyl)-2-{[(4-methoxypyridin-3-yl)amino]sulfonyl}-N-methylbenzamide | (400 MHz, CHLOROFORM-d) d ppm 8.27(d, J=4.78Hz, 1H) 8.15(s, 1H) 7.76(s, 1H) 7.53-7.66(m, 2H) 7.32-7.54(m, 2H) 7.07(d, J=5.04Hz, 1H) 3.56-3.86 (m, 3H) 3.29-3.54(m, 4H) 3.22(s, 1H) 3.03(s, 2H) 2.24(d, J=2.01Hz, 3H) LCMS ESI: 364.20 MH+ |
| 162 | 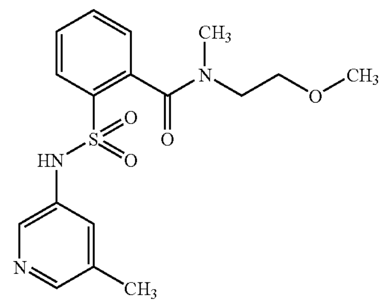 | N-(2-methoxyethyl)-N-methyl-2-{[(5-methylpyridin-3-yl)amino]sulfonyl}benzamide | (400 MHz, CHLOROFORM-d) d ppm 8.27(d, J=4.78Hz, 1H) 8.15(s, 1H) 7.76(s, 1H) 7.53-7.66(m, 2H) 7.32-7.54(m, 2H) 7.07(d, J=5.04Hz, 1H) 3.56-3.86 (m, 3H) 3.29-3.54(m, 4H) 3.22(s, 1H) 3.03(s, 2H) 2.24(d, J=2.01Hz, 3H) LCMS ESI: 364.20 MH+ |
| 163 | 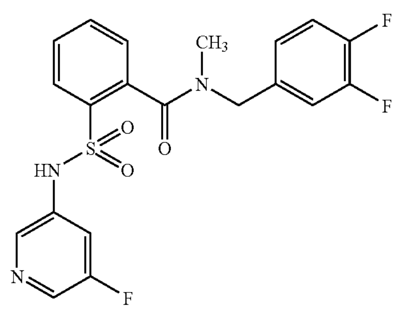 | N-(3,4-difluorobenzyl)-2-{[(5-fluoropyridin-3-yl)amino]sulfonyl}-N-methylbenzamide | (400 MHz, CHLOROFORM-d) d ppm 8.25(s, 1H) 8.20(s, 1H) 8.13(s, 1H) 7.70(d, J=7.81 Hz, 1H) 7.51-7.65(m, 1H) 7.35-7.51(m, 3H) 6.97-7.33(m, 3H) 4.27-4.95(m, 2H) 3.08(s, 1H) 2.87(s, 2H) LCMS ESI: 436.20 MH+ |
| 164 | 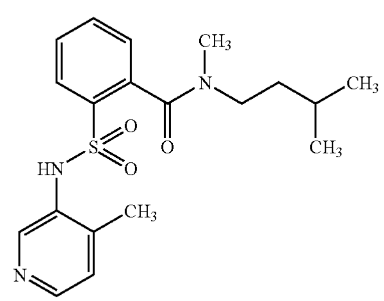 | N-methyl-N-(3-methylbutyl)-2-{[(4-methylpyridin-3-yl)amino]sulfonyl}benzamide | (400 MHz, CHLOROFORM-d) d ppm 8.27(d, J=5.04Hz, 1H) 8.13(s, 1H) 7.81(d, J=14.86Hz, 1H) 7.56-7.65 (m, 2H) 7.35-7.45(m, 2H) 7.07(d, J=4.78Hz, 1H) 3.62(s, 1H) 3.17-3.24(m, 2H) 3.16(s, 1H) 2.92(s, 2H) 2.25(d, J=3.78Hz, 3H) 1.65-1.79(m, 1H) 1.38-1.52(m, 1H) 1.01(d, J=6.04Hz, 3H) 0.78(dd, J=14.35, 6.04Hz, 3H) LCMS ESI: 376.20 MH+ |

| Example No. | Structure | Name | ¹H NMR |
|---|---|---|---|
| 165 | 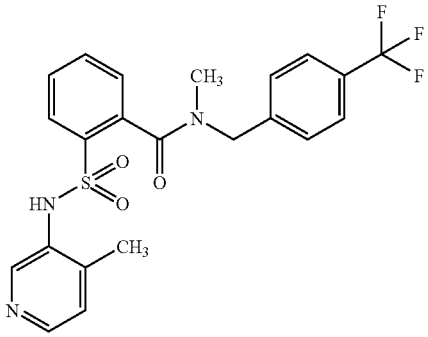 | N-methyl-2-{[(4-methylpyridin-3-yl)amino]sulfonyl}-N-[4-(trifluoromethyl)benzyl]benzamide | (400 MHz, CHLOROFORM-d) d ppm 8.29(d, J=5.04Hz, 1H) 8.10-8.20(m, 1H) 7.75(s, 1H) 7.50-7.72(m, 5H) 7.38-7.49(m, 3H) 7.10(d, J=4.78Hz, 1H) 4.47-5.08 (m, 2H) 3.11(s, 1H) 2.89 (s, 2H) 2.28(s, 3H) LCMS ESI: 464.20 MH+ |
| 166 | 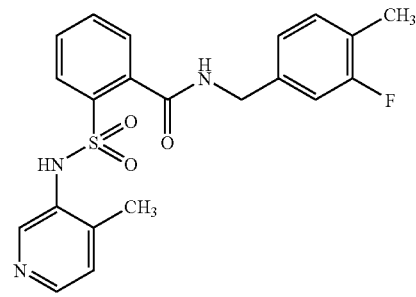 | N-(3-fluoro-4-methylbenzyl)-2-{[(4-methylpyridin-3-yl)amino]sulfonyl}benzamide | (400 MHz, CHLOROFORM-d) d ppm 7.08(s, 1H) 7.00(d, J=4.78 Hz, 1H) 6.92(s, 1H) 6.44 (d, J=7.55Hz, 1H) 6.29-6.38(m, 2H) 6.15-6.26(m, 1H) 5.94(t, J=7.68Hz, 1H) 5.77-5.90(m, 3H) 5.17-5.31(m, 1H) 3.41(d, J=5.79Hz, 2H) 1.04(s, 3H) 1.01(s, 3H) LCMS ESI: 414.20 MH+ |
| 167 | 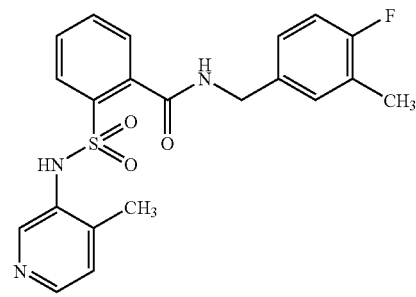 | N-(4-fluoro-3-methylbenzyl)-2-{[(4-methylpyridin-3-yl)amino]sulfonyl}benzamide | (400 MHz, CHLOROFORM-d) d ppm 8.37(s, 1H) 8.27(d, J=4.78 Hz, 1H) 8.18(s, 1H) 7.70 (d, J=7.81Hz, 1H) 7.53-7.65(m, 2H) 7.42-7.49(m, 1H) 7.24-7.31(m, 1H) 7.17-7.25(m, 1H) 7.10(d, J=5.04Hz, 1H) 6.95-7.05 (m, 1H) 6.42(t, J=5.41Hz, 1H) 4.65(d, J=5.79Hz, 2H) 2.31(s, 3H) 2.30(d, J=1.76Hz, 3H) LCMS ESI: 414.20 MH+ |
| 168 | 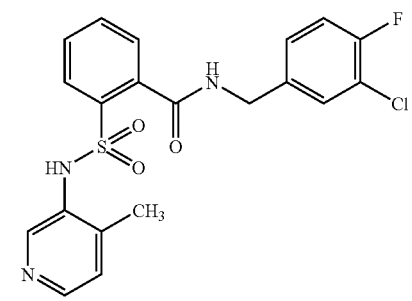 | N-(3-chloro-4-fluorobenzyl)-2-{[(4-methylpyridin-3-yl)amino]sulfonyl}benzamide | (400 MHz, CHLOROFORM-d) d ppm 8.27(d, J=4.78Hz, 2H) 8.18(s, 1H) 7.70(d, J=7.81 Hz, 1H) 7.55-7.66(m, 2H) 7.45-7.52(m, 2H) 7.32-7.40(m, 1H) 7.17(t, J=8.69 Hz, 1H) 7.10(d, J=4.78Hz, 1H) 6.52(s, 1H) 4.68(d, J=5.79Hz, 2H) 2.30(s, 3H) LCMS ESI: 434.15 MH+ |

| Example No. | Structure | Name | ¹H NMR |
|---|---|---|---|
| 169 | 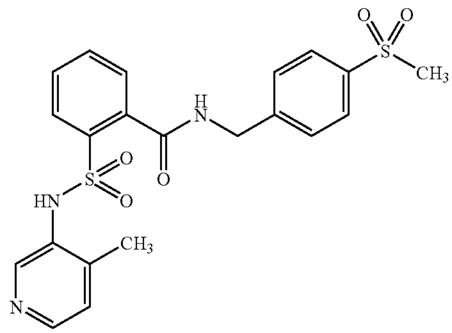 | 2-{[(4-methylpyridin-3-yl)amino]sulfonyl}-N-[4-(methylsulfonyl)benzyl]benzamide | (400 MHz, CHLOROFORM-d) d ppm 8.26(d, J=5.04Hz, 2H) 8.16(s, 1H) 7.90(d, J=8.31 Hz, 2H) 7.60-7.70(m, 5H) 7.44-7.54(m, 1H) 7.09(d, J=5.04Hz, 1H) 6.89(t, J=6.17Hz, 1H) 4.82(d, J=6.04Hz, 2H) 3.03(s, 3H) 2.28(s, 3H) LCMS ESI: 460.20 MH+ |
| 170 | 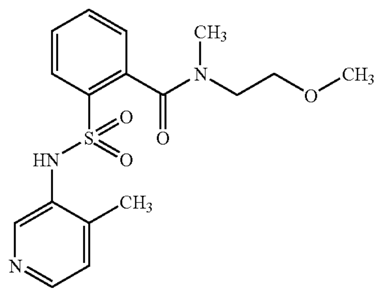 | N-(2-methoxyethyl)-N-methyl-2-{[(4-methylpyridin-3-yl)amino]sulfonyl}benzamide | (400 MHz, CHLOROFORM-d) d ppm 8.27(d, J=4.78Hz, 1H) 8.15(s, 1H) 7.76(s, 1H) 7.53-7.66(m, 2H) 7.32-7.54(m, 2H) 7.07(d, J=5.04Hz, 1H) 3.56-3.86 (m, 3H) 3.29-3.54(m, 4H) 3.22(s, 1H) 3.03(s, 2H) 2.24(d, J=2.01Hz, 3H) LCMS ESI: 364.20 MH+ |
| 171 | 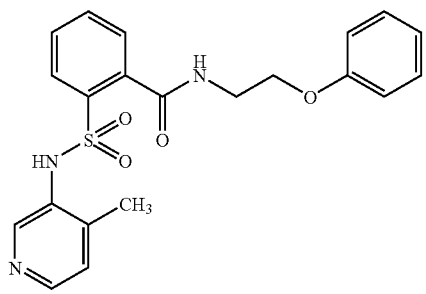 | 2-{[(4-methylpyridin-3-yl)amino]sulfonyl}-N-(2-phenoxyethyl)benzamide | (400 MHz, CHLOROFORM-d) d ppm 8.34(s, 1H) 8.28(d, J=4.78 Hz, 1H) 8.20(s, 1H) 7.71 (d, J=7.81Hz, 1H) 7.54-7.66(m, 2H) 7.43-7.53(m, 1H) 7.28-7.35(m, 2H) 7.10(d, J=4.78Hz, 1H) 7.00(t, J=7.43Hz, 1H) 6.90-6.97(m, 2H) 6.62(s, 1H) 4.23(t, J=5.04Hz, 2H) 3.96 (q, J=5.46Hz, 2H) 2.30(s, 3H) LCMS ESI: 412.20 MH+ |
| 172 | 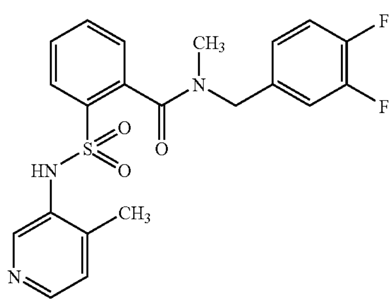 | N-(3,4-difluorobenzyl)-N-methyl-2-{[(4-methylpyridin-3-yl)amino]sulfonyl}benzamide | (400 MHz, CHLOROFORM-d) d ppm 8.30(s, 1H) 8.18(s, 1H) 7.71-7.81(m, 1H) 7.53-7.67(m, 2H) 7.37-7.49(m, 2H) 7.01-7.36(m, 4H) 4.31-4.98(m, 2H) 3.08(s, 1H) 2.88(s, 2H) 2.27(s, 3H) LCMS ESI: 432.20 MH+ |
| 173 | 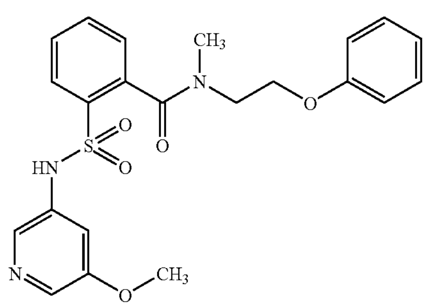 | 2-{[(5-methoxypyridin-3-yl)amino]sulfonyl}-N-methyl-N-(2-phenoxyethyl)benzamide | (400 MHz, CHLOROFORM-d) d ppm 8.07(d, J=2.27Hz, 1H) 7.92-7.99(m, 1H) 7.83-7.92(m, 1H) 7.64(d, J=8.06Hz, 1H) 7.48-7.59 (m, 2H) 7.28-7.40(m, 3H) 7.18(t, J=2.27Hz, 1H) 6.93-7.03(m, 2H) 6.87(d, J=8.56Hz, 1H) 3.82-4.44 (m, 3H) 3.77-3.81(m, 3H) 3.51-3.76(m, 1H) 3.28(s, 1H) 3.08(s, 2H) LCMS ESI: 442.20 MH+ |

| Example No. | Structure | Name | ¹H NMR |
|---|---|---|---|
| 174 | 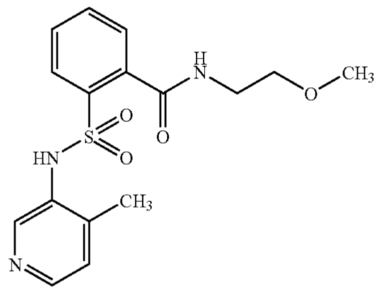 | N-(2-methoxyethyl)-2-{[(4-methylpyridin-3-yl)amino]sulfonyl}benzamide | (400 MHz, CHLOROFORM-d) d ppm 8.42(s, 1H) 8.27(d, J=4.78 Hz, 1H) 8.18(s, 1H) 7.71 (d, J=7.81Hz, 1H) 7.57-7.65(m, 2H) 7.42-7.51(m, 1H) 7.08(d, J=4.78Hz, 1H) 6.61(s, 1H) 3.67-3.76 (m, 2H) 3.64(t, J=5.04Hz, 2H) 3.35-3.43(m, 3H) 2.29(s, 3H) LCMS ESI: 350.15 MH+ |
| 175 | 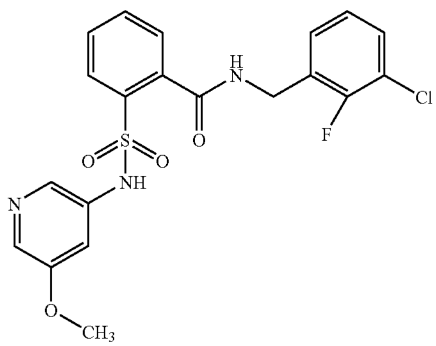 | N-(3-chloro-2-fluorobenzyl)-2-{[(5-methoxypyridin-3-yl)amino]sulfonyl}benzamide | (400 MHz, DMSO-d6) d ppm 9.87(s, 1H), 9.31(s, 1H) 7.98(d, J=2.53Hz, 1H), 7.92(d, J=2.02Hz, 1H), 7.78-7.83(m, 1H), 7.67-7.74(m, 1H), 7.60(t, J=7.20Hz, 2H), 7.52(t, J=7.45Hz, 2H), 7.24(t, J=7.83Hz, 1H), 7.11(t, J=2.27Hz, 1H), 4.57(d, J=5.56Hz, 2H), 3.74(s, 3H) |
| 176 | 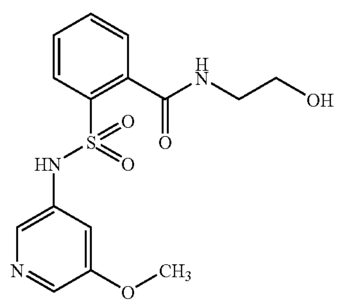 | N-(2-hydroxyethyl)-2-{[(5-methoxypyridin-3-yl)amino]sulfonyl}benzamide | (400 MHz, DMSO-d6) d ppm 9.89(s, 1H) 8.70(t, J=5.54Hz, 1H) 7.99(d, J=2.52Hz, 1H) 7.91(d, J=2.01Hz, 1H) 7.76-7.83 (m, 1H) 7.65-7.73(m, 1H) 7.53-7.62(m, 2H) 7.11(t, J=2.39Hz, 1H) 4.87(s, 1H) 3.76(s, 3H) 3.57(t, J=6.29 Hz, 2H) 3.32-3.41(m, 2H) LCMS ESI: 352.20 MH+ |
| 177 | 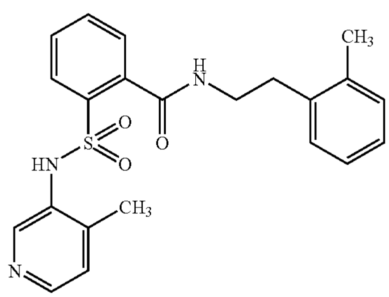 | N-[2-(2-methylphenyl)ethyl]-2-{[(4-methylpyridin-3-yl)amino]sulfonyl}benzamide | (400 MHz, CHLOROFORM-d) d ppm 8.43(s, 1H) 8.26(d, J=5.04 Hz, 1H) 8.17(s, 1H) 7.67 (d, J=7.81Hz, 1H) 7.52-7.61(m, 1H) 7.38-7.49(m, 2H) 7.22-7.29(m, 1H) 7.12-7.22(m, 3H) 7.09(d, J=5.04Hz, 1H) 6.23(s, 1H) 3.76(q, J=7.05Hz, 2H) 3.03(t, J=7.05Hz, 2H) 2.39 (s, 3H) 2.30(s, 3H) LCMS ESI: 410.20 MH+ |
| 178 | 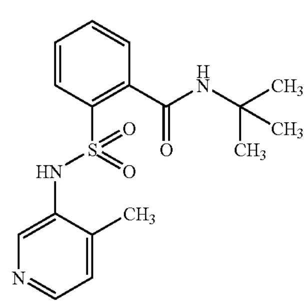 | N-(tert-butyl)-2-{[(4-methylpyridin-3-yl)amino]sulfonyl}benzamide | (400 MHz, CHLOROFORM-d) d ppm 8.37(s, 1H) 8.27(d, J=4.78 Hz, 1H) 8.12(s, 1H) 7.65 (d, J=7.81Hz, 1H) 7.50-7.63(m, 2H) 7.37-7.47(m, 1H) 7.09(d, J=4.78Hz, 1H) 5.91(s, 1H) 2.30(s, 3H) 1.48-1.57(m, 9H) LCMS ESI: 348.20 MH+ |

| Example No. | Structure | Name | $^1$H NMR |
|---|---|---|---|
| 179 | 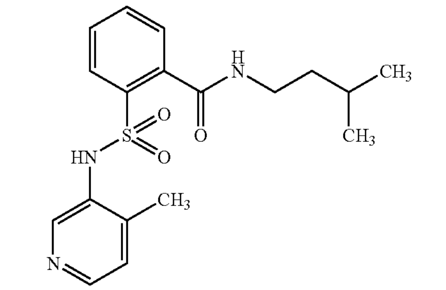 | N-(3-methylbutyl)-2-{[(4-methylpyridin-3-yl)amino]sulfonyl}benzamide | (400 MHz, CHLOROFORM-d) d ppm 8.43(s, 1H) 8.27(d, J=5.04 Hz, 1H) 8.18(s, 1H) 7.69 (d, J=8.06Hz, 1H) 7.58-7.64(m, 1H) 7.52-7.57(m, 1H) 7.41-7.50(m, 1H) 7.09(d, J=5.04Hz, 1H) 6.08(s, 1H) 3.51-3.59(m, 2H) 2.30(s, 3H) 1.68-1.81 (m, 1H) 1.50-1.68(m, 2H) 0.99(d, J=6.55Hz, 6H) LCMS ESI: 362.20 MH+ |
| 180 | 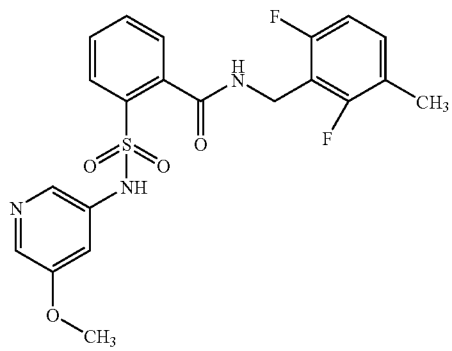 | N-(2,6-difluoro-3-methylbenzyl)-2-{[(5-methoxypyridin-3-yl)amino]sulfonyl}benzamide | (400 MHz, DMSO-d6) d ppm 9.84(s, 1H), 9.16(t, J=4.42Hz, 1H), 7.98(d, J=2.78Hz, 1H), 7.90(d, J=2.02Hz, 1H), 7.76(d, J=7.83Hz, 1H), 7.66(td, J=7.58, 1.26Hz, 1H), 7.56 (td, J=7.71, 1.52Hz, 1H), 7.43(dd, J=7.58, 1.01Hz, 1H), 7.24-7.32(m, 1H), 7.12(t, J=2.27Hz, 1H), 7.01(t, J=8.84Hz, 1H), 4.54(d, J=5.05Hz, 2H), 3.76(s, 3H), 2.22(s, 3H) |
| 181 | 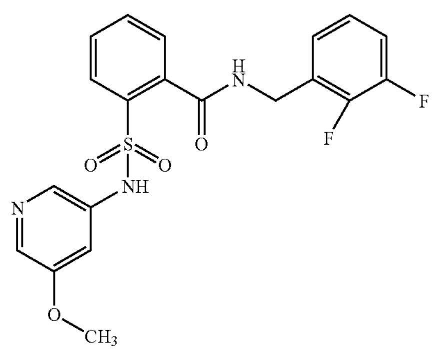 | N-(2,3-difluorobenzyl)-2-{[(5-methoxypyridin-3-yl)amino]sulfonyl}benzamide | (400 MHz, DMSO-d6) d ppm 9.85(s, 1H), 9.32(t, J=4.80Hz, 1H), 7.98(d, J=2.53Hz, 1H), 7.91(d, J=2.02Hz, 1H), 7.81(d, J=7.83Hz, 1H), 7.66-7.73 (m, 1H), 7.56-7.62(m, 2H), 7.31-7.39(m, 2H), 7.17-7.24(m, 1H), 7.11(t, J=2.40Hz, 1H), 4.58(d, J=5.81Hz, 2H), 3.72-3.76 (m, 3H) |
| 182 | 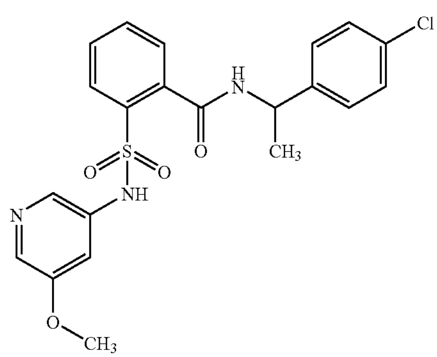 | N-[1-(4-chlorophenyl)ethyl]-2-{[(5-methoxypyridin-3-yl)amino]sulfonyl}benzamide | (400 MHz, DMSO-d6) d ppm 9.82(s, 1H), 9.22(d, J=8.08Hz, 1H), 7.98(d, J=2.53Hz, 1H), 7.91(d, J=2.27Hz, 1H), 7.80(s, 1H), 7.78(d, J=1.01Hz, 1H), 7.70(td, J=7.45, 1.26Hz, 1H) 7.52-7.61(m, 2H), 7.39-7.49(m, 4H), 7.11(t, J=2.40Hz, 1H), 5.18(qd, J=7.24, 7.07Hz, 1H), 3.74 (s, 3H), 1.44(d, J=6.82Hz, 3H) |

| Example No. | Name | 1H NMR |
|---|---|---|
| 183 | N-(2-chloro-4-fluorobenzyl)-2-{[(5-methoxypyridin-3-yl)amino]sulfonyl}benzamide | (400 MHz, DMSO-d6) d ppm 9.84(s, 1H), 9.27-9.36(m, 1H), 7.98(d, J=2.53Hz, 1H), 7.92(d, J=2.02Hz,1H), 7.83(d, J=6.82Hz, 1H), 7.81(s, 1H), 7.72(td, J=7.45, 1.26 Hz, 1H), 7.58-7.66(m, 2H), 7.48(dd, J=8.84, 2.53 Hz, 1H), 7.25(td, J=8.53, 2.65Hz, 1H), 7.12(t, J=2.40Hz, 1H), 4.54(d, J=5.56Hz, 2H), 3.75(s, 3H) |
| 184 | N-(3,5-difluorobenzyl)-2-{[(5-methoxypyridin-3-yl)amino]sulfonyl}benzamide | (400 MHz, DMSO-d6) d ppm 9.88(s, 1H), 9.33(t, J=5.81Hz, 1H), 7.99(d, J=2.53Hz, 1H), 7.93(d, J=2.02Hz, 1H), 7.82(d, J=7.83Hz, 1H), 7.72(td, J=7.45, 1.01Hz, 1H), 7.63 (dd, J=7.71, 6.19Hz, 2H), 7.59(d, J=1.52Hz, 1H), 7.09-7.19(m, 3H), 4.55(d, J=5.81Hz, 2H), 3.74(s, 3H) |
| 185 | N-(2,3-dichlorobenzyl)-2-{[(5-methoxypyridin-3-yl)amino]sulfonyl}benzamide | (400 MHz, DMSO-d6) d ppm 10.03(s, 1H), 9.34(t, J=5.81Hz, 1H), 8.04(s, 1H), 7.97(s, 1H), 7.86(d, J=7.83Hz, 1H), 7.74 (td, J=7.45, 1.26Hz, 1H), 7.62-7.68(m, 2H), 7.54-7.61(m, 2H), 7.39(t, J=7.83Hz, 1H), 7.21(d, J=2.02Hz, 1H), 4.60(d, J=5.56Hz, 2H), 4.58(s, 1H), 3.73-3.78(m, 3H) |
| 186 | N-(2-methoxybenzyl)-2-{[(5-methoxypyridin-3-yl)amino]sulfonyl}benzamide | (400 MHz, CHLOROFORM-d) d ppm 9.49(s, 1H), 8.13(d, J=1.77 Hz, 1H), 8.04(d, J=2.53Hz, 1H), 7.80(d, J=7.58Hz, 1H), 7.79(s, 1H), 7.64(d, J=1.26Hz, 1H), 7.58-7.63 (m, 2H), 7.55(s, 1H), 7.51 (qd, J=7.62, 1.14Hz, 1H), 7.40(dd, J=7.45, 1.64Hz, 1H), 7.34(td, J=7.83, 1.77 Hz, 1H), 6.97-7.02(m, 1H), 6.95(d, J=8.08Hz, 1H), 6.80(t, J=5.68Hz, 1H), 4.71(d, J=5.81Hz, 2H), 3.87-3.92(m, 6H) |

| Example No. | Structure | Name | ¹H NMR |
|---|---|---|---|
| 187 | 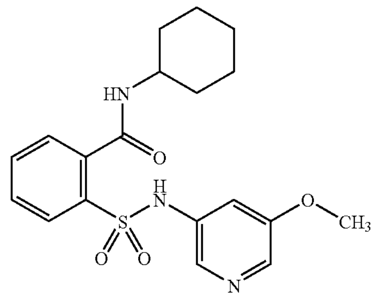 | N-cyclohexyl-2-{[(5-methoxypyridin-3-yl)amino]sulfonyl}benzamide | (400 MHz, CHLOROFORM-d) d ppm 1.17-1.28(m, 3H) 1.33-1.45(m, 2H) 1.59 (d, J=4.04Hz, 1H) 1.67-1.77(m, 2H) 2.04(s, 2H) 3.75(s, 3H) 3.90-3.99 (m, 1H) 5.91(s, 1H) 7.21(t, J=2.27Hz, 1H) 7.36(td, J=7.58, 1.52Hz, 1H) 7.41-7.47(m, 1H) 7.50(td, J=7.45, 1.26Hz, 1H) 7.65(d, J=7.83Hz, 1H) 7.91(s, 1H) 7.98(d, J=2.27Hz, 1H) 8.67(s, 1H) |
| 188 | 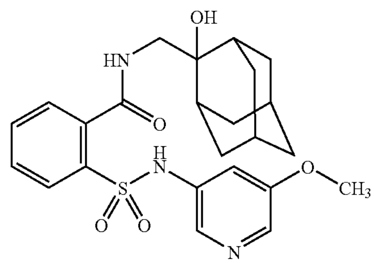 | N-[(2-hydroxy-2-adamantyl)methyl]-2-{[(5-methoxypyridin-3-yl)amino]sulfonyl}benzamide | (400 MHz, DMSO-d6) d ppm 1.45(d, J=11.62Hz, 2H) 1.62-1.71(m, 4H) 1.74-1.83(m, 4H) 1.95(d, J=12.63Hz, 2H) 2.21(d, J=11.12Hz, 2H) 3.61(d, J=5.81Hz, 2H) 3.76(s, 3H) 4.39(s, 1H) 5.76(s, 1H) 7.11(s, 1H) 7.55-7.62(m, 2H) 7.70(t, J=7.20Hz, 1H) 7.79(d, J=7.83Hz, 1H) 7.91(s, 1H) 7.99(s, 1H) 8.41(s, 1H) 9.87(s, 1H) |
| 189 | 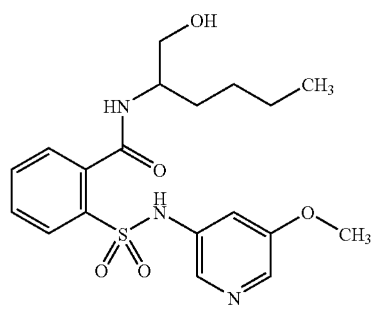 | N-[1-(hydroxymethyl)pentyl]-2-{[(5-methoxypyridin-3-yl)amino]sulfonyl}benzamide | (400 MHz, DMSO-d6) d ppm 0.76(t, J=6.95Hz, 3H) 1.16-1.25(m, 3H) 1.28(d, J=6.32Hz, 1H) 1.45-1.55 (m, 1H) 3.24-3.32(m, 1H) 3.34-3.45(m, 1H) 3.63 (s, 3H) 3.81(d, J=4.55Hz, 1H) 4.74(s, 1H) 6.97(s, 1H) 7.44(t, J=7.20Hz, 2H) 7.56(d, J=7.33Hz, 1H) 7.65(d, J=7.33Hz, 1H) 7.77(s, 1H) 7.86(s, 1H) 8.36(s, 1H) 9.72(s, 1H) |
| 190 | 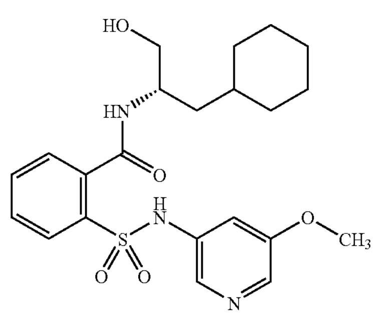 | N-[(1S)-2-cyclohexyl-1-(hydroxymethyl)ethyl]-2-{[(5-methoxypyridin-3-yl)amino]sulfonyl}benzamide | (400 MHz, CHLOROFORM-d) d ppm 0.92-1.04(m, 2H) 1.22-1.31(m, 3H) 1.42-1.53(m, 3H) 1.66-1.78 (m, 5H) 1.89(d, J=12.38 Hz, 1H) 3.69(dd, J=11.37, 6.06Hz, 1H) 3.83(s, 3H) 4.00(dd, J=11.37, 3.54Hz, 1H) 4.38(s, 1H) 6.37(d, J=8.59Hz, 1H) 7.45-7.53 (m, 1H) 7.55-7.65(m, 2H) 7.81(d, J=7.83Hz, 1H) 8.01(dd, J=1 2.00, 2.15Hz, 2H) |

-continued

| Example No. | Structure | Name | ¹H NMR |
|---|---|---|---|
| 191 | 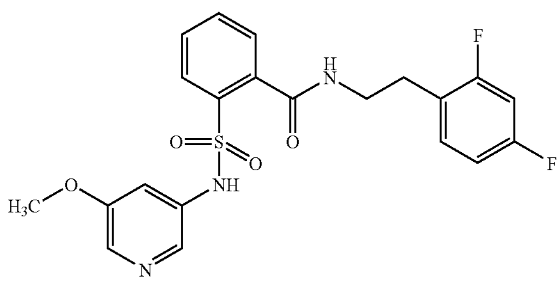 | N-[2-(2,4-difluorophenyl)ethyl]-2-{[(5-methoxypyridin-3-yl)amino]sulfonyl}benzamide | (400 MHz, CHLOROFORM-D) d ppm 8.59(bs, 1H) 8.02 (d, J=2.78Hz, 1H) 7.92(d, J=2.27Hz, 1H) 7.68(d, J=7.83Hz, 1H) 7.50-7.57 (m, 1H) 7.37-7.45(m, 2H) 7.28-7.35(m, 1H) 7.18-7.22(m, 1H) 6.79-6.87(m, 2H) 6.40(m, 1H) 3.81(s, 3H) 3.74(q, J=6.65Hz, 2H) 3.02(t, J=6.69Hz, 2H) |
| 192 | 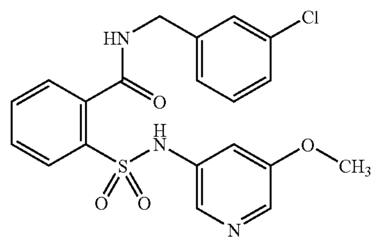 | N-(3-chlorobenzyl)-2-{[(5-methoxypyridin-3-yl)amino]sulfonyl}benzamide | (400 MHz, CHLOROFORM-d) d ppm 3.84(s, 3H) 4.71 (d, J=5.81Hz, 2H) 6.48(s, 1H) 7.28-7.31(m, 1H) 7.31-7.37(m, 3H) 7.43 (s, 1H) 7.44-7.51(m, 1H) 7.53-7.63(m, 2H) 7.76(d, J=7.58Hz, 1H) 7.98(d, J=1.77Hz, 1H) 8.07(d, J=2.27Hz, 1H) 8.61(s, 1H) |
| 193 | 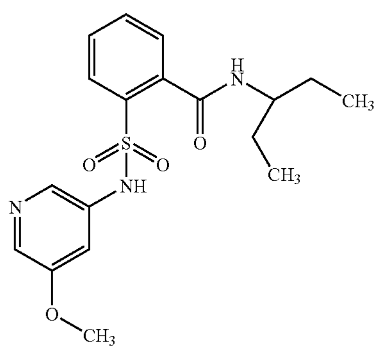 | N-(1-ethylpropyl)-2-{[(5-methoxypyridin-3-yl)amino]sulfonyl}benzamide | (400 MHz, CHLOROFORM-d) d ppm 9.45(s, 1H), 8.10(s, 1H), 8.03(d, J=2.53Hz, 1H), 7.73-7.82(m, 1H), 7.55-7.65(m, 3H), 7.47-7.53 (m, 1H), 6.08(d, J=8.84Hz, 1H), 4.00-4.09(m, 1H), 3.91(s, 3H), 1.68-1.79(m, 2H), 1.53-1.64(m, 2H), 1.03-1.08(m, 6H) |
| 194 | 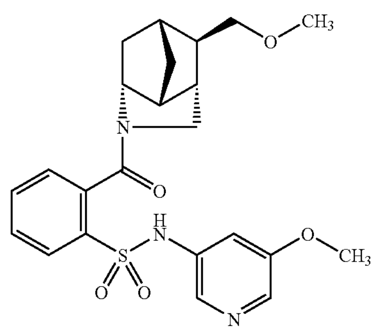 | 2-{[(3R,3aR,5R,6aR,7R)-7-(methoxymethyl)hexahydro-3,5-methanocyclopenta[b]pyrrol-1(2H)-yl]carbonyl}-N-(5-methoxypyridin-3-yl)benzenesulfonamide | (400 MHz, CHLOROFORM-d) d ppm 1.17(d, J=11.62 Hz, 1H), 1.35(d, J=10.61 Hz, 1H), 1.56-1.70(m, 2H), 1.80(s, 1H), 2.01(s, 1H), 2.05-2.14(m, 1H), 2.61-2.67(m, 1H), 3.02-3.11(m, 1H), 3.19-3.23 (m, 2H), 3.23-3.28(m, 1H 3.30(s, 1H), 3.35(d, J=7.58Hz, 1H), 3.42(s, 1H), 3.71-3.76(m, 2H), 4.30(s, 1H), 7.15-7.18(m, 1H), 7.27-7.33(m, 1H), 7.33-7.38(m, 1H), 7.44-7.53(m, 1H), 7.59(d, J=8.08Hz, 1H), 7.88-7.96 (m, 1H), 7.99(d, J=2.27Hz, 1H), 8.29(s, 1H) |

| Example No. | Structure | Name | ¹H NMR |
|---|---|---|---|
| 195 | 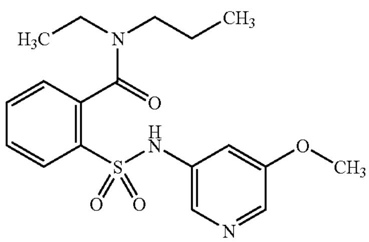 | N-ethyl-2-{[(5-methoxypyridin-3-yl)amino]sulfonyl}-N-propylbenzamide | (400 MHz, CHLOROFORM-d) δ ppm 0.81(t, J=7.45Hz, 1H), 1.06(t, J=7.45Hz, 1H), 1.18(t, J=7.20Hz, 1H), 1.35(t, J=7.07Hz, 1H), 1.52-1.65(m, 1H),1.66-1.92(m, 2H), 3.02-3.12(m, 1H), 3.14-3.27(m, 1H), 3.28-3.39(m, 1H), 3.47-3.60(m, 1H), 3.68-3.77(m, 1H), 3.83(s, 2H), 7.26(t, J=2.15Hz, 1H), 7.36-7.45(m, 2H), 7.59(t, J=7.58Hz, 1H), 7.64-7.69(m, 1H), 8.00(s, 1H), 8.09(s, 1H), 8.15(d, J=10.36 Hz, 1H) |
| 196 | 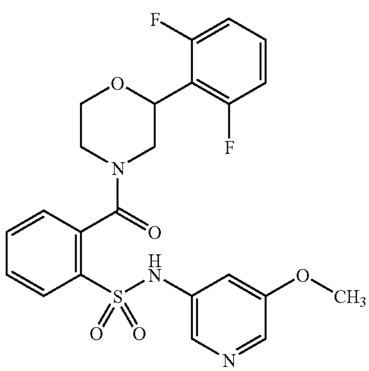 | 2-{[2-(2,6-difluorophenyl)morpholin-4-yl]carbonyl}-N-(5-methoxypyridin-3-yl)benzenesulfonamide | (400 MHz, CHLOROFORM-d) δ ppm 3.24-3.36(m, 1H), 3.38-3.51(m, 1H), 3.53-3.64(m, 1H), 3.84(d, J=1.26Hz, 1H), 3.85(s, 1H), 3.89-3.94(m, 1H), 3.96-4.01(m, 1H), 4.02-4.07(m, 1H), 4.15(dd, J=11.37, 3.54Hz, 1H), 4.29(dd, J=12.13, 3.03Hz, 1H), 4.52-4.63(m, 1H), 4.81(dd, J=12.88, 2.02Hz, 1H), 4.93-5.06(m, 1H), 5.09-5.19(m, 1H), 6.87(q, J=8.25Hz, 1H), 6.94-7.01(m, 1H), 7.30-7.37(m, 1H), 7.38-7.52(m, 1H), 7.54-7.61(m, 1H), 7.61-7.66(m, 1H), 7.68-7.74(m, 1H), 7.97-8.03(m, 1H), 8.08-8.15(m, 1H) |
| 197 | 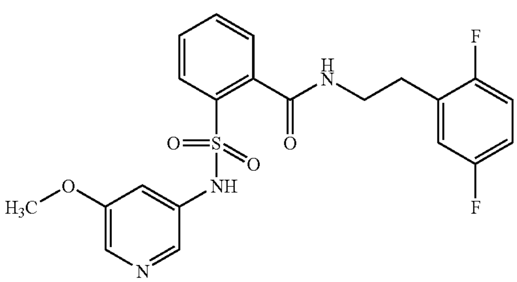 | N-[2-(2,5-difluorophenyl)ethyl]-2-{[(5-methoxypyridin-3-yl)amino]sulfonyl}benzamide | (400 MHz, CHLOROFORM-D) δ ppm 8.57(bs, 1H) 8.02(d, J=2.53Hz, 1H) 7.91(d, J=2.27Hz, 1H) 7.67(dd, J=7.83, 1.01Hz, 1H) 7.54(td, J=7.58, 1.26Hz, 1H) 7.43(m, 1H) 7.40(m, 1H) 7.15-7.22(m, 1H) 7.06(m, 1H) 6.98-7.03(m, 1H) 6.87-6.96(m, 1H) 6.48(m, 1H) 3.80(s, 3H) 3.76(q, J=6.74Hz, 2H) 3.03(t, J=6.69Hz, 2H) |
| 198 | 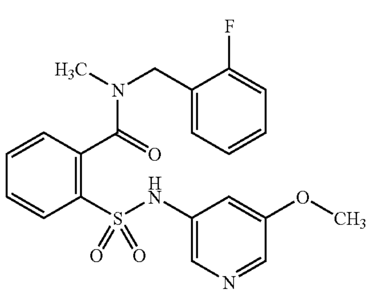 | N-(2-fluorobenzyl)-2-{[(5-methoxypyridin-3-yl)amino]sulfonyl}-N-methylbenzamide | (400 MHz, CHLOROFORM-d) δ ppm 2.91(s, 2.1H), 3.13(s, 1H), 3.84(s, 3H), 4.40-4.50(m, 0.4H), 4.56-4.65(m, 0.3H), 4.72-4.82(m, 0.7H), 5.03-5.16(m, 0.6H), 7.04-7.18(m, 1.2H), 7.20-7.27(m, 1.3H), 7.31-7.48(m, 3.5H), 7.52-7.65(m, 1.9H), 7.67-7.73(m, 1H), 7.97-8.06(m, 1.3H), 8.10(d, J=2.27Hz, 1.6H) |

-continued

| Example No. | Name | $^1$H NMR |
|---|---|---|
| 199 | N-[1-(4-chlorobenzyl)-2-hydroxyethyl]-2-{[(5-methoxypyridin-3-yl)amino]sulfonyl}benzamide | (400 MHz, DMSO-d6) d ppm 2.71(s, 1H) 2.93(s, 1H) 3.39(s, 1H) 3.51(s, 1H) 3.70(s, 3H) 4.10(s, 1H) 4.99(s, 1H) 7.04(s, 1H) 7.25-7.35(m, 5H) 7.48-7.56(m, 1H) 7.63(t, J=7.45 Hz, 1H) 7.74(d, J=7.83Hz, 1H) 7.85(s, 1H) 7.93(s, 1H) 8.59(s, 1H) 9.81(s, 1H) |
| 200 | N-(cyclohexylmethyl)-2-{[(5-methoxypyridin-3-yl)amino]sulfonyl}benzamide | (400 MHz, CHLOROFORM-d) d ppm 9.79(s, 1H), 8.09-8.20(m, 1H), 8.03(d, J=2.27Hz, 1H), 7.75-7.83 (m, 1H), 7.58-7.68(m, 2H), 7.49-7.55(m, 1H), 6.50(d, J=4.80Hz, 1H), 3.96(s, 3H), 3.32-3.40(m, 2H), 1.76-1.87(m, 4H), 1.67-1.74(m, J=10.80, 7.33, 3.69, 3.69 Hz, 2H), 1.22-1.33(m, 3H), 1.00-1.11(m, 2H) |
| 201 | N-2-adamantyl-2-{[(5-methoxypyridin-3-yl)amino]sulfonyl}benzamide | (400 MHz, CHLOROFORM-d) d ppm 1.23-1.29(m, 1H) 1.61(s, 1H) 1.73-1.81 (m, 4H) 1.84(s, 3H) 2.04 (s, 1H) 2.18(s, 2H) 3.80(s, 3H) 4.28(s, 1H) 6.38(m, 1H) 7.21-7.24(m, 1H) 7.42 (s, 1H) 7.44(d, J=7.83Hz, 1H) 7.56(d, J=1.52Hz, 1H) 7.57(dd, J=7.07, 1.26 Hz, 1H) 7.71(d, J=7.83Hz, 1H) 7.95(d, J=2.02Hz, 1H) 8.05(d, J=2.53Hz, 1H) 8.61(s, 1H) |
| 202 | 2-{[(5-methoxypyridin-3-yl)amino]sulfonyl}-N-(3-methylcyclohexyl)benzamide | (400 MHz, CHLOROFORM-d) d ppm 9.71(s, 1H), 8.11-8.20(m, 1H), 8.04(d, J=2.27Hz, 1H), 7.81(dd, J=5.81, 2.78Hz, 1H), 7.79(s, 1H), 7.71(d, J=2.27 Hz, 1H), 7.56-7.68(m, 2H), 7.49-7.54(m, 1H), 6.23(t, J=6.69Hz, 1H), 3.91-4.02(m, 3H), 2.16(d, J=2.02Hz, 1H), 2.14(d, J=4.04Hz, 1H), 1.79-1.90 (m, 1H), 1.71(s, 1H), 1.60 (s, 1H), 1.58(d, J=2.02Hz, 1H), 1.40-1.52(m, 1H), 0.94-1.01(m, 3H), 0.83-0.94(m, 1H) |

| Example No. | Structure | Name | ¹H NMR |
|---|---|---|---|
| 203 | 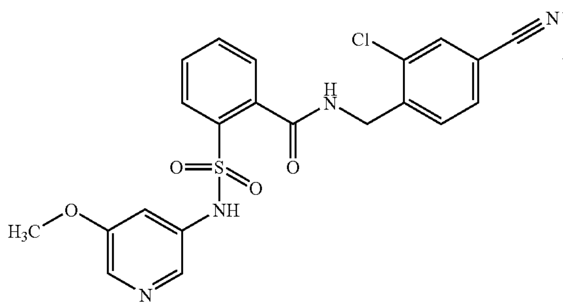 | N-(2-chloro-4-cyanobenzyl)-2-{[(5-methoxypyridin-3-yl)amino]sulfonyl}benzamide | (400 MHz, CHLOROFORM-d) d ppm 3.80(s, 3H) 4.83 (d, J=6.06Hz, 2H) 7.00-7.08(m, 1H) 7.18(m, 1H) 7.39-7.46(m, 1H) 7.55-7.64(m, 3H) 7.67-7.73(m, 2H) 7.77(m, 1H) 7.86(d, J=2.02Hz, 1H) 8.01(d, J=2.53Hz, 1H) |
| 204 | 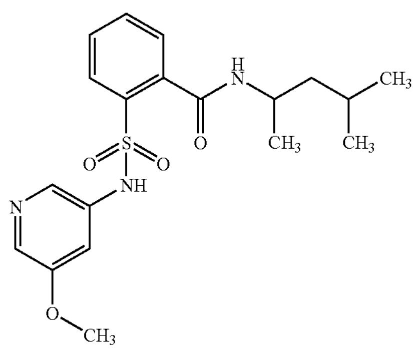 | N-(1,3-dimethylbutyl)-2-{[(5-methoxypyridin-3-yl)amino]sulfonyl}benzamide | (400 MHz, DMSO-d6) d ppm 9.75(s, 1H), 8.59 (d, J=8.08Hz, 1H), 8.00(d, J=2.53Hz, 1H), 7.91(d, J=2.02Hz, 1H), 7.74(d, J=7.83Hz, 1H), 7.69(t, J=7.07Hz, 1H), 7.56(t, J=7.20Hz, 1H), 7.49(d, J=7.33Hz, 1H), 7.12(t, J=2.40Hz, 1H), 4.05-4.15 (m, 1H), 3.76(s, 3H) 1.68-1.79(m, 1H), 1.45-1.55 (m, 1H), 1.23(ddd, J=13.58, 8.40, 5.56Hz, 1H), 1.15(d, J=6.57Hz, 3H), 0.91(dd, J=9.60, 6.57Hz, 6H) |
| 205 | 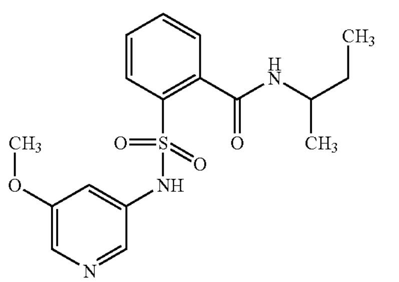 | N-(sec-butyl)-2-{[(5-methoxypyridin-3-yl)amino]sulfonyl}benzamide | (400 MHz, CHLOROFORM-d) d ppm 1.04m, 3H) 1.31 (m, 3H) 1.66(m, 2H) 3.80 (s, 3H) 4.08-4.19(m, 1H) 6.02(m, 1H) 7.21 m, 1H) 7.38-7.46(m, 1H) 7.49-7.58(m, 2H) 7.70(m, 1H) 7.94(m, 1H) 8.04(m, 1H) 8.64(s, 1H) |
| 206 | 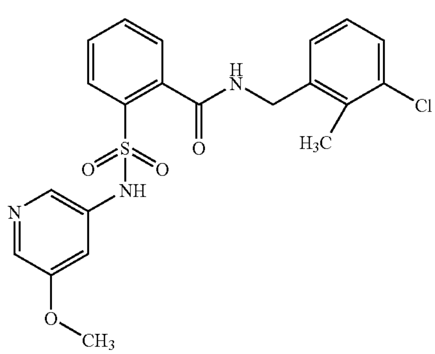 | N-(3-chloro-2-methylbenzyl)-2-{[(5-methoxypyridin-3-yl)amino]sulfonyl}benzamide | (400 MHz, CHLOROFORM-d) d ppm 7.98(s, 2H), 7.75 (d, J=8.08Hz, 1H), 7.56-7.63(m, 2H), 7.44-7.50 (m, 1H), 7.41(s, 1H), 7.33(dd, J=11.62, 7.83Hz, 2H), 7.16(t, J=7.71Hz, 1H), 6.73(s, 1H), 4.73(d, J=5.56Hz, 2H), 3.86(s, 3H), 2.47(s, 3H) |

| Example No. | Structure | Name | ¹H NMR |
|---|---|---|---|
| 207 | 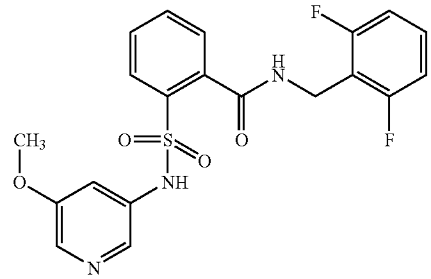 | N-(2,6-difluorobenzyl)-2-{[(5-methoxypyridin-3-yl)amino]sulfonyl}benzamide | (400 MHz, CHLOROFORM-d) d ppm 3.81(s, 3H) 4.74 (d J=6.06Hz, 2H) 6.5(m, 1H) 6.98-7.10(m, 2H) 7.16-7.23(m, 1H) 7.45(m, 1H) 7.52-7.61(m, 3H) 7.74(d, J=7.83Hz, 1H) 7.94(d, J=2.27Hz, 1H) 8.06(d, J=2.78Hz, 1H) |
| 208 | 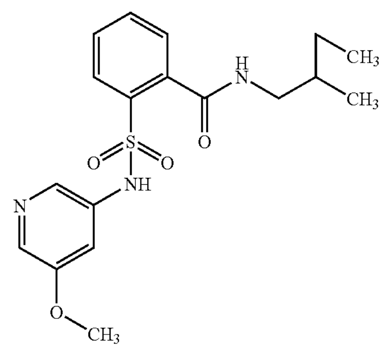 | 2-{[(5-methoxypyridin-3-yl)amino]sulfonyl}-N-(2-methylbutyl)benzamide | (400 MHz, DMSO-d6) d ppm 9.77(s, 1H), 8.76(t, J=5.56Hz, 1H), 8.00(d, J=2.53Hz, 1H), 7.91(d, J=2.02Hz, 1H), 7.76(d, J=7.83Hz, 1H), 7.69(t, J=7.45Hz, 1H), 7.51-7.59 (m, 2H), 7.12(t, J=2.27Hz, 1H), 3.76(s, 3H), 3.21 (ddd, J=12.88, 6.32, 6.06 Hz, 1H), 3.08(dt, J=13.14, 6.57Hz, 1H), 1.68(dt, J=19.39, 6.73Hz, 1H), 1.41-1.52(m, 1H), 1.16(ddd, J=13.89, 7.33, 7.07Hz, 1H), 0.89-0.93(m, 6H) |
| 209 | 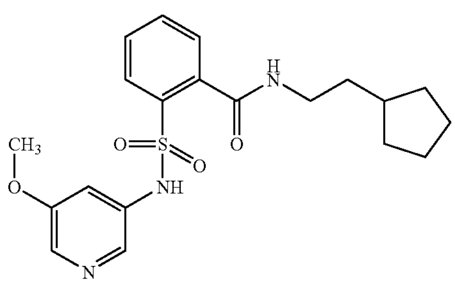 | N-(2-cyclopentylethyl)-2-{[(5-methoxypyridin-3-yl)amino]sulfonyl}benzamide | (400 MHz, CHLOROFORM-d) d ppm 1.18(dd, J=11.62, 7.58Hz, 2H) 1.26(t, J=7.07 Hz, 1H) 1.54-1.60(m, 1H) 1.62-1.73(m, 4H) 1.81-1.92(m, 3H) 3.52(td, J=7.33, 6.06Hz, 2H) 3.80 (s, 3H) 6.28(m, 1H) 7.20(t, J=2.40Hz, 1H) 7.40(td, J=7.52, 1.64Hz, 1H) 7.53 (qd, J=7.37, 1.39Hz, 2H) 7.68(d, J=7.07Hz, 1H) 7.94(d, J=2.02Hz, 1H) 8.04(d, J=2.78Hz, 1H) 8.66(s, 1H) |
| 210 | 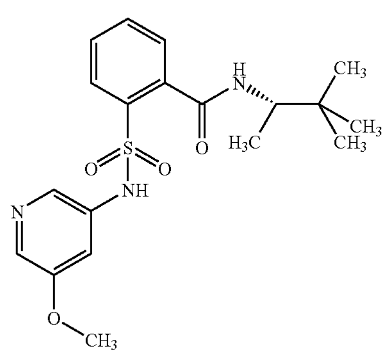 | 2-{[(5-methoxypyridin-3-yl)amino]sulfonyl}-N-[(1S)-122-trimethylpropyl]benzamide | (400 MHz, CHLOROFORM-d) d ppm 8.16(d, J=2.02Hz, 1H), 8.05(d, J=2.53Hz, 1H), 7.81(s, 1H), 7.79(d, J=1.01Hz,1H), 7.70(s, 1H), 7.67(td, J=7.77, 1.64 Hz, 2H), 7.49-7.59(m, 1H), 6.13(d, J=9.85Hz, 1H), 4.10-4.17(m, 1H), 3.94(s, 3H), 1.23-1.28(m, 3H), 1.00-1.06(m, 9H) |

| Example No. | Structure | Name | $^1$H NMR |
|---|---|---|---|
| 211 | 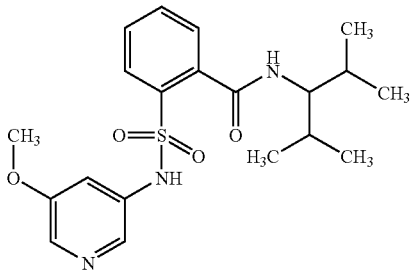 | N-(1-isopropyl-2-methylpropyl)-2-{[(5-methoxypyridin-3-yl)amino]sulfonyl}benzamide | (400 MHz, CHLOROFORM-d) d ppm 0.99-1.09(m, 12H) 1.90-2.00(m, 2H) 3.81(s, 3H) 3.82-3.87(m, 1H) 5.85(m, 1H) 7.20-7.25(m, 1H) 7.26(s, 1H) 7.40-7.49(m, 1H) 7.54-7.61(m, 2H) 7.76(d, J=8.08Hz, 1H) 7.96(d, J=2.02Hz, 1H) 8.04(d, J=2.53Hz,1H) 8.76(s, 1H) |
| 212 | 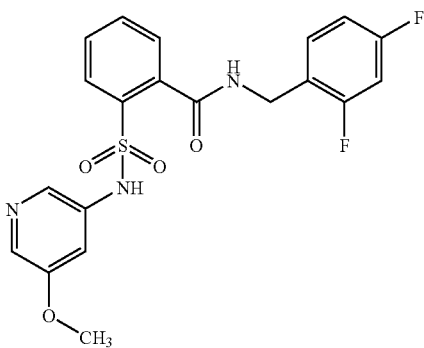 | N-(2,4-difluorobenzyl)-2-{[(5-methoxypyridin-3-yl)amino]sulfonyl}benzamide | (400 MHz, CHLOROFORM-d ppm 8.00(s, 2H), 7.74 (d, J=7.83Hz, 1H), 7.56-7.63(m, 2H), 7.51-7.54 (m, 1H), 745-7.50(m, 1H), 7.42(t, J=2.27Hz, 1H), 6.89-6.95(m, 2H), 6.83-6.89(m, 1H), 4.72(d, J=6.06Hz, 2H), 3.87(s, 3H) |
| 213 | 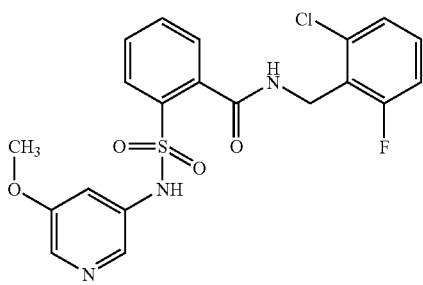 | N-(2-chloro-6-fluorobenzyl)-2-{[(5-methoxypyridin-3-yl)amino]sulfonyl}benzamide | (400 MHz, CHLOROFORM-d) d ppm 3.80(s, 3H) 4.90 (d, J=5.56Hz, 2H) 6.52(m, 1H) 7.03-7.12(m, 1H) 7.21(m. 1H) 7.25-7.33(m, 1H) 7.41(td, J=7.58, 1.52 Hz, 1H) 7.48-7.56(m, 2H) 7.70(d, J=7.83Hz, 1H) 7.94(d, J=2.02Hz, 1H) 8.04(d, J=2.53Hz, 1H) |
| 214 | 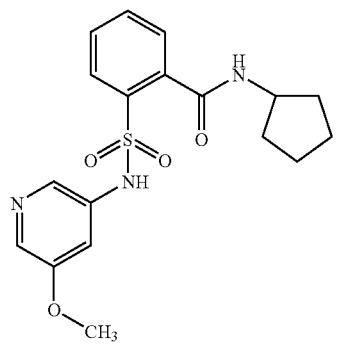 | N-cyclopentyl-2-{[(5-methoxypyridin-3-yl)amino]sulfonyl}benzamide | (400 MHz, CHLOROFORM-d) d ppm 8.03-8.09(m, 1H), 7.96(t, J=1.89Hz, 1H), 7.70(d, J=7.83Hz, 1H), 7.48-7.59(m, 2H), 7.38-7.45(m, 1H), 7.22(q, J=2.27Hz, 1H), 6.13(d, J=6.57Hz, 1H), 4.43(td, J=12.69, 5.68Hz, 1H), 3.81 (d, J=2.02Hz, 3H), 3.58-3.65(m, 1H), 2.10-2.19(m, 2H), 1.96-2.06(m, 2H), 1.83-1.94(m, 1H), 1.69-1.78(m, 2H), 1.61-1.67 (m, 2H) |

| Example No. | Structure | Name | ¹H NMR |
|---|---|---|---|
| 215 | 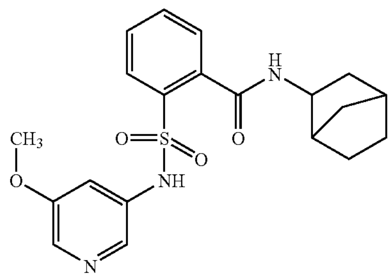 | N-bicyclo[2.2.1]hept-2-yl-2-{[(5-methoxypyridin-3-yl)amino]sulfonyl}benzamide | (400 MHz, CHLOROFORM-d) d ppm 1.00-1.12(m, 3H) 1.16-1.26(m, 1H) 1.27-1.36(m, 1H) 1.37-1.48 (m, 3H) 1.53(m, 1H) 1.58-1.67(m, 1H) 1.90-1.97(m, 1H) 2.21(bs, 1H) 2.36(bs, 1H) 2.47(m, 1H) 2.80(m, 1H) 3.31(s, 1H) 3.80(s, 3H) 3.94 m, 1H) 6.10(m, 1H) 7.20(t, J=2.40Hz, 1H) 7.37-(m, 1H) 7.47-7.51 (m, 1H) 7.55(t, J=7.45Hz, 1H) 7.68(d, J=7.83Hz, 1H) 7.95(d, J=2.02Hz, 1H) 8.04(d, J=2.78Hz, 1H) |
| 216 | 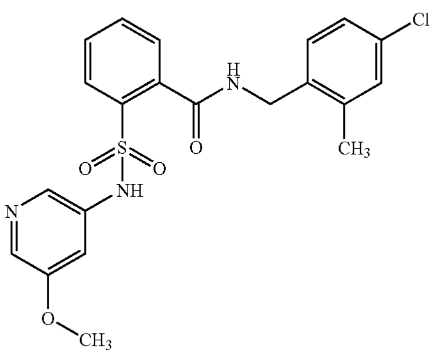 | N-(4-chloro-methylbenzyl)-2-{[(5-methoxypyridin-3-yl)amino]sulfonyl}benzamide | (400 MHz, CHLOROFORM-d) d ppm 7.96(s, 2H), 7.73 (d J=7.58Hz, 1H), 7.57-7.63(m, 2H), 7.47(td, J=5.43, 2.78Hz, 1H), 7.40(d, J=2.02Hz, 1H), 7.33(d, J=8.08Hz, 1H), 7.20(s, 1H), 7.15-7.19(m, 1H), 6.77(t, J=5.31Hz, 1H), 4.66(d, J=5.56Hz, 2H), 3.84-3.89(m, 3H), 2.41(s, 3H) |
| 217 | 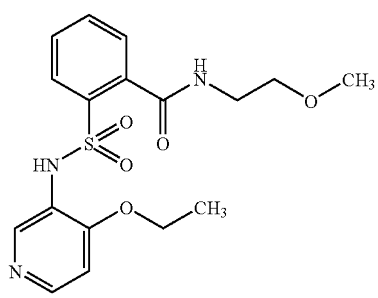 | 2-{[(4-ethoxypyridin-3-yl)amino]sulfonyl}-N-(2-methoxyethyl)benzamide | (400 MHz, CHLOROFORM-d) d ppm 8.64(s, 2H) 8.25(d, J=5.54 Hz, 1H) 7.77(d, J=7.81Hz, 1H) 7.51-7.67(m, 2H) 7.37-7.51(m, 1H) 6.54-6.87(m, 2H) 3.88(q, J=6.88Hz, 2H) 3.59-3.76 (m, 4H) 3.29-3.44(m, 3H) 1.09-1.22(m, 3H) |
| 218 | 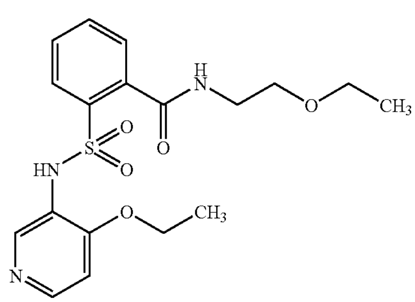 | N-(2-ethoxyethyl)-2-{[(4-ethoxypyridin-3-yl)amino]sulfonyl}benzamide | (400 MHz, CHLOROFORM-d) d ppm 8.65(s, 2H) 8.26(d, J=5.54 Hz, 1H) 7.76(d, J=8.31Hz, 1H) 7.50-7.65(m, 2H) 7.30-7.49(m, 1H) 6.36-6.80(m, 2H) 3.87(q, J=6.88Hz, 2H) 3.64-3.76 (m, 4H) 3.58(q, J=6.97Hz, 2H) 1.04-1.26(m, 6H) |

| Example No. | Structure | Name | ¹H NMR |
|---|---|---|---|
| 219 | 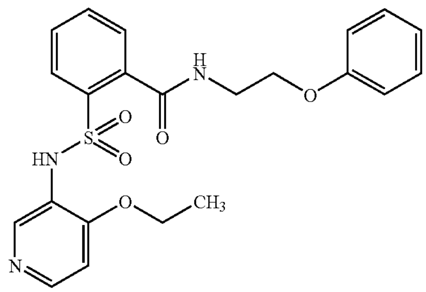 | 2-{[(4-ethoxypyridin-3-ylamino]sulfonyl}-N-(2-phenoxyethyl)benzamide | (400 MHz, CHLOROFORM-d) d ppm 8.65(s, 1H) 8.60-8.60(m, 1H) 8.25(d, J=5.79Hz, 1H) 7.77(d, J=8.06Hz, 1H) 7.51-7.62(m, 2H) 7.38-7.49(m, 1H) 7.20-7.34(m, 2H) 6.88-7.03(m, 3H) 6.64(d, J=5.54Hz, 2H) 4.23(t, J=5.04Hz, 2H) 3.72-4.03(m, 4H) 0.89-1.25 (m, 3H) |
| 220 | 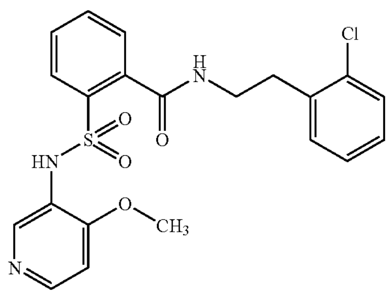 | N-[2-(2-chlorophenyl)ethyl]-2-{[(4-methoxypyridin-3-yl)amino]sulfonyl}benzamide | (400 MHz, CHLOROFORM-d) d ppm 8.42(dd, J=4.66, 1.38Hz, 1H) 8.36(d, J=1.76Hz, 1H) 7.42-7.52(m, 1H) 7.11-7.24(m, 2H) 6.75(dd, J=7.43, 5.92Hz, 2H) 5.85 (s, 1H) 4.44-4.66(m, 1H) 4.03(q, J=7.05Hz, 2H) 2.87-3.00(m, 4H) 2.34-2.49(m, 2H) 1.80-1.92(m, 2H) 1.71-1.81(m, 2H) 1.31-1.44(m, 3H) LCMS ESI: 446.10 MH+ |
| 221 | 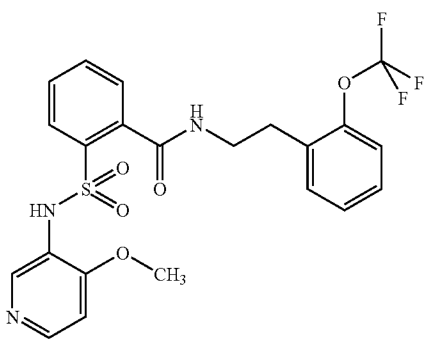 | 2-{[(4-methoxypyridin-3-yl)amino]sulfonyl}-N-{2-[2-(trifluoromethoxy) phenyl]ethyl}benzamide | (400 MHz, CHLOROFORM-d) d ppm 8.63(s, 1H) 8.48-8.58(m, 1H) 8.26(d, J=5.54Hz, 1H) 7.72-7.82(m, 1H) 7.50-7.59(m, 1H) 7.39-7.47 (m, 3H) 7.19-7.31(m, 3H) 6.67(d, J=5.79Hz, 1H) 6.07-6.25(m, 1H) 3.77(q, J=6.80Hz, 2H) 3.47-3.67 (m, 3H) 3.09(t, J=6.92Hz, 2H) |
| 222 | 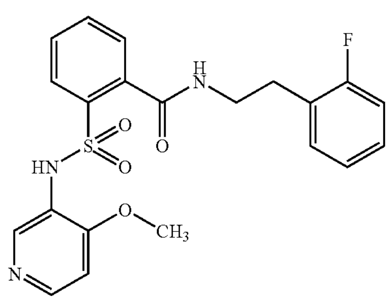 | N-[2-(2-fluorophenyl)ethyl]-2-{[(4-methoxypyridin-3-ylamino]sulfonyl}benzamide | (400 MHz, CHLOROFORM-d) d ppm 8.63(s, 1H) 8.49-8.59(m, 1H) 8.26(d, J=5.79Hz, 1H) 7.75-7.81(m, 1H) 7.49-7.59(m, 1H) 7.39-7.46 (m, 2H) 7.30-7.38(m, 1H) 7.18-7.28(m, 3H) 6.98-7.14(m, 2H) 3.78(q, J=6.55Hz, 2H) 3.54-3.63 (m, 3H) 3.06(t, J=6.67Hz, 2H) |
| 223 | 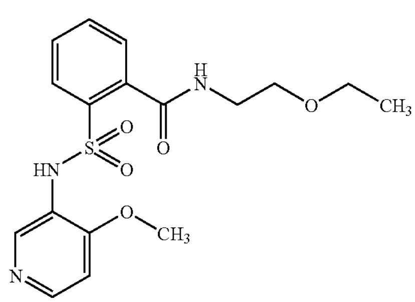 | N-(2-ethoxyethyl)-2-{[(4-methoxypyridin-3-yl)amino]sulfonyl}benzamide | (400 MHz, CHLOROFORM-d) d ppm 8.64(s, 2H) 8.28(d, J=5.54 Hz, 1H) 7.79(d, J=7.81Hz, 1H) 7.51-7.69(m, 2H) 7.37-7.50(m, 1H) 6.86(s, 1H), 6.67(d, J=5.54Hz, 1H) 3.67-3.75(m, 4H) 3.52-3.63(m, 5H) 1.06-1.24 (m, 3H) |

| Example No. | Structure | Name | ¹H NMR |
|---|---|---|---|
| 224 | 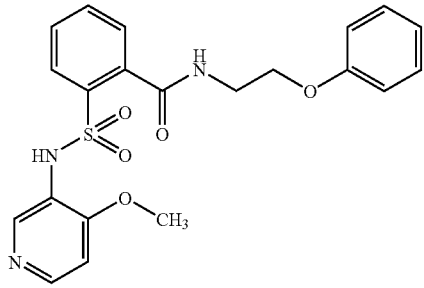 | 2-{[(4-methoxypyridin-3-yl)amino]sulfonyl}-N-(2-phenoxyethyl)benzamide | (400 MHz, CHLOROFORM-d) d ppm 8.63(s, 1H) 8.48(s, 1H) 8.26(d, J=5.54Hz, 1H) 7.79(d, J=7.55Hz, 1H) 7.53-7.63(m, 2H) 7.40-7.49(m, 1H) 7.23-7.34(m, 2H) 6.88-7.01(m, 3H) 6.72-6.81(m, 1H) 6.65(d, J=5.54Hz, 1H) 4.09-4.28 (m, 2H) 3.94(q, J=5.46Hz, 2H) 3.25-3.71(m, 3H) |
| 225 | 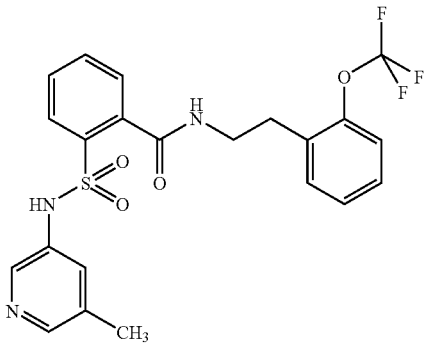 | 2-{[(5-methylpyridin-3-yl)amino]sulfonyl}-N-{2-[2-(trifluoromethoxy)phenyl]ethyl}benzamide | (400 MHz, CHLOROFORM-d) d ppm 8.54(s, 1H) 8.17(dd, J=5.29, 1.76Hz, 2H) 7.69 (d, J=7.81Hz, 1H) 7.49-7.57(m, 1H) 7.37-7.47(m, 4H) 7.23-7.33(m, 3H) 6.22(t, J=5.92Hz, 1H) 3.78 (q, J=6.80Hz, 2H) 3.10(t, J=6.92Hz, 2H) 2.28(s, 3H) |
| 226 | 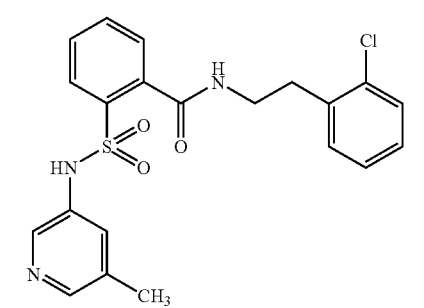 | N-[2-(2-chlorophenyl)ethyl]-2-{[(5-methylpyridin-3-yl)amino]sulfonyl}benzamide | (400 MHz, CHLOROFORM-d) d ppm 8.57(s, 1H) 8.16(d, J=4.28 Hz 2H) 7.69(d, J=7.81Hz, 1H) 7.53(t, J=7.43Hz, 1H) 7.36-7.47(m, 5H) 7.11-7.26(m, 2H) 6.14-6.32(m, 1H) 3.81(q, J=6.55Hz, 2H) 3.16(t, J=6.67Hz, 2H) 2.28(s, 3H) |
| 227 | 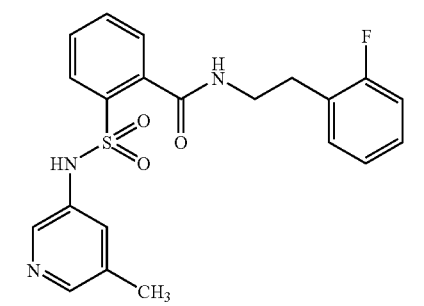 | N-[2-(2-fluorophenyl)ethyl]-2-{[(5-methylpyridin-3-yl)amino]sulfonyl}benzamide | (400 MHz, CHLOROFORM-d) d ppm 8.55(s, 1H) 8.17(dd, J=4.91, 1.89Hz, 2H) 7.69 (d, J=7.81Hz, 1H) 7.52-7.55(m, 1H) 7.46(s, 1H) 7.30-7.43(m, 3H) 7.21-7.29(m, 1H) 7.04-7.15(m, 2H) 6.21(s, 1H) 3.79(q, J=6.55Hz, 2H) 3.07(t, J=6.67Hz, 2H) 2.28(s, 3H) |

| Example No. | Structure | Name | $^1$H NMR |
|---|---|---|---|
| 228 | 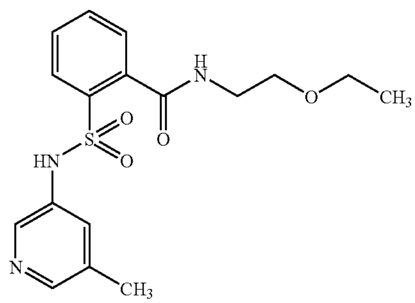 | N-(2-ethoxyethyl)-2-{[(5-methylpyridin-3-yl)amino]sulfonyl}benzamide | (400 MHz, CHLOROFORM-d) d ppm 8.75(s, 1H) 8.17(s, 2H) 7.77(d, J=7.55Hz, 1H) 7.53-7.61(m, 2H) 7.37-7.47(m, 2H) 6.72(s, 1H) 3.66-3.80(m, 4H) 3.59(q, J=7.05Hz, 2H) 2.26(s, 3H) 1.13-1.35(m, 3H) |
| 229 | 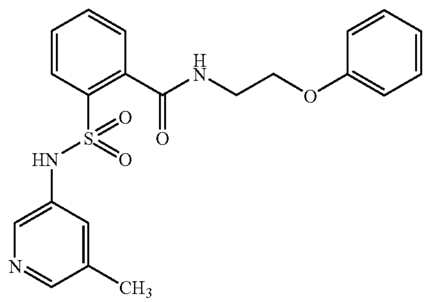 | 2-{[(5-methylpyridin-3-yl)amino]sulfonyl}-N-(2-phenoxyethyl)benzamide | (400 MHz, CHLOROFORM-d) d ppm 8.52(s, 1H) 8.05-8.27(m, 2H) 7.72(d, J=7.55Hz, 1H) 7.51-7.65(m, 2H) 7.40-7.47(m, 2H) 7.28-7.35(m, 2H) 6.89-7.03(m, 3H) 6.63(s, 1H) 4.24(t, J=5.04Hz, 2H) 3.95(q, J=5.20Hz, 2H) 2.12-2.40(m, 3H) |
| 230 | 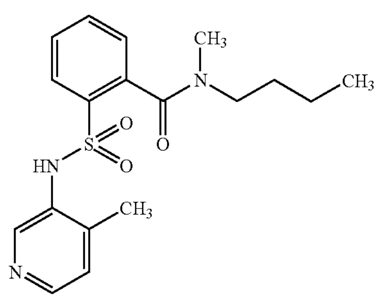 | N-butyl-N-methyl-2-{[(4-methylpyridin-3-yl)amino]sulfonyl}benzamide | (400 MHz, CHLOROFORM-d) d ppm 8.27(d, J=4.78Hz, 1H) 8.14(s, 1H) 7.81(d, J=10.07Hz, 1H) 7.57-7.66(m, 2H) 7.36-7.45(m, 2H) 7.07(d, J=5.04Hz, 1H) 3.53-3.67(m, 1H) 3.17-3.24(m, 1H) 3.16(s, 1H) 2.93(s, 2H) 2.25(d, J=3.27 Hz, 3H) 1.37-1.86(m, 3H) 1.14-1.30(m, 1H) 1.02(t, J=7.30Hz, 3H) LCMS ESI: 362.20 MH+ |
| 231 | 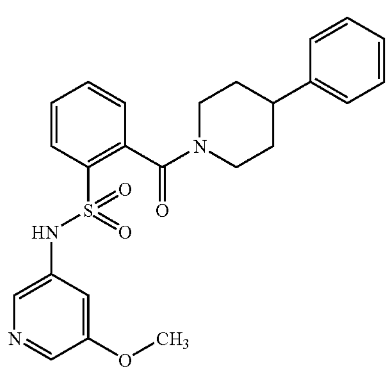 | N-(5-methoxypyridin-3-yl)-2-[(4-phenylpiperidin-1-yl)carbonyl]benzenesulfonamide | (400 MHz, CHLOROFORM-d) d ppm 8.19(s, 1H) 8.08(d, J=2.52 Hz, 1H) 7.97(d, J=2.01Hz, 1H) 7.62-7.71(m, 1H) 752-7.62(m, 1H) 7.28-7.47(m, 4H) 7.17-7.29(m, 4H) 4.71-5.04(m, 1H) 3.76-3.85(m, 3H) 3.57-3.75(m, 1H) 3.12-3.34(m, 1H) 2.89-3.08(m, 1H) 2.68-2.90(m, 1H) 1.51-2.19(m, 4H) LCMS ESI: 452.20 MH+ |

| Example No. | Structure | Name | ¹H NMR |
|---|---|---|---|
| 232 | 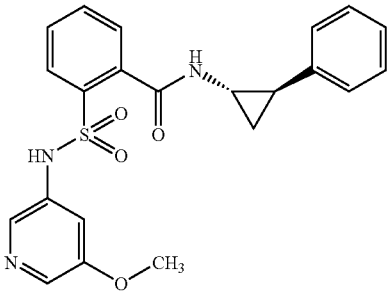 | 2-{[(5-methoxypyridin-3-yl)amino]sulfonyl}-N-[(1S2R)-2-phenylcyclopropyl]benzamide | (400 MHz, CHLOROFORM-d) d ppm 8.46(s, 1H) 8.06(d, J=2.77 Hz, 1H) 7.97(d, J=2.01Hz, 1H) 7.70(d, J=7.81Hz, 1H) 7.54-7.60(m, 1H) 7.50-7.54(m, 1H) 7.39-7.46(m, 1H) 7.32(t, J=7.43Hz, 2H) 7.18-7.28(m, 4H) 6.40(s, 1H) 3.81(s, 3H) 3.08-3.16(m, 1H) 2.26-2.36(m, 1H) 1.35-1.45(m, 2H) 2H) LCMS ESI: 424.20 MH+ |
| 233 | 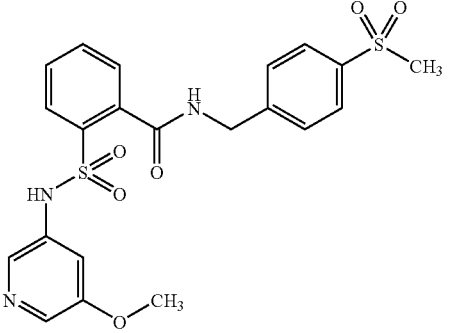 | 2-{[(5-methoxypyridin-3-yl)amino]sulfonyl}-N-[4-(methylsulfonyl)benzyl]benzamide | (400 MHz, CHLOROFORM-d) d ppm 8.49(s, 1H) 8.05(d, J=2.52 Hz, 1H) 7.84-7.96(m, 3H) 7.72(d, J=7.81Hz, 1H) 7.56-7.66(m, 4H) 7.42-7.50(m, 1H) 7.19-7.22(m, 1H) 6.90(t, J=6.04Hz, 1H) 4.81(d, J=6.04Hz, 2H) 3.81(s, 3H) 3.03(s, 3H) LCMS ESI: 476.20 MH+ |
| 234 | 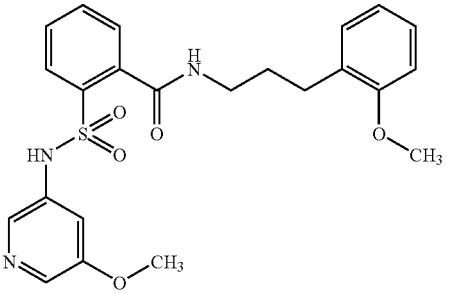 | N-[3-(2-methoxyphenyl)propyl]-2-{[(5-methoxypyridin-3-yl)amino]sulfonyl}benzamide | (400 MHz, CHLOROFORM-d) d ppm 8.73(s, 1H) 8.05(d, J=2.52 Hz, 1H) 7.95(d, J=2.01Hz, 1H) 7.72(d, J=7.81Hz, 1H) 7.50-7.59(m, 1H) 7.37-7.47(m, 2H) 7.15-7.24(m, 3H) 6.89-6.99(m, 1H) 6.87(d, J=8.06Hz, 1H) 6.46(t, J=5.54Hz, 1H) 3.80(s, 3H) 3.78(s, 3H) 3.49(q, J=6.55Hz, 2H) 2.79(t, J=7.18Hz, 2H) 1.93-2.06(m, 2H) LCMS ESI: 456.20 MH+ |
| 235 | 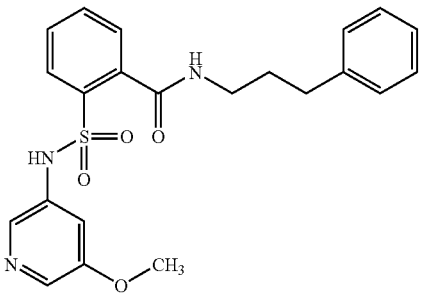 | 2-{[(5-methoxypyridin-3-yl)amino]sulfonyl}-N-(3-phenylpropyl)benzamide | (400 MHz, CHLOROFORM-d) d ppm 8.63(s, 1H) 8.05(d, J=2.52 Hz, 1H) 7.94(d, J=1.76Hz, 1H) 7.69(d, J=7.81Hz, 1H) 7.52(t, J=7.55Hz, 1H) 7.27-7.45(m, 4H) 7.16-7.28(m, 4H) 6.09-6.23(m, 1H) 3.80(s, 3H) 3.55(q, J=6.63Hz, 2H) 2.78(t, J=7.43Hz, 2H) 1.96-2.10(m, 2H) LCMS ESI: 426.20 MH+ |

| Example No. | Structure | Name | $^1$H NMR |
|---|---|---|---|
| 236 | 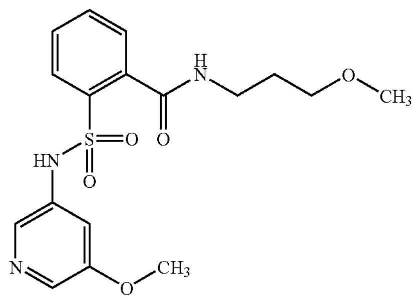 | N-(3-methoxypropyl)-2-{[(5-methoxypyridin-3-yl)amino]sulfonyl}benzamide | (400 MHz, CHLOROFORM-d) d ppm 8.81(s, 1H) 8.05(d, J=1.76 Hz, 1H) 7.95(s, 1H) 7.73 (d, J=8.06Hz, 1H) 7.49-7.61(m, 2H) 7.34-7.47(m, 1H) 7.22(t, J=2.27Hz, 1H) 6.90(s, 1H) 3.81(s, 3H) 3.65(q, J=5.96Hz, 2H) 3.60(t, J=5.54Hz, 2H) 3.35 (s, 3H) 1.90-2.01(m, 2H) LCMS ESI: 380.20 MH+ |
| 237 | 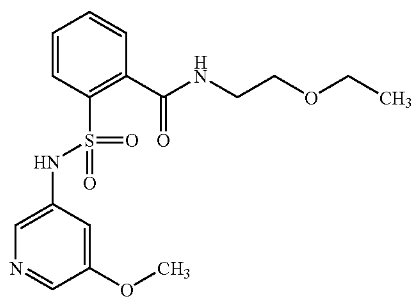 | N-(2-ethoxyethyl)-2-{[(5-methoxypyridin-3-yl)amino]sulfonyl}benzamide | (400 MHz, CHLOROFORM-d) d ppm 8.84(s, 1H) 8.05(d, J=2.52 Hz, 1H) 7.96(d, J=2.01Hz, 1H) 7.81(d, J=7.81Hz, 1H) 7.59(d, J=4.03Hz, 2H) 7.41-7.49(m, 1H) 7.19(t, J=2.39Hz, 1H) 6.67(s, 1H) 3.80(s, 3H) 3.68-3.76(m, 4H) 3.60(q, J=7.05Hz, 2H) 1.23(t, J=7.05Hz, 3H) LCMS ESI: 380.20 MH+ |
| 238 | 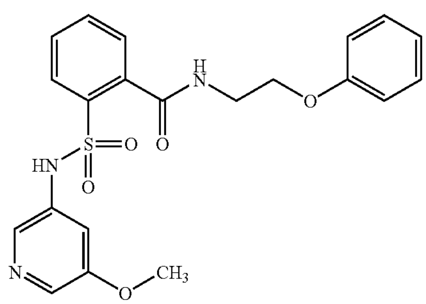 | 2-{[(5-methoxypyridin-3-yl)amino]sulfonyl}-N-(2-phenoxyethyl)benzamide | (400 MHz, CHLOROFORM-d) d ppm 8.57(s, 1H) 8.06(d, J=2.77 Hz, 1H) 7.94(d, J=2.01Hz, 1H) 7.74(d, J=8.06Hz, 1H) 7.49-7.62(m, 2H) 7.36-7.49(m, 1H) 7.31(t, J=8.06Hz, 2H) 7.22(t, J=2.27Hz, 1H) 6.91-7.04 (m, 3H) 6.65(s, 1H) 4.23(t, J=5.04Hz, 2H) 3.95(q, J=5.46Hz, 2H) 3.81(s, 3H) LCMS ESI: 428.20 MH+ |
| 239 | 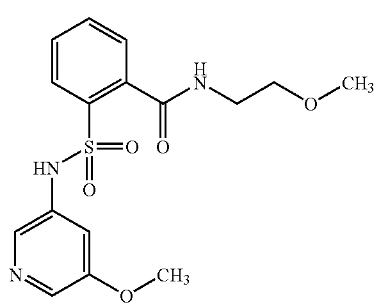 | N-(2-methoxyethyl)-2-{[(5-methoxypyridin-3-yl)amino]sulfonyl}benzamide | (400 MHz, CHLOROFORM-d) d ppm 8.82(s, 1H) 8.05(d, J=2.52 Hz, 1H) 7.96(d, J=2.01Hz, 1H) 7.80(d, J=7.81Hz, 1H) 7.55-7.61(m, 2H) 7.39-7.49(m, 1H) 7.20(t, J=2.27Hz, 1H) 6.63(s, 1H) 3.80(s, 3H) 3.70-3.77(m, 2H) 3.63-3.70(m, 2H) 3.43(s, 3H) LCMS ESI: 366.20 MH+ |
| 240 | 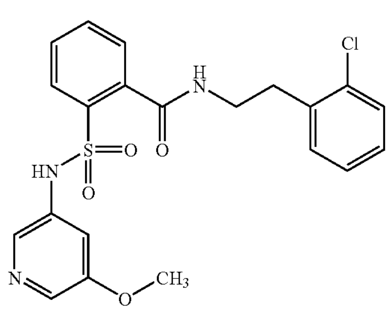 | N-[2-(2-chlorophenyl)ethyl]-2-{[(5-methoxypyridin-3-yl)amino]sulfonyl}benzamide | (400 MHz, CHLOROFORM-d) d ppm 8.42(dd, J=4.66, 1.38Hz, 1H) 8.36(d, J=1.76Hz, 1H) 7.42-7.52(m, 1H) 7.11-7.24(m, 2H) 6.75(dd, J=7.43, 5.92Hz, 2H) 5.85 (s, 1H) 4.44-4.66(m, 1H) 4.03(q, J=7.05Hz, 2H) 2.87-3.00(m, 4H) 2.34-2.49(m, 2H) 1.80-1.92(m, 2H) 1.71-1.81(m, 2H) 1.31-1.44(m, 3H) LCMS ESI: 446.10 MH+ |

| Example No. | Structure | Name | ¹H NMR |
|---|---|---|---|
| 241 | 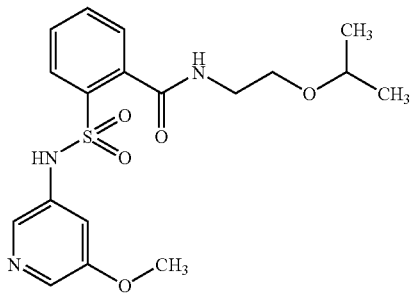 | N-(2-isopropoxyethyl)-2-{[(5-methoxypyridin-3-yl)amino]sulfonyl}benzamide | (400 MHz, CHLOROFORM-d) d ppm 8.83(s, 1H) 8.05(d, J=2.52 Hz, 1H) 7.97(d, J=2.01Hz, 1H) 7.80(d, J=7.55Hz, 1H) 7.54-7.62(m, 2H) 7.41-7.50(m, 1H) 7.16-7.23 (m, 1H) 6.66(s, 1H) 3.80 (s, 3H) 3.65-3.74(m, 5H) 1.19(d, J=6.29Hz, 6H) LCMS ESI: 394.20 MH+ |
| 242 | 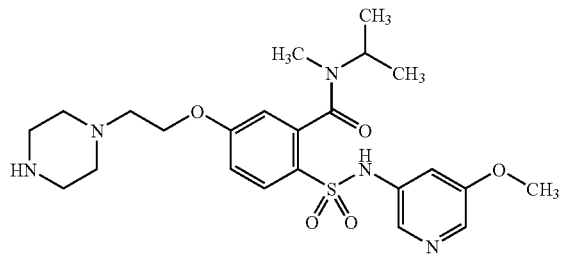 | N-isopropyl-2-{[(5-methoxypyridin-3-yl)amino]sulfonyl}-N-methyl-5-(2-piperazin-1-ylethoxy)benzamide | (400 MHz, CHLOROFORM-d) d ppm 1.23(dd, J=6.69, 2.40Hz, 3.5H), 1.29(d, J=6.82Hz, 2.9H), 2.77(s, 1.6H) 2.82-2.186(m, 3.5H) 2.89(t, J=5.18Hz, 2H), 3.01(s, 1.9H), 3.16-3.25 (m, 3.7H), 3.50(s, 1.2H), 3.79-3.95(m, 3.6H), 4.02-4.22(m, 2H), 4.84-5.03 (m, 0.4H), 6.71-6.78(m, 1H), 6.81(d, J=2.53Hz, 1H), 7.20-7.25(m, 1.2H), 7.50-7.60(m, 1H), 7.88-7.99 (m, 1.7H), 8.07(s, 1.1H) |
| 243 | 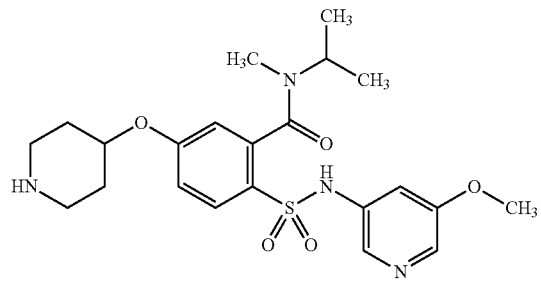 | N-isopropyl-2-{[(5-methoxypyridin-3-yl)amino]sulfonyl}-N-methyl-5-(piperidin-4-yloxy)benzamide | (400 MHz, CHLOROFORM-d) d ppm 1.24(dd, J=6.57, 3.28Hz, 4H), 1.27-1.34 (m, 2.4H), 1.95-2.14(m, 3H), 2.15-2.32(m, 1.6H), 2.78(s, 1.3H), 3.02(s, 1.6H), 3.13-3.23(m, 1.9H), 3.31(t, J=11.24Hz, 1.7H), 3.80-3.89(m, 3.5H), 4.63-4.71(m, 1H), 4.88-4.98 (m, 0.6H), 6.73-6.80(m, 1H), 6.82(t, J=2.15Hz, 1H), 7.23-7.26(m, 1H), 7.58 (dd, J=8.72, 3.41Hz, 1H), 7.91-8.00(m, 1H), 8.07(d, J=2.02Hz, 1H) |
| 244 | 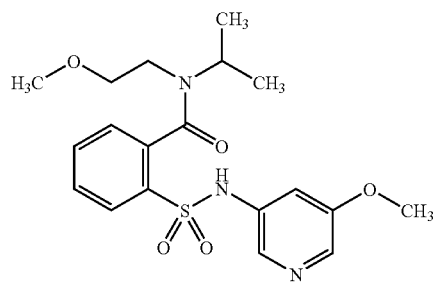 | N-isopropyl-N-(2-methoxyethyl)-2-{[(5-methoxypyridin-3-yl)amino]sulfonyl}benzamide | (400 MHz, CHLOROFORM-d) d ppm 1.22(dd, J=6.69, 2.91Hz, 4H), 1.36-1.48 (m, 1H), 3.23-3.26(m, 1H), 3.32-3.41(m, 1H), 3.44(s, 2H), 3.45-3.52(m, 1H), 3.52-3.62(m, 1H), 3.62-3.72(m, 1H), 3.76-3.91 3H), 4.47-4.63 (m, 1H), 7.13-7.20(m, 1H), 7.30-7.40(m, 1H), 7.40-7.45(m, 1H), 7.52-7.60(m, 1H), 7.64(d, J=7.83Hz, 1H), 7.87-7.95 (m, 1H), 8.00(s, 1H), 8.07 (d, J=2.53Hz, 1H) |

| Example No. | Structure | Name | $^1$H NMR |
|---|---|---|---|
| 245 | 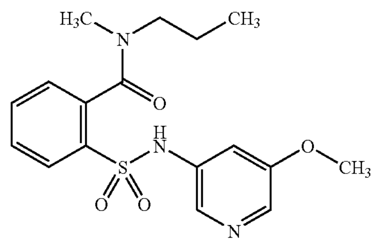 | 2-{[(5-methoxypyridin-3-yl)amino]sulfonyl}-N-methyl-N-propylbenzamide | (400 MHz, CHLOROFORM-d) δ ppm 0.81(t, J=7.33Hz, 1H), 1.05(t, J=7.45Hz, 1H), 1.64-1.97(m, 1H), 2.92(s, 1H), 3.10-3.25(m, 2H), 3.50-3.62(m, 1H), 3.79(s, 2H), 7.11-7.21(m, 1H), 7.32-7.43(m, 2H), 7.52-7.60(m, 1H), 7.60-7.72(m, 1H), 7.95(dd, J=5.05, 2.02Hz, 1H), 7.99(s, 1H), 8.07(d, J=2.53Hz, 1H) |
| 246 | 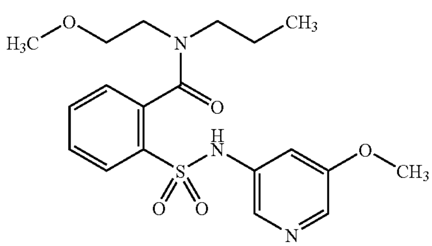 | N-(2-methoxyethyl)-2-{[(5-methoxypyridin-3-yl)amino]sulfonyl}-N-propylbenzamide | (400 MHz, CHLOROFORM-d) δ ppm 0.77(t, J=7.33Hz, 1H), 1.03(t, J=7.45Hz, 1H), 1.49-1.57(m, 1H), 1.64-1.92(m, 1H), 3.03-3.19(m, 1H), 3.23-3.31(m, 1H), 3.32(s, 1H), 3.36-3.49(m, 2H), 3.53-3.68(m, 1H), 3.72-3.77(m, 1H), 3.79(s, 2H), 3.88-4.02(m, 1H), 7.17(t, J=2.40Hz, 1H), 7.31-7.42(m, 1H), 7.46(dd, J=7.58, 1.26Hz, 1H), 7.52-7.59(m, 1H), 7.62(s, 1H), 7.66-7.74(m, 1H), 7.94(d, J=2.02Hz, 1H), 8.06(dd, J=5.43, 2.65 Hz, 1H), 8.12(s, 1H) |
| 247 | 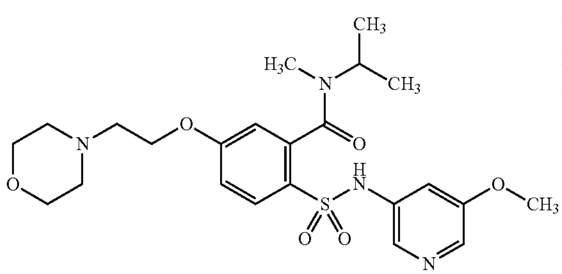 | N-isopropyl-2-{[(5-methoxypyridin-3-yl)amino]sulfonyl}-N-methyl-5-(2-morpholin-4-ylethoxy)benzamide | (400 MHz, CHLOROFORM-d) δ ppm 1.22(dd, J=6.57, 2.27Hz, 3.4H), 1.28(d, J=6.82Hz, 2.9H), 2.51-2.60(m, 4.1H), 2.76(s, 1.4H), 2.80(t, J=5.43Hz, 2.1H), 3.01(s, 1.7H), 3.68-3.76(m, 4.1H), 3.81(s, 3H), 3.82-3.89(m, 0.7H), 4.03-4.17(m, 2.1H), 4.86-4.99(m, 0.4H), 6.72-6.79(m, 1H), 6.82(t, J=2.27Hz, 1H), 7.21(t, J=2.27Hz, 1H), 7.54(dd, J=8.59, 3.79 Hz, 1H), 7.75-7.91(m, 1H), 7.93-7.98(m, 1H), 8.04-8.11(m, 1H) |
| 248 | 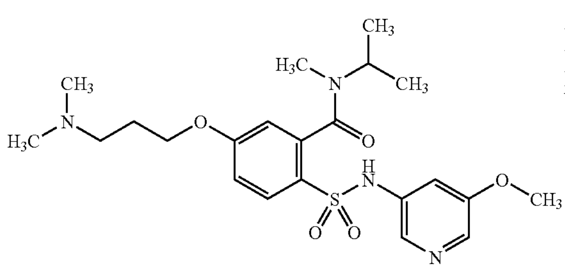 | 5-[3-(dimethylamino)propoxy]-N-isopropyl-2-{[(5-methoxypyridin-3-yl)amino]sulfonyl}-N-methylbenzamide | (400 MHz, CHLOROFORM-d) δ ppm 1.22(dd, J=6.69, 4.42Hz, 3.5H), 1.28(d, J=6.82Hz, 2.7H), 1.93-2.01(m, 3.3H), 2.27(d, J=1.52Hz, 6.2H), 2.44-2.51(m, 2.2H), 2.76(s, 1.3H), 3.01(s, 1.6H), 3.81(s, 2.8H), 3.82-3.91(m, 0.6H), 3.96-4.08(m, 1.9H), 4.89-4.97(m, 0.4H), 6.73-6.78(m, 0.9H), 6.80(t, J=2.27Hz, 1H), 7.21(t, J=2.40Hz, 1H), 7.53(dd, J=8.59, 4.55Hz, 1H), 7.96(t, J=2.27Hz, 1H), 8.06(dd, J=2.53, 1.26Hz, 1H) |

-continued

| Example No. | Structure | Name | $^1$H NMR |
|---|---|---|---|
| 249 | 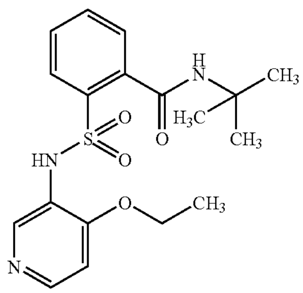 | N-(tert-butyl)-2-{[(4-ethoxy-pyridin-3-yl)amino]sulfonyl}benzamide | (400 MHz, CHLOROFORM-d) d ppm 8.69(s, 1H) 8.62(s, 1H) 8.22(d, J=5.79Hz, 1H) 7.76(d, J=7.81Hz, 1H) 7.36-7.58(m, 3H) 6.63(d, J=5.54Hz, 1H) 5.88(s, 1H) 3.85(q, J=7.05Hz, 2H) 1.52(s, 9H) 1.17(t, J=6.92Hz, 3H) |
| 250 | 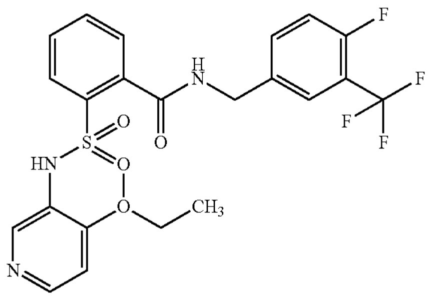 | 2-{[(4-ethoxypyridin-3-yl)amino]sulfonyl}-N-[4-fluoro-3-(trifluoromethyl)benzyl]benzamide | (400 MHz, CHLOROFORM-d) d ppm 8.64(s, 1H) 8.39-8.62(m, 1H) 8.21(d, J=5.54Hz, 1H) 7.74(d, J=7.05Hz, 1H) 7.61-7.72(m, 2H) 7.50-7.60(m, 2H) 7.38-7.47(m, 1H) 7.22(t, J=9.19Hz, 1H) 6.70(s, 1H) 6.63(d, J=5.54 Hz, 1H) 4.71(d, J=6.04Hz, 2H) 3.84(q, J=6.88Hz, 2H) 0.99-1.18(m, 3H) |
| 251 | 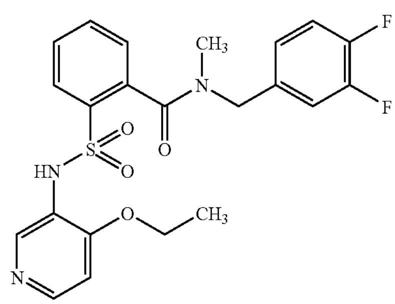 | N-(3,4-difluorobenzyl)-2-{[(4-ethoxypyridin-3-yl)amino]sulfonyl}-N-methylbenzamide | (400 MHz, CHLOROFORM-d) d ppm 8.57-8.74(m, 1H) 8.15-8.33(m, 1H) 7.95(s, 1H) 7.67-7.78(m, 1H) 7.52-7.63(m, 1H) 7.28-7.47(m, 3H) 6.96-7.23(m, 2H) 6.65(d, J=5.79Hz, 1H) 4.24-4.94(m, 2H) 3.60-4.09(m, 2H) 3.06(s, 1H) 2.83(s, 2H) 1.02-1.30(m, 3H) |
| 252 | 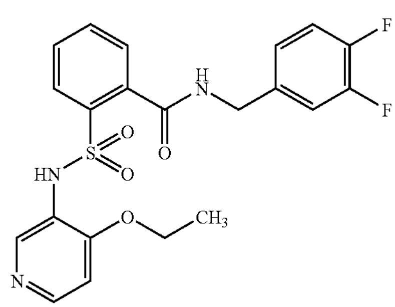 | N-(3,4-difluorobenzyl)-2-{[(4-ethoxypyridin-3-yl)amino]sulfonyl}benzamide | (400 MHz, CHLOROFORM-d) d ppm 8.66(s, 1H) 8.40-8.62(m, 1H) 8.23(d, J=5.54Hz, 1H) 7.79(d, J=7.81Hz, 1H) 7.41-7.67(m, 3H) 7.25-7.34(m, 1H) 7.01-7.22(m, 2H) 6.65(d, J=5.29Hz, 1H) 6.33-6.57(m, 1H) 4.66(d, J=5.79Hz, 2H) 3.87(q, J=6.63Hz, 2H) 1.07-1.27(m, 3H) |

| Example No. | Structure | Name | ¹H NMR |
|---|---|---|---|
| 253 | 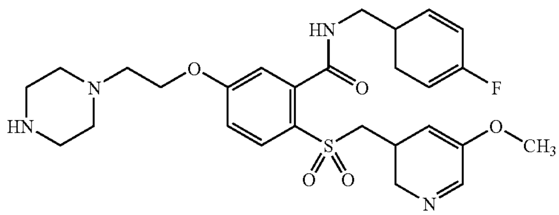 | N-(4-fluorobenzyl)-2-{[(5-methoxypyridin-3-yl)amino]sulfonyl}-5-(2-piperazin-1-ylethoxy)benzamide | (400 MHz, MeOD) d ppm 2.72(d, J=4.29Hz, 4H) 2.86(t, J=5.18Hz, 2H) 3.04-3.13(m, 4H) 3.83(s, 3H) 4.21(t, J=5.31Hz, 2H) 4.62(s, 2H) 7.04(dd, J=8.84, 2.53Hz, 1H) 7.07-7.13(m, 2H) 7.14(d, J=2.78Hz, 1H) 7.26-7.35 (m, 1H) 7.47-7.57(m, 2H) 7.74(d, J=8.84 Hz, 1H) 7.93(dd, J=8.97, 2.40Hz, 2H) |
| 254 | 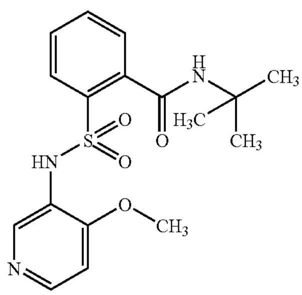 | N-(tert-butyl)-2-{[(4-methoxypyridin-3-yl)amino]sulfonyl}benzamide | (400 MHz, MeOD): d 8.123 (s, 2H), 7.812(d, J=7.2Hz, 1H), 7.658(m, 1H), 7.543 (m, 3H), 3,891(s, 3H), 1474 (s, 9H). |
| 255 | 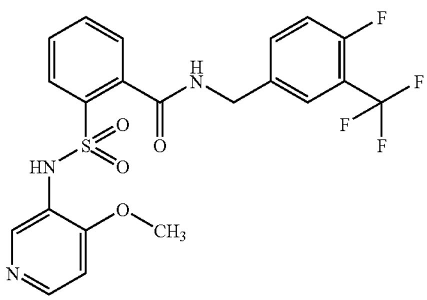 | N-[4-fluoro-3-(trifluoromethyl)benzyl]-2-{[(4-methoxypyridin-3-yl)amino]sulfonyl}benzamide | (400 MHz, CHLOROFORM-d) d ppm 8.64(s, 1H) 8.41(s, 1H) 8.25(d, J=5.54Hz, 1H) J=7.81Hz, 1H) 7.63-7.75(m, 2H) 7.53-7.63(m, 2H) 7.41-7.51(m, 1H) 7.19-7.24(m, 1H) 6.68(d, J=5.54Hz, 1H) 6.49-6.61(m, 1H) 4.73(d, J=6.04Hz, 2H) 3.47-3.70 (m, 3H) |
| 256 | 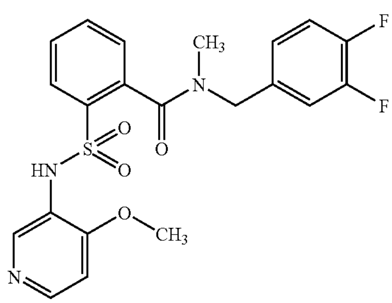 | N-(3,4-difluorobenzyl)-2-{[(4-methoxypyridin-3-yl)amino]sulfonyl}-N-methylbenzamide | (400 MHz, CHLOROFORM-d) d ppm 8.52-8.74(m, 1H) 8.29(d, J=5.54Hz, 1H) 7.88(s, 1H) 7.53-7.66(m, 1H) 7.28-7.47(m, 4H) 6.95-7.23(m, 2H) 6.68(d, J=5.54Hz, 1H) 4.19-4.97(m, 2H) 3.48-3.76(m, 3H) 3.07(s, 1H) 2.83(s, 2H) |
| 257 | 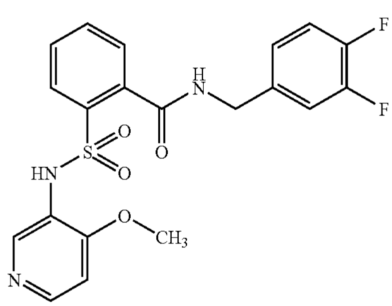 | N-(3,4-difluorobenzyl)-2-{[(4-methoxypyridin-3-yl)amino]sulfonyl}benzamide | (400 MHz, CHLOROFORM-d) d ppm 8.61(s, 1H) 8.24(d, J=5.79 Hz, 1H) 7.77(d, J=7.30Hz, 1H) 7.51-7.62(m, 2H) 7.43-7.49(m, 1H) 7.24-7.33(m, 2H) 7.05-7.22(m, 2H) 6.57-6.73(m, 2H) 4.66(d, J=6.04Hz, 2H) |

| Example No. | Structure | Name | ¹H NMR |
|---|---|---|---|
| 258 | 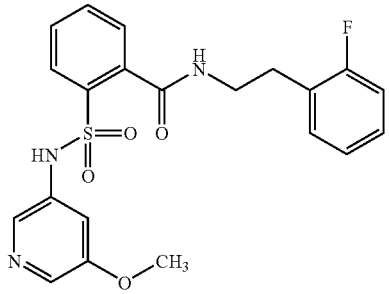 | N-[2-(2-fluorophenyl)ethyl]-2-{[(5-methoxypyridin-3-yl)amino]sulfonyl}benzamide | (400 MHz, CHLOROFORM-d) d ppm 8.64(s, 1H) 8.06(d, J=2.52 Hz, 1H) 7.96(d, J=2.01Hz, 1H) 7.67-7.77(m, 1H) 7.49-7.59(m, 1H) 7.38-7.45(m, 2H) 7.35(t, J=7.43 Hz, 1H) 7.19-7.29(m, 2H) 7.02-7.16(m, 2H) 6.10-6.21(m, 1H) 3.73-3.87(m, 5H) 3.07(t, J=6.55Hz, 2H) LCMS ESI: 430.20 MH+ |
| 259 | 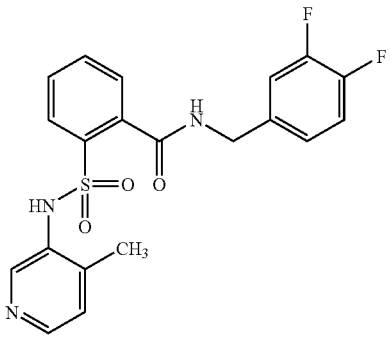 | N-(3,4-difluorobenzyl)-2-{[(4-methylpyridin-3-yl)amino]sulfonyl}benzamide | (400 MHz, CHLOROFORM-d) d ppm 8.27(d, J=5.04Hz, 2H) 8.17(s, 1H) 7.71(d, J=8.06 Hz, 1H) 7.56-7.66(m, 2H) 7.44-7.52(m, 1H) 7.27-7.34(m, 1H) 7.14-7.22(m, 2H) 7.10(d, J=4.78Hz, 1H) 6.51(s, 1H) 4.68(d, J=6.04Hz, 2H) 2.30(s, 3H) LCMS ESI: 418.15 MH+ |
| 260 | 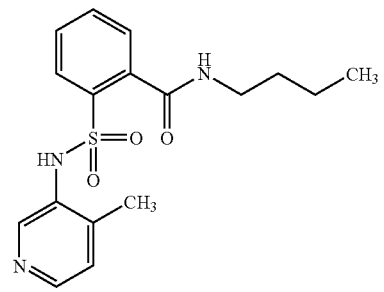 | N-butyl-2-{[(4-methylpyridin-3-yl)amino]sulfonyl}benzamide | (400 MHz, CHLOROFORM-d) d ppm 8.43(s, 1H) 8.26(d, J=4.78 Hz, 1H) 8.17(s, 1H) 7.66 (d, J=7.55Hz, 1H) 7.58-7.63(m, 1H) 7.49-7.58(m, 1H) 7.40-7.49(m, 1H) 7.08(d, J=5.04Hz, 1H) 6.21(s, 1H) 3.45-3.59(m, 2H) 2.29(s, 3H) 1.61-1.73 (m, 2H) 1.40-1.53(m, 2H) 1.00(t, J=7.43Hz, 3H) LCMS ESI: 348.20 MH+ |
| 261 | 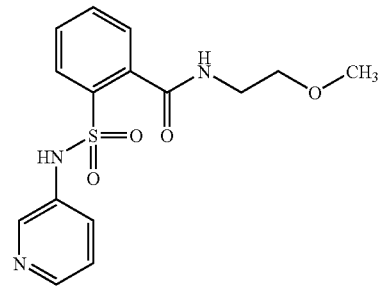 | N-(2-methoxyethyl)-2-[(pyridin-3-ylamino)sulfonyl]benzamide | (400 MHz, CHLOROFORM-d) d ppm 8.80(s, 1H) 8.37 (d, J=2.52Hz, 1H) 8.34(d, J=4.78Hz, 1H) 7.76(d, J=7.81Hz, 1H) 7.51-7.65 (m, 3H) 7.39-7.49(m, 1H) 7.17(dd, J=8.06, 4.78Hz, 1H) 6.68(s, 1H) 3.70-3.80 (m, 2H) 3.65-3.70(m, 2H) 3.43(s, 3H) LCMS ESI: 336.20 MH+ |

| Example No. | Structure | Name | $^1$H NMR |
|---|---|---|---|
| 262 | 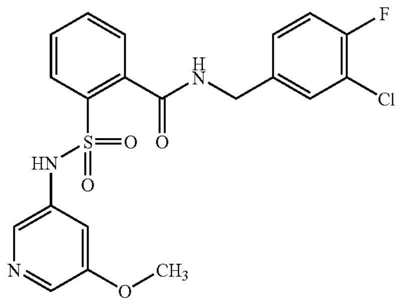 | N-(3-chloro-4-fluorobenzyl)-2-{[(5-methoxypyridin-3-yl)amino]sulfonyl}benzamide | (400 MHz, CHLOROFORM-d) d ppm 8.48(s, 1H) 8.06(d, J=2.52 Hz, 1H) 7.94(d, J=2.01Hz, 1H) 7.74(d, J=7.81Hz, 1H) 7.52-7.63(m, 2H) 7.41-7.53(m, 2H) 7.30-7.39 (m, 1H) 7.21-7.29(m, 1H) 7.17(t, J=8.69Hz, 1H) 6.48 (s, 1H) 4.67(d, J=6.04Hz, 2H) 3.82(s, 3H) LCMS ESI: 450.10 MH+ |
| 263 | 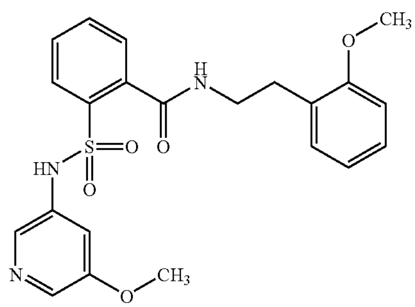 | N-[2-(2-methoxyphenyl)ethyl]-2-{[(5-methoxypyridin-3-yl)amino]sulfonyl}benzamide | (400 MHz, CHLOROFORM-d) d ppm 8.79(s, 1H) 8.05(d, J=2.77 Hz, 1H) 7.96(d, J=2.01 Hz, 1H) 7.72(dd, J=7.68, 1.13 Hz, 1H) 7.47-7.56(m, 1H) 7.32-7.44(m, 2H) 7.20-7.30(m, 3H) 6.95(t, J=7.30 Hz, 1H) 6.91(d, J=8.56Hz, 1H) 6.43(s, 1H) 3.83(s, 3H) 3.81(s, 3H) 3.71-3.80 (m, 2H) 3.02(t, J=6.42Hz, 2H) LCMS ESI: 442.20 MH+ |
| 264 | 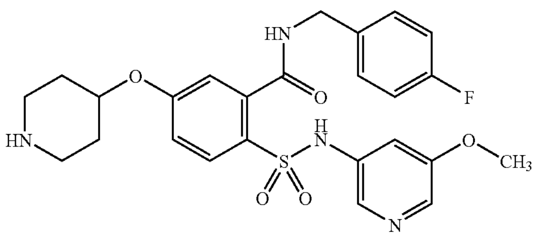 | N-(4-fluorobenzyl)-2-{[(5-methoxypyridin-3-yl)amino]sulfonyl}-5-(piperidin-4-yloxy)benzamide | (400 MHz, MeOD) d ppm 1.80-1.90(m, 2H) 2.05-2.16(m, 2H) 2.93-3.05(m, 2H) 3.18-3.28(m, 2H) 3.81(s, 3H) 4.61(s, 2H) 4.68-4.79(m, 1H) 7.05-7.15(m, 3H) 7.17(d, J=2.53Hz, 1H) 7.21-7.31 (m, 1H) 7.46-7.56(m, 2H) 7.78(d, J=8.84Hz, 1H) 7.87(d, J=1.26Hz, 2H) |
| 265 | 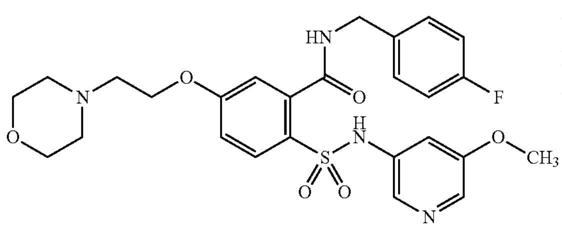 | N-(4-fluorobenzyl)-2-{[(5-methoxypyridin-3-yl)amino]sulfonyl}-5-(2-morpholin-4-ylethoxy)benzamide | (400 MHz, MeOD) d ppm 2.58(d, J=4.29Hz, 4H) 2.81(t, J=5.43Hz, 2H) 3.67-3.77(m, 4H) 3.83(s, 3H) 4.21(t, J=5.43Hz, 2H) 4.62(s, 2H) 7.04(dd, J=8.84, 2.53Hz, 1H) 7.07-7.14(m, 2H) 7.15(d, J=2.53Hz, 1H) 7.26-7.37 (m, 1H) 7.47-7.57(m, 2H) 7.72(d, J=8.84 Hz, 1H) 7.93-8.04(m, 2H) |
| 266 | 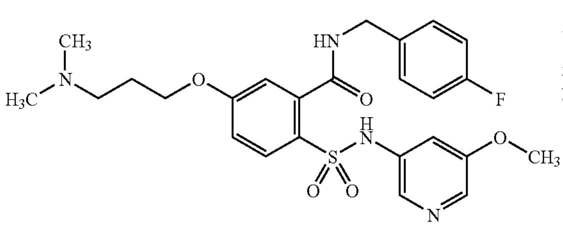 | 5-[3-(dimethylamino)propoxy]-N-(4-fluorobenzyl)-2-{[(5-methoxypyridin-3-yl)amino]sulfonyl}benzamide | (400 MHz, MeOD) d ppm 1.93(dt, J=1 5.09, 6.09Hz, 2H) 2.35(s, 6H) 2.57-2.67 (m, 2H) 3.70(s, 3H) 4.00(t, J=6.06Hz, 2H) 4.49 (s, 2H) 6.90(dd, J=8.84, 2.53Hz, 1H) 6.94-7.02(m, 3H) 7.13-7.20(m, 1H) 7.33-7.40(m, 2H) 7.60(d, J=8.84Hz, 1H) 7.82(dd, J=9.35, 2.27Hz, 2H) |

-continued

| Example No. | Structure | Name | ¹H NMR |
|---|---|---|---|
| 267 | 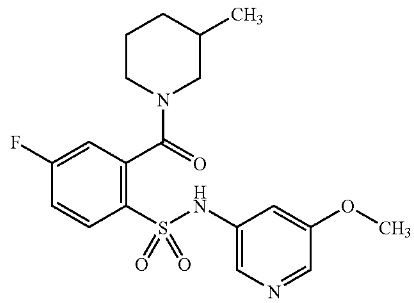 | 4-fluoro-N-(5-methoxypyridin-3-yl)-2-[(3-methylpiperidin-1-yl)carbonyl]benzenesulfonamide | (400 MHz, CHLOROFORM-d) d ppm 0.81(dd, J=19.33, 6.44Hz, 1.5H) 1.02(dd, J=17.94, 6.57Hz, 1.5H) 1.12-1.28(m, 1.3H) 1.72-1.84(m, 1.5H) 1.85-2.01 (m, 1.9H) 2.49(dd, J=12.51, 10.99Hz, 0.3H) 2.63-2.89(m, 1.2H) 2.98-3.14(m, 0.6H) 3.30-3.59 (m, 1.1H) 3.81(s, 3H) 4.44 (dd, J=12.76, 3.66Hz, 0.2H) 4.55-4.72(m, 0.8H) 6.94-7.12(m, 1.9H) 7.18 (d, J=2.02Hz, 0.9H) 7.65 (dd, J=8.97, 4.67Hz, 1.3H) 7.94-8.01(m, 1.3H) 8.09 (s, 1.2H) |
| 268 | 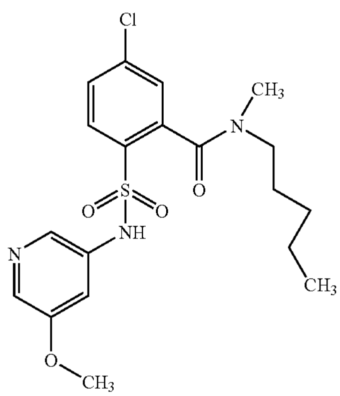 | 5-chloro-2-{[(5-methoxypyridin-3-yl)amino]sulfonyl}-N-methyl-N-pentylbenzamide | (400 MHz, CHLOROFORM-d) d ppm 8.86(s, 1H), 8.28 (s, 1H), 8.20(s, 1H), 7.75 (t, J=8.34Hz, 1H), 7.66(s, 1H), 7.44(ddd, J=8.34, 4.67, 1.89Hz, 1H), 7.36 (dd, J=5.05, 2.02Hz, 1H), 3.95(s, 3H), 3.57(t, J=7.71 Hz, 1H), 3.16-3.22(m, 1H), 3.15(s, 1H), 2.93-2.96 (m, 2H), 1.71(s, 1H), 1.42 (d, J=2.53Hz, 3H), 1.16-1.27(m, 2H), 0.96(t, J=6.82Hz, 2H), 0.87(t, J=7.07Hz, 1H) |
| 269 | 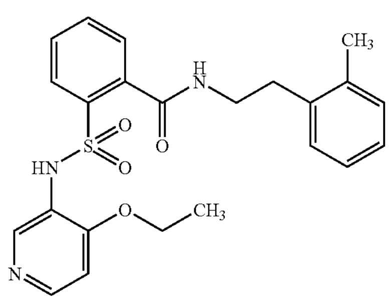 | 2-{[(4-ethoxypyridin-3-yl)amino]sulfonyl}-N-[2-(2-methylphenyl)ethyl]benzamide | (400 MHz, CHLOROFORM-d) d ppm 8.65(s, 2H) 8.13-8.29(m, 1H) 7.70-7.92(m, 1H) 7.48-7.62(m, 1H) 7.42(t, J=7.05Hz, 1H) 7.12-7.25 (m, 3H) 6.63(t, J=5.04Hz, 1H) 5.97-6.21(m, 1H) 3.85(q, J=6.97Hz, 2H) 3.74(q, J=7.05Hz, 2H) 3.02(t, J=7.05Hz, 2H) 2.27-2.47(m, 2H) 1.64(s, 3H) 1.06-1.23(m, 3H) |
| 270 | 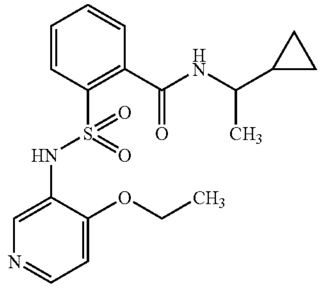 | N-(1-cyclopropylethyl)-2-{[(4-ethoxypyridin-3-yl)amino]sulfonyl}benzamide | (400 MHz, CHLOROFORM-d) d ppm 8.63(s, 2H) 8.23(d, J=5.79 Hz, 1H) 7.78(d, J=7.81Hz, 1H) 7.49-7.64(m, 2H) 736-7.48(m, 1H) 6.62(d, J=5.54Hz, 1H) 6.09(d, J=7.55Hz, 1H) 3.85(q, J=7.05Hz, 2H) 3.49-3.68 (m, 1H) 1.64(s, 3H) 1.38 (d, J=6.55Hz, 2H) 1.06-1.22(m, 2H) 0.85-1.04(m, 1H) 0.42-0.60(m, 2H) 0.26-0.42(m, 1H) |

| Example No. | Name | ¹H NMR |
|---|---|---|
| 271 | 2-{[(4-ethoxypyridin-3-yl)amino]sulfonyl}-N-(3-methylbutyl)benzamide | (400 MHz, CHLOROFORM-d) d ppm 8.71(s, 1H) 8.61(s, 1H) 8.22(d, J=5.54Hz, 1H) 7.70(d, J=7.81Hz, 1H) 7.46-7.60(m, 2H) 740(t, J=7.43Hz, 1H) 6.62(d, J=5.54Hz, 1H) 6.27(t, J=5.04Hz, 1H) 3.83(q, J=6.88Hz, 2H) 3.37-3.60 (m, 2H) 1.66-1.84(m, 2H) 1.46-1.63(m, 2H) 1.06-1.20(m, 3H) 0.84-1.05(m, 5H) |
| 272 | 2-{[(4-ethoxypyridin-3-yl)amino]sulfonyl}-N-methyl-N-pentylbenzamide | (400 MHz, CHLOROFORM-d) d ppm 8.60(t, J=5.79Hz, 1H) 8.24 (d, J=5.54Hz, 1H) 7.90-8.06(m, 1H) 7.65-7.79(m, 1H) 7.49-7.62(m, 1H) 7.32-7.46(m, 2H) 6.63(d, J=5.54Hz, 1H) 3.71-4.00 (m, 2H) 3.46-3.68(m, 1H) 3.03-3.20(m, 2H) 2.78-2.98(m, 1H) 1.60-1.84(m, 3H) 1.35-1.46(m, 2H) 1.23-1.29(m, 2H) 1.09-1.20(m, 3H) 0.91-1.01(m, 2H) 0.84(t, J=7.18Hz, 1H) |
| 273 | 2-{[(4-ethoxypyridin-3-yl)amino]sulfonyl}-N-methylbenzamide | (400 MHz, CHLOROFORM-d) d ppm 8.00-8.07(m, 2H) 7.89-7.98(m, 2H) 7.52-7.66(m, 2H) 7.29-7.40(m, 2H) 7.17(t, J=2.27Hz, 1H) 3.72-4.10(m, 3H) 3.03(s, 2H) 2.75(s, 1H) 1.39(t, J=7.05 Hz, 3H) 1.29(d, J=6.80Hz, 2H) 1.22(dd, J=6.55, 3.78 Hz, 3H) |
| 274 | N-butyl-2-{[(4-ethoxypyridin-3-yl)amino]sulfonyl}-N-methylbenzamide | (400 MHz, CHLOROFORM-d) d ppm 8.60(t, J=5.79Hz, 1H) 8.24 (d, J=5.54Hz, 1H) 7.90-8.06(m, 1H) 7.65-7.79(m, 1H) 749-7.62(m, 1H) 7.32-7.46(m, 2H) 6.63(d, J=5.54Hz, 1H) 3.71-4.00 (m, 2H) 3.46-3.68(m, 1H) 3.03-3.20(m, 2H) 2.78-2.98(m, 1H) 1.60-1.84(m, 3H) 1.35-1.46(m, 2H) 1.23-1.29(m, 2H) 1.09-1.20(m, 3H) 0.84(t, J=7.18 Hz, 1H) |
| 275 | 2-{[(4-methoxypyridin-3-yl)amino]sulfonyl}-N-[2-(2-methylphenyl)ethyl]benzamide | (400 MHz, CHLOROFORM-d) d ppm 8.52-8.68(m, 2H) 8.15-8.30(m, 1H) 7.74(d, J=7.81Hz, 1H) 7.49-7.60 (m, 1H) 7.36-7.48(m, 2H) 7.21-7.27(m, 1H) 7.08-7.20(m, 3H) 6.66(d, J=5.54Hz, 1H) 6.30(t, J=5.67Hz, 1H) 3.74(q, J=7.05Hz, 2H) 3.44-3.65 (m, 3H) 3.02(t, J=7.18Hz, 2H) 2.31-2.47(m, 3H) |

| Example No. | Structure | Name | ¹H NMR |
|---|---|---|---|
| 276 | 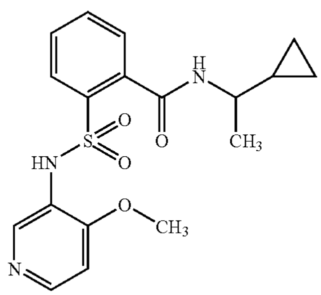 | N-(1-cyclopropylethyl)-2-{[(4-methoxypyridin-3-yl)amino]sulfonyl}benzamide | (400 MHz, CHLOROFORM-d) d ppm 8.61(s, 1H) 8.05(d, J=2.52 Hz, 1H) 7.95(d, J=2.01Hz, 1H) 7.72(d, J=8.06Hz, 1H) 7.50-7.61(m, 2H) 7.36-7.45(m, 1H) 7.23(t, J=2.27Hz, 1H) 6.12(s, 1H) 3.81(s, 3H) 3.56-3.70(m, 1H) 1.39(d, J=6.55Hz, 3H) 0.88-1.02(m, 1H) 0.44-0.70(m, 3H) 0.29-0.43(m, 1H) |
| 277 | 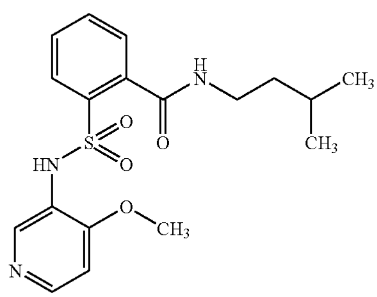 | 2-{[(4-methoxypyridin-3-yl)amino]sulfonyl}-N-(3-methylbutyl)benzamide | (400 MHz, CHLOROFORM-d) d ppm 8.51-8.67(m, 2H) 8.25(d, J=5.54Hz, 1H) 7.74(d, J=7.81Hz, 1H) 7.49-7.61 (m, 2H) 7.27-7.47(m, 1H) 6.66(d, J=5.54Hz, 1H) 6.16(s, 1H) 3.42-3.64(m, 5H) 1.63-1.80(m, 2H) 1.49-1.63(m, 2H) 0.98(d, J=6.55Hz, 5H) |
| 278 | 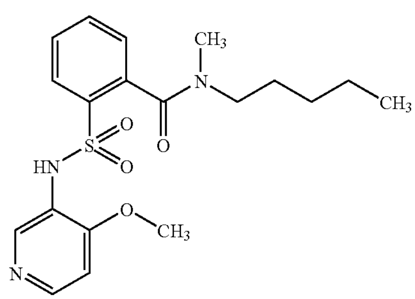 | 2-{[(4-methoxypyridin-3-yl)amino]sulfonyl}-N-methyl-N-pentylbenzamide | (400 MHz, CHLOROFORM-d) d ppm 8.60(d, J=10.07Hz, 1H) 8.27(dd, J=5.54, 1.26Hz, 1H) 7.93(s, 1H) 7.70(dd, J=7.30, 6.04Hz, 1H) 7.50-7.63(m, 1H) 7.32-7.44(m, 2H) 6.66(dd, J=5.54, 1.26 Hz, 1H) 4.12(q, J=7.05Hz, 1H) 3.58(s, 4H) 3.08-3.20 (m, 2H) 2.89(s, 1H) 2.05 (s, 1H) 1.50-1.83(m, 2H) 1.38-1.45(m, 1H) 1.07-1.29(m, 3H) 0.95(t, J=6.80 Hz, 1H) 0.83(t, J=7.18Hz, 1H) |
| 279 | 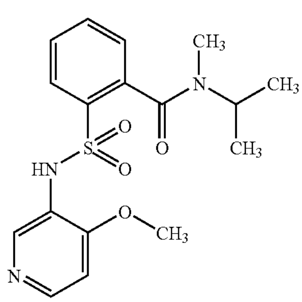 | N-isopropyl-2-{[(4-methoxypyridin-3-yl)amino]sulfonyl-N-methylbenzamide | (400 MHz, CHLOROFORM-d) d ppm 8.61(s, 1H) 8.27(d, J=5.54 Hz, 1H) 7.97(d, J=26.19 Hz, 1H) 7.71(t, J=7.43Hz, 1H) 7.57(t, J=7.55Hz, 1H) 7.31-7.44(m, 2H) 6.66 (dd, J=5.54, 2.52Hz, 1H) 4.87-5.13(m, 1H) 3.59(d, J=5.54Hz, 2H) 3.02(s, 2H) 2.73(s, 1H) 1.67(s, 2H) 1.05-1.35(m, 5H) |
| 280 | 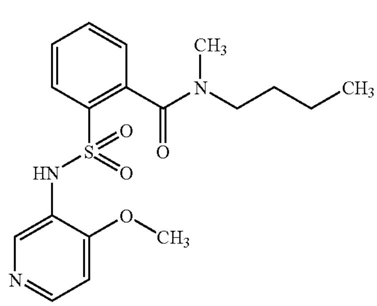 | N-butyl-2-{[(4-methoxypyridin-3-yl)amino]sulfonyl}-N-methylbenzamide | (400 MHz, CHLOROFORM-d) d ppm 8.60(d, J=1 0.07Hz, 1H) 8.27(dd, J=5.54, 1.26Hz, 1H) 7.93(s, 1H) 7.70(dd, J=7.30, 6.04Hz, 1H) 7.50-7.63(m, 1H) 7.32-7.44(m, 2H) 6.66(dd, J=5.54, 1.26 Hz, 1H) 4.12(q, J=7.05Hz, 1H) 3.58(s, 4H) 3.08-3.20 (m, 2H) 2.89(s, 1H) 2.05 (s, 1H) 1.38-1.45(m, 1H) 1.07-1.29(m, 3H) 0.95(t, J=6.80Hz, 1H) 0.83(t, J=7.18Hz, 1H) |

| Example No. | Structure | Name | ¹H NMR |
|---|---|---|---|
| 281 | 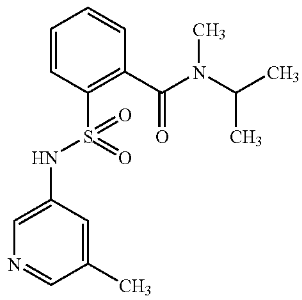 | N-isopropyl-N-methyl-2-{[(5-methylpyridin-3-yl)amino]sulfonyl}benzamide | (400 MHz, CHLOROFORM-d) d ppm 8.10-8.26(m, 2H) 7.96(d, J=25.43Hz, 1H) 7.51-7.67 (m, 2H) 7.41(s, 1H) 7.31-7.39(m, 2H) 4.91-5.03(m, 1H) 3.03(s, 2H) 2.75(s, 1H) 2.26(s, 3H) 1.71(s, 1H) 1.30(d, J=6.80Hz, 2H) 1.18-1.25(m, 3H) |
| 282 | 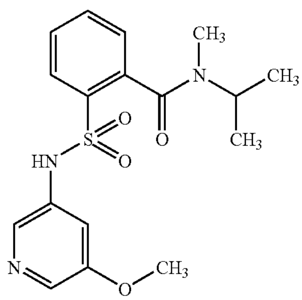 | N-isopropyl-2-{[(5-methoxypyridin-3-yl)amino]sulfonyl}-N-methylbenzamide | (400 MHz, CHLOROFORM-d) d ppm 8.03-8.09(m, 1H) 7.92-8.00(m, 1H) 7.63(dd, J=7.93, 4.66Hz, 1H) 7.53-7.59(m, 1H) 7.31-7.40(m, 2H) 7.14-7.20(m, 1H) 3.74-3.86(m, 4H) 3.03(s, 2H) 2.75(s, 1H) 1.65(s, 2H) 1.30(d, J=6.80Hz, 2H) 1.22(dd, J=6.55, 3.78Hz, 3H) |
| 283 | 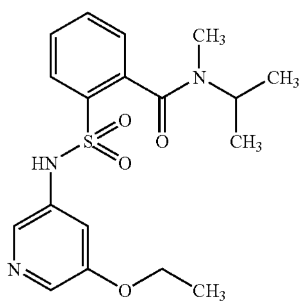 | 2-{[(5-ethoxypyridin-3-yl)amino]sulfonyl}-N-methylbenzamide | (400 MHz, CHLOROFORM-d) d ppm 8.00-8.07(m, 2H) 7.89-7.98(m, 2H) 7.52-7.66(m, 2H) 7.29-7.40(m, 2H) 7.17(t, J=2.27Hz, 1H) 3.72-4.10(m, 3H) 3.03(s, 2H) 2.75(s, 1H) 1.39(t, J=7.05 Hz, 3H) 1.29(d, J=6.80Hz, 2H) 1.22(dd, J=6.55, 3.78 Hz, 3H) |
| 284 | 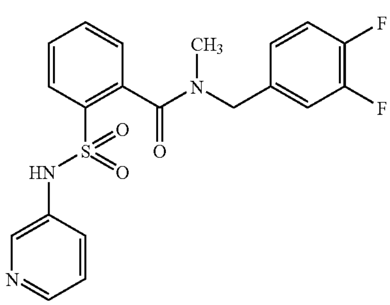 | N-(3,4-difluorobenzyl)-N-methyl-2-[(pyridin-3-ylamino)sulfonyl]benzamide | (400 MHz, CHLOROFORM-d) d ppm 8.25-8.51(m, 2H) 7.94(s, 1H) 7.49-7.68(m, 3H) 7.37(q, J=7.39Hz, 2H) 7.28-7.37(m, 1H) 7.05-7.28(m, 3H) 5.05(none, 1H) 4.25-4.97(m, 2H) 3.08 (s, 1H) 2.65-2.94(m, 2H) |
| 285 | 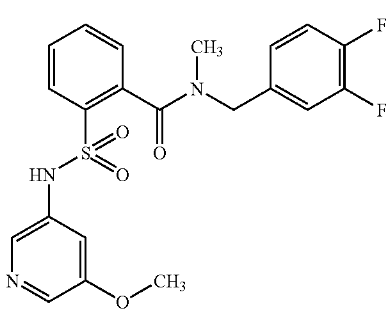 | N-(3,4-difluorobenzyl)-2-{[(5-methoxypyridin-3-yl)amino]sulfonyl}-N-methylbenzamide | (400 MHz, CHLOROFORM-d) d ppm 8.09(d, J=1.51Hz, 1H) 788-8.00(m, 2H) 7.67(d, J=8.06Hz, 1H) 7.49-7.63 (m, 1H) 7.34-7.45(m, 2H) 7.23-7.34(m, 1H) 7.08-7.22(m, 3H) 4.63-4.94(m, 1H) 4.40(d, J=9.32Hz, 1H) 3.77-3.83(m, 3H) 3.08 (s, 1H) 2.86(s, 2H) |

| Example No. | Structure | Name | $^1$H NMR |
|---|---|---|---|
| 286 | 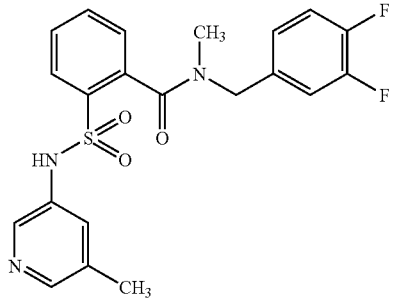 | N-(3,4-difluorobenzyl)-N-methyl-2-{[(5-methylpyridin-3-yl)amino]sulfonyl}benzamide | (400 MHz, CHLOROFORM-d) d ppm 8.21(s, 1H) 8.17(d, J=2.01 Hz, 1H) 7.87(s, 1H) 7.65 (d, J=8.31Hz, 1H) 7.57-7.62(m, 1H) 7.44(s, 1H) 7.35-7.42(m, 2H) 7.28-7.34(m, 1H) 7.11-7.23(m, 2H) 4.79(d, J=55.90Hz, 1H) 4.40(d, J=9.82Hz, 1H) 2.86(s, 3H) 2.28(s, 3H) |
| 287 | 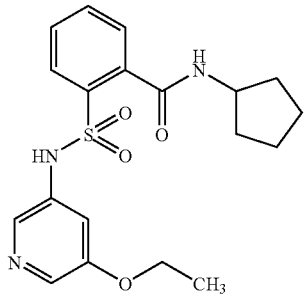 | N-cyclopentyl-2-{[(5-ethoxypyridin-3-yl)amino]sulfonyl}benzamide | Mass point = LCMS 390.6 MH+ |
| 288 | 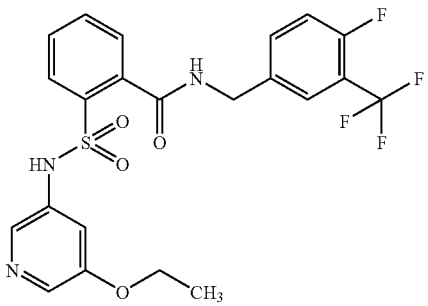 | 2-{[(5-ethoxypyridin-3-yl)amino]sulfonyl}-N-[4-fluoro-3-(trifluoromethyl)benzyl]benzamide | (400 MHz, CHLOROFORM-d) d ppm 8.42(s, 1H) 8.03(d, J=2.52 Hz, 1H) 7.90(d, J=2.01Hz, 1H) 7.63-7.78(m, 3H) 7.50-7.62(m, 2H) 7.41-7.49(m, 1H) 7.18-7.26(m, 2H) 6.64(t, J=5.79Hz, 1H) 4.73(d, J=6.04Hz, 2H) 4.03(q, J=7.05Hz, 2H) 1.40(t, J=7.05Hz, 3H) |
| 289 | 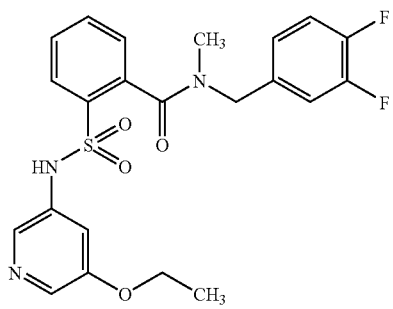 | N-(3,4-difluorobenzyl)-2-{[(5-ethoxypyridin-3-yl)amino]sulfonyl}-N-methylbenzamide | (400 MHz, CHLOROFORM-d) d ppm 8.07(d, J=2.52Hz, 1H) 7.85-7.95(m, 2H) 7.67(d, J=7.30Hz, 1H) 7.50-7.63 (m, 1H) 7.34-7.45(m, 2H) 7.31(d, J=9.57Hz, 1H) 7.00-7.24(m, 4H) 4.79(d, J=67.73Hz, 1H) 3.93-4.11 (m, 2H) 2.86(s, 3H) 1.34-1.48(m, 3H) |

-continued

| Example No. | Structure | Name | ¹H NMR |
|---|---|---|---|
| 290 | 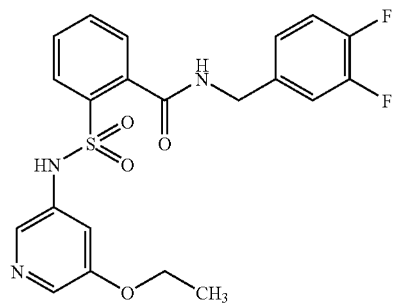 | N-(3,4-difluorobenzyl)-2-{[(5-ethoxypyridin-3-yl)amino]sulfonyl}benzamide | (400 MHz, CHLOROFORM-d) d ppm 8.46(s, 1H) 8.03(d, J=2.52 Hz, 1H) 7.91(d, J=1.51Hz, 1H) 7.72(d, J=7.81Hz, 1H) 7.50-7.62(m, 2H) 7.38-7.47(m, 1H) 7.26-7.33 (m, 1H) 7.11-7.23(m, 3H) 6.54(t, J=5.54Hz, 1H) 4.67 (d, J=6.04Hz, 2H) 4.03(q, J=6.97Hz, 2H) 1.41(t, J=6.92Hz, 3H) |
| 291 | 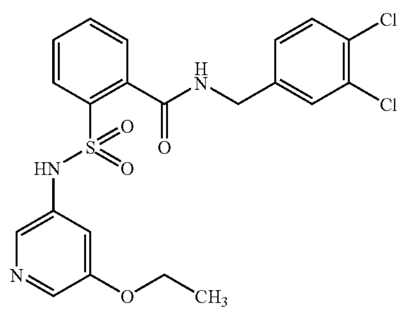 | N-(3,4-dichlorobenzyl)-2-{[(5-ethoxypyridin-3-yl)amino]sulfonyl}benzamide | (400 MHz, CHLOROFORM-d) d ppm 8.44(s, 1H) 8.04(d, J=2.52 Hz, 1H) 7.92(d, J=1.76Hz, 1H) 7.73(d, J=7.81Hz, 1H) 7.51-7.62(m, 3H) 7.40-7.50(m, 2H) 7.31(dd, J=8.18, 1.64Hz, 1H) 7.21 (t, J=2.14Hz, 1H) 6.52(t, J=5.67Hz, 1H) 4.67(d, J=6.04Hz, 2H) 4.03(q, J=6.97Hz, 2H) 1.41(t, J=6.92Hz, 3H) |
| 292 | 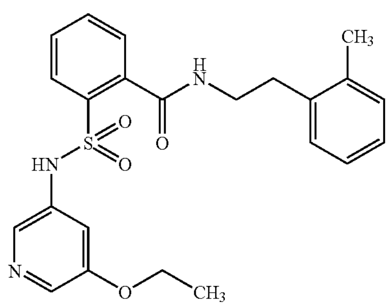 | 2-{[(5-ethoxypyridin-3-yl)amino]sulfonyl}-N-[2-(2-methylphenyl)ethyl]benzamide | (400 MHz, CHLOROFORM-d) d ppm 8.63(s, 1H) 8.05(d, J=2.52 Hz, 1H) 7.94(d, J=2.01Hz, 1H) 7.65-7.76(m, 1H) 7.50-7.59(m, 1H) 7.33-7.45(m, 2H) 7.13-7.26(m, 5H) 6.14(s, 1H) 4.03(q, J=7.05Hz, 2H) 3.76(q, J=6.80Hz, 2H) 3.03(t, J=6.92Hz, 2H) 2.40(s, 3H) 1.41(t, J=7.05Hz, 3H) |
| 293 | 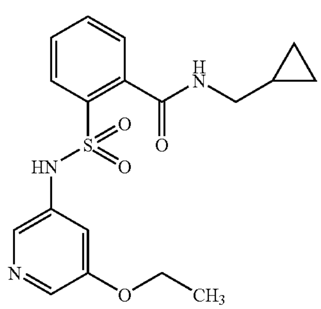 | N-(cyclopropylmethyl)-2-{[(5-ethoxypyridin-3-yl)amino]sulfonyl}benzamide | (400 MHz, CHLOROFORM-d) d ppm 8.61(s, 1H) 8.04(d, J=2.52 Hz, 1H) 7.93(d, J=2.01Hz, 1H) 7.71(d, J=7.81Hz, 1H) 7.52-7.61(m, 2H) 7.35-7.47(m, 1H) 7.20(t, J=2.27Hz, 1H) 6.28(s, 1H) 4.02(q, J=7.05Hz, 2H) 3.39(dd, J=7.18, 5.67Hz, 2H) 1.28-1.51(m, 3H) 1.00-1.17(m, 1H) 0.49-0.67 (m, 2H) 0.33(q, J=4.78Hz, 2H) |
| 294 | 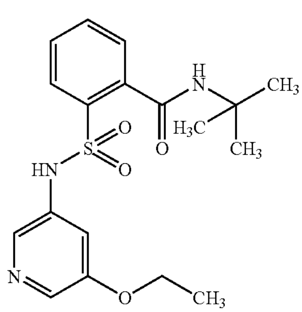 | N-(tert-butyl)-2-{[(5-ethoxy-pyridin-3-yl)amino]sulfonyl} benzamide | (400 MHz, CHLOROFORM-d) d ppm 8.55(s, 1H) 8.04(d, J=2.52 Hz, 1H) 7.93(d, J=1.76Hz, 1H) 7.67(d, J=7.81Hz, 1H) 7.47-7.58(m, 2H) 7.35-7.42(m, 1H) 7.18-7.22 (m, 1H) 5.92(s, 1H) 4.02 (q, J=6.88Hz, 2H) 1.53(s, 9H) 1.32-1.44(m, 3H) |

| Example No. | Structure | Name | ¹H NMR |
|---|---|---|---|
| 295 | 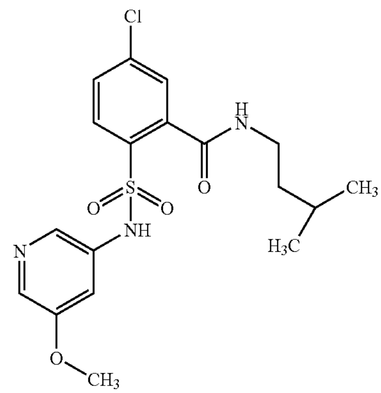 | 5-chloro-2-{[(5-methoxypyridin-3-yl)amino]sulfonyl}-N-(3-methylbutyl)benzamide | (400 MHz, DMSO-d6) d ppm 9.98(s, 1H), 8.74(t, J=5.31Hz, 1H), 8.03(d, J=2.53Hz, 1H), 7.93(d, J=1.77Hz, 1H), 7.78(d, J=8.59Hz, 1H), 7.66(dd, J=8.46, 2.15Hz, 1H), 7.59(d, J=2.27Hz, 1H), 7.15(t, J=2.27Hz, 1H), 3.78(s, 3H), 3.24-3.32(m, 2H), 1.62-1.73(m, J=13.34, 6.95, 6.71, 6.71, 6.71Hz, 1H), 1.43(q, J=7.16Hz, 2H), 1.17(s, 1H), 0.91(d, J=6.57 Hz, 6H) |
| 296 | 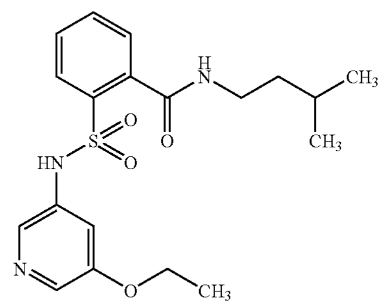 | 2-{[(5-ethoxypyridin-3-yl)amino]sulfonyl}-N-(3-methylbutyl)benzamide | (400 MHz, CHLOROFORM-d) d ppm 8.62(s, 1H) 8.04(d, J=2.52 Hz, 1H) 7.93(d, J=2.01Hz, 1H) 7.70(d, J=7.81Hz, 1H) 7.48-7.61(m, 2H) 7.33-7.46(m, 1H) 7.20(t, J=2.27Hz, 1H) 6.13(s, 1H) 3.92-4.12(m, 2H) 3.41-3.64(m, 2H) 1.67-1.83(m, 1H) 1.53-1.63(m, 2H) 1.23-1.43(m, 3H) 0.88-1.03(m, 6H) |
| 297 | 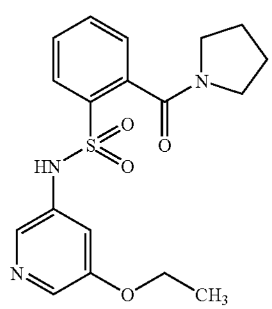 | N-(5-ethoxypyridin-3-yl)-2-(pyrrolidin-1-ylcarbonyl)benzenesulfonamide | (400 MHz, CHLOROFORM-d) d ppm 8.15(s, 1H) 8.05(d, J=2.27 Hz, 1H) 7.97(d, J=1.51Hz, 1H) 7.65(d, J=7.81Hz, 1H) 7.57(t, J=7.55Hz, 1H) 7.33-7.44(m, 2H) 7.18(s, 1H) 4.00(q, J=7.05Hz, 2H) 3.72(s, 1H) 3.48(q, J=6.97Hz, 1H) 3.29(t, J=6.55Hz, 2H) 1.92-2.08(m, 3H) 1.39(t, J=6.92Hz, 2H) 1.14-1.32(m, 2H) |
| 298 | 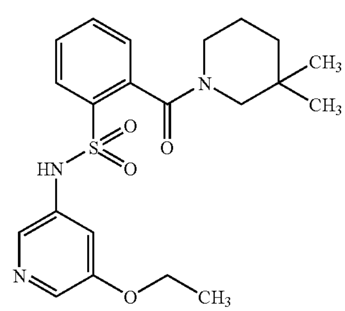 | 2-[(3,3-dimethylpiperidin-1-yl)carbonyl]-N-(5-ethoxypyridin-3-yl)benzenesulfonamide | Mass point = LCMS 418.7 MH+ |

| Example No. | Name | ¹H NMR |
|---|---|---|
| 299 | N-(1-cyclopropylethyl)-2-{[(5-ethoxypyridin-3-yl)amino]sulfonyl}benzamide | (400 MHz, CHLOROFORM-d) d ppm 8.60(s, 1H) 8.02(d, J=2.52 Hz, 1H) 7.92(d, J=2.01Hz, 1H) 7.71(d, J=7.81Hz, 1H) 7.51-7.59(m, 2H) 7.36-7.46(m, 1H) 7.08-7.24 (m, 1H) 6.25(d, J=7.81Hz, 1H) 3.92-4.08(m, 2H) 1.31-1.48(m, 6H) 0.83-1.04(m, 1H) 0.45-0.69(m, 4H) 0.22-0.43(m, 1H) |
| 300 | N-(1,1-dimethylpropyl)-2-{[(5-ethoxypyridin-3-yl)amino]sulfonyl}benzamide | (400 MHz, CHLOROFORM-d) d ppm 0.99(t, J=7.43Hz, 3H) 1.16 (t, J=6.92Hz, 3H) 1.47(s, 6H) 1.89(q, J=7.55Hz, 2H) 3.83(q, J=6.97Hz, 2H) 5.75(s, 1H) 6.62(d, J=5.54 Hz, 1H) 7.33-7.47(m, 1H) 7.48-7.64(m, 2H) 7.76(d, J=7.81Hz, 1H) 8.23(d, J=5.54Hz, 1H) 8.62(s, 1H) 8.73(s, 1H) |
| 301 | N-cyclopropyl-2-{[(5-ethoxypyridin-3-yl)amino]sulfonyl}benzamide | (400 MHz, CHLOROFORM-d) d ppm 8.50(s, 1H) 7.99-8.07(m, 1H) 7.89-7.96(m, 1H) 7.63(d, J=7.81Hz, 1H) 7.49-7.56(m, 1H) 7.43-7.49(m, 1H) 7.33-7.41(m, 1H) 7.18(t, J=2.39Hz, 1H) 6.53(s, 1H) 3.94-4.10(m, 2H) 2.89-3.02(m, 1H) 1.29-1.45(m, 3H) 0.87-0.98(m, 2H) 0.70-0.80(m, 2H) |
| 302 | N-cyclohexyl-2-{[(5-ethoxypyridin-3-yl)amino]sulfonyl}benzamide | (400 MHz, CHLOROFORM-d) d ppm 8.62(s, 1H) 7.99-8.10(m, 1H) 7.93(d, J=2.01Hz, 1H) 7.69(d, J=7.81Hz, 1H) 7.47-7.58(m, 2H) 7.35-7.45(m, 1H) 7.20(t, J=2.27 Hz, 1H) 6.09(d, J=8.06Hz, 1H) 3.92-4.10(m, 3H) 2.06-2.17(m, 2H) 1.62-1.87(m, 4H) 1.14-1.51(m, 7H) |
| 303 | 5-fluoro-2-{[(5-methoxypyridin-3-yl)amino]sulfonyl}-N-(3-methylbutyl)benzamide | (400 MHz, CHLOROFORM-d) d ppm 0.99(d, J=6.57Hz, 6H) 1.74(ddd, J=13.26, 6.82, 6.69Hz, 1H) 3.54(td, J=7.39, 5.94Hz, 2H) 3.82(s, 3H) 6.05(s, 1H) 7.09(td, J=8.21, 2.53Hz, 1H) 7.17-7.24(m, 2H) 7.73 (dd, J=8.59, 5.31Hz, 1H) 7.97(d, J=2.02Hz, 1H) 8.08(d, J=2.53Hz, 1H) 8.45(s, 1H) |

-continued

| Example No. | Structure | Name | ¹H NMR |
|---|---|---|---|
| 304 | 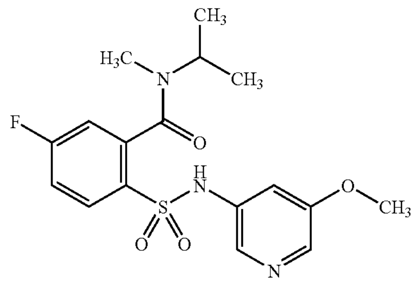 | 5-fluoro-N-isopropyl-2-{[(5-methoxypyridin-3-yl)amino]sulfonyl}-N-methylbenzamide | (400 MHz, CHLOROFORM-d) d ppm 1.21-1.27(m, 3H) 1.29(d, J=6.82Hz, 3H) 2.77(s, 1H) 3.02(s, 2H) 3.77-3.85(m, 4H) 6.99-7.07(m, 2H) 7.18(t, J=2.27 Hz, 1H) 7.61-7.68(m, 1H) 7.93-8.00(m, 1H) 8.06-8.11 (m, 1H) |
| 305 | 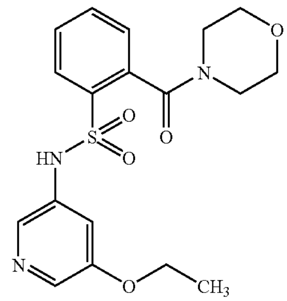 | N-(5-ethoxypyridin-3-yl)-2-(morpholin-4-ylcarbonyl)benzenesulfonamide | (400 MHz, CHLOROFORM-d) d ppm 8.06(d, J=2.52Hz, 1H) 7.92(d, J=1.76Hz, 1H) 7.87(d, 1H) 7.65(d, J=7.81 Hz, 1H) 7.54-7.61(m, 1H) 7.30-7.41(m, 2H) 7.18(t, J=2.27Hz, 1H) 4.16-4.25 (m, 1H) 3.95-4.08(m, 2H) 3.82-3.88(m, 2H) 3.71-3.79(m, 1H) 3.60-3.69(m, 1H) 3.49-3.60(m, 1H) 3.24-3.44(m, 2H) 1.33-1.45(m, 3H) |
| 306 | 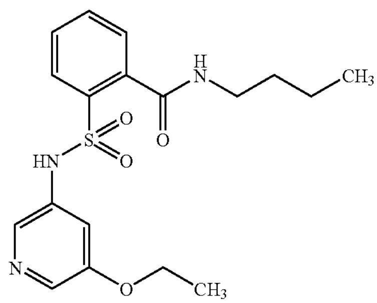 | N-butyl-2-{[(5-ethoxypyridin-3-yl)amino]sulfonyl}benzamide | (400 MHz, CHLOROFORM-d) d ppm 8.62(s, 1H) 8.04(d, J=2.52 Hz, 1H) 7.94(d, J=1.76Hz, 1H) 7.71(d, J=7.81Hz, 1H) 7.48-7.60(m, 2H) 7.38-7.45(m, 1H) 7.21(t, J=2.27Hz, 1H) 6.12(s, 1H) 4.02(q, J=7.05Hz, 2H) 3.42-3.59(m, 2H) 1.58-1.72(m, 2H) 1.43-1.53(m, 2H) 1.40(t, J=6.92Hz, 3H) 1.00(t, J=7.30Hz, 3H) |
| 307 | 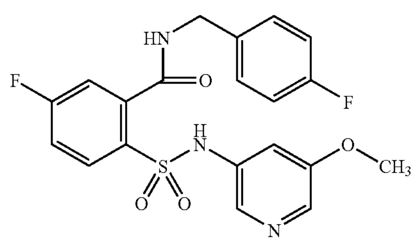 | 5-fluoro-N-(4-fluorobenzyl)-2-{[(5-methoxypyridin-3-yl)amino]sulfonyl}benzamide | (400 MHz, CHLOROFORM-d) d ppm 3.83(s, 3H) 4.68 (d, J=5.81Hz, 2H) 6.43(s, 1H) 7.06-7.17(m, 3H) 7.19-7.26(m, 2H) 7.41 (dd, J=8.59, 5.31Hz, 2H) 7.75(dd, J=8.72, 5.18Hz, 1H) 7.96(d, J=2.02Hz, 1H) 8.08(d, J=2.53Hz, 1H) 8.37(s, 1H) |
| 308 | 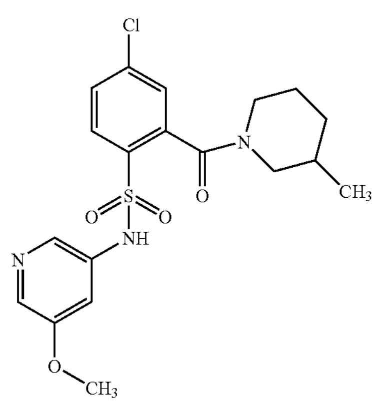 | 4-chloro-N-(5-methoxypyridin-3-yl)-2-[(3-methylpiperidin-1-yl)carbonyl]benzenesulfonamide | (400 MHz, CHLOROFORM-d) d ppm 8.57(s, 1H), 8.23 (s, 1H), 8.16(s, 1H), 7.65-7.72(m, 1H), 7.45-7.53 (m, 1H), 7.30-7.42(m, 2H), 3.90(s, 3H), 3.04-3.15 (m, 1H), 2.77-2.85(m, 1H), 2.71(dd, J=11.37, 6.32 Hz, 1H), 2.45-2.55(m, 1H), 1.92(d, J=4.29Hz, 1H), 1.77(d, J=4.29Hz, 1H), 1.73(s, 1H), 1.58(d, J=13.64Hz, 1H), 1.26(s, 1H), 1.14-1.23(m, 1H), 1.04(dd, J=19.58, 6.44Hz, 1H), 0.78-0.90(m, 1H) |

| Example No. | Structure | Name | ¹H NMR |
|---|---|---|---|
| 309 | 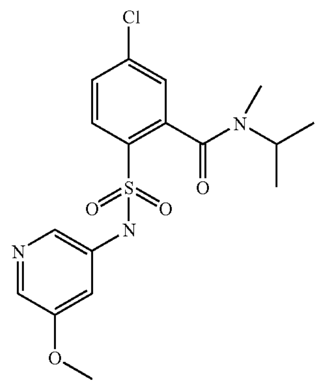 | 5-chloro-N-isopropyl-2-{[(5-methoxypyridin-3-yl)amino]sulfonyl}-N-methylbenzamide | (400 MHz, CHLOROFORM-d) d ppm 8.21(d, J=2.27Hz, 1H), 8.13(s, 1H), 7.65(dd, J=8.34, 5.56Hz, 1H), 7.43 (t, J=2.15Hz, 1H), 7.39 (ddd, J=8.34, 4.04, 2.02Hz, 1H), 7.34(t, J=1.89Hz, 1H), 3.89(s, 3H), 3.03(s, 1H), 2.90(s, 3H), 2.78(s, 1H), 1.25-1.34(m, 4H), 1.23(d, J=6.57Hz, 1H) |
| 310 | 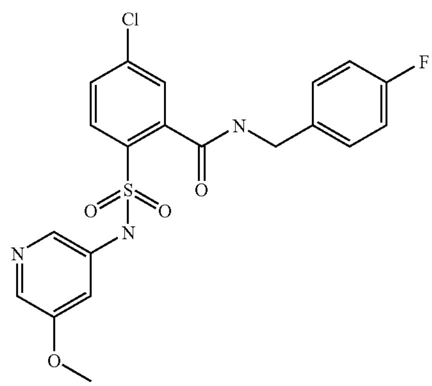 | 5-chloro-N-(4-fluorobenzyl)-2-{[(5-methoxypyridin-3-yl)amino]sulfonyl}benzamide | (400 MHz, DMSO-d6) d ppm 10.07(s, 1H), 9.29(t, J=5.81Hz, 1H), 8.03(d, J=2.78Hz, 1H), 7.95(d, J=2.02Hz, 1H), 7.82(d, J=8.34Hz, 1H), 7.65-7.72 (m, 2H), 7.45(dd, J=8.34, 5.56Hz, 2H), 7.20(s, 1H), 7.17(ddd, J=4.61, 2.21, 2.02Hz, 2H), 4.49(d, J=5.81Hz, 2H), 3.77(s, 3H) |
| 311 | 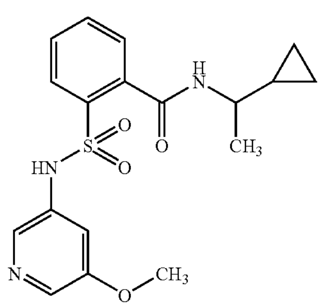 | N-(1-cyclopropylethyl)-2-{[(5-methoxypyridin-3-yl)amino]sulfonyl}benzamide | (400 MHz, CHLOROFORM-d) d ppm 8.61(s, 1H) 8.05(d, J=2.52 Hz, 1H) 7.95(d, J=2.01Hz, 1H) 7.72(d, J=8.06Hz, 1H) 7.50-7.61(m, 2H) 7.36-7.45(m, 1H) 7.23(t, J=2.27Hz, 1H) 6.12(s, 1H) 3.81(s, 3H) 3.56-3.70(m, 1H) 1.39(d, J=6.55Hz, 3H) 0.88-1.02(m, 1H) 0.44-0.70(m, 3H) 0.29-0.43(m, 1H) |
| 312 | 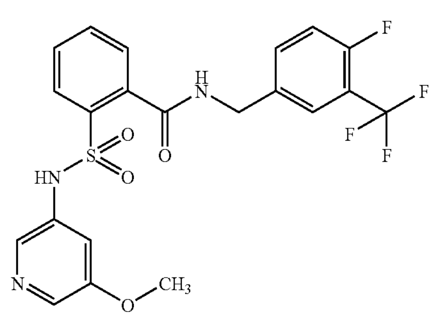 | N-[4-fluoro-3-(trifluoromethyl)benzyl]-2-{[(5-methoxypyridin-3-yl)amino]sulfonyl}benzamide | (400 MHz, CHLOROFORM-d) d ppm 8.37(s, 1H) 8.15(dd, J=9.69,1.64Hz, 2H) 7.64-7.74(m, 3H) 7.50-7.60(m, 2H) 7.39-7.47(m, 2H) 7.20-7.26(m, 1H) 6.67(t, J=5.67Hz, 1H) 4.73(d, J=5.79Hz, 2H) 2.28(s, 3H) |

-continued

| Example No. | Structure | Name | ¹H NMR |
|---|---|---|---|
| 313 | 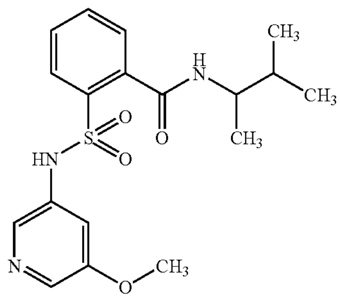 | N-(1,2-dimethylpropyl)-2-{[(5-methoxypyridin-3-yl)amino]sulfonyl}benzamide | (400 MHz, CHLOROFORM-d) d ppm 8.39(d, J=2.27Hz, 1H) 8.16(dd, J=8.44, 1.64Hz, 2H) 7.70(d, J=7.55Hz, 1H) 7.51-7.61(m, 3H) 7.39-7.49(m, 3H) 7.31(dd, J=8.31, 2.01Hz, 1H) 6.59(t, J=5.79Hz, 1H) 4.67(d, J=6.04Hz, 2H) 2.28(s, 3H) |
| 314 | 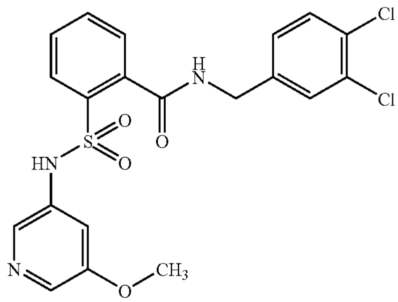 | N-(3,4-dichlorobenzyl)-2-{[(5-methoxypyridin-3-yl)amino]sulfonyl}benzamide | (400 MHz, CHLOROFORM-d) d ppm 8.39(d, J=2.27Hz, 1H) 8.16(dd, J=8.44, 1.64 Hz 2H) 7.70(d, J=7.55Hz, 1H) 7.51-7.61(m, 3H) 7.39-7.49(m, 3H) 7.31(dd, J=8.31, 2.01Hz, 1H) 6.59(t, J=5.79Hz, 1H) 4.67(d, J=6.04Hz, 2H) 2.28(s, 3H) |
| 315 | 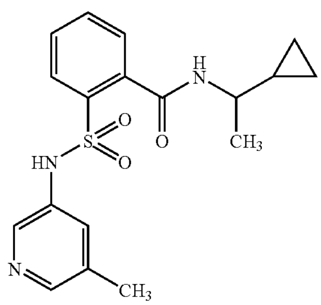 | N-(1-cyclopropylethyl)-2-{[(5-methylpyridin-3-yl)amino]sulfonyl}benzamide | (400 MHz, CHLOROFORM-d) d ppm 8.54(s, 1H) 8.18(s, 2H) 7.70(d, J=7.81Hz, 1H) 7.50-7.60(m, 2H) 7.36-7.48(m, 2H) 6.12(s, 1H) 3.57-3.70(m, 1H) 2.27(s, 3H) 1.39(d, J=6.55Hz, 3H) 0.90-1.01(m, 1H) 0.45-0.66(m, 3H) 0.30-0.43(m, 1H) |
| 316 | 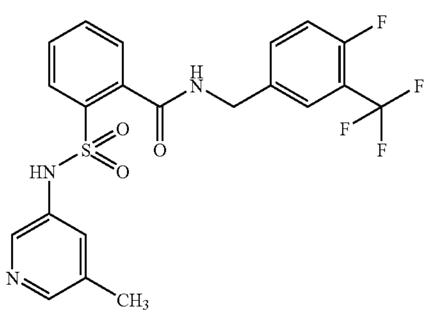 | N-[4-fluoro-3-(trifluoromethyl)benzyl]-2-{[(5-methylpyridin-3-yl)amino]sulfonyl}benzamide | (400 MHz, CHLOROFORM-d) d ppm 8.37(s, 1H) 8.15(dd, J=9.69, 1.64Hz, 2H) 7.64-7.74(m, 3H) 7.50-7.60(m, 2H) 7.39-7.47(m, 2H) 7.20-7.26(m, 1H) 6.67(t, J=5.67Hz, 1H) 4.73(d, J=5.79Hz, 2H) 2.28(s, 3H) |
| 317 | 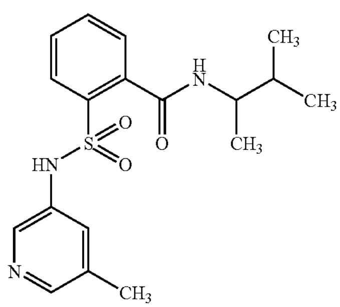 | N-(1,2-dimethylpropyl)2{[(5-methylpyridin-3-yl)amino]sulfonyl}benzamide | (400 MHz, CHLOROFORM-d) d ppm 8.39(d, J=2.27Hz, 1H) 8.16(dd, J=8.44, 1.64Hz, 2H) 7.70(d, J=7.55Hz, 1H) 7.51-7.61(m, 3H) 7.39-7.49(m, 3H) 7.31(dd, J=8.31, 2.01Hz, 1H) 6.59(t, J=5.79Hz, 1H) 4.67(d, J=6.04Hz, 2H) 2.28(s, 3H) |

| Example No. | Structure | Name | ¹H NMR |
|---|---|---|---|
| 318 | 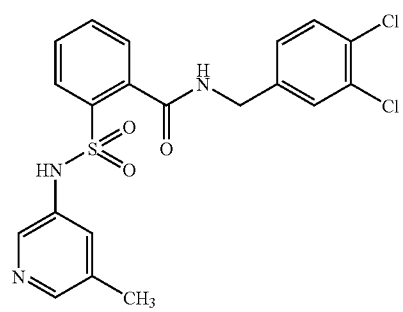 | N-(3,4-dichlorobenzyl)-2-{[(5-methylpyridin-3-yl)amino]sulfonyl}benzamide | (400 MHz, CHLOROFORM-d) d ppm 8.39(d, J=2.27Hz, 1H) 8.16(dd, J=8.44, 1.64 Hz 2H) 7.70(d, J=7.55Hz, 1H) 7.51-7.61(m, 3H) 7.39-7.49(m, 3H) 7.31 (dd, J=8.31, 2.01Hz, 1H) 6.59(t, J=5.79Hz, 1H) 4.67 (d, J=6.04Hz, 2H) 2.28(s, 3H) |
| 319 | 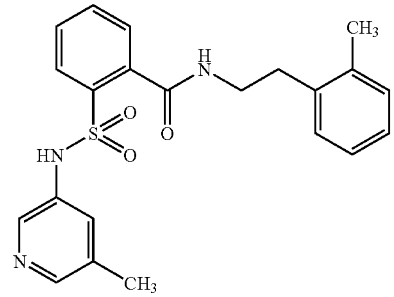 | N-[2-(2-methylphenyl)ethyl]-2-{[(5-methylpyridin-3-yl)amino]sulfonyl}benzamide | (400 MHz, CHLOROFORM-d) d ppm 2.15-2.46(m, 3H) 2.80-2.98(m, 3H) 3.39-3.51(m, 2H) 3.50-3.70(m, 2H) 5.90-6.41(m, 1H) 6.98-7.31(m, 7H) 7.36-7.71(m, 3H) 8.01(s, 1H) 8.49(dd, J=9.69, 3.15Hz, 1H) |
| 320 | 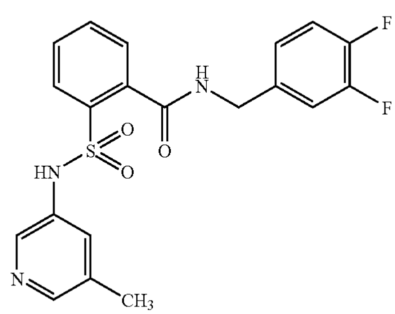 | N-(3,4-difluorobenzyl)-2-{[(5-methylpyridin-3-yl)amino]sulfonyl}benzamide | (400 MHz, CHLOROFORM-d) d ppm 8.39(d, J=2.27Hz, 1H) 8.16(dd, J=8.44, 1.64 Hz 2H) 7.70(d, J=7.55Hz, 1H) 7.51-7.61(m, 3H) 7.39-7.49(m, 3H) 7.31 (dd, J=8.31, 2.01Hz, 1H) 6.59(t, J=5.79Hz, 1H) 4.67 (d, J=6.04Hz, 2H) 2.28(s, 3H) |
| 321 | 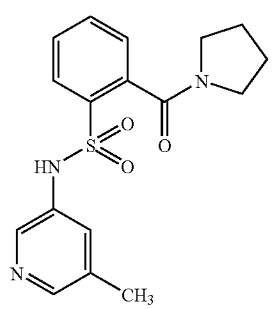 | N-(5-methylpyridin-3-yl)-2-(pyrrolidin-1-ylcarbonyl)benzenesulfonamide | (400 MHz, CHLOROFORM-d) d ppm 8.50(d, J=2.52Hz, 2H) 7.52-7.70(m, 2H) 7.39(d, J=7.55Hz, 1H) 7.31-7.37 (m, 2H) 7.20-7.29(m, 1H) 3.63(s, 2H) 3.33-3.38(m, 3H) 3.23-3.32(m, 1H) 3.03(s, 1H) 1.80-2.07(m, 4H) |
| 322 | 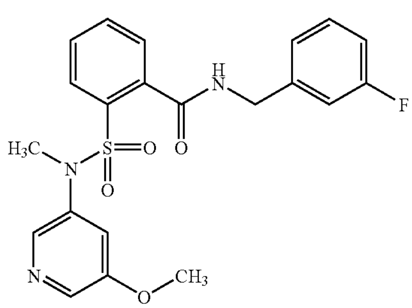 | N-(3-fluorobenzyl)-2-{[(5-methoxypyridin-3-yl)(methyl)amino]sulfonyl}benzamide | (400 MHz, MeOD) δ 8.300 (s, 2H), 7.744-6.972(m, 9H), 4.441(s, 2H), 3.913(s, 3H), 3.324(s, 3H) |

-continued

| Example No. | Structure | Name | ¹H NMR |
|---|---|---|---|
| 323 | 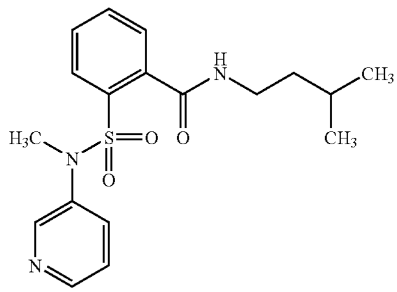 | N-(3-methylbutyl)-2-{[methyl(pyridin-3-yl)amino]sulfonyl}benzamide | (400 MHz, MeOD) δ8.470 (m, 2H), 7.743(m, 2H), 7.514 9m, 5H), 3.364(m, 5H), 1.735(m, 1H), 1.514 (m, 2H), 0.963(d, J=8.8Hz, 6H) |
| 324 | 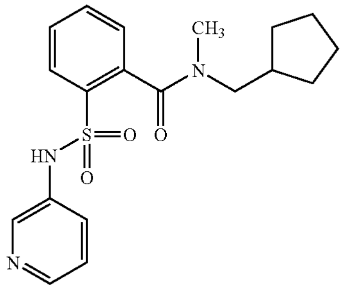 | N-(cyclopentylmethyl)-N-methyl-2-[(pyridin-3-ylamino)sulfonyl]benzamide | (400 MHz, MeOD) δ 8.600 (s, 1H), 8.450 9s, 1H), 8.153 (m, 1H), 7.982(m, 1H), 7.771(m, 2H), 7.611(m, 1H), 7.441(m, 1H), 3.713 (m, 1H), 3.294(m, 2H), 2.854(s, 2H), 2.419(m, 1H), 1.863-1.000(m, 8H) |
| 325 | 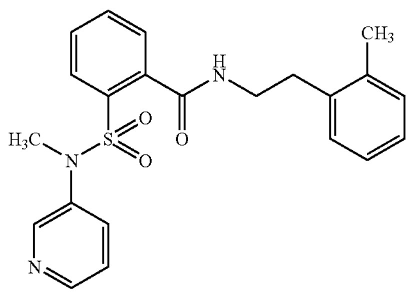 | N-[2-(2-methylphenyl)ethyl]-2-{[methyl(pyridin-3-yl)amino]sulfonyl}benzamide | (400 MHz, CHLOROFORM-d) d ppm 2.15-2.46(m, 3H) 2.80-2.98(m, 3H) 3.39-3.51(m, 2H) 3.50-3.70(m, 2H) 5.90-6.41(m, 1H) 6.98-7.31(m, 7H) 7.36-7.71(m, 3H) 8.01(s, 1H) 8.49(dd, J=9.69, 3.15Hz, 1H) |
| 326 | 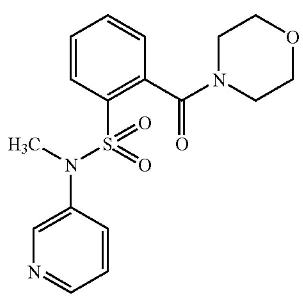 | N-methyl-2-(morpholin-4-ylcarbonyl)-N-pyridin-3-ylbenzenesulfonamide | (400 MHz, CHLOROFORM-d) d ppm 2.61-3.03(m, 3H) 3.02-3.19(m, 1H) 3.17-3.29(m, 1H) 3.43-3.59(m, 1H) 3.65-3.90(m, 5H) 7.00-7.48(m, 4H) 7.53-7.76(m, 2H) 8.39-8.66(m, 2H) |
| 327 | 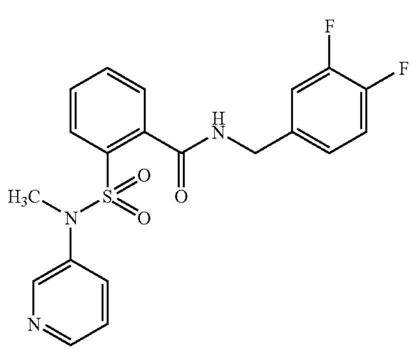 | N-(3,4-difluorobenzyl)-2-{[methyl(pyridin-3-yl)amino]sulfonyl}benzamide | (400 MHz, CHLOROFORM-d) d ppm 2.92-3.03(m, 3H) 3.21-3.39(m, 2H) 4.47(d, J=5.79Hz, 1H) 6.32(s, 1H) 6.99-7.32(m, 3H) 7.35-7.48(m, 1H) 7.50-7.68(m, 4H) 8.01(s, 1H) 8.50(d, J=2.77Hz, 1H) |

| Example No. | Structure | Name | ¹H NMR |
|---|---|---|---|
| 328 | 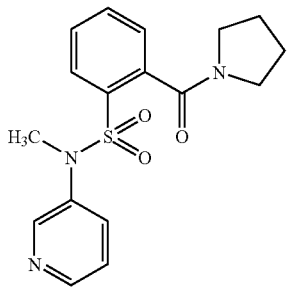 | N-methyl-N-pyridin-3-yl-2-(pyrrolidin-1-ylcarbonyl)benzenesulfonamide | (400 MHz, CHLOROFORM-d) d ppm 8.50(d, J=2.52Hz, 2H) 7.52-7.70(m, 2H) 7.39(d, J=7.55Hz, 1H) 7.31-7.37 (m, 2H) 7.20-7.29(m, 1H) 3.63(s, 2H) 3.33-3.38(m, 3H) 3.23-3.32(m, 1H) 3.03(s, 1H) 1.80-2.07(m, 4H) |
| 329 | 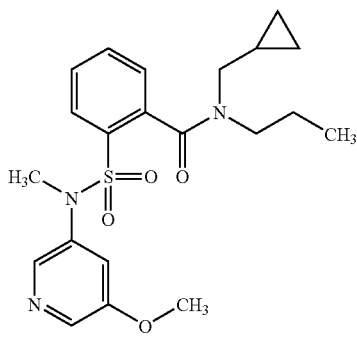 | N-(cyclopropylmethyl)-2-{[(5-methoxypyridin-3-yl)(methyl)amino]sulfonyl}-N-propylbenzamide | (400 MHz, MeOD) δ 8.453 (m, 2H), 7.802(m, 3H), 7.667(m, 1H), 7.432(m, 1H), 3.956(s, 3H), 3.594(m, 1H), 3.344(s, 3H), 3.294-2.868(m, 3H), 1.685-1.579 (m, 2H), 0.974(m, 3H), 0.700--0.100(m, 5H) |
| 330 | 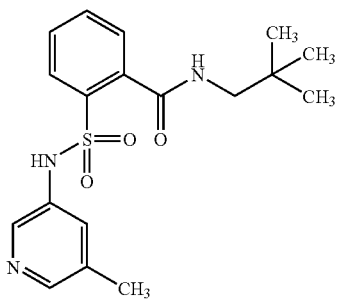 | N-(2,2-dimethylpropyl)-2-{[(5-methylpyridin-3-yl)amino]sulfonyl}benzamide | (400 MHz, MeOD) δ 8.440 (s, 1H), 8.312(s, 1H), 7.939 (m, 2H), 7.705(m, 1H), 7.610(m, 2H), 3.237(s, 2H), 2.416(s, 3H), 1.029(s, 9H) |
| 331 | 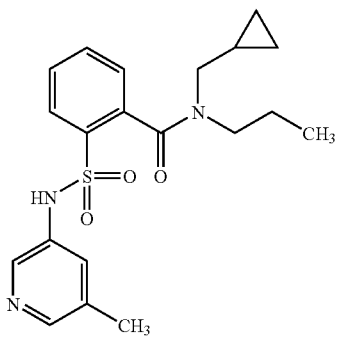 | N-(cyclopropylmethyl)-2-{[(5-methylpyridin-3-yl)amino]sulfonyl}-N-propylbenzamide | (400 MHz, MeOD) δ8.453 (s, 1H), 8.340(s, 1H), 7.977 (m, 2H), 7.740(m, 1H), 7.694(m, 1H), 7.449(m, 1H), 3.631(m, 2H), 3.024 (m, 2H), 2.439(s, 3H), 1.818-1.500(m, 2H), 1.300-0.348(m, 8H) |

| Example No. | Name | ¹H NMR |
|---|---|---|
| 332 | N-(cyclopentylmethyl)-2-{[methyl(pyridin-3-yl)amino]sulfonyl}benzamide | (400 MHz, MeOD) δ 8.799 (m, 1H), 8.620(d, 1H), 8.333(m, 1H), 7.938-7.434 (m, 5H), 3.366(s, 3H), 3.166 (d, J=9.6Hz, 2H), 2.130(m, 1H), 1.831-1.587(m, 6H), 1.300(m, 2H) |
| 333 | 2-[(3,5-dimethylpiperidin-1-yl)carbonyl]-N-(5-methylpyridin-3-yl)benzenesulfonamide | (400 MHz, MeOD): δ 8.458 (m, 1H), 8.320(s, 1H), 7.936 (m, 2H), 7.746-7.395(m, 3H), 4.672(m, 1H), 3.243 (m, 1H), 2.689(m, 1H), 2.433(s, 3H), 2.365(m, 1H), 1.902-1.649(m, 3H), 1.012 (m, 3H), 0.952(m, 1H), 0.752(m, 3H) |
| 334 | N-(cyclopentylmethyl)-2-{[(5-methylpyridin-3-yl)amino]sulfonyl}benzamide | (400 MHz, MeOD) δ 8.446 (s, 1H), 8.325(s, 1H), 7.954 (s, 1H), 7.898(m, 1H), 7.717 (m, 1H), 7.591(m, 2H), 3.346(m, 2H), 2.419(s, 3H), 2.305(m, 1H), 1.897-1.337 (m, 8H) |
| 335 | N-benzyl-N-methyl-2-{[(5-methylpyridin-3-yl)amino]sulfonyl}benzamide | (400 MHz, MeOD): δ 8.400 (s, 1H), 8.290(s, 1H), 7.900 (m, 2H), 7.71 7-7.210(m, 8H), 4.878(s, 2H), 2.981(s, 1H), 2.716(s, 2H), 2.373(s, 3H). |

| Example No. | Structure | Name | ¹H NMR |
|---|---|---|---|
| 336 | 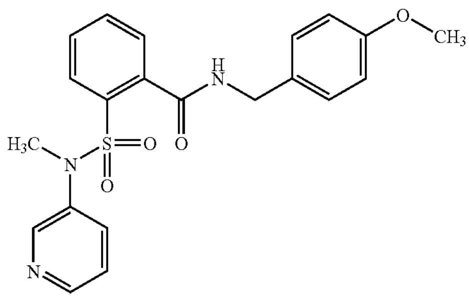 | N-(4-methoxybenzyl)-2-{[methyl(pyridin-3-yl)amino]sulfonyl}benzamide | (400 MHz, MeOD) δ 8.750 (m, 1H), 8.580(m, 1H), 8.238(m, 1H), 7.825-7.470 (m, 5H), 7.265(d, J=6.0Hz, 2H), 6.872(d, J=9.2Hz, 2H), 4.326(s, 1H), 3.766(s, 3H), 3.325(s, 3H) |
| 337 | 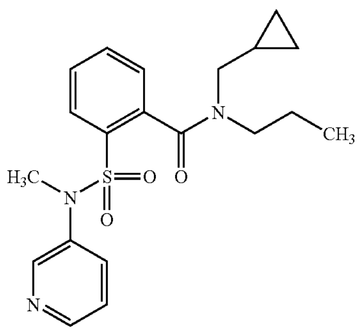 | N-(cyclopropylmethyl)-2-{[methyl(pyridin-3-yl)amino]sulfonyl}-N-propylbenzamide | (400 MHz, MeOD) δ 8.755 (s, 1H), 8.651(m, 1H), 8.320 (m, 1H), 7.936-7.620(m, 4H), 7.414(m, 1H), 3.522-2.856(m, 7H), 1.651(m, 2H), 1.017(m, 3H), 0.700--0.100(m, 5H) |
| 338 | 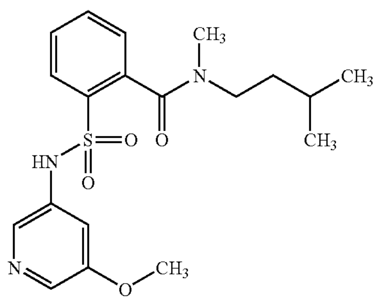 | 2-{[(5-methoxypyridin-3-yl)amino]sulfonyl}-N-methyl-N-(3-methylbutyl)benzamide | (400 MHz, MeOD) δ 8.159 (s, 2H), 7.987(m, 1H), 7.746 (m, 1H), 7.696(m, 2H), 7.460(m, 1H), 3.926(s, 3H), 3.611(m, 1H), 3.128(m, 2H), 2.831(2H), 1.722-1.364(m, 3H), 1.017(d, J=8.8Hz, 3H), 0.752(m, 3H) |
| 339 | 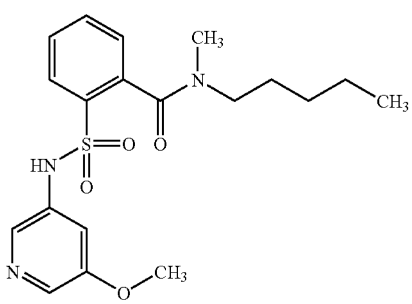 | 2-{[(5-methoxypyridin-3-yl)amino]sulfonyl}-N-methyl-N-pentylbenzamide | (400 MHz, MeOD) δ 8.121 (m, 2H), 7.987(m, 1H), 7.732(m, 1H), 7.605(m, 2H), 7.447(m, 1H), 3.899(s, 3H), 3.563(m, 1H), 3.102 (m, 2H), 2.827(s, 2H), 1.742-1.399(m, 4H), 1.194 (m, 2H), 0.990(m, 2H), 0.840(m, 1H) |
| 340 | 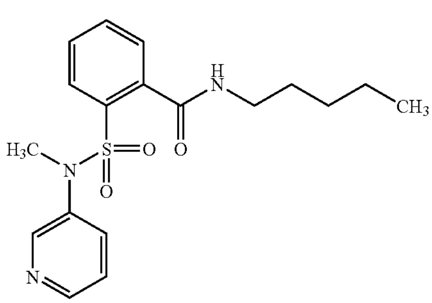 | 2-{[methyl(pyridin-3-yl)amino]sulfonyl}-N-pentylbenzamide | (400 MHz, MeOD) δ 8.800 (s, 1H), 8.643(d, J=6.8Hz, 1H), 8.377(m, 1H), 7.964-7.428(m, 5H), 3.367(s, 3H), 3.186(m, 2H), 1.540(m 2H), 1.361(m, 4H), 0.949 (m, 3H) |

| Example No. | Structure | Name | ¹H NMR |
|---|---|---|---|
| 341 | 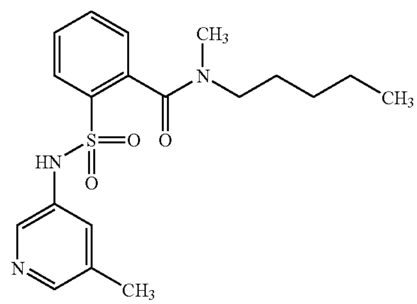 | N-methyl-2-{[(5-methylpyridin-3-yl)amino]sulfonyl}-N-pentylbenzamide | (400 MHz, MeOD) δ 8.480 (s, 1H), 8.350(s, 1H), 8.010 (m, 2H), 7.752(m, 2H), 7.445(m, 1H), 3.597(m, 1H), 3.114(m, 2H), 2.833(s, 2H), 2.447(s, 3H), 1.744-1.402(m, 4H), 1.202(m, 2H), 0.992(m, 2H), 0.853 (m, 1H) |
| 342 | 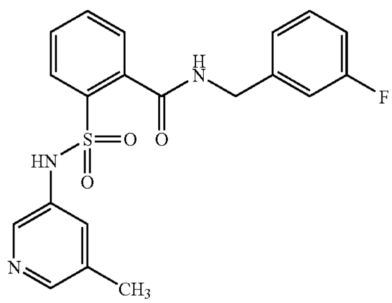 | N-(3-fluorobenzyl)-2-{[(5-methylpyridin-3-yl)amino]sulfonyl}benzamide | (400 MHz, MeOD) δ 8.500 (s, 1H), 8.300(s, 1H), 7.955 (m, 2H), 7.738-7.562(m, 3H), 7.398-7.192(m, 3H), 7.032(m, 1H), 4.623(s, 2H), 2.420(s, 3H) |
| 343 | 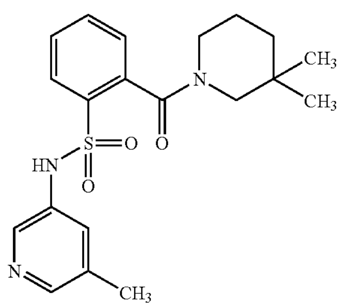 | 2-[(3,3-dimethylpiperidin-1-yl)carbonyl]-N-(5-methylpyridin-3-yl)benzenesulfonamide | (400 MHz, MeOD) δ 8.408 (m, 1H), 8.308(m, 1H), 7.965(m, 2H), 7.719(m, 1H), 7.586(m, 1H), 7.421 (m, 1H), 3.580(m, 1H), 3.170(m, 2H), 2.862(s, 1H), 2.422(s, 3H), 1.800-1.498 (m, 4H), 1.086(s, 6H) |
| 344 | 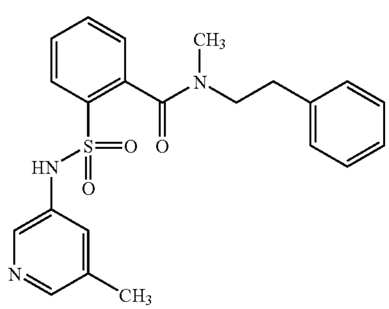 | N-methyl-2-{[(5-methylpyridin-3-yl)amino]sulfonyl}-N-(2-phenylethyl)benzamide | (400 MHz, MeOD): δ 8.490 (dd, 2H), 8.350(d, 2H), 8.050(m, 4H), 7.708-7.449 (m 4H), 7.336-7.221(m, 9H), 6.997(m, 2H), 6.592 (m, 1H), 4.000-3.600(m, 2H), 3.334(m, 2H), 3.265(s, 3H), 3.164-2.814(m, 4H), 2.764(s, 3H), 2.433(s, 3H), 2.406(s, 3H). |
| 345 | 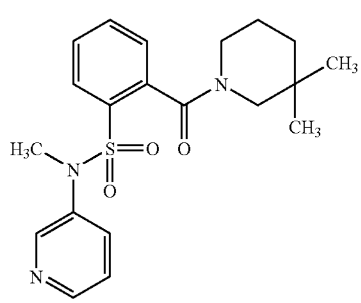 | 2-[(3,3-dimethylpiperidin-1-yl)carbonyl]-N-methyl-N-pyridin-3-ylbenzenesulfonamide | (400 MHz, MeOD) δ 8.800 (s, 1H), 8.650(d, 1H), 8.300 (m, 1H), 7.800-7.610(m, 4H), 7.402(d, J=10Hz, 1H), 3.370(m, 4H), 3.100(m, 2H), 2.737(m, 1H), 1.626 (m, 4H), 1.100-0.700(m, 6H) |

| Example No. | Name | 1H NMR |
|---|---|---|
| 346 | N-(3-fluorobenzyl)-2-{[(5-methoxypyridin-3-yl)amino]sulfonyl}-N-methylbenzamide | (400 MHz, MeOD) δ 8.180 (s, 2H), 7.950(d, 1H), 7.704-7.232(m, 6H), 7.102 (m, 2H), 4.817(m, 2H), 3.895(s, 3H), 3.034(s, 1H), 2.773(s, 2H) |
| 347 | N-(cyclopentylmethyl)-N-methyl-2-{[(5-methylpyridin-3-yl)amino]sulfonyl}benzamide | (400 MHz, MeOD) δ 8.445 (s, 1H), 8.342(s, 1H), 7.992 (m, 2H), 7.753(m, 2H), 7.440(m, 1H), 3.694(m, 1H), 3.119(m, 2H), 2.857(s, 2H), 2.441(m, 4H), 1.872-1.000(m, 9H) |
| 348 | N-methyl-N-(3-methylbutyl)-2-{[(5-methylpyridin-3-yl)amino]sulfonyl}benzamide | (400 MHz, MeOD) δ 8.500 (s, 1H), 8.350(s, 1H), 8.024 (m, 2H), 7.750(m, 2H), 7.454(m, 1H), 3.617(m, 1H) 3.132(m, 2H), 2.454(s, 2H), 1.732(m, 2H), 1.397 (m, 1H), 1.018(d, J=8.4Hz, 3H), 0.753(m, 3H) |
| 349 | N-(3-fluorobenzyl)-N-methyl-2-{[(5-methylpyridin-3-yl)amino]sulfonyl}benzamide | (400 MHz, MeOD) δ 8.480 (s, 1H), 8.320(s, 1H), 7.987 (m, 2H), 7.766-7.228(m, 5H), 7.102(m, 2H), 4.802(s, 2H), 3.032(s, 1H), 2.777(s, 2H), 2.436(s, 3H) |
| 350 | N-(3-fluorobenzyl)-N-methyl-2-[(pyridin-3-ylamino)sulfonyl]benzamide | (400 MHz, MeOD) δ 8.650 (br, 1H), 8.485(br, 1H), 8.181(m, 1H), 7.996(m, 1H), 7.749-6.998(m, 8H), 4.801(s, 2H), 2.767(s, 3H) |

| Example No. | Name | ¹H NMR |
|---|---|---|
| 351 | N-butyl-2-{[methyl(pyridin-3-yl)amino]sulfonyl}benzamide | (400 MHz, MeOD) δ 8.800 (s, 1H), 8.655(d, J=7.2Hz, 1H), 8.415(m, 1H), 7.980-7.627(m, 4H) 7.459(d, J=10H), 3.307(s, 3H), 3.192(m, 2H), 1.564(m, 4H), 0.937(m, 3H) |
| 352 | N-butyl-N-methyl-2-{[(5-methylpyridin-3-yl)amino]sulfonyl}benzamide | (400 MHz, MeOD) δ 8.450 (s, 1H), 8.352(s, 1H), 7.995 (m, 2H), 7.749(m, 2H), 7.415(m, 1H), 3.578(m, 1H), 3.120(m, 2H), 2.830(s, 2H), 2.446(s, 3H), 1.731-1.414(m, 3H), 1.196(m, 1H), 1.041(m, 2H), 0.819 (m, 1H) |
| 353 | N-butyl-2-{[(5-methoxypyridin-3-yl)amino]sulfonyl}-N-methylbenzamide | (400 MHz, MeOD) δ 8.200 (s, 2H), 7.980(m, 1H), 7.745 (m, 1H), 7.625(m, 2H), 7.451(m, 1H), 3.925(s, 3H), 3.578(m, 1H), 3.116(s, 2H), 2.836(s, 2H), 1.734-1.412 (m, 3H), 1.195(m, 1H), 1.039(m, 2H), 0.810(m, 1H) |
| 354 | N-(tert-butyl)-2-{[(5-methyl-pyridin-3-yl)amino]sulfonyl}benzamide | (400 MHz, MeOD) δ 8.466 (s, 1H), 8.330(s, 1H), 7.971 (m, 2H), 7.863(m, 1H), 7.666(m, 1H), 7.550(m, 1H), 2.426(s, 3H), 1.468(s, 9H) |
| 355 | N-benzyl-N-methyl-2-{[methyl(pyridin-3-yl)amino]sulfonyl}benzamide | (400 MHz MeOD) δ 8.800 (s, 1H), 8.650(m, 1H), 8.365 (m, 1H), 8.000-7.163(m, 10H), 4.667(m, 1H), 4.259 (m, 1H), 3.468(s, 3H), 2.808 (s, 1H), 2.638(s, 2H) |

| Example No. | Structure | Name | ¹H NMR |
|---|---|---|---|
| 356 | 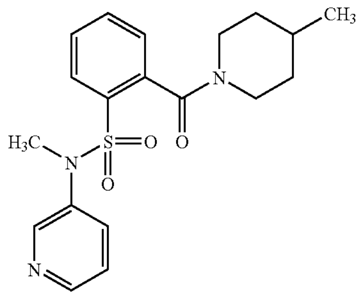 | N-methyl-2-[(4-methylpiperidin-1-yl)carbonyl]-N-pyridin-3-ylbenzenesulfonamide | (400 MHz, MeOD) δ 8.800 (m, 1H), 8.650(d, 1H), 8.400(m, 1H), 7.980-7.625 (m, 4H), 7.422 9m, 1H), 4.327(m, 1H), 3.392(s, 3H), 3.296-2.567(m, 3H), 1.800-0.900(m, 9H) |
| 357 | 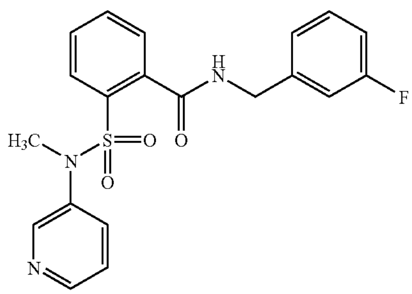 | N-(3-fluorobenzyl)-2-{[methyl(pyridin-3-yl)amino]sulfonyl}benzamide | (400 MHz, MeOD) δ 8.780 (m, 1H), 8.590(m, 1H), 8.258(m, 1H), 7.900-6.942 (m, 9H), 4.403(s, 2H), 3.314 (s, 3H) |
| 358 | 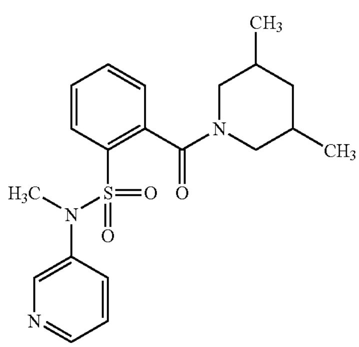 | 2-[(3,5-dimethylpiperidin-1-yl)carbonyl]-N-methyl-N-pyridin-3-ylbenzenesulfonamide | (400 MHz, MeOD) δ 8.800 (d, 1H), 8.650(d, 1H), 8.350 (m, 1H), 7.914-7.628(m, 4H), 7.388(m, 1H), 4.368 (m, !H), 3.362(s, 3H), 3.116 (m, 1H), 2.565(m, 1H), 2.226(m, 1H), 1.913-1.670 (m, 3H), 1.000-0.600(m, 7H) |
| 359 | 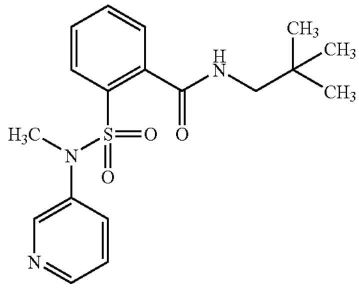 | N-(2,2-dimethylpropyl)-2-{[methyl(pyridin-3-yl)amino]sulfonyl}benzamide | (400 MHz, MeOD) δ 8.821 (d, J=3.2Hz, 1H), 8.631(d, 1H), 8.370(m, 1H), 7.919 (m, 2H), 7.753(m, 2H), 7.478(m, 1H), 3.373(s, 3H), 2.996(s, 2H), 0.919(s, 9H) |

| Example No. | Name | ¹H NMR |
|---|---|---|
| 360 | 2-{[(5-methylpyridin-3-yl)amino]sulfonyl}-N-pentylbenzamide | (400 MHz, MeOD) δ 8.462 (s, 1H), 8.334(s, 1H), 7.978 (m, 2H), 7.713(m, 1H), 7.586(m, 2H), 3.413(m, 2H), 2.430(s, 3H), 1.662(m, 2H), 1.418(m, 4H), 0.957 (m, 3H) |
| 361 | N-(4-methoxybenzyl)-2-{[(5-methylpyridin-3-yl)amino]sulfonyl}benzamide | (400 MHz, MeOD) δ 8.439 (s, 1H), 8.305(s, 1H), 7.934 (m, 2H), 7.681(m, 1H), 7.592(m, 2H), 7.372(d, J=12Hz, 2H), 6.920(d, J=12Hz, 2H), 4.544(s, 2H), 3.783(s, 3H), 2.405(s, 3H) |
| 362 | N-(3-methylbutyl)-2-{[(5-methylpyridin-3-yl)amino]sulfonyl}benzamide | (400 MHz, MeOD) δ 8.437 (s, 1H), 8.312(s, 1H), 7.950 (m, 2H), 7.715(m, 1H), 7.585(m, 2H), 3.452(m, 2H), 2.417(s, 3H), 1.767(m, 12H), 1.581(m, 2H), 0.992 (d, J=8.8Hz, 6H) |
| 363 | 2-[(4-methylpiperidin-1-yl)carbonyl]-N-(5-methylpyridin-3-yl)benzenesulfonamide | (400 MHz, MeOD) δ 8.500-8.300(m, 2H), 7.948(m, 2H), 7.747-7.384(m, 3H), 4.695(m, 1H), 3.402(m, 1H), 3.297-2.809(m, 2H), 2.437(s, 3H), 1.853-1.100 (m, 5H), 1.000(m, 3H) |

| Example No. | Structure | Name | $^1$H NMR |
|---|---|---|---|
| 364 | 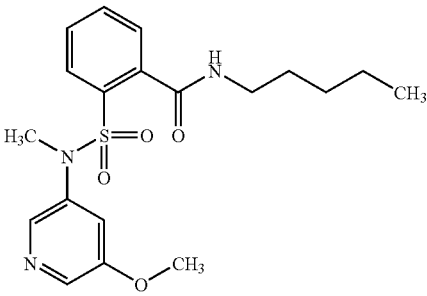 | 2-{[(5-methoxypyridin-3-yl)(methyl)amino]sulfonyl}-N-pentylbenzamide | (400 MHz, MeOD) δ 8.285 (m, 2H), 7.744-7.455(m, 5H), 3.912(s, 3H), 3.331(s, 3H), 3.292(m, 2H), 1.590 (m, 2H), 1.385(m, 4H), 0.934(m, 3H) |
| 365 | 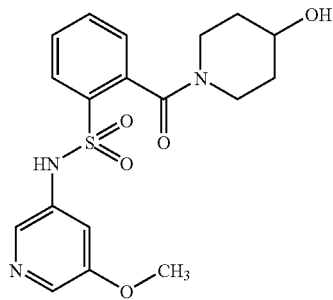 | 2-[(4-hydroxypiperidin-1-yl)carbonyl]-N-(5-methoxypyridin-3-yl)benzenesulfonamide | (400 MHz, CHLOROFORM-d) d ppm 8.05-8.10(m, 1H) 8.02-8.05(m, 1H) 7.94(dd, J=4.66, 1.64Hz, 1H) 7.64 (dd, J=8.06, 3.78Hz, 1H) 7.53-7.60(m, 1H) 7.31-7.40(m, 2H) 7.14-7.22(m, 1H) 4.07-4.17(m, 1H) 3.83-3.98(m, 1H) 3.80(d, J=2.27Hz, 3H) 3.50-3.64 (m, 1H) 3.10-3.31(m, 2H) 1.95-2.17(m, 2H) 1.59-1.84(m, 3H) |
| 366 | 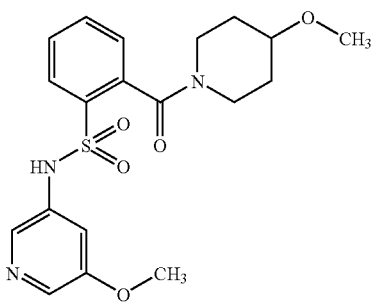 | 2-[(4-methoxypiperidin-1-yl)carbonyl]-N-(5-methoxypyridin-3-yl)benzenesulfonamide | (400 MHz, CHLOROFORM-d) d ppm 8.07(d, J=2.52Hz, 2H) 7.92-7.97(m, 1H) 7.64(d, J=7.81Hz, 1H) 7.52-7.59 (m, 1H) 7.32-7.40(m, 2H) 7.14-7.21(m, 1H) 3.98-4.25(m, 1H) 3.79(s, 3H) 3.63-3.75(m, 1H) 3.42-3.59(m, 2H) 3.33-3.39(m, 3H) 3.13-3.29(m, 1H) 1.72-2.04(m, 3H) 1.52-1.68(m, 1H) |
| 367 | 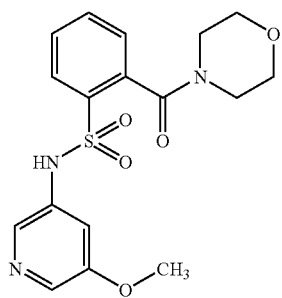 | N-(5-methoxypyridin-3-yl)-2-(morpholin-4-ylcarbonyl)benzenesulfonamide | (400 MHz, CHLOROFORM-d) d ppm 8.08(d, J=2.52Hz, 1H) 7.88-7.97(m, 2H) 7.65(d, J=7.81Hz, 1H) 7.58(t, J=7.55Hz, 1H) 7.32-7.42 (m, 2H) 7.19(s, 1H) 4.15-4.25(m, 1H) 3.85(t, J=3.90 Hz, 2H) 3.80(s, 3H) 3.71-3.79(m, 1H) 3.61-3.69(m, 1H) 3.50-3.59(m, 1H) 3.28-3.44(m, 2H) |

| Example No. | Structure | Name | ¹H NMR |
|---|---|---|---|
| 368 | 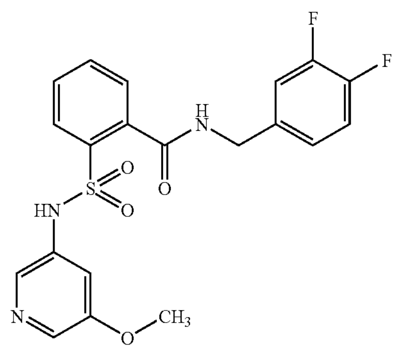 | N-(3,4-difluorobenzyl)-2-{[(5-methoxypyridin-3-yl)amino]sulfonyl}benzamide | (400 MHz, CHLOROFORM-d) d ppm 8.48(s, 1H) 8.05(d, J=2.52 Hz, 1H) 7.93(d, J=2.01Hz, 1H) 7.73(d, J=8.06Hz, 1H) 7.52-7.64(m, 2H) 7.41-7.48(m, 1H) 7.27-7.32 (m, 2H) 7.23(t, J=2.27Hz, 1H) 7.15-7.20(m, 2H) 4.67(d, J=5.79Hz, 2H) 3.82(s, 3H) |
| 369 | 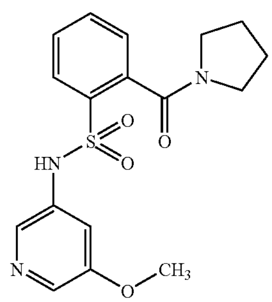 | N-(5-methoxypyridin-3-yl)-2-(pyrrolidin-1-ylcarbonyl)benzenesulfonamide | (400 MHz, CHLOROFORM-d) d ppm 8.17(s, 1H) 8.06(t, J=2.39 Hz, 1H) 7.98(s, 1H) 7.65 (d, J=7.81Hz, 1H) 7.52-761(m, 1H) 7.31-7.46(m, 2H) 7.19(d, J=2.27Hz, 1H) 3.66-3.84(m, 5H) 3.29 (t, J=6.29Hz, 2H) 1.85-2.08(m, 4H) |
| 370 | 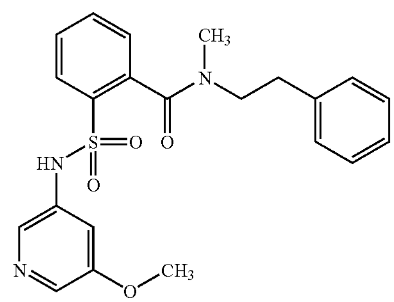 | 2-{[(5-methoxypyridin-3-yl)amino]sulfonyl}-N-methyl-N-(2-phenylethyl)benzamide | (400 MHz, MeOD) δ 8.100 (m, 2H), 7.900(m, 1H), 7.649-7.450(3H), 7.362-7.217(m, 4H), 6.991(m, 1H), 3.899(s, 3H), 3.332(m, 21H), 3.173(s, 3H), 3.074 (m, 2H) |
| 371 | 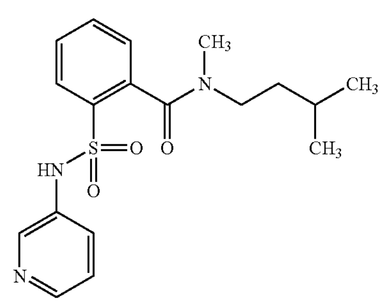 | N-methyl-N-(3-methylbutyl)-2-[(pyridin-3-ylamino)sulfonyl]benzamide | (400 MHz, MeOD) δ 8.630 (s, 1H), 8.485(m, 1H), 8.121 (m, 1H), 7.997(m, 1H), 7.805-7.388(m, 4H), 3.642 (m, 1H), 3.130(s, 2H), 2.823 (s, 2H), 1.719-1.343(m, 3H), 1.013(d, J=8.8Hz, 3H), 0.749(m, 3H) |

-continued

| Example No. | Structure | Name | ¹H NMR |
|---|---|---|---|
| 372 | 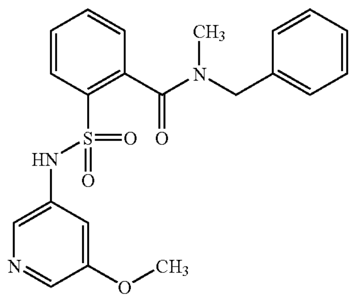 | N-benzyl-2-{[(5-methoxypyridin-3-yl)amino]sulfonyl}-N-methylbenzamide | (400 MHz, MeOD) δ 8.150 (s, 2H), 7.900(m, 1H), 7.800-7.245(m, 9H), 4.731 (m, 1H), 4.370(m, 1H), 3.899(s, 3H), 3.020(s, 1H), 2.749(s, 2H) |
| 373 | 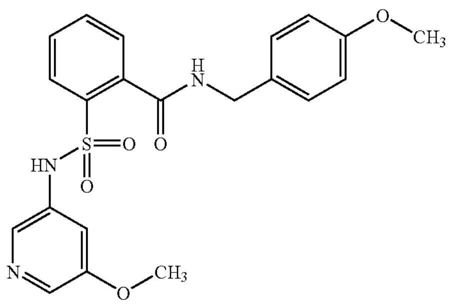 | N-(4-methoxybenzyl)-2-{[(5-methoxypyridin-3-yl)amino]sulfonyl}benzamide | (400 MHz, MeOD) δ 8.163 (br, 2H), 7.920(d, J=9.6Hz, 1H), 7.710(m, 4H), 7.371 (d, J=8.8Hz, 2H), 6.911(d, J=8.8Hz, 2H), 4.540(s, 2H), 3.904(s, 3H), 3.782(s, 3H) |
| 374 | 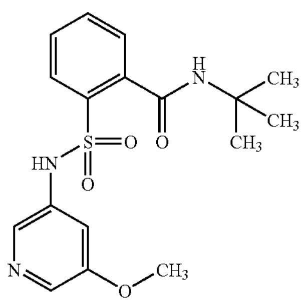 | N-(tert-butyl)-2-{[(5-methoxypyridin-3-yl)amino]sulfonyl}benzamide | (400 MHz, MeOD) δ 8.123 (s, 2H), 7.812(d, J=7.2Hz, 1H), 7.658(m, 1H), 7.543 (m, 3H), 3.891(s, 3H), 1.474 (s, 9H) |
| 375 | 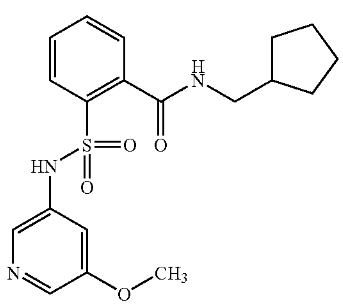 | N-(cyclopentylmethyl)-2-{[(5-methoxypyridin-3-yl)amino]sulfonyl}benzamide | (400 MHz, MeOD) δ 8.071 (br, 2H), 7.836-7.458(m, 5H), 3.867(s, 3H), 3.311 (m, 2H), 2.283(m, 1H), 1.898(m, 2H), 1.718(m, 4), 1.393(m, 2H) |
| 376 | 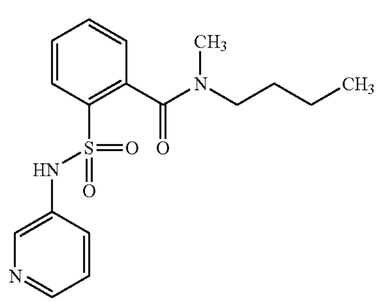 | N-butyl-N-methyl-2-[(pyridin-3-ylamino)sulfonyl]benzamide | (400 MHz, MeOD) δ 8.700 (s, 1H), 8.500(m, 1H), 8.255 (m, 1H), 8.035(m, 1H), 7.905(m, 1H), 7.747(m, 1H), 7.636(m, 1H), 7.440 (m, 1H), 3.606(m, 1H), 3.119(m, 2H), 2.830(s, 2H), 1.721-1.400(m, 3H), 1.189 (m, 1H), 1.025(m, 2H), 0.800(m, 1H) |

| Example No. | Structure | Name | ¹H NMR |
|---|---|---|---|
| 377 | 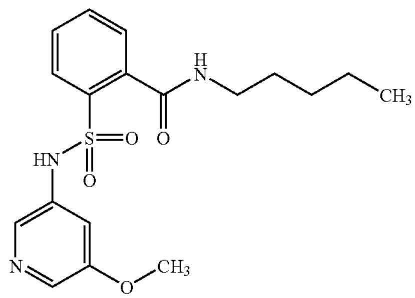 | 2-{[(5-methoxypyridin-3-yl)amino]sulfonyl}-N-pentylbenzamide | (400 MHz, MeOD) δ 8.134 (s, 2H), 7.880(m, 1H), 7.710(m, 1H), 7.579(m, 3H), 3.896(s, 3H), 3.418(m, 2H), 1.683(m, 2H), 1.441 (m, 4H), 0.977(m, 3H) |
| 378 | 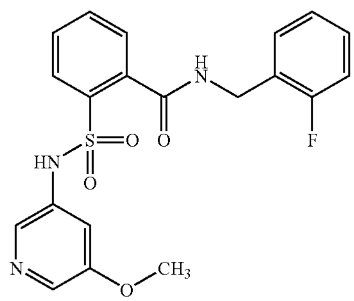 | N-(2-fluorobenzyl)-2-{[(5-methoxypyridin-3-yl)amino]sulfonyl}benzamide | |
| 379 | 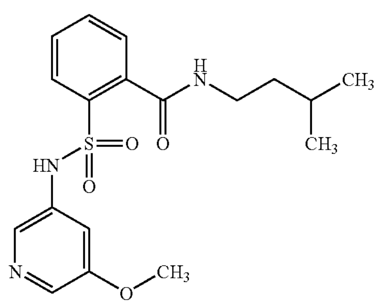 | 2-{[(5-methoxypyridin-3-yl)amino]sulfonyl}-N-(3-methylbutyl)benzamide | (400 MHz, MeOD) δ 8.132 (s, 2H), 7.881(m, 1H), 7.713(m, 1H), 7.584(m, 3H), 3.905(s, 3H), 3.453(m, 2H), 1.766(m, 1H), 1.581 (m, 2H), 0.999(d, J=8.8Hz, 6H) |
| 380 | 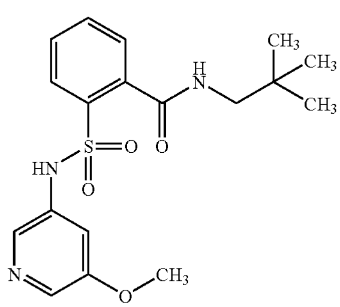 | N-(2,2-dimethylpropyl)-2-{[(5-methoxypyridin-3-yl)amino]sulfonyl}benzamide | (400 MHz, MeOD) δ 8.099 (s, 2H), 7.852(d, J=9.2Hz, 1H), 7.671(m, 1H), 7.581 (m, 3H), 3.865(s, 3H), 3.207 (s, 2H), 0.987(s, 9H) |
| 381 | 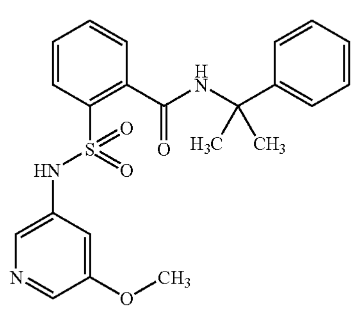 | 2-{[(5-methoxypyridin-3-yl)amino]sulfonyl}-N-(1-methyl-1-phenylethyl)benzamide | (400 MHz, CHLOROFORM-d) d ppm 8.47(d, J=2.52Hz, 1H) 8.42(d, J=1.76Hz, 1H) 8.33(s, 1H) 8.18(d, J=7.30 Hz, 1H) 8.00-8.06(m, 1H) 7.91-7.99(m, 2H) 7.88(d, J=2.01Hz, 1H) 7.70(d, J=7.81Hz, 1H) 7.54-7.63 (m, 2H) 7.38-7.47(m, 2H) 7.32(d, J=7.30Hz, 1H) |

| Example No. | Structure | Name | ¹H NMR |
|---|---|---|---|
| 382 | 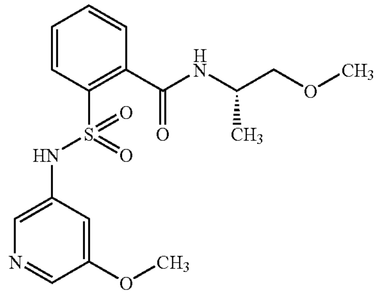 | N-[(1S)-2-methoxy-1-methylethyl]-2-{[(5-methoxypyridin-3-yl)amino]sulfonyl}benzamide | (400 MHz, CHLOROFORM-d) d ppm 8.14(d, J=2.77Hz, 1H) 8.01(s, 1H) 7.88(d, J=8.31 Hz, 2H) 7.46(d, J=8.31Hz, 2H) 7.32(dd, J=8.18, 5.92 Hz, 1H) 6.99(d, J=1.76Hz, 1H) 6.84-6.94(m, 1H) 4.61(s, 3H) 3.82(s, 3H) 2.99-3.12(m, 4H) 2.79-2.95(m, 2H) |
| 383 | 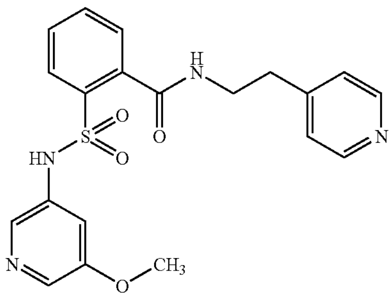 | 2-{[(5-methoxypyridin-3-yl)amino]sulfonyl}-N-(2-pyridin-4-ylethyl)benzamide | (400 MHz, CHLOROFORM-d) d ppm 8.66(s, 1H) 8.21(d, J=4.53 Hz, 2H) 8.06(d, J=2.27Hz, 1H) 7.96(s, 1H) 7.73(d, J=7.55Hz, 1H) 7.52(t, J=7.43Hz, 1H) 7.37-7.48 (m, 2H) 7.23-7.28(m, 1H) 7.17(t, J=5.54Hz, 3H) 3.73-3.84(m, 5H) 2.99(t, J=6.29Hz, 2H) |
| 384 | 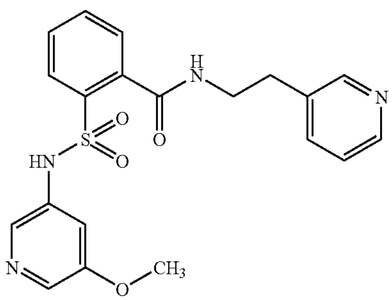 | 2-{[(5-methoxypyridin-3-yl)amino]sulfonyl}-N-(2-pyridin-3-ylethyl)benzamide | (400 MHz, CHLOROFORM-d) d ppm 8.50(d, J=1.76Hz, 1H) 8.41(d, J=4.78Hz, 1H) 8.06(d, J=2.52Hz, 1H) 7.95(s, 1H) 7.72(d, J=7.81 Hz, 1H) 7.66(d, J=7.81Hz, 1H) 7.53(t, J=7.43Hz, 1H) 7.42(t, J=7.43Hz, 2H) 7.20-7.26(m, 2H) 6.47(s, 1H) 3.73-3.84(m, 5H) 3.03(t, J=6.80Hz, 2H) |
| 385 | 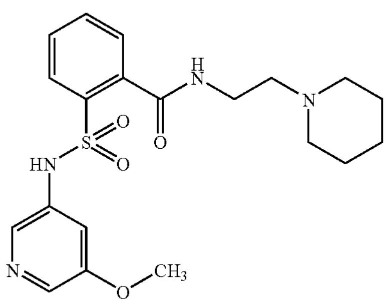 | 2-{[(5-methoxypyridin-3-yl)amino]sulfonyl}N-(2-piperidin-1-ylethyl)benzamide | (400 MHz, CHLOROFORM-d) d ppm 7.93-8.01(m, 3H) 7.84-7.93(m, 1H) 7.68(dd, J=7.55, 1.26Hz, 1H) 7.48-7.56(m, 1H) 7.40-7.46(m, 1H) 7.18(t, J=2.27Hz, 5H) 2.96-3.00(m, 2H) 2.74(s, 6H) 1.62-1.68(m, 4H) 1.47(s, 2H) |
| 386 | 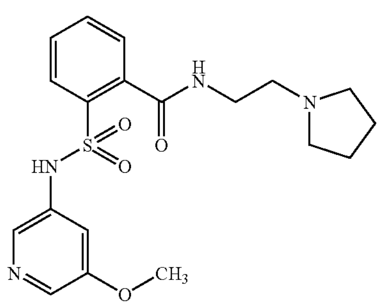 | 2-{[(5-methoxypyridin-3-yl)amino]sulfonyl}-N-(2-pyrrolidin-1-ylethyl)benzamide | (400 MHz, CHLOROFORM-d) d ppm 7.96(d, J=9.32Hz, 3H) 7.80(s, 1H) 7.66(d, J=7.55 Hz, 1H) 7.50(t, J=7.43Hz, 1H), 7.42(t, J=7.68Hz, 1H) 7.13(s, 1H) 3.74(s, 6H) 3.14(t, J=5.04Hz, 2H) 2.95 (s, 3H) 1.80(s, 5H) |

| Example No. | Structure | Name | ¹H NMR |
|---|---|---|---|
| 387 | 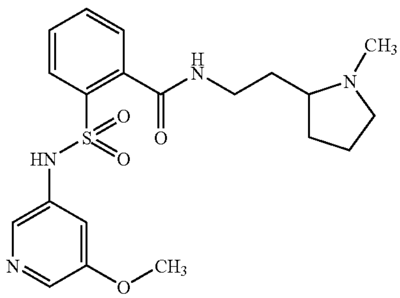 | 2-{[(5-methoxypyridin-3-yl)amino]sulfonyl}N[2-(1-methylpyrrolidin-2-yl)ethyl]benzamide | (400 MHz, CHLOROFORM-d) d ppm 8.19(s, 1H) 7.72-7.92(m, 3H) 7.28-7.52(m, 3H) 7.04(s, 1H) 3.73(s, 4H) 3.43(s, 1H) 2.93(s, 1H) 1.47-2.48(m, 12H) |
| 388 | 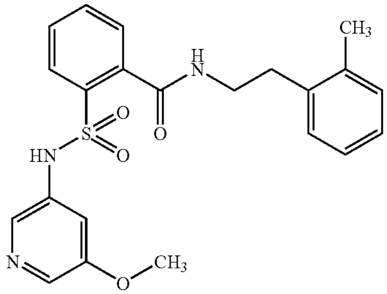 | 2-{[(5-methoxypyridin-3-yl)amino]sulfonyl}-N-[2-(2-methylphenyl)ethyl]benzamide | (400 MHz, CHLOROFORM-d) d ppm 8.66(s, 1H) 8.05(d, J=2.52 Hz, 1H) 7.95(d, J=2.01Hz, 1H) 7.67-7.73(m, 1H) 7.48-7.57(m, 1H) 7.37-7.44(m, 2H) 7.10-7.25(m, 5H) 6.23(s, 1H) 3.81(s, 3H) 3.75(q, J=6.97Hz, 2H) 3.03(t, J=7.05Hz, 2H) 2.39 (s, 3H) |
| 389 | 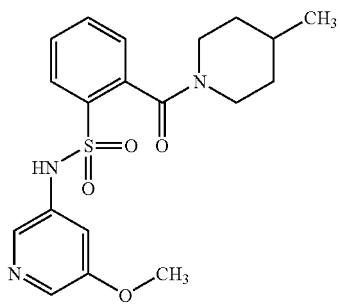 | N-(5-methoxypyridin-3-yl)-2-[(4-methylpiperidin-1-yl)carbonyl]benzenesulfonamide | (400 MHz, MeOD) δ 8.120 (m, 2H), 7.939(m, 1H), 7.735(m, 1H), 7.603-7.395 (m, 3H), 4.663(m, 1H), 3.900(s, 3H), 3.413(m, 1H), 3.134-2.845(m, 2H), 1.810-1.160(m, 5H), 0.988(m, 3H) |
| 390 | 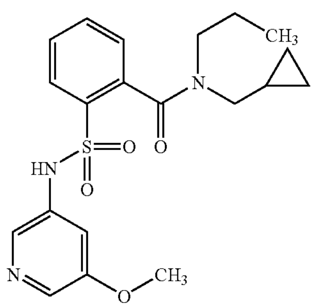 | N-(cyclopropylmethyl)-2-{[(5-methoxypyridin-3-yl)amino]sulfonyl}-N-propylbenzamide | (400 MHz, MeOD) δ 8.177 (s, 2H), 7.959(m, 1H), 7.741(m, 1H), 7.620(m, 2H), 7.430(d, J=10Hz), 3.929(s, 3H), 3.649(m, 2H), 3.260(m, 2H), 1.824(m, 2H), 1.041(m, 3H), 0.753 (m, 1H), 0.625(m, 3H), 0.185(m, 1H) |
| 391 | 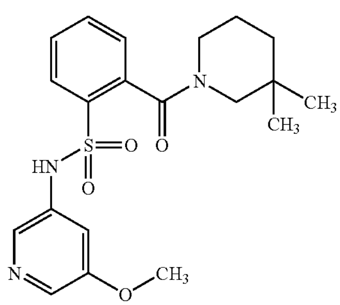 | 2-[(3,3-dimethylpiperidin-1-yl)carbonyl]-N-(5-methoxypyridin-3-yl)benzenesulfonamide | (400 MHz, MeOD) δ 8.150 (s, 2H), 7.946(d, J=10Hz, 1H), 7.746(m, 1H), 7.615 (m, 2H), 7.422(m, 1H), 3.909(s, 3H), 3.602(m, 1H), 3.326(m, 2H), 2.856(s, 1H), 1.726-1.467(m, 4H), 1.083 (d, J=16.8Hz, 3H), 0.909(d, J=37.2Hz, 3H) |

| Example No. | Structure | Name | ¹H NMR |
|---|---|---|---|
| 392 | 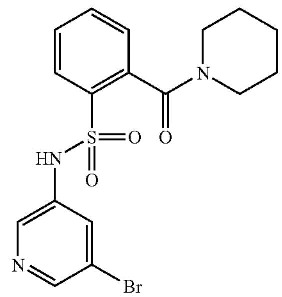 | N-(5-bromopyridin-3-yl)-2-(piperidin-1-ylcarbonyl)benzenesulfonamide | (400 MHz, CHLOROFORM-d) d ppm 8.43(d, J=2.02Hz, 1H) 8.32(d, J=2.27Hz, 1H) 8.27(s, 1H) 7.83(t, J=2.15Hz, 1H) 7.69 (dd,J=7.83, 1.01Hz, 1H) 7.60(td, J=7.52, 1.14Hz, 1H) 7.41(td, J=7.71, 1.26Hz, 1H) 7.37(dd, J=7.45, 1.14 Hz, 1H) 3.97-4.05(m, 1H) 3.55-3.64(m, 1H) 3.24-3.40(m, 2H) 1.65-1.89(m, 5H) 1.24-1.33(m, 1H) |
| 393 | 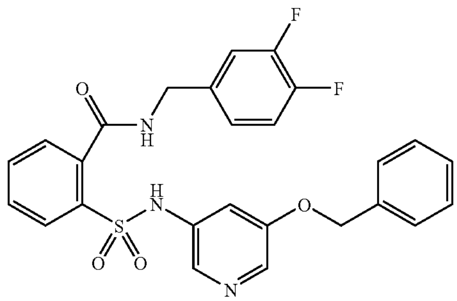 | 2-({[5-(benzyloxy) pyridin-3-yl]amino}sulfonyl)-N-(3,4-diflorobenzyl)benzamide | (400 MHz, CHLOROFORM-d) d ppm 4.69(d, J=5.81Hz, 2H), 5.10(s, 2H), 6.50(t, J=5.68Hz, 1H), 7.16-7.23 (m, 2H), 7.29-7.33(m, 1H), 7.36-7.46(m, 7H), 7.53-7.56(m, 1H), 7.59 (td, J=7.39, 1.14Hz, 1H), 7.65(dd, J=7.83, 0.76Hz, 1H), 7.96(d, J=2.02Hz, 1H), 8.14(d, J=2.53Hz, 1H), 8.51(s, 1H) |

Example G

In Vitro Activity Data for Examples

1. Determination of compound $K_{iapp}$

A determination of the $K_{iapp}$ of the compounds of the invention against recombinant CYP3A4 enzyme was performed as follows. The assay was performed in a 100 mM sodium phosphate buffer pH 7.0, 5 mM TCEP and containing 2% dimethylformamide (final concentration) upon addition of substrate and inhibitor. A typical reaction for the determination of $K_{iapp}$ values was carried at room temperature in a solid black Costar u-bottom 96-well polypropylene plate. In each well, recombinant CYP3A4 enzyme (5.5 nM or 8 nM, final concentration depending on the commercial source of the enzyme) was pre-incubated in the presence of the inhibitor for at least 30 minutes in the assay buffer. When pre-incubation was completed (~30 min), the reaction was initiated by adding NADPH (200 uM, final concentration), and 7-benzyloxy-4-(trifluoromethyl)-coumarin (BFC) (5 uM, final concentration). The oxidation of the coumarin substrate was recorded by a 96-well plate reader POLARstar (BMG LABTECH, Offenburg, Germany).

The initial reaction velocities were measured during the first 5 min of the reaction when the release of the fluorescent product is linear with time, in the absence and in the presence of various concentrations of inhibitors. For non-partial & partial inhibitors, the $K_{iapp}$ values were determined by using the equation for tight-binding inhibitor developed by Morrison, J F (Morrison J F. *Biochim Biophys Acta*. 1969, 185: 269-86) and by Szedlaseck S E et al. (Szedlascek, S. E., Ostafe, V., Serban, M., and Vlad, M.O. Biochem. J. 1988, 254:311-312), respectively.

The fluorescent substrate BFC was purchased from Sigma (St Louis, Mo.). Two commercial sources of recombinant enzymes were used in this study: recombinant CYP3A4–b5 enzyme (Baculosomes®) was purchased from Invitrogen (Carlsbad, Calif.) and the recombinant CYP3A4+b5 enzyme (Supersomes®) was purchased from BD Biosciences (Woburn, Mass.).

2. Determination of $IC_{50}$ Against CYP3A4 by Measurement of Inhibition of Testosterone Metabolism This assay was performed using a standard 96 well plate design. IC50 values are calculated from the percent inhibition determined for each test compound at 6 concentrations (for example: 750, 250, 83.3, 27.8, 9.3 and 3.1 nM). The incubation substrate mix contains 25 μM testosterone, 0.1 mg/mL human liver microsomes, 1 mM NADPH, and potassium phosphate buffer (100 mM, pH 7.4). Quantitation of metabolite peak area ratio against an internal standard is determined by LC-MS/MS analysis. The production of 6-β-OH-testosterone from testosterone metabolism is determined after incubation for eight minutes by comparison to a standard curve generated for the metabolite Samples were analyzed in the MRM mode using a Sciex API 3000 mass spectrometer (Applied Biosystems, Foster City, Calif.) with a Paradigm MS4 binary pump (Michrom BioResources Inc., Auburn, Calif.) and a LEAP CTC PAL autosampler (LEAP Technologies, Carrboro, N.C.). A Phenomenex Synergi, 4μ, Polar-RP, 10×2.0 mm column (Phenomenex, Torrance, Calif.) was used for separation with a mobile phase composition of: 0.1% formic acid in water (A) and: 0.1% formic acid in methanol (B). The following gradient was used:

| Time (minutes) | % B | Flow rate (mL/min) |
| --- | --- | --- |
| 0.0 | 0 | 0.8 |
| 0.1 | 95 | 0.8 |
| 0.55 | 95 | 0.8 |
| 0.6 | 0 | 0.8 |

The sample injection volume was 10 μL and flow was split post-column with 0.4 mL/min going to the mass spectrometer. Analysis was performed using the following API 3000 mass spectrometer settings:

Instrument Settings

| | |
| --- | --- |
| Ionization Method | ESI, positive |
| Interface | Turbo-ionspray |
| Desolvation Temperature (TEM) | 450° C. |
| Ionspray Voltage (IS) | 5000 |
| Curtain Gas (CUR) | 15 |
| Nebulizer (NEB) | 10 |
| Collision Gas (CAD) | 6 |
| Entrance Potential (EP) | 10 |

| Compound | | Transition (m/z) | DP | FP | CE | CXP | Ret. Time (min) |
| --- | --- | --- | --- | --- | --- | --- | --- |
| 6-OH-Testosterone | Analyte | 305.4 > 269.2 | 56 | 170 | 21 | 18 | 0.44 |

3. Determination of $IC_{50}$ Against CYP3A4 by Measurement of Inhibition of Midazolam Metabolism This assay was performed using a standard 96 well plate design. IC50s are calculated from the percent inhibition determined for each test compound at 6 concentrations (for example: 750, 250, 83.3, 27.8, 9.3 and 3.1 nM). The incubation substrate mix contains 2 μM midazolam, 0.1 mg/mL human liver microsomes, 1 mM NADPH, and potassium phosphate buffer (100 mM, pH 7.4). Quantitation of metabolite peak area ratio against internal standard is determined by LC-MS/MS analysis. The production of 1-hydroxymidazolam from midazolam metabolism is determined after incubation for eight minutes by comparison to a standard curve generated for the metabolite.

Samples were analyzed in the MRM mode using a Sciex API 3000 mass spectrometer (Applied Biosystems, Foster City, Calif.) with a Paradigm MS4 binary pump (Michrom BioResources Inc., Auburn, Calif.) and a LEAP CTC PAL autosampler (LEAP Technologies, Carrboro, N.C.). A Phenomenex Synergi, 4μ, Polar-RP, 10×2.0 mm column (Phenomenex, Torrance, Calif.) was used for separation with a mobile phase composition of: 0.1% formic acid in water (A) and: 0.1% formic acid in methanol (B). The following gradient was used:

| Time (minutes) | % B | Flow rate (mL/min) |
| --- | --- | --- |
| 0.0 | 0 | 0.8 |
| 0.1 | 95 | 0.8 |
| 0.55 | 95 | 0.8 |
| 0.6 | 0 | 0.8 |

The sample injection volume was 10 μL and flow was split post-column with 0.4 mL/min going to the mass spectrometer. Analysis was performed using the following API 3000 mass spectrometer settings:

Instrument Settings

| | |
| --- | --- |
| Ionization Method | ESI, positive |
| Interface | Turbo-ionspray |
| Desolvation Temperature (TEM) | 450° C. |
| Ionspray Voltage (IS) | 5000 |
| Curtain Gas (CUR) | 15 |
| Nebulizer (NEB) | 10 |
| Collision Gas (CAD) | 6 |
| Entrance Potential (EP) | 10 |

| Compound | | Transition (m/z) | DP | FP | CE | CXP | Ret. time |
| --- | --- | --- | --- | --- | --- | --- | --- |
| 1-hydroxymidazolam | Analyte | 342.2 > 203.1 | 46 | 130 | 29 | 18 | 0.44 |

| Ex. No. | Kiapp (BFC, Baculo.) (μM) | Kiapp (BFC, Super.) (μM) | IC50 (Testo.) (μM) | IC50 (Midazolam) (μM) |
| --- | --- | --- | --- | --- |
| 1 | 0.538 | 0.662 | <0.003 | 0.39 |
| 2 | 0.901 | 0.57 | >0.750 | >0.750 |
| 3 | 0.858 | >1.00 | >0.750 | >0.750 |
| 4 | 0.167 | 0.0436 | 0.096 | 0.052 |
| 5 | 0.0559 | 0.0058 | 0.066 | 0.041 |
| 6 | | | | 0 |
| 7 | >1.00 | >1.00 | >0.750 | >0.750 |
| 8 | 0.46 | 0.0446 | 0.067 | 0.063 |
| 9 | 0.173 | 0.004 | 0.009 | 0.011 |
| 10 | >1.00 | 0.558 | >0.750 | 0.279 |
| 11 | >1.00 | 0.563 | >0.750 | >0.750 |
| 12 | 0.27 | 0.0105 | 0.029 | 0.031 |
| 13 | 0.251 | | 0.024 | |
| 14 | 0.503 | | 0.06 | |
| 15 | | | | 0 |
| 16 | 0.433 | | 0.117 | 0.065 |
| 17 | 0.133 | | 0.062 | 0.026 |
| 18 | 0.57 | | 0.349 | 0.146 |
| 19 | 0.329 | | 0.169 | 0.069 |
| 20 | >1.00 | | 0.445 | 0.379 |
| 21 | >1.00 | | >0.750 | >0.750 |
| 22 | >1.00 | | >0.750 | >0.750 |
| 23 | >1.00 | 0.28 | 0.325 | 0.103 |
| 24 | >1.00 | | >0.750 | 0.567 |
| 25 | 0.239 | | 0.077 | 0.045 |
| 26 | >1.00 | | 0.691 | 0.494 |
| 27 | >1.00 | | >0.750 | 0.658 |
| 28 | >1.00 | | >0.750 | >0.750 |
| 29 | 0.324 | | 0.172 | 0.076 |
| 30 | 0.69 | | 0.125 | 0.056 |
| 31 | 0.0701 | | 0.038 | 0.023 |
| 32 | No Data | | >0.750 | 0.413 |
| 33 | >1.00 | | 0.473 | 0.111 |
| 34 | >1.00 | | >0.750 | >0.750 |
| 35 | >1.00 | | >0.750 | >0.750 |
| 36 | >1.00 | | >0.750 | >0.750 |
| 37 | >1.00 | | >0.750 | >0.750 |
| 38 | 0.644 | | 0.084 | 0.068 |
| 39 | >1.00 | | >0.500 | >0.500 |
| 40 | >1.00 | | 0.34 | 0.179 |
| 41 | 0.486 | 0.0303 | 0.0834 | 0.0628 |
| 42 | 0.378 | 0.0225 | 0.0515 | 0.0359 |
| 43 | 0.269 | 0.0165 | 0.0217 | 0.0134 |

| Ex. No. | Kiapp (BFC, Baculo.) (μM) | Kiapp (BFC, Super.) (μM) | IC50 (Testo.) (μM) | IC50 (Midazolam) (μM) |
|---|---|---|---|---|
| 44 | 0.617 | | 0.167 | 0.072 |
| 45 | 0.382 | | 0.042 | 0.02 |
| 46 | 0.325 | | 0.023 | 0.023 |
| 47 | 0.332 | | 0.03 | 0.026 |
| 48 | >1.00 | | 0.335 | 0.327 |
| 49 | >1.00 | | >0.500 | 0.328 |
| 50 | >1.00 | | 0.371 | 0.254 |
| 51 | 0.68 | | 0.057 | 0.034 |
| 52 | 0.56 | | 0.073 | 0.027 |
| 53 | 0.613 | | 0.049 | 0.024 |
| 54 | 0.239 | | 0.026 | 0.015 |
| 55 | 0.385 | 0.0142 | 0.0545 | 0.0406 |
| 56 | 0.34 | 0.0224 | 0.062 | 0.0489 |
| 57 | 0.353 | 0.035 | 0.0933 | 0.0696 |
| 58 | 0.15 | 0.0091 | 0.0253 | 0.0265 |
| 59 | 0.838 | 0.0574 | 0.117 | 0.109 |
| 60 | 0.151 | | 0.024 | 0.017 |
| 61 | 0.131 | 0.0077 | 0.0302 | 0.0268 |
| 62 | >1.00 | 0.0833 | 0.211 | 0.184 |
| 63 | 0.449 | 0.0424 | 0.0841 | 0.0842 |
| 64 | 0.19 | 0.0128 | 0.0318 | 0.0305 |
| 65 | 0.92 | | 0.214 | 0.254 |
| 66 | >1.00 | 0.21 | 0.302 | 0.146 |
| 67 | 0.844 | 0.062 | 0.247 | 0.11 |
| 68 | 0.116 | | 0.036 | 0.017 |
| 69 | >1.00 | | 0.179 | 0.105 |
| 70 | 0.8 | | 0.421 | |
| 71 | 0.245 | 0.0051 | <0.003 | 0.029 |
| 72 | 0.164 | 0.0129 | <0.003 | 0.027 |
| 73 | 0.124 | 0.0107 | <0.003 | 0.038 |
| 74 | 0.174 | 0.0048 | <0.003 | 0.023 |
| 75 | 0.043 | 0.0024 | 0.013 | 0.016 |
| 76 | 0.0767 | 0.0094 | 0.029 | 0.024 |
| 77 | 0.131 | 0.0056 | 0.192 | 0.023 |
| 78 | 0.158 | 0.0138 | >0.750 | 0.022 |
| 79 | 0.144 | 0.0262 | 0.177 | 0.03 |
| 80 | 0.206 | 0.0041 | 0.071 | 0.025 |
| 81 | >1.00 | 0.276 | <0.003 | 0.501 |
| 82 | 0.743 | 0.0209 | 0.025 | 0.028 |
| 83 | 0.127 | 0.0128 | 0.028 | 0.035 |
| 84 | >1.00 | 0.464 | 0.028 | >0.750 |
| 85 | 0.105 | 0.0121 | 0.041 | 0.016 |
| 86 | >1.00 | 0.209 | 0.027 | 0.118 |
| 87 | 0.09 | 0.0063 | 0.01 | 0.03 |
| 88 | 0.362 | 0.0476 | 0.028 | 0.185 |
| 89 | >1.00 | 0.218 | 0.06 | 0.054 |
| 90 | 0.313 | 0.0252 | 0.036 | 0.01 |
| 91 | 0.058 | 0.0172 | | 0.018 |
| 92 | 0.0457 | 0.0175 | | 0.022 |
| 93 | 0.166 | 0.0147 | | 0.01 |
| 94 | 0.182 | 0.0257 | | 0.016 |
| 95 | 0.078 | 0.0254 | | 0.008 |
| 96 | 0.124 | 0.0223 | | 0.009 |
| 97 | 0.421 | 0.157 | | 0.107 |
| 98 | 0.506 | 0.196 | | 0.051 |
| 99 | 0.406 | 0.223 | | 0.09 |
| 100 | 0.0883 | 0.0357 | | 0.014 |
| 101 | 0.244 | 0.0548 | | 0.026 |
| 102 | 0.375 | 0.056 | | 0.055 |
| 103 | 0.129 | 0.026 | | 0.021 |
| 104 | 0.141 | 0.0235 | | 0.035 |
| 105 | 0.0831 | 0.0286 | | 0.021 |
| 106 | 0.345 | 0.0875 | | 0.051 |
| 107 | 0.214 | 0.044 | | 0.057 |
| 108 | 0.506 | 0.115 | | 0.098 |
| 109 | 0.213 | 0.0372 | | 0.035 |
| 110 | 0.156 | 0.0504 | | 0.026 |
| 111 | 0.0273 | 0.0068 | | 0.01 |
| 112 | 0.438 | 0.119 | | 0.046 |
| 113 | 0.698 | 0.0975 | | 0.09 |
| 114 | 0.466 | 0.105 | | 0.134 |
| 115 | 0.124 | 0.026 | | 0.023 |
| 116 | 0.317 | 0.0509 | | 0.033 |
| 117 | 0.159 | 0.0148 | | 0.02 |
| 118 | 0.103 | 0.0135 | | 0.018 |
| 119 | 0.249 | 0.0712 | | 0.045 |
| 120 | 0.487 | 0.14 | | 0.086 |
| 121 | 0.49 | 0.0712 | | 0.031 |
| 122 | 0.0495 | 0.01 | | 0.031 |
| 123 | 0.0725 | 0.0152 | | 0.01 |
| 124 | 0.136 | 0.018 | | 0.014 |
| 125 | 0.185 | 0.0312 | | 0.02 |
| 126 | 0.194 | 0.0848 | | 0.053 |
| 127 | 0.694 | 0.282 | | 0.107 |
| 128 | 0.448 | 0.0549 | | 0.067 |
| 129 | 0.0876 | 0.0096 | | 0.012 |
| 130 | 0.134 | 0.0628 | | 0.022 |
| 131 | >1.00 | 0.329 | | >0.750 |
| 132 | 0.0406 | 0.0084 | | 0.008 |
| 133 | 0.0678 | 0.0116 | | 0.018 |
| 134 | 0.0697 | 0.0087 | | 0.014 |
| 135 | 0.0248 | 0.0049 | | 0.018 |
| 136 | 0.0598 | 0.0048 | | 0.01 |
| 137 | 0.115 | 0.0073 | | 0.018 |
| 138 | 0.0196 | 0.0027 | | 0.016 |
| 139 | 0.388 | 0.0511 | | 0.048 |
| 140 | 0.16 | 0.0173 | | 0.056 |
| 141 | 0.172 | 0.0211 | | 0.036 |
| 142 | 0.111 | 0.0118 | | 0.026 |
| 143 | 0.169 | 0.029 | | 0.058 |
| 144 | 0.327 | 0.039 | | 0.072 |
| 145 | 0.0439 | 0.0059 | | 0.018 |
| 146 | 0.0546 | 0.0086 | | 0.011 |
| 147 | 0.209 | 0.0192 | | 0.016 |
| 148 | 0.0181 | 0.0049 | 0.015 | <0.00300 |
| 149 | 0.208 | 0.0123 | 0.021 | 0.012 |
| 150 | 0.0522 | 0.0092 | 0.015 | 0.038 |
| 151 | 0.12 | 0.0122 | 0.016 | 0.028 |
| 152 | 0.0461 | 0.0064 | 0.023 | 0.013 |
| 153 | 0.262 | 0.0271 | 0.019 | 0.005 |
| 154 | 0.0115 | 0.0032 | 0.023 | 0.006 |
| 155 | 0.0028 | 0.0016 | 0.015 | 0.008 |
| 156 | 0.084 | 0.005 | 0.011 | 0.013 |
| 157 | 0.0494 | 0.0013 | 0.008 | 0.008 |
| 158 | 0.0197 | 0.0009 | 0.01 | 0.006 |
| 159 | 0.751 | 0.144 | 0.129 | 0.064 |
| 160 | >1.00 | 0.163 | 0.202 | 0.129 |
| 161 | >1.00 | 0.418 | 0.371 | 0.308 |
| 162 | 0.469 | 0.0999 | 0.17 | 0.093 |
| 163 | 0.263 | 0.058 | 0.082 | 0.049 |
| 164 | 0.281 | 0.0343 | 0.047 | 0.024 |
| 165 | 0.163 | 0.0296 | 0.054 | 0.043 |
| 166 | 0.196 | 0.0351 | 0.026 | 0.023 |
| 167 | 0.159 | 0.0174 | 0.016 | 0.009 |
| 168 | 0.066 | 0.0117 | 0.018 | 0.009 |
| 169 | >1.00 | 0.187 | 0.395 | 0.139 |
| 170 | >1.00 | 0.427 | 0.285 | 0.557 |
| 171 | 0.299 | 0.0491 | 0.038 | 0.035 |
| 172 | 0.173 | 0.0217 | 0.034 | 0.044 |
| 173 | 0.104 | 0.0099 | 0.018 | 0.016 |
| 174 | >1.00 | 0.392 | 0.356 | 0.451 |
| 175 | 0.024 | 0.0013 | 0.009 | 0.009 |
| 176 | >1.00 | 0.625 | >0.750 | 0.406 |
| 177 | 0.0706 | 0.0035 | 0.012 | 0.011 |
| 178 | >1.00 | 0.106 | 0.097 | 0.07 |
| 179 | 0.314 | 0.0637 | 0.058 | 0.045 |
| 180 | 0.0928 | 0.007 | 0.011 | 0.004 |
| 181 | 0.0718 | 0.0108 | 0.013 | 0.007 |
| 182 | 0.0374 | 0.0035 | 0.013 | 0.006 |
| 183 | 0.0226 | 0.002 | 0.011 | 0.005 |
| 184 | 0.0545 | 0.0059 | 0.011 | 0.013 |
| 185 | 0.0171 | 0.0028 | 0.01 | 0.011 |
| 186 | 0.171 | 0.0097 | 0.007 | 0.006 |
| 187 | 0.257 | 0.0359 | 0.028 | 0.022 |
| 188 | 0.0364 | 0.0034 | 0.012 | 0.008 |
| 189 | 0.175 | 0.0274 | 0.048 | 0.024 |
| 190 | 0.0169 | 0.0034 | 0.016 | 0.007 |
| 191 | 0.0597 | 0.005 | 0.015 | 0.01 |

| Ex. No. | Kiapp (BFC, Baculo.) (μM) | Kiapp (BFC, Super.) (μM) | IC50 (Testo.) (μM) | IC50 (Midazolam) (μM) | Ex. No. | Kiapp (BFC, Baculo.) (μM) | Kiapp (BFC, Super.) (μM) | IC50 (Testo.) (μM) | IC50 (Midazolam) (μM) |
|---|---|---|---|---|---|---|---|---|---|
| 192 | 0.0237 | 0.0027 | 0.007 | 0.007 | 266 | 0.145 | 0.0268 | 0.109 | 0.054 |
| 193 | 0.0412 | 0.0217 | 0.027 | 0.013 | 267 | 0.27 | 0.0432 | 0.216 | 0.12 |
| 194 | 0.376 | 0.0685 | 0.099 | 0.073 | 268 | 0.11 | 0.0194 | 0.063 | 0.044 |
| 195 | 0.0708 | 0.0356 | 0.032 | 0.015 | 269 | 0.0181 | 0.00331 | 0.013 | 0.009 |
| 196 | 0.379 | 0.0745 | 0.058 | 0.051 | 270 | 0.352 | 0.0398 | 0.052 | 0.022 |
| 197 | 0.0695 | 0.0201 | 0.018 | 0.004 | 271 | 0.118 | 0.0172 | 0.021 | 0.018 |
| 198 | 0.0417 | 0.0166 | 0.01 | <0.00300 | 272 | 0.0673 | 0.00568 | 0.019 | 0.012 |
| 199 | 0.0127 | 0.0105 | 0.011 | 0.006 | 273 | 0.513 | 0.0377 | 0.112 | 0.084 |
| 200 | 0.0361 | 0.0099 | 0.021 | 0.012 | 274 | 0.0701 | 0.00885 | 0.046 | 0.025 |
| 201 | 0.0293 | 0.008 | 0.016 | 0.009 | 275 | 0.0429 | 0.00376 | 0.007 | 0.009 |
| 202 | 0.0842 | 0.0334 | 0.007 | <0.00300 | 276 | 0.563 | 0.0629 | 0.134 | 0.071 |
| 203 | 0.101 | 0.0258 | 0.012 | 0.005 | 277 | 0.459 | 0.0479 | 0.065 | 0.053 |
| 204 | 0.0525 | 0.0126 | 0.012 | <0.00300 | 278 | 0.131 | 0.0119 | 0.066 | 0.031 |
| 205 | 0.206 | 0.0419 | 0.027 | <0.0155 | 279 | >1.00 | 0.0952 | 0.337 | 0.123 |
| 206 | 0.0036 | 0.0029 | 0.006 | <0.00300 | 280 | 0.4 | 0.0525 | 0.095 | 0.039 |
| 207 | 0.105 | 0.0191 | 0.024 | 0.005 | 281 | 0.468 | 0.0426 | 0.065 | 0.031 |
| 208 | 0.0573 | 0.0161 | 0.019 | 0.0095 | 282 | 0.33 | 0.0577 | 0.062 | 0.049 |
| 209 | 0.0182 | 0.0061 | 0.005 | 0.004 | 283 | 0.314 | 0.0272 | 0.046 | 0.031 |
| 210 | 0.286 | 0.0396 | 0.049 | 0.01 | 284 | 0.0998 | 0.0142 | 0.049 | 0.015 |
| 211 | 0.0336 | 0.0079 | 0.019 | 0.004 | 285 | 0.026 | 0.00724 | 0.028 | 0.019 |
| 212 | 0.0203 | 0.006 | 0.008 | <0.00300 | 286 | 0.0272 | 0.00406 | 0.0095 | 0.00767 |
| 213 | 0.0272 | 0.0098 | 0.013 | <0.00300 | 287 | 0.216 | 0.0477 | 0.099 | 0.043 |
| 214 | 0.355 | 0.0473 | 0.066 | 0.014 | 288 | 0.0022 | 0.00308 | 0.018 | 0.012 |
| 215 | 0.216 | 0.0433 | 0.058 | 0.025 | 289 | 0.0059 | 0.00497 | 0.027 | 0.015 |
| 216 | 0.0069 | 0.0035 | 0.007 | 0.005 | 290 | 0.0146 | 0.00394 | 0.016 | 0.004 |
| 217 | 0.965 | 0.216 | 0.23 | 0.179 | 291 | 0.0045 | 0.00298 | 0.027 | 0.021 |
| 218 | 0.748 | 0.146 | 0.189 | 0.096 | 292 | 0.0016 | 0.000618 | 0.016 | <0.00300 |
| 219 | 0.108 | 0.0403 | 0.032 | 0.027 | 293 | 0.268 | 0.0581 | 0.145 | 0.081 |
| 220 | 0.0137 | 0.0091 | 0.011 | 0.006 | 294 | 0.135 | 0.0321 | 0.057 | 0.024 |
| 221 | 0.016 | 0.0089 | 0.012 | 0.011 | 295 | 0.184 | 0.042 | 0.231 | 0.042 |
| 222 | 0.207 | 0.0127 | 0.034 | 0.015 | 296 | 0.0358 | 0.00932 | 0.09 | 0.012 |
| 223 | >1.00 | 0.326 | 0.745 | 0.26 | 297 | 0.444 | 0.11 | >0.750 | 0.17 |
| 224 | 0.399 | 0.0568 | 0.056 | 0.029 | 298 | 0.0585 | 0.0156 | 0.135 | 0.031 |
| 225 | 0.0157 | 0.0017 | 0.009 | 0.007 | 299 | 0.0565 | 0.0206 | 0.053 | 0.026 |
| 226 | 0.0164 | 0.0026 | 0.008 | <0.00300 | 300 | 0.0576 | 0.0195 | 0.039 | 0.016 |
| 227 | 0.0868 | 0.0086 | 0.011 | 0.005 | 301 | 0.409 | 0.152 | >0.750 | 0.14 |
| 228 | >1.00 | 0.12 | 0.161 | 0.053 | 302 | 0.0789 | 0.0245 | 0.11 | 0.023 |
| 229 | 0.203 | 0.0243 | 0.037 | 0.016 | 303 | 0.118 | 0.0316 | 0.156 | 0.03 |
| 230 | 0.373 | 0.0784 | 0.087 | 0.042 | 304 | 0.536 | 0.171 | >0.750 | 0.119 |
| 231 | 0.0591 | 0.0089 | 0.031 | 0.02 | 305 | 0.753 | 0.27 | >0.750 | 0.347 |
| 232 | 0.0994 | 0.0115 | 0.032 | 0.028 | 306 | 0.0778 | 0.0249 | 0.048 | 0.032 |
| 233 | >1.00 | 0.182 | 0.195 | 0.067 | 307 | 0.143 | 0.0168 | 0.036 | 0.044 |
| 234 | 0.0379 | 0.0081 | >0.750 | >0.750 | 308 | 0.513 | 0.042 | 0.095 | 0.062 |
| 235 | 0.107 | 0.0087 | 0.019 | 0.01 | 309 | 0.808 | 0.145 | 0.427 | 0.149 |
| 236 | >1.00 | 0.142 | 0.223 | 0.132 | 310 | 0.14 | 0.0283 | 0.064 | 0.053 |
| 237 | 0.979 | 0.142 | 0.215 | 0.125 | 311 | 0.209 | 0.0762 | 0.073 | 0.034 |
| 238 | 0.23 | 0.018 | 0.031 | 0.017 | 312 | 0.0086 | 0.0035 | 0.012 | 0.013 |
| 239 | 0.849 | 0.191 | 0.301 | 0.163 | 313 | 0.197 | 0.0487 | 0.055 | 0.019 |
| 240 | 0.022 | 0.0032 | 0.009 | 0.004 | 314 | 0.0187 | 0.0045 | 0.017 | 0.017 |
| 241 | 0.751 | 0.097 | 0.15 | 0.077 | 315 | 0.25 | 0.0422 | 0.043 | 0.022 |
| 242 | 0.246 | 0.2 | 0.289 | 0.254 | 316 | 0.0084 | 0.0012 | 0.027 | 0.017 |
| 243 | 0.0284 | 0.0858 | 0.264 | 0.069 | 317 | 0.144 | 0.0516 | 0.019 | 0.015 |
| 244 | 0.0456 | 0.0268 | 0.052 | <0.0160 | 318 | 0.0099 | 0.0019 | 0.165 | 0.145 |
| 245 | 0.164 | 0.0187 | 0.063 | 0.029 | 319 | 0.0043 | 0.0072 | 0.011 | 0.01 |
| 246 | 0.0503 | 0.0185 | 0.072 | 0.036 | 320 | 0.0101 | 0.0284 | 0.008 | 0.006 |
| 247 | 0.0484 | 0.0889 | 0.108 | 0.054 | 321 | 0.195 | 0.46 | 0.129 | 0.094 |
| 248 | 0.439 | 0.193 | 0.235 | 0.108 | 322 | 0.0544 | 0.0198 | 0.015 | 0.011 |
| 249 | 0.0601 | 0.0377 | 0.045 | 0.0285 | 323 | 0.21 | 0.221 | 0.059 | 0.028 |
| 250 | 0.0043 | 0.00314 | 0.007 | 0.01 | 324 | 0.0851 | 0.0217 | 0.02 | 0.011 |
| 251 | 0.0086 | 0.00531 | 0.012 | 0.01 | 325 | 0.035 | 0.0086 | 0.084 | 0.119 |
| 252 | 0.0171 | 0.00541 | 0.009 | 0.009 | 326 | 0.884 | 0.273 | 0.164 | 0.132 |
| 253 | 0.203 | 0.0352 | 0.08 | 0.05 | 327 | 0.0864 | 0.0198 | | |
| 254 | 0.284 | 0.122 | 0.12 | 0.04 | 328 | >1.00 | 0.484 | >0.750 | >0.750 |
| 255 | 0.0227 | 0.00406 | 0.009 | 0.007 | 329 | 0.034 | 0.0177 | 0.058 | 0.032 |
| 256 | 0.0302 | 0.00525 | 0.016 | 0.0145 | 330 | 0.204 | 0.0227 | 0.055 | 0.06 |
| 257 | 0.101 | 0.0141 | 0.014 | 0.015 | 331 | 0.0752 | 0.0109 | 0.014 | 0.012 |
| 258 | 0.0509 | 0.00649 | 0.011 | 0.006 | 332 | 0.334 | 0.0612 | 0.013 | 0.013 |
| 259 | 0.135 | 0.0125 | 0.015 | 0.015 | 333 | 0.0692 | 0.0229 | 0.013 | 0.024 |
| 260 | 0.485 | 0.0715 | 0.065 | 0.047 | 334 | 0.0826 | 0.0091 | 0.017 | 0.012 |
| 261 | >1.00 | 0.453 | 0.627 | 0.256 | 335 | 0.0977 | 0.0168 | 0.028 | 0.02 |
| 262 | 0.0102 | 0.00163 | 0.0075 | 0.005 | 336 | 0.319 | 0.0682 | 0.019 | 0.037 |
| 263 | 0.0547 | 0.0054 | 0.011 | 0.009 | 337 | 0.285 | 0.0613 | 0.064 | 0.088 |
| 264 | 0.0347 | 0.00988 | 0.058 | 0.026 | 338 | 0.024 | 0.0068 | 0.03 | 0.023 |
| 265 | 0.0296 | 0.0126 | 0.041 | 0.023 | 339 | 0.0354 | 0.0061 | 0.026 | 0.014 |

| Ex. No. | Kiapp (BFC, Baculo.) (μM) | Kiapp (BFC, Super.) (μM) | IC50 (Testo.) (μM) | IC50 (Midazolam) (μM) |
|---|---|---|---|---|
| 340 | 0.338 | 0.0922 | 0.044 | 0.041 |
| 341 | 0.0366 | 0.0131 | 0.026 | 0.022 |
| 342 | 0.063 | 0.0131 | 0.015 | 0.011 |
| 343 | 0.206 | 0.0603 | 0.08 | 0.037 |
| 344 | 0.0544 | 0.0212 | 0.009 | 0.007 |
| 345 | 0.409 | 0.135 | 0.048 | 0.075 |
| 346 | 0.052 | 0.0132 | 0.011 | 0.019 |
| 347 | 0.0347 | 0.0054 | 0.026 | 0.013 |
| 348 | 0.0308 | 0.0047 | 0.012 | 0.007 |
| 349 | 0.0564 | 0.0074 | 0.025 | 0.011 |
| 350 | 0.139 | 0.0214 | 0.039 | 0.02 |
| 351 | 0.456 | 0.138 | 0.11 | 0.113 |
| 352 | 0.0704 | 0.0226 | 0.031 | 0.016 |
| 353 | 0.0281 | 0.0115 | 0.031 | 0.018 |
| 354 | 0.305 | 0.0253 | 0.061 | 0.031 |
| 355 | 0.181 | 0.0449 | 0.064 | 0.063 |
| 356 | 0.483 | 0.148 | 0.114 | 0.083 |
| 357 | 0.123 | 0.0304 | 0.043 | 0.032 |
| 358 | 0.592 | 0.137 | 0.1 | 0.068 |
| 359 | 0.593 | 0.14 | 0.26 | 0.101 |
| 360 | 0.0808 | 0.0218 | 0.043 | 0.025 |
| 361 | 0.274 | 0.0414 | 0.04 | 0.016 |
| 362 | 0.0944 | 0.0229 | 0.044 | 0.026 |
| 363 | 0.169 | 0.0364 | 0.076 | 0.037 |
| 364 | 0.0868 | 0.0234 | 0.049 | 0.033 |
| 365 | >1.00 | 0.515 | >0.750 | >0.750 |
| 366 | 0.553 | 0.0651 | >0.750 | 0.253 |
| 367 | 0.57 | 0.148 | >0.750 | 0.317 |
| 368 | 0.0076 | 0.0011 | 0.018 | 0.006 |
| 369 | 0.35 | 0.0532 | 0.181 | 0.098 |
| 370 | 0.0529 | 0.019 | 0.008 | 0.012 |
| 371 | 0.248 | 0.0588 | 0.01 | 0.005 |
| 372 | 0.079 | 0.018 | 0.023 | 0.015 |
| 373 | 0.221 | 0.045 | 0.049 | 0.037 |
| 374 | 0.483 | 0.0745 | 0.079 | 0.029 |
| 375 | 0.142 | 0.0316 | 0.042 | 0.022 |
| 376 | 0.117 | 0.073 | 0.043 | 0.027 |
| 377 | 0.0763 | 0.0176 | 0.033 | 0.021 |
| 378 | 0.078 | 0.0187 | 0.014 | 0.013 |
| 379 | 0.12 | 0.0246 | 0.007 | 0.008 |
| 380 | 0.215 | 0.0607 | 0.029 | 0.021 |
| 381 | 0.052 | 0.00279 | 0.064 | 0.03 |
| 382 | 0.505 | 0.0201 | 0.263 | 0.068 |
| 383 | 0.912 | 0.031 | 0.348 | 0.067 |
| 384 | 0.56 | 0.0192 | 0.178 | 0.043 |
| 385 | >1.00 | 0.216 | >0.750 | >0.750 |
| 386 | >1.00 | 0.174 | >0.750 | >0.750 |
| 387 | >1.00 | 0.224 | >0.750 | >0.750 |
| 388 | 0.016 | <0.00100 | 0.003 | 0.009 |
| 389 | 0.241 | 0.00281 | 0.057 | 0.024 |
| 390 | 0.0849 | 0.00178 | 0.07 | 0.018 |
| 391 | 0.317 | 0.00626 | 0.063 | 0.027 |
| 392 | >1.00 | 0.32 | 0.009 | 0.065 |
| 393 | | | | 0.008 |

We claim:

1. A compound of formula (I),

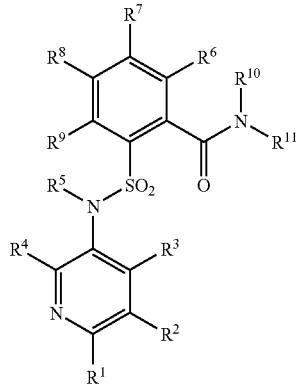

wherein:

$R^1$, $R^2$, $R^3$, $R^4$ are independently selected from hydrogen, $C_1$-$C_6$ alkyl, —$(CR^{12a}R^{12b})_t$halo, —$(CR^{12a}R^{12b})_t$CN, —$(CR^{12a}R^{12b})_t$OR$^{12a}$, —$(CR^{12a}R^{12b})_t$N(R$^{12a}$R$^{12b}$), —$(CR^{12a}R^{12b})_t$CF$_3$, and —$(CR^{12a}R^{12b})_t$C$_6$-C$_{10}$ aryl;

$R^5$ is hydrogen or $C_1$-$C_6$ alkyl;

$R^6$, $R^7$, $R^8$, and $R^9$ are independently selected from hydrogen, $C_1$-$C_6$ alkyl, —(CR$^{12a}$R$^{12b}$)$_t$halo, —(CR$^{12a}$R$^{12b}$)$_t$CN, —(CR$^{12a}$R$^{12b}$)$_t$CF$_3$, —(CR$^{12a}$R$^{12b}$)$_t$OR$^{12a}$, —(CR$^{12a}$R$^{12b}$)$_t$N(R$^{12a}$R$^{12b}$), —(CR$^{12a}$R$^{12b}$)$_t$R$^{12a}$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —O(CR$^{12a}$R$^{12b}$)$_t$R$^{12a}$, —O(CR$^{12a}$R$^{12b}$)$_t$C$_3$-C$_{11}$ cycloalkyl, —O(CR$^{12a}$R$^{12b}$)$_t$C$_6$-C$_{10}$ aryl, —O(CR$^{12a}$R$^{12b}$)$_t$OR$^{12a}$, and —O(CR$^{12a}$R$^{12b}$)$_t$N(R$^{12a}$R$^{12b}$), wherein each of said $C_1$-$C_6$ alkyl, $C_3$-$C_{11}$ cycloalkyl, and $C_6$-$C_{10}$ aryl, is optionally substituted with one or more R$^{14}$;

$R^{10}$ and $R^{11}$ are independently selected from hydrogen, —(CR$^{12a}$R$^{12b}$)$_t$C$_1$-C$_6$ alkyl, —(CR$^{12a}$R$^{12b}$)$_t$C$_3$-C$_{11}$ cycloalkyl, —(CR$^{12a}$R$^{12b}$)$_t$C$_6$-C$_{10}$ aryl, and wherein each of said $C_1$-$C_6$ alkyl, $C_3$-$C_{11}$ cycloalkyl, and $C_6$-$C_{10}$ aryl, groups is optionally substituted with one or more R$^{13}$;

each R$^{12a}$ and R$^{12b}$ is independently selected from hydrogen and $C_1$-$C_6$ alkyl; or R$^{12a}$ and R$^{12b}$, together with the atom to which they are attached, form a $C_3$-$C_{11}$ cycloalkyl;

each R$^{13}$ is independently selected from $C_1$-$C_6$ alkyl, halogen, —(CR$^{12a}$R$^{12b}$)$_t$CN, —(CR$^{12a}$R$^{12b}$)$_t$CF$_3$, —(CR$^{12a}$R$^{12b}$)$_t$OCF$_3$, —(CR$^{12a}$R$^{12b}$)$_t$C$_3$-C$_{11}$ cycloalkyl, —(CR$^{12a}$R$^{12b}$)$_t$C$_6$-C$_{10}$ aryl, —O(CR$^{12a}$R$^{12b}$)$_t$R$^{12a}$, —O(CR$^{12a}$R$^{12b}$)$_t$C$_6$-C$_{10}$ aryl, —(CR$^{12a}$R$^{12b}$)$_t$CO$_2$ (C$_1$-C$_6$ alkyl), —(CR$^{12a}$R$^{12b}$)$_t$N(R$^{12a}$R$^{12b}$), —(CR$^{12a}$R$^{12b}$)$_t$C(O)NR$^{12a}$R$^{12b}$, —(CR$^{12a}$R$^{12b}$)$_t$OR$^{12a}$, —(CR$^{12a}$R$^{12b}$)$_t$S(O)R$^{12a}$, and —(CR$^{12a}$R$^{12b}$)$_t$S(O)$_2$R$^{12a}$, wherein each of said $C_1$-$C_6$ alkyl, $C_3$-$C_{11}$ cycloalkyl, and groups is optionally substituted with one or more R$^{14}$;

each R$^{14}$ is independently selected from $C_1$-$C_6$ alkyl, halogen, —CN, —CF$_3$, and —OR$^{12a}$; and each t is independently selected from 0, 1, 2, 3, 4, 5, and 6; or a pharmaceutically acceptable salt thereof.

2. A compound according to claim 1, wherein:

$R^1$, $R^2$, $R^3$, $R^4$ are independently selected from hydrogen, $C_1$-$C_6$ alkyl, —(CR$^{12a}$R$^{12b}$)$_t$halo, —(CR$^{12a}$R$^{12b}$)$_t$CN, —$(CR^{12a}R^{12b})_rOR^{12a}$, —$(CR^{12a}R^{12b})_rN(R^{12a}R^{12b})$, and —$(CR^{12a}R^{12b})_rCF_3$; and $R^{10}$ and $R^{11}$ are independently selected from hydrogen, —$(CR^{12a}R^{12b})_rC_1$-$C_6$ alkyl, —$(CR^{12a}R^{12b})_rC_3$-$C_{11}$ cycloalkyl, —$(CR^{12a}R^{12b})_rC_6$-$C_{10}$ aryl, wherein each of said $C_1$-$C_6$ alkyl, $C_3$-$C_{11}$ cycloalkyl, and $C_6$-$C_{10}$ aryl, groups is optionally substituted with one or more $R^{13}$; or a pharmaceutically acceptable salt thereof.

3. A compound according to claim 2, wherein:
$R^1$, $R^2$, $R^3$, $R^4$ are independently selected from hydrogen, $C_1$-$C_6$ alkyl, halo, —CN, —$OR^{12a}$, and —$CF_3$; and
$R^5$ is hydrogen; or
a pharmaceutically acceptable salt thereof.

4. A compound according to claim 3, wherein:
$R^{10}$ is hydrogen or $C_1$-$C_6$ alkyl; and
$R^{11}$ is selected from —$(CR^{12a}R^{12b})_rC_1$-$C_6$ alkyl, —$(CR^{12a}R^{12b})_rC_3$-$C_{11}$ cycloalkyl, —$(CR^{12a}R^{12b})_rC_6$-$C_{10}$ aryl, wherein each of said $C_1$-$C_6$ alkyl, $C_3$-$C_{11}$ cycloalkyl, and $C_6$-$C_{10}$ aryl groups is optionally substituted with one or more $R^{13}$; or
a pharmaceutically acceptable salt thereof.

5. A compound according to claim 4, wherein $R^6$, $R^7$, $R^8$, and $R^9$ are hydrogen, or a pharmaceutically acceptable salt thereof.

6. A compound according to claim 5, wherein:
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$;
$R^{12a}$ is hydrogen or $C_1$-$C_6$ alkyl; and
each $R^{13}$ is independently selected from $C_1$-$C_6$ alkyl, halogen, —CN, —$CF_3$, and —$OCF_3$; or
a pharmaceutically acceptable salt thereof.

7. A compound according to claim 6, wherein:
$R^1$, $R^2$, and $R^4$ are hydrogen;
$R^3$ is $C_1$-$C_6$ alkyl, —Cl, —F, —CN, —$OCH_3$, —$OCH_2CH_3$, or —$CF_3$;
$R^{10}$ is hydrogen or —$CH_3$; and
each $R^{13}$ is independently selected from $C_1$-$C_6$ alkyl, —Cl, —F, —CN, —$CF_3$, and —$OCF_3$; or
a pharmaceutically acceptable salt thereof.

8. A compound according to claim 1, wherein:
$R^1$, $R^2$, and $R^4$ are hydrogen;
$R^3$ is —$CH_3$, —$OCH_3$ or —$OCH_2CH_3$;
$R^5$ is hydrogen;
$R^6$, $R^7$, $R^8$, and $R^9$ are hydrogen;
$R^{10}$ is hydrogen or —$CH_3$;
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more $R^{13}$; and
each $R^{13}$ is independently selected from $C_1$-$C_6$ alkyl, —Cl, —F, —CN, —$CF_3$, and —$OCF_3$; or a pharmaceutically acceptable salt thereof.

9. A compound according to claim 1, wherein:
$R^1$, $R^2$, and $R^4$ are hydrogen;
$R^3$ is —$OCH_3$ or —$OCH_2CH_3$;
$R^5$ is hydrogen;
$R^6$, $R^7$, $R^8$, and $R^9$ are hydrogen;
$R^{10}$ is hydrogen or —$CH_3$; and
$R^{11}$ is —$(CH_2)C_6$-$C_{10}$ aryl or —$(CH_2)_2C_6$-$C_{10}$ aryl, wherein said $C_6$-$C_{10}$ aryl is optionally substituted with one or more substituents independently selected from —Cl and —F; or
a pharmaceutically acceptable salt thereof.

10. A compound selected from N-(3,4-difluorobenzyl)-2-{[(5-methoxypyridin-3-yl)amino]sulfonyl}benzamide; N-[2-(2-methylphenyl)ethyl]-2-{[(5-methylpyridin-3-yl)amino]sulfonyl}benzamide; N-(3,4-dichlorobenzyl)-2-{[(5-methylpyridin-3-yl)amino]sulfonyl}benzamide; N-[4-fluoro-3-(trifluoromethyl)benzyl]-2-{[(5-methylpyridin-3-yl)amino]sulfonyl}benzamide; N-[4-fluoro-3-(trifluoromethyl)benzyl]-2-{[(5-methoxypyridin-3-yl)amino]sulfonyl}benzamide; 2-{[(5-ethoxypyridin-3-yl)amino]sulfonyl}-N-[2-(2-methylphenyl)ethyl]benzamide; N-(3,4-dichlorobenzyl)-2-{[(5-ethoxypyridin-3-yl)amino]sulfonyl}benzamide; N-(3,4-difluorobenzyl)-2-{[(5-ethoxypyridin-3-yl)amino]sulfonyl}-N-methylbenzamide; 2-{[(4-ethoxypyridin-3-yl)amino]sulfonyl}-N-[4-fluoro-3-(trifluoromethyl)benzyl]benzamide; 2-{[(5-ethoxypyridin-3-yl)amino]sulfonyl}-N-[4-fluoro-3-(trifluoromethyl)benzyl]benzamide; N-(3,4-difluorobenzyl)-2-{[(4-ethoxypyridin-3-yl)amino]sulfonyl}-N-methylbenzamide; N-(4-chloro-2-methylbenzyl)-2-{[(5-methoxypyridin-3-yl)amino]sulfonyl}benzamide; N-(3-chloro-2-methylbenzyl)-2-{[(5-methoxypyridin-3-yl)amino]sulfonyl}benzamide; N-(3,5-dichlorobenzyl)-2-{[(5-methylpyridin-3-yl)amino]sulfonyl}benzamide; and N-(3,4-difluorobenzyl)-2-{[(4-methoxypyridin-3-yl)amino]sulfonyl}-N-methylbenzamide; or a pharmaceutically acceptable salt thereof.

11. A compound selected from N-(3,4-difluorobenzyl)-2-{[(4-methoxypyridin-3-yl)amino]sulfonyl}-N-methylbenzamide; N-(3,4-difluorobenzyl)-2-{[(4-methoxypyridin-3-yl)amino]sulfonyl}benzamide; N-[2-(2-fluorophenyl)ethyl]-2-{[(5-methoxypyridin-3-yl)amino]sulfonyl}benzamide; N-[4-fluoro-3-(trifluoromethyl)benzyl]-2-{[(4-methoxypyridin-3-yl)amino]sulfonyl}benzamide; N-(3,4-difluorobenzyl)-2-{[(4-ethoxypyridin-3-yl)amino]sulfonyl}benzamide; and N-(3,4-difluorobenzyl)-2-{[(4-ethoxypyridin-3-yl)amino]sulfonyl}-N-methylbenzamide; or a pharmaceutically acceptable salt thereof.

12. A pharmaceutical composition, comprising an effective amount of one or more compounds according to claim 1, and a pharmaceutically acceptable carrier.

* * * * *